United States Patent
Condon et al.

(10) Patent No.: US 8,415,486 B2
(45) Date of Patent: Apr. 9, 2013

(54) IAP INHIBITORS

(75) Inventors: Stephen M. Condon, Malvern, PA (US); Yijun Deng, Malvern, PA (US); Matthew D. Alexander, Malvern, PA (US); Matthew G. Laporte, Malvern, PA (US)

(73) Assignee: TetraLogic Pharmaceuticals Corp., Malvern, PA (US)

( * ) Notice: Subject to any disclaimer, the term of this patent is extended or adjusted under 35 U.S.C. 154(b) by 0 days.

(21) Appl. No.: 13/322,709

(22) PCT Filed: May 27, 2010

(86) PCT No.: PCT/US2010/036320
§ 371 (c)(1),
(2), (4) Date: Dec. 7, 2011

(87) PCT Pub. No.: WO2010/138666
PCT Pub. Date: Dec. 2, 2010

(65) Prior Publication Data
US 2012/0135990 A1    May 31, 2012

Related U.S. Application Data

(60) Provisional application No. 61/181,914, filed on May 28, 2009.

(51) Int. Cl.
*C07D 239/02*  (2006.01)
*C07D 487/02*  (2006.01)
*C07D 211/32*  (2006.01)
*C07D 413/14*  (2006.01)
*A61K 31/505*  (2006.01)
*A61K 31/40*  (2006.01)
*A61K 31/445* (2006.01)
*A61K 31/535* (2006.01)

(52) U.S. Cl.
USPC ........... 548/453; 546/199; 544/144; 544/323; 514/421; 514/326; 514/234.5; 514/275

(58) Field of Classification Search .................. None
See application file for complete search history.

(56) References Cited

U.S. PATENT DOCUMENTS

2011/0237517 A1*  9/2011  Condon et al. ............... 514/18.9
2012/0094917 A1*  4/2012  Condon et al. ............... 514/18.7

FOREIGN PATENT DOCUMENTS

WO     2005097791 A1    10/2005
WO     2008014240 A2     1/2008
WO     2008/134679      11/2008

OTHER PUBLICATIONS

Liu et al., Structural basis for binding of Smac/DIABLO to the XIAP BIR3 domain, 2000, Nature vol. 408, pp. 1004-1008; p. 1004-p. 1007.
Extended European Search Report dated Nov. 22, 2012 in EP Application No. 10781180.

* cited by examiner

*Primary Examiner* — Kamal Saeed
*Assistant Examiner* — Nyeemah A Grazier
(74) *Attorney, Agent, or Firm* — Banner & Witcoff, Ltd.

(57) ABSTRACT

The present invention describes compounds, processes for their preparation, pharmaceutical compositions containing them, and their use in therapy.

33 Claims, No Drawings

IAP INHIBITORS

BACKGROUND OF THE INVENTION

1. Field of the Invention

The present invention describes compounds that are inhibitors of IAPs (inhibitors of apoptosis proteins), processes for their preparation, pharmaceutical compositions containing them, and their use in therapy. The compounds of the present invention are useful in the treatment of cancer, autoimmune diseases and other disorders.

2. Description of Related Art

Apoptosis (programmed cell death) plays a central role in the development and homeostasis of all multi-cellular organisms. Apoptosis can be initiated within a cell from an external factor such as a chemokine (an extrinsic pathway) or via an intracellular event such a DNA damage (an intrinsic pathway). Alterations in apoptotic pathways have been implicated in many types of human pathologies, including developmental disorders, cancer, autoimmune diseases, as well as neurodegenerative disorders. One mode of action of chemotherapeutic drugs is cell death via apoptosis.

Apoptosis is conserved across species and executed primarily by activated caspases, a family of cysteine proteases with aspartate specificity in their substrates. These cysteine containing aspartate specific proteases ("caspases") are produced in cells as catalytically inactive zymogens and are proteolytically processed to become active proteases during apoptosis. Once activated, effector caspases are responsible for proteolytic cleavage of a broad spectrum of cellular targets that ultimately lead to cell death. In normal surviving cells that have not received an apoptotic stimulus, most caspases remain inactive. If caspases are aberrantly activated, their proteolytic activity can be inhibited by a family of evolutionarily conserved proteins called IAPs (inhibitors of apoptosis proteins).

The IAP family of proteins suppresses apoptosis by preventing the activation of procaspases and inhibiting the enzymatic activity of mature caspases. Several distinct mammalian IAPs including XIAP, c-IAP1, c-IAP2, ML-IAP, NAIP (neuronal apoptosis inhibiting protein), Bruce, and survivin, have been identified, and they all exhibit anti-apoptotic activity in cell culture. IAPs were originally discovered in baculovirus by their functional ability to substitute for P35 protein, an anti-apoptotic gene. IAPs have been described in organisms ranging from Drosophila to human, and are known to be overexpressed in many human cancers. Generally speaking, IAPs comprise one to three Baculovirus IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion. It is the BIR domain that is believed to cause the anti-apoptotic effect by inhibiting the caspases and thus inhibiting apoptosis. XIAP is expressed ubiquitously in most adult and fetal tissues. Overexpression of XIAP in tumor cells has been demonstrated to confer protection against a variety of pro-apoptotic stimuli and promotes resistance to chemotherapy. Consistent with this, a strong correlation between XIAP protein levels and survival has been demonstrated for patients with acute myelogenous leukemia. Down-regulation of XIAP expression by antisense oligonucleotides has been shown to sensitize tumor cells to death induced by a wide range of pro-apoptotic agents, both in vitro and in vivo In normal cells signaled to undergo apoptosis, however, the IAP-mediated inhibitory effect must be removed, a process at least in part performed by a mitochondrial protein named Smac (second mitochondrial activator of caspases). Smac (or, DIABLO), is synthesized as a precursor molecule of 239 amino acids; the N-terminal 55 residues serve as the mitochondria targeting sequence that is removed after import. The mature form of Smac contains 184 amino acids and behaves as an oligomer in solution. Smac and various fragments thereof have been proposed for use as targets for identification of therapeutic agents.

Smac is synthesized in the cytoplasm with an N-terminal mitochondrial targeting sequence that is proteolytically removed during maturation to the mature polypeptide and is then targeted to the inter-membrane space of mitochondria. At the time of apoptosis induction, Smac is released from mitochondria into the cytosol, together with cytochrome c, where it binds to IAPs, and enables caspase activation, therein eliminating the inhibitory effect of IAPs on apoptosis. Whereas cytochrome c induces multimerization of Apaf-1 to activate procaspase-9 and -3, Smac eliminates the inhibitory effect of multiple IAPs. Smac interacts with essentially all IAPs that have been examined to date including XIAP, c-IAP1, c-IAP2, ML-IAP, and survivin. Thus, Smac appears to be a master regulator of apoptosis in mammals.

It has been shown that Smac promotes not only the proteolytic activation of procaspases, but also the enzymatic activity of mature caspase, both of which depend upon its ability to interact physically with IAPs. X-ray crystallography has shown that the first four amino acids (AVPI) of mature Smac bind to a portion of IAPs. This N-terminal sequence is essential for binding IAPs and blocking their anti-apoptotic effects.

Currently, there are drug discovery efforts aimed at identifying compounds that interfere with the role played by IAPs in disease states where a defect in apoptosis is implicated, such as in cancers and autoimmune diseases. Indeed, a number of IAP inhibitors that mimic the interactions of the Smac tetrapeptide are now known and possess pro-apoptotic activity in vitro and in vivo. The art continues to look for additional compounds that may function as IAP inhibitors.

SUMMARY OF THE INVENTION

The present invention provides IAP inhibitors (Smac mimetics), as well as therapeutic methods of using these inhibitors to modulate apoptosis.

In one embodiment, which can be practiced either separately, or in combination with the other embodiments disclosed below, the present invention provides compounds of Formula (I):

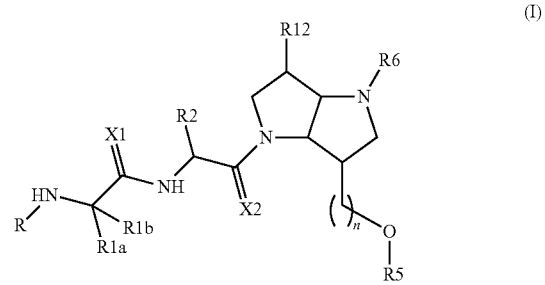

wherein:
X1 and X2 are each independently O, or S:
n is 0 or 1;

R is selected from H, alkyl, substituted alkyl, alkenyl, substituted alkenyl, cycloalkyl, substituted cycloalkyl, aryl, substituted aryl, heteroaryl, or substituted heteroaryl;

R1a and R1b are each independently selected from H, alkyl, or substituted alkyl;

R2 is selected from H, alkyl, substituted alkyl, cycloalkyl, substituted cycloalkyl, heterocycloalkyl, substituted heterocycloalkyl, aryl, substituted aryl, heteroaryl, or substituted heteroaryl;

R5 is selected from H, alkyl, substituted alkyl, cycloalkyl, substituted cycloalkyl, aryl, substituted aryl, heterocycloalkyl, substituted heterocycloalkyl, heteroaryl, or substituted heteroaryl;

R6 is selected from H, alkyl, substituted alkyl, alkoxy, substituted alkoxy, alkylsulfonyl, arylsulfonyl, cycloalkyl, substituted cycloalkyl, heterocycloalkyl, substituted heterocycloalkyl, aryl, substituted aryl, heteroaryl, or substituted heteroaryl; and R12 is selected from H or hydroxy, In another embodiment, the various elements of which can be practiced either separately, or in combination with the other embodiments disclosed above and below, the various substituents of Formula (I) are defined as follows:

X1 and X2 are O, or S;

R is selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R1a and R1b are each independently selected from H, alkyl, or substituted alkyl, wherein the substitutents are selected from the group consisting of halogen, hydroxy, oxo, mercapto, carboxyl, cycloalkyl, aryl, alkoxy, amino, heteroaryl, and nitro;

R2 is alkyl; substituted alkyl, wherein the substituents are selected from the group consisting of halogen, hydroxy, oxo, alkoxy, cycloalkyl, aryl, heterocycloalkyl and heteroaryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl, or substituted heteroaryl wherein the substituents are selected from the group consisting of halogen, hydroxy, mercapto, carboxyl, alkyl, cycloalkyl, aryl, alkoxy, amino, heteroaryl, and nitro;

R5 is selected from H; alkyl; substituted alkyl, wherein the alkyl substituents are selected from the groups consisting of oxo, amino, alkoxy, carboxy, carboalkoxy, cycloalkyl, aryl, and substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl, or substituted heteroaryl, wherein the substituents are selected from the group consisting of halogen, hydroxy, mercapto, carboxyl, alkyl, cycloalkyl, aryl, alkoxy, amino, heteroaryl, and nitro;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; and R12 is selected from H or hydroxy.

In another embodiment, the various elements of which can be practiced either separately, or in combination with the other embodiments disclosed above and below, the various substituents of Formula (I) are defined as follows:

R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro;

R1a and R1b are each independently selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

R2 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R5 is selected from H; alkyl; substituted alkyl, wherein the alkyl substituents are selected from the groups consisting of oxo, amino, aryl, and substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; aryl; substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; or heterocycloalkyl;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; and R12 is selected from H or hydroxy.

In another embodiment, the various elements of which can be practiced either separately, or in combination with the other embodiments disclosed above and below, various substituents of Formula (I) are defined as follows:

R is selected from H, or lower alkyl;

R1a and R1b are each independently selected from H, or lower alkyl optionally substituted with halogen;

R2 is selected from H; lower alkyl; cycloalkyl, or substituted lower alkyl wherein the substituents are selected from the group consisting of hydroxy, cycloalkyl and alkoxy;

R5 is selected from H; alkyl; substituted alkyl, wherein the alkyl substituents are selected from the groups consisting of oxo, amino, aryl, and substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; aryl; substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; or heterocycloalkyl;

R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen, and R12 is H, or hydroxy.

In still another embodiment, the various elements of which can be practiced either separately, or in combination with the other embodiments disclosed above and below, various substituents of Formula (I) are defined as follows:

X1 and X2 are O;

R is methyl;

R1a is H and R1b is selected from methyl or fluoromethyl;

R2 is selected from iso-propyl, t-butyl, 2-methoxy ethyl (e.g.,

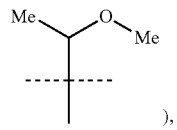

), or cyclohexyl;

R5 is selected from H; alkyl; substituted alkyl, wherein the alkyl substituents are selected from the groups consisting of oxo, amino, heterocycloalkyl, and aryl optionally substituted with halogen; cycloalkyl; aryl; or substituted aryl wherein the aryl substituents are selected from the groups consisting of halogen and phenyl;

R6 is selected from H; lower alkylsulfonyl; lower alkyl; substituted lower alkyl, wherein the substituents are selected from the groups consisting of oxo, lower alkoxy, amino, and heteroaryl optionally substituted with lower alkyl or halogen; cycloalkyl; heterocycloalkyl; or heteroaryl, and R12 is H, or hydroxy.

In another embodiment, the various elements of which can be practiced either separately, or in combination with the other embodiments disclosed above and below, the various substituents of Formula (I) are defined as follows:

X1 and X2 are O.

In yet another embodiment, the various elements of which can be practiced either separately, or in combination with the other embodiments disclosed above and below, amino comprises a group having a formula —NHR3 or —NR3R4, where the R3 and R4 groups can be the same or different and are selected from the groups consisting of alkyl, substituted alkyl, aryl, substituted aryl, cycloalkyl and heterocycloalkyl.

In another embodiment, the various elements of which can be practiced either separately, or in combination with the other embodiments disclosed above and below, R5 is selected from H; phenyl, biphenyl, fluorophenyl, naphthyl, tetrahydronaphthyl, benzyl, fluorobenzyl, pyrrolidinyl carbonyl, piperidyl carbonyl, morpholinyl carbonyl, benzyl carbamoyl, phenyl carbamoyl, naphthyl carbamoyl, ethyl carbamoyl, n-butyl carbamoyl, isopropyl carbamoyl, tert-butyl carbamoyl, cyclopropyl carbamoyl, cyclohexyl carbamoyl, diphenylamino carbonyl, or methyl-phenyl amino carbonyl.

In still another embodiment, the various elements of which can be practiced either separately, or in combination with the other embodiments disclosed above and below, R6 is selected from H, ethyl, cyclopropyl, cyclohexyl, acetyl, tert-butoxy carbonyl, 3-methyl butyryl, 2-oxo-propionyl, methylsulfonyl, 2-methyl-propylsulfonyl, methyl carbamoyl, isopropyl carbamoyl, dimethyl carbamoylbenzyl carbamoyl, tetrahydro pyanyl, or pyrimidinyl.

In one embodiment, the separate elements of which can be practiced either separately, or in combination with the other embodiments disclosed above and below, the compounds of Formula (I), particularly those where X1 and X2 are O and R1a is H, or their pharmaceutically acceptable salts, have the absolute configuration of formula (I-S) as follows (with the various substituents having the same definitions presented above in connection with all of the embodiments associated with formula (I)):

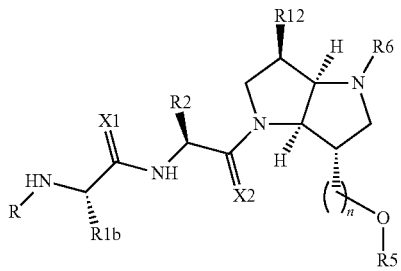

(I-S)

In related compounds, the separate elements of which can be practiced either separately, or in combination with the other embodiments disclosed above and below, the compounds and pharmaceutically acceptable salts of Formula (I), particularly those where X1 and X2 are O and R1a is H have the absolute configuration of formula (I-R) as follows (with the various substituents having the same definitions presented above in connection with all of the embodiments associated with formula (I)):

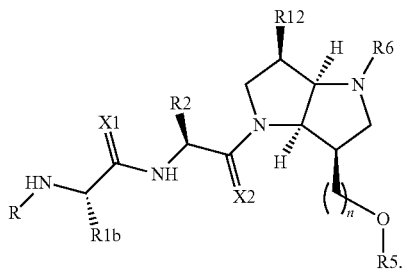

(I-R)

In all of the embodiments identified above and below, dimers are also encompassed within the scope of this invention. Dimerization of monomeric Smac mimetics has been shown to provide useful Smac mimetics. See, e.g., U.S. Pat. No. 7,517,906, US20080020986, WO200814236, WO200814238, and WO200814240, all of which are incorporated herein by reference as though fully set forth.

Dimeric Smac mimetics of the invention generally comprise the formula "Formula (I)-L-Formula (I)", as depicted here:

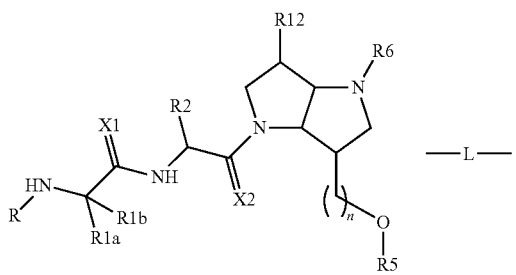

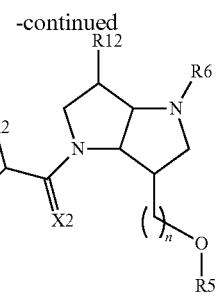

or Formula (I-S)-L- Formula (I-S) or Formula (I-S)-L- Formula (I-R).

L is a "Linker" (L), i.e., a bond or a linking group whereby two chemical moieties are directly covalently linked one to the other or are indirectly linked via a chemical moiety that covalently links the two chemical moieties, in either case, to form a homo- or heterodimer. A Linker, therefore, is a single or double covalent bond or is a contiguous chain, branched or unbranched, substituted or unsubstituted, of 1 to about 100 atoms, typically 1 to about 30 atoms and typically up to about 500 MW, e.g., optionally substituted alkyl, alkylene, alkylyne, cycloalkyl, alkylcycloalkyl, alkylarylalkyl chain of 2 to 20 atoms with 1-4 heteroatoms selected from —O—, —NH— and —S—. Illustrative Linkers are described, e.g., in U.S. Pat. No. 7,517,906, U.S. Pat. No. 7,309,792, US20080020986, WO200814236, WO200814238, and WO200814240, US 20050197403, U.S. Pat. No. 7,589,118, WO2010031171, WO2007131366, WO2007104162, and WO2008134679 all of which are incorporated herein by reference as though fully set forth.

Illustrative -L- groups include the following:
1) —C1-C10 alkyl-,
2) —C2-C6 alkenyl-,
3) —C2-C4 alkynyl-,
4) —C3-C7 cycloalkyl-,
5) -phenyl-,
6) -biphenyl-,
7) -heteroaryl-,
8) -heterocyclyl-,
9) —C1-C6 alkyl-(C2-C6 alkenyl)-C1-C6 alkyl-,
10) —C1-C6 alkyl-(C2-C4 alkynyl)-C1-C6 alkyl-,
11) —C1-C6 alkyl-(C3-C7 cycloalkyl)-C1-C6 alkyl-,
12) —C1-C6 alkyl-phenyl-C1-C6 alkyl-,
13) —C1-C6 alkyl-biphenyl-C1-C6 alkyl-,
14) —C1-C6 alkyl-heteroaryl-C1-C6 alkyl-,
15) —C1-C6 alkyl-heterocyclyl-C1-C6 alkyl-,
16) —C1-C6 alkyl-O—C1-C6 alkyl-,
17) —C(O)—N—C(O)— wherein N is cyclohexyl, phenyl, naphthyl or biphenyl optionally substituted with Rx and Rx is C1-C6 alkyl or C6-C10 aryl optionally substituted with C1-C6 alkyl,
18) —C(O)CH$_2$NHC(O)C(O)NHCH$_2$C(O)—.

For additional linkers, see, e.g., WO2007131366 and WO2007104162.

More specifically, in this embodiment., the invention provides a compound that is a dimer of two monomers of Formula (I), or two monomers of Formula (I-S) or one monomer of Formula (I-S) and one monomer of Formula (I-R), or a pharmaceutically acceptable salt thereof, wherein
X1 and X2 are each independently O, or S:
n is 0 or 1;
R is selected from H, alkyl, substituted alkyl, alkenyl, substituted alkenyl, cycloalkyl, substituted cycloalkyl, aryl, substituted aryl, heteroaryl, or substituted heteroaryl;

R1a and R1b are each independently selected from H, alkyl, or substituted alkyl;

R5 is selected from H, alkyl, substituted alkyl, cycloalkyl, substituted cycloalkyl, aryl, substituted aryl, heterocycloalkyl, substituted heterocycloalkyl, heteroaryl, or substituted heteroaryl;

both R2 groups together, or both R6 groups together, form -L-, linking the two monomers;

when both R6 groups together form -L-, then each R2 is selected from H, alkyl, substituted alkyl, cycloalkyl, substituted cycloalkyl, heterocycloalkyl, substituted heterocycloalkyl, aryl, substituted aryl, heteroaryl, or substituted heteroaryl;

when both R2 groups together form -L-, then each R6 is selected from H, alkyl, substituted alkyl, alkoxy, substituted alkoxy, alkylsulfonyl, arylsulfonyl, cycloalkyl, substituted cycloalkyl, heterocycloalkyl, substituted heterocycloalkyl, aryl, substituted aryl, heteroaryl, or substituted heteroaryl;

R12 is selected from H or hydroxyl, and

L is a single or double covalent bond, or is a contiguous chain, branched or unbranched, substituted or unsubstituted, of 1 to about 100 atoms.

In other embodiments, the elements of which can be practiced either separately, or in combination with the other embodiments disclosed above and below, the present invention provides a compound that is a dimer of two monomers of Formula (I), or two monomers of Formula (I-S) or one monomer of Formula (I-S) and one monomer of Formula (I-R), or a pharmaceutically acceptable salt thereof, wherein:

X1 and X2 are O, or S;

R is selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R1a and R1b are each independently selected from H, alkyl, or substituted alkyl, wherein the substitutents are selected from the group consisting of halogen, hydroxy, oxo, mercapto, carboxyl, cycloalkyl, aryl, alkoxy, amino, heteroaryl, and nitro;

R5 is selected from H; alkyl; substituted alkyl, wherein the alkyl substituents are selected from the groups consisting of oxo, amino, alkoxy, carboxy, carboalkoxy, cycloalkyl, aryl, and substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl, or substituted heteroaryl, wherein the substituents are selected from the group consisting of halogen, hydroxy, mercapto, carboxyl, alkyl, cycloalkyl, aryl, alkoxy, amino, heteroaryl, and nitro;

when both R6 groups together form -L-, then each R2 is alkyl; substituted alkyl, wherein the substituents are selected from the group consisting of halogen, hydroxy, oxo, alkoxy, cycloalkyl, aryl, heterocycloalkyl and heteroaryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl, or substituted heteroaryl wherein the substituents are selected from the group consisting of halogen, hydroxy, mercapto, carboxyl, alkyl, cycloalkyl, aryl, alkoxy, amino, heteroaryl, and nitro;

when both R2 groups together form -L-, then each R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro;

R12 is selected from H or hydroxyl, and

L is a single or double covalent bond, or is a contiguous chain, branched or unbranched, substituted or unsubstituted, of 1 to about 100 atoms.

In other embodiments, the elements of which can be practiced either separately, or in combination with the other embodiments disclosed above and below, the present invention provides a compound that is a dimer of two monomers of Formula (I), or two monomers of Formula (I-S) or one monomer of Formula (I-S) and one monomer of Formula (I-R), or a pharmaceutically acceptable salt thereof, wherein:

R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro;

R1a and R1b are each independently selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

R5 is selected from H; alkyl; substituted alkyl, wherein the alkyl substituents are selected from the groups consisting of oxo, amino, aryl, and substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; aryl; substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; or heterocycloalkyl;

when both R6 groups together form -L-, then each R2 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

when both R2 groups together form -L-, then each R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro;

R12 is selected from H or hydroxyl, and

L is a single or double covalent bond, or is a contiguous chain, branched or unbranched, substituted or unsubstituted, of 1 to about 100 atoms.

In other embodiments, the elements of which can be practiced either separately, or in combination with the other embodiments disclosed above and below, the present invention provides a compound that is a dimer of two monomers of Formula (I), or two monomers of Formula (I-S) or one monomer of Formula (I-S) and one monomer of Formula (I-R), or a pharmaceutically acceptable salt thereof, wherein:

X1 and X2 are O;

R is selected from H, or lower alkyl;

R1a and R1b are each independently selected from H, or lower alkyl optionally substituted with halogen;

R2 is selected from H; lower alkyl; cycloalkyl, or substituted lower alkyl wherein the substituents are selected from the group consisting of hydroxy, cycloalkyl and alkoxy;

R5 is selected from H; alkyl; substituted alkyl, wherein the alkyl substituents are selected from the groups consisting of oxo, amino, aryl, and substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; aryl; substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; or heterocycloalkyl;

both R6 groups together form -L-,

R12 is H, or hydroxyl, and

L is a single or double covalent bond, or is a contiguous chain, branched or unbranched, substituted or unsubstituted, of 1 to about 100 atoms.

In other embodiments, the elements of which can be practiced either separately, or in combination with the other embodiments disclosed above and below, the present invention provides a compound that is a dimer of two monomers of Formula (I), or two monomers of Formula (I-S) or one monomer of Formula (I-S) and one monomer of Formula (I-R), or a pharmaceutically acceptable salt thereof, wherein:

X1 and X2 are O;

R is methyl;

R1a is H and R1b is selected from methyl or fluoromethyl;

when both R6 groups together form -L-, then each R2 is selected from iso-propyl, t-butyl, 2-methoxy ethyl, or cyclohexyl;

R5 is selected from H; alkyl; substituted alkyl, wherein the alkyl substituents are selected from the groups consisting of oxo, amino, heterocycloalkyl, and aryl optionally substituted with halogen; cycloalkyl; aryl; or substituted aryl wherein the aryl substituents are selected from the groups consisting of halogen and phenyl;

when both R2 groups together form -L-, then each R6 is selected from H; lower alkylsulfonyl; lower alkyl; substituted lower alkyl, wherein the substituents are selected from the groups consisting of oxo, lower alkoxy, amino, and heteroaryl optionally substituted with lower alkyl or halogen; cycloalkyl; heterocycloalkyl; or heteroaryl, R12 is H, or hydroxyl, and L is optionally substituted alkyl, alkylene, alkylyne, cycloalkyl, alkylcycloalkyl, alkylarylalkyl chain of 2 to 20 atoms with 1-3 heteroatoms selected from —O—, —NH— and —S—.

In other embodiments, the elements of which can be practiced either separately, or in combination with the other embodiments disclosed above and below, the present invention provides a compound that is a dimer of two monomers of Formula (I), or two monomers of Formula (I-S) or one monomer of Formula (I-S) and one monomer of Formula (I-R), or a pharmaceutically acceptable salt thereof, wherein:

X1 and X2 are O;

R is methyl;

R1a is H and R1b is selected from methyl or fluoromethyl;

when both R6 groups together form -L-, then each R2 is selected from iso-propyl, t-butyl, 2-methoxy ethyl (e.g.,

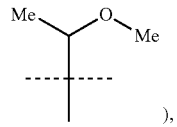

), or cyclohexyl;

R5 is selected from H, phenyl, biphenyl, fluorophenyl, naphthyl, tetrahydronaphthyl, benzyl, fluorobenzyl, pyrrolidinyl carbonyl, piperidyl carbonyl, morpholinyl carbonyl, benzyl carbamoyl, phenyl carbamoyl, naphthyl carbamoyl, ethyl carbamoyl, n-butyl carbamoyl, isopropyl carbamoyl, tert-butyl carbamoyl, cyclopropyl carbamoyl, cyclohexyl carbamoyl, diphenylamino carbonyl, or methyl-phenyl amino carbonyl when both R2 groups together form -L-, then each R6 is selected from H, ethyl, cyclopropyl, cyclohexyl, acetyl, tert-butoxy carbonyl, 3-methyl butyryl, 2-oxo-propionyl, methylsulfonyl, 2-methyl-propylsulfonyl, methyl carbamoyl, isopropyl carbamoyl, dimethyl carbamoylbenzyl carbamoyl, tetrahydro pyanyl, or pyrimidinyl, and L is —C(O)CH$_2$NHC(O)C(O)NHCH$_2$C(O)—.

In still other embodiments, the various elements of which can be practiced either separately, or in combination with the other embodiments disclosed above, R5 is selected from H,

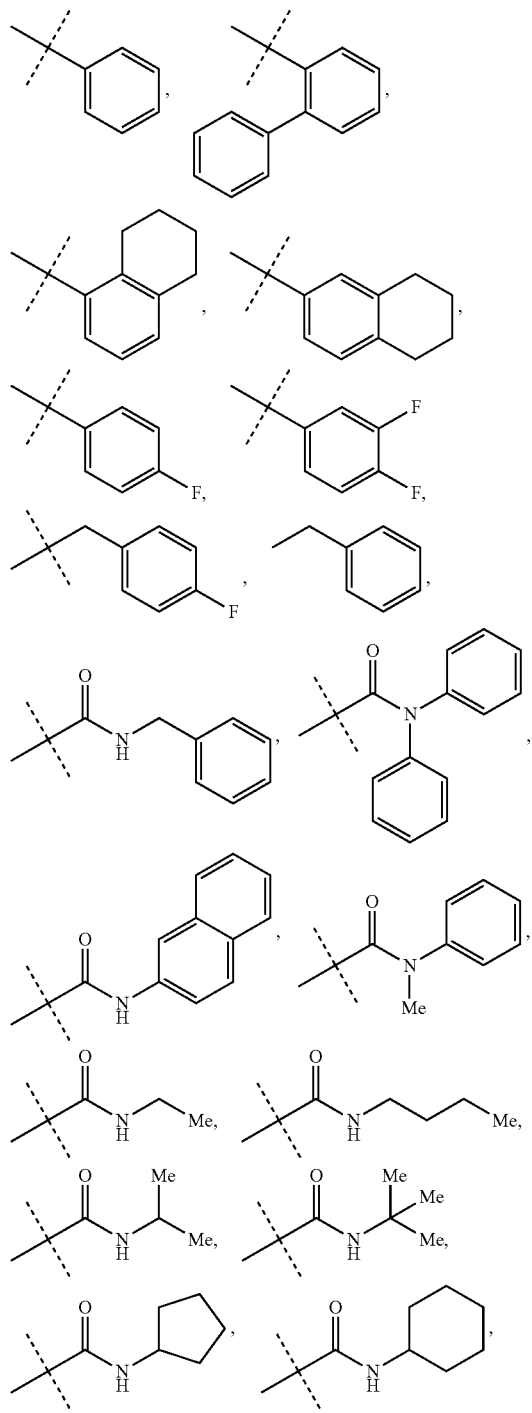

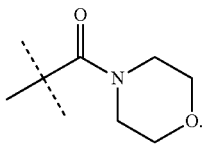

In all of the embodiments identified above, the pharmaceutically acceptable salts of the compounds embraced by the foregoing formulae are also included in each of the embodiments.

For simplicity and illustrative purposes, the principles of the invention are described by referring mainly to specific illustrative embodiments thereof. In addition, in the following description, numerous specific details are set forth in order to provide a thorough understanding of the invention. It will be apparent however, to one of ordinary skill in the art, that the invention may be practiced without limitation to these specific details. In other instances, well known methods and structures have not been described in detail so as not to unnecessarily obscure the invention.

DEFINITIONS

"Alkyl" (monovalent) and "alkylene" (divalent) when alone or as part of another term (e.g., alkoxy) mean branched or unbranched, saturated aliphatic hydrocarbon group, having up to 12 carbon atoms unless otherwise specified. Examples of particular alkyl groups include, but are not limited to, methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The term, "lower," when used to modify alkyl, alkenyl, etc., means 1 to 4 carbon atoms, branched or linear so that, e.g., the terms "lower alkyl", "C$_1$-C$_4$ alkyl" and "alkyl of 1 to 4 carbon atoms" are synonymous and used interchangeably to mean methyl, ethyl, 1-propyl, isopropyl, 1-butyl, sec-butyl or t-butyl. Examples of alkylene groups include, but are not limited to, methylene, ethylene, n-propylene, n-butylene and 2-methyl-butylene.

The term substituted alkyl refers to alkyl moieties having substituents replacing one or more hydrogens on one or more (often no more than four) carbon atoms of the hydrocarbon backbone. Such substituents are independently selected from the group consisting of: a halogen (e.g., I, Br, Cl, or F, particularly fluoro(F)), hydroxy, amino, cyano, mercapto, alkoxy (such as a C$_1$-C$_6$ alkoxy, or a lower (C$_1$-C$_4$ alkoxy, e.g., methoxy or ethoxy to yield an alkoxyalkyl), aryloxy (such as phenoxy to yield an aryloxyalkyl), nitro, oxo (e.g., to form a carbonyl), carboxyl (which is actually the combination of an oxo and hydroxy substituent on a single carbon atom), carbamoyl (also known as an aminocarbonyl such as NR$_2$C(O)—, which is the substitution of an oxo and an amino on a single carbon atom), cycloalkyl (e.g., a cycloalkylalkyl), aryl (resulting for example in aralkyls such as benzyl or phenylethyl), heterocyclylalkyl (e.g., heterocycloalkylalkyl), heteroaryl (e.g., heteroarylalkyl), alkylsulfonyl (including lower alkylsulfonyl such as methylsulfonyl), arylsulfonyl (such as phenylsulfonyl), and —OCF$_3$ (which is a halogen substituted alkoxy). The invention further contemplates that several of these alkyl substituents, including specifically alkoxy, cycloalkyl, aryl, heterocyclyalkyl and heteroaryl, are optionally further substituted as defined in connection with each of their respective definitions provided below. In addition, certain alkyl substituent moieties result from a combination of such substitutions on a single carbon atom. For example, an ester moiety, e.g., an alkoxycarbonyl such as methoxycarbonyl, or tert-butoxycarbonyl (Boc) results from such substitution. In particular, methoxycarbonyl and Boc are substituted alkyls that result from the substitution on a methyl group (—$CH_3$) of both an oxo (═O) and an unsubstituted alkoxy, e.g., a methoxy($CH_3$—O) or a tert-butoxy(($CH_3$)$_3$C—O—), respectively replacing the three hydrogens. Similarly, an amide moiety, e.g., an alkylaminocarbonyl, such as dimethylaminocarbonyl or methylaminocarbonyl, is a substituted alkyl that results from the substitution on a methyl group (—$CH_3$) of both an oxo (═O) and a mono-unsubstitutedalkylamino or, diunsubstitutedalkylamino, e.g., dimethylamino (—N—($CH_3$)$_2$), or methylamino (—NH—($CH_3$)) replacing the three hydrogens (similarly an arylaminocarbonyl such as diphenylaminocarbonyl is a substituted alkyl that results from the substitution on a methyl group (—$CH_3$) of both an oxo (═O) and a mono-unsubstitutedaryl(phenyl)amino). Exemplary substituted alkyl groups further include cyanomethyl, nitromethyl, hydroxyalkyls such as hydroxymethyl, trityloxymethyl, propionyloxymethyl, aminoalkyls such as aminomethyl, carboxylalkyls such as carboxymethyl, carboxyethyl, carboxypropyl, 2,3-dichloropentyl, 3-hydroxy-5-carboxyhexyl, acetyl (e.g., an alkanoyl, where in the case of acetyl the two hydrogen atoms on the —$CH_2$ portion of an ethyl group are replaced by an oxo (═O)), 2-aminopropyl, pentachlorobutyl, trifluoromethyl, methoxyethyl, 3-hydroxypentyl, 4-chlorobutyl, 1,2-dimethyl-propyl, pentafluoroethyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro (n-butyl), 2-amino (iso-propyl), cycloalkylcarbonyl (e.g., cuclopropylcarbonyl) and 2-carbamoyloxyethyl. Particular substituted alkyls are substituted methyl groups. Examples of substituted methyl group include groups such as hydroxymethyl, protected hydroxymethyl (e.g., tetrahydropyranyloxymethyl), acetoxymethyl, carbamoyloxymethyl, trifluoromethyl, chloromethyl, carboxymethyl, carboxyl (where the three hydrogen atoms on the methyl are replaced, two of the hydrogens are replaced by an oxo (═O) and the other hydrogen is replaced by a hydroxy (—OH)), tert-butoxycarbonyl (where the three hydrogen atoms on the methyl are replaced, two of the hydrogens are replaced by an oxo (═O) and the other hydrogen is replaced by a tert-butoxy (—O—C($CH_3$)$_3$), bromomethyl and iodomethyl. When the specification and especially the claims refer to a particular substituent for an alkyl, that substituent can potentially occupy one or more of the substitutable positions on the allyl. For example, reciting that an alkyl has a fluoro substituent, would embrace mono-, di-, and possibly a higher degree of substitution on the alkyl moiety.

The term substituted alkylene refers to alkylene moieties having substituents replacing one or more hydrogens on one or more (often no more than four) carbon atoms of the hydrocarbon backbone where the alkylene is similarly substituted with groups as set forth above for alkyl.

Alkoxy is —O-alkyl. A substituted alkoxy is —O-substituted alkyl, where the alkoxy is similarly substituted with groups as set forth above for alkyl. One substituted alkoxy is acetoxy where two of the hydrogens in ethoxy (e.g., —O—$CH_2$—$CH_3$) are replaced by an oxo, (═O) to yield —O—C(O)—$CH_3$; another is an aralkoxy where one of the hydrogens in the alkoxy is replaced by an aryl, such as benzyloxy, and another is a carbamate where two of the hydrogens on methoxy (e.g., —O—$CH_3$) are replaced by oxo (═O) and the other hydrogen is replaced by an amino (e.g., —$NH_2$, —NHR or —NRR) to yield, for example, —O—C(O)—$NH_2$. A lower alkoxy is —O-lower alkyl.

"Alkenyl" (monovalent) and "alkenylene" (divalent) when alone or as part of another term mean an unsaturated hydrocarbon group containing at least one carbon-carbon double bond, typically 1 or 2 carbon-carbon double bonds, which may be linear or branched and which have at least 2 and up to 12 carbon atoms unless otherwise specified. Representative alkenyl groups include, by way of example, vinyl, allyl, isopropenyl, but-2-enyl, n-pent-2-enyl, and n-hex-2-enyl.

The terms substituted alkenyl and substituted alkenylene refer to alkenyl and alkenylene moieties having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as $C_1$-$C_6$ alkoxy), aryloxy (such as phenoxy), nitro, mercapto, carboxyl, oxo, carbamoyl, cycloalkyl, aryl, heterocyclyl, heteroaryl, alkylsulfonyl, arylsulfonyl and —$OCF_3$.

"Alkynyl" means a monovalent unsaturated hydrocarbon group containing at least one carbon-carbon triple bond, typically 1 carbon-carbon triple bond, which may be linear or branched and which have at least 2 and up to 12 carbon atoms unless otherwise specified. Representative alkynyl groups include, by way of example, ethynyl, propargyl, and but-2-ynyl.

"Cycloalkyl" when alone or as part of another term means a saturated or partially unsaturated cyclic aliphatic hydrocarbon group (carbocycle group), having up to 12 carbon atoms unless otherwise specified, such as cyclopropyl, cyclobutyl, cyclopentyl and cyclohexyl, and further includes polycyclic, including fused cycloalkyls such as 1,2,3,4-tetrahydronaphthalenyls (1,2,3,4-tetrahydronaphthalen-1-yl, and 1,2,3,4-tetrahydronaphthalen-2-yl), indanyls (indan-1yl, and indan-2-yl), isoindenyls (isoinden-1-yl, isoinden-2-yl, and isoinden-3-yl) and indenyls (inden-1-yl, inden-2-yl and inden-3-yl). A lower cycloalkyl has from 3 to 6 carbon atoms and includes cyclopropyl, cyclobutyl, cyclopentyl and cyclohexyl.

The term substituted cycloalkyl refers to cycloalkyl moieties having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, mercapto, carboxyl, oxo, carbamoyl, alkyl, substituted alkyls such as trifluoromethyl, aryl, substituted aryls, heterocyclyl, heteroaryl, alkylsulfonyl, arylsulfonyl and —$OCF_3$. When the specification and especially the claims refer to a particular substituent for a cycloalkyl, that substituent can potentially occupy one or more of the substitutable positions on the cycloalkyl. For example, reciting that a cycloalkyl has a fluoro substituent, would embrace mono-, di-, and a higher degree of substitution on the cycloalkyl moiety. Examples of cycloalkyls include cyclopropy, cyclobutyl, cyclopentyl, cyclohexyl, tetrahydronaphthyl and indanyl.

"Amino" denotes primary (i.e., —$NH_2$), secondary (i.e., —NHR) and tertiary (i.e., —NRR) amines, where the R groups can be the same or different and can be selected from a variety of moieties, usually an alkyl, a substituted alkyl, an aryl, a substituted aryl, a cycloalkyl, or a substituted cycloalkyl and especially a lower alkyl and an aryl (phenyl), including substituted phenyl. Particular secondary and tertiary aminos are alkylaminos, dialkylaminos, arylaminos, diarylaminos, aralkylaminos and diaralkylaminos. Particular secondary and tertiary amines are methylamino, ethylamino, propylamino, isopropylamino, phenylamino, benzylamino dimethylamino, diethylamino, dipropylamino and disopropylamino.

"Aryl" when used alone or as part of another term means an aromatic carbocyclic group whether or not fused having the number of carbon atoms designated, or if no number is designated, from 6 up to 14 carbon atoms. Particular aryl groups include phenyl, naphthyl, biphenyl, phenanthrenyl, naphthacenyl, and the like (see e.g. Lang's Handbook of Chemistry (Dean, J. A., ed) 13$^{th}$ ed. Table 7-2 [1985]). Phenyl and naphthyl groups are generally preferred.

The term substituted aryl refers to aryl moieties having substituents replacing one or more hydrogens on one or more (usually no more than six) carbon atoms of the aromatic hydrocarbon core. Such substituents are independently selected from the group consisting of: halo (e.g., I, Br, Cl, F), hydroxy, amino, cyano, alkoxy (such as $C_1$-$C_6$ alkoxy and particularly lower alkoxy), substituted alkoxy, aryloxy (such as phenoxy), nitro, mercapto, carboxyl, carbamoyl, alkyl, substituted alkyl (such as trifluoromethyl), aryl, —$OCF_3$, alkylsulfonyl (including lower alkylsulfonyl), arylsulfonyl, heterocyclyl and heteroaryl. Examples of such substituted phenyls include but are not limited to a mono- or di (halo)-substituted phenyl groups such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl; 3-fluorophenyl, 4-fluorophenyl, 3,4-difluorophenyl, a mono- or di (hydroxy) phenyl group such as 4-hydroxyphenyl, 3-hydroxyphenyl, 2,4-dihydroxyphenyl, the protected-hydroxy derivatives thereof; a nitrophenyl group such as 3-or 4-nitrophenyl; a cyanophenyl group, for example, 4-cyanophenyl; a mono-or di (lower alkyl)phenyl group such as 4-methylphenyl, 2,4-dimethylphenyl, 2-methylphenyl, 4-(iso-propyl)phenyl, 4-ethylphenyl, 3-(n-propyl)phenyl; a mono or di (alkoxy) phenyl group, for example, 3,4-dimethoxyphenyl, 3-methoxy-4-benzyloxyphenyl, 3-methoxy-4-(1-chloromethyl) benzyloxy-phenyl, 3-ethoxyphenyl, 4-(isopropoxy)phenyl, 4-(t-butoxy)phenyl, 3-ethoxy-4-methoxyphenyl; 3-or 4-trifluoromethylphenyl; a mono- or dicarboxyphenyl or (protected carboxy)phenyl group such 4-carboxyphenyl; a mono- or di (hydroxymethyl)phenyl or (protected hydroxymethyl) phenyl such as 3-(protected hydroxymethyl)phenyl or 3,4-di (hydroxymethyl)phenyl; a mono-or di (aminomethyl)phenyl or (protected aminomethyl)phenyl such as 2-(aminomethyl) phenyl or 2,4-(protected aminomethyl)phenyl; or a mono-or di (N-(methylsulfonylamino)) phenyl such as 3-(N-methylsulfonylamino) phenyl. Also, the substituents, such as in a disubstituted phenyl groups, can be the same or different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, as well as for trisubstituted phenyl groups where the substituents are different, as for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Particular substituted phenyl groups are 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. When the specification and especially the claims refer to a particular substituent for an aryl, that substituent can potentially occupy one or more of the substitutable positions on the aryl. For example, reciting that an aryl has a fluoro substituent, would embrace mono-, di-, tri, tetra and a higher degree of substitution on the aryl moiety. Fused aryl rings may also be substituted with the substituents specified herein, for example with 1, 2 or 3 substituents, in the same manner as substituted alkyl groups. The terms aryl and substituted aryl do not include moieties in which an aromatic ring is fused to a saturated or partially unsaturated aliphatic ring.

Aryloxy is —O-aryl. A substituted aryloxy is —O-substituted aryl, where the suitable substituents are those described for a substituted aryl.

"Heterocyclic group", "heterocyclic", "heterocycle", "heterocyclyl", "heterocycloalkyl" or "heterocyclo" alone and when used as a moiety in a complex group, are used interchangeably and refer to any mono-, bi-, or tricyclic, saturated or unsaturated, non-aromatic hetero-atom-containing ring system having the number of atoms designated, or if no number is specifically designated then from 5 to about 14 atoms, where the ring atoms are carbon and at least one heteroatom and usually not more than four heteroatoms (i.e., nitrogen, sulfur or oxygen). Included in the definition are any bicyclic groups where any of the above heterocyclic rings are fused to an aromatic ring (i.e., an aryl (e.g., benzene) or a heteroaryl ring). The heterocycloalkyl can be bonded to the structure through either a ring carbon or a ring heteroatom, as appropriate. In a particular embodiment the group incorporates 1 to 4 heteroatoms. Typically, a 5-membered ring has 0 to 1 double bonds and a 6-or 7-membered ring has 0 to 2 double bonds and the nitrogen or sulfur heteroatoms may optionally be oxidized (e.g. SO, $SO_2$), and any nitrogen heteroatom may optionally be quaternized. Particular unsubstituted non-aromatic heterocycles include morpholinyl (morpholino), pyrrolidinyls, oxiranyl, indolinyls (e.g., 2,3-dihydroindolyl), isoindolinyls, tetrahydroquinolinyls, tetrahydroisoquinolinyls, oxetanyl, tetrahydrofuranyls, 2,3-dihydrofuranyl, 2H-pyranyls, tetrahydropyranyls, aziridinyls, azetidinyls, 1-methyl-2-pyrrolyl, piperazinyls and piperidinyls.

The term substituted heterocycloalkyl refers to heterocycloalkyl moieties having substituents replacing one or more hydrogens on one or more (usually no more than six) atoms of the heterocycloalkyl backbone. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, carboxyl, oxo, carbamoyl, alkyl, substituted alkyl (such as trifluoromethyl), —$OCF_3$, aryl, substituted aryl, alkylsulfonyl (including lower alkylsulfonyl), and arylsulfonyl. When the specification and especially the claims refer to a particular substituent for a heterocycloalkyl, that substituent can potentially occupy one or more of the substitutable positions on the heterocycloalkyl. For example, reciting that a heterocycloalkyl has a fluoro substituent, would embrace mono-, di-, tri, tetra and a higher degree of substitution on the heterocycloalkyl moiety.

"Heteroaryl" alone and when used as a moiety in a complex group refers to any mono-, bi-, or tricyclic aromatic ring system having the number of atoms designated, or if no number is specifically designated then at least one ring is a 5-, 6-or 7-membered ring and the total number of atoms is from 5 to about 14 and containing from one to four heteroatoms selected from the group consisting of nitrogen, oxygen, and sulfur (Lang's Handbook of Chemistry, supra). Included in the definition are any bicyclic groups where any of the above heteroaryl rings are fused to a benzene ring. The heteraryl can be bonded to the structure through either a ring carbon or a ring heteroatom, as appropriate. The following ring systems are examples of the heteroaryl groups denoted by the term "heteroaryl": thienyls (alternatively called thiophenyl), furyls, imidazolyls, pyrazolyls, thiazolyls, isothiazolyls, oxazolyls, isoxazolyls, triazolyls, thiadiazolyls, oxadiazolyls, tetrazolyls, thiatriazolyls, oxatriazolyls, pyridyls, pyrimidinyls (e.g., pyrimidin-2-yl), pyrazinyls, pyridazinyls, thiazinyls, oxazinyls, triazinyls, thiadiazinyls, oxadiazinyls, dithiazinyls, dioxazinyls, oxathiazinyls, tetrazinyls, thiatriazinyls, oxatriazinyls, dithiadiazinyls, imidazolinyls, dihydropyrimidyls, tetrahydropyrimidyls, tetrazolo[1,5-b]pyridazinyl and purinyls, as well as benzo-fused derivatives, for example benzoxazolyls, benzofuryls, benzothienyls, benzothiazolyls, benzothiadiazolyl, benzotriazolyls, benzoimidazolyls, isoindolyls, indazolyls, indolizinyls, indolyls, naphthyridines, pyridopyrimidines, phthalazinyls, quinolyls, isoquinolyls and quinazolinyls.

The term substituted heteroaryl refers to heteroaryl moieties (such as those identified above) having substituents replacing one or more hydrogens on one or more (usually no more than six) atoms of the heteroaryl backbone. Such substituents are independently selected from the group consisting of: halo (e.g., I, Br, Cl, F), hydroxy, amino, cyano, alkoxy (such as $C_1$-$C_6$ alkoxy), aryloxy (such as phenoxy), nitro, mercapto, carboxyl, carbamoyl, alkyl, substituted alkyl (such as trifluoromethyl), —$OCF_3$, aryl, substituted aryl, alkylsulfonyl (including lower alkylsulfonyl), and arylsulfonyl. When the specification and especially the claims refer to a particular substituent for a heteroaryl, that substituent can potentially occupy one or more of the substitutable positions on the heteroaryl. For example, reciting that a heteroaryl has a fluoro substituent, would embrace mono-, di-, tri, tetra and a higher degree of substitution on the heteroaryl moiety.

Particular "heteroaryls" (including "substituted heteroaryls") include; 1H-pyrrolo[2,3-b]pyridine, 1,3-thiazol-2-yl, 4-(carboxymethyl)-5-methyl-1,3-thiazol-2-yl, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino) eth-2-yl)-1H-tetrazol-5-yl, 1-(carboxymethyl)-1H-tetrazol-5-yl, 1-(methylsulfonic acid)-1H-tetrazol-5-yl, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl, 2,5-dihydro-5-oxo-6-hydroxy-2-methyl-astriazin-3-yl, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl, 8-aminotetrazolo[1,5-b]-pyridazin-6-yl, quinol-2-yl, quinol-3-yl, quinol-4-yl, quinol-5-yl, quinol-6-yl, quinol-8-yl, 2-methyl-quinol-4-yl, 6-fluoro-quinol-4-yl, 2-methyl, 8-fluoro-quinol-4-yl, isoquinol-5-yl, isoquinol-8-yl, isoquinol-1-yl, and quinazolin-4-yl. An alternative group of "heteroaryl" includes: 5-methyl-2-phenyl-2H-pyrazol-3-yl, 4-(carboxymethyl)-5-methyl-1,3-thiazol-2-yl, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(methylsulfonic acid)-1H-tetrazol-5-yl, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

"IAP Inhibitor" or "IAP antagonist" means a compound (1) which interferes with the physiological function of an IAP protein, including the binding of IAP proteins to caspase proteins, for example by reducing or preventing the binding of IAP proteins to caspase proteins, or (2) which reduces or prevents the inhibition of apoptosis by an IAP protein, or (3) which binds to an IAP BIR domain in a manner similar to the binding of the amino terminal portion of Smac, or (4) has any two, or all three of the preceding functions.

As used herein, the terms "pharmaceutically acceptable", "physiologically tolerable" and grammatical variations thereof, as they refer to compositions, excipients, carriers, diluents and reagents, are used interchangeably and represent that the materials can be administered to a subject or patient, especially a human patient.

"Pharmaceutically acceptable salts" include both acid and base addition salts.

"Pharmaceutically acceptable acid addition salt" refers to those non-toxic salts which retain the biological effectiveness and essential properties of the associated free bases and which are not biologically or otherwise undesirable, and are formed with inorganic acids and with organic acids. The acid addition salts of the basic compounds are prepared by contacting the free base form of the compound with a sufficient amount of the desired acid to produce the salt in the conventional manner. The free base form may be regenerated by contacting the salt form with a base and isolating the free base in the conventional manner. The free base forms generally differ from their respective salt forms somewhat in certain physical properties such as solubility in polar solvents.

"Pharmaceutically acceptable base addition salts" refer to those non-toxic salts which retain the biological effectiveness and essential properties of the associated free acids and which are not biologically or otherwise undesirable and are formed with metals or amines, such as alkali and alkaline earth metal hydroxides, or with organic amines. The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms usually differ from their respective salt forms somewhat in certain physical properties such as solubility in polar solvents.

The terms "treating", "treat" or "treatment" and the like include preventative (e.g., prophylactic) and palliative treatment.

As used herein "subject" or "patient" refers to an animal or mammal including, but not limited to, human, dog, cat, horse, cow, pig, sheep, goat, chicken, monkey, rabbit, rat, and mouse.

As used herein, the term "therapeutic" refers to the amelioration of, the prevention of, an improvement of, or a delay in the onset of one or more symptoms of an unwanted condition or disease of a patient. Embodiments of the present invention are directed to therapeutic treatments by promoting apoptosis, and thus cell death.

The terms "therapeutically effective amount" or "effective amount", as used herein, means an amount of a compound, or a pharmaceutically acceptable salt thereof, often as part of a pharmaceutical composition, sufficient to inhibit, halt, ameliorate, attenuate, delay the onset of, or cause an improvement in one or more symptoms of the disease being treated when administered alone or in conjunction with another pharmaceutical agent for treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "excipient" means any pharmaceutically acceptable additive, carrier, diluent, adjuvant, or other ingredient, other than the active pharmaceutical ingredient (API), which is typically included for formulation and/or administration to a patient.

DETAILED DESCRIPTION OF THE INVENTION

It has been demonstrated in accordance with the present invention that the IAP-binding compounds of the present invention, which are Smac mimetics, are capable of potentiating apoptosis of cells.

Compounds of the present invention can be used in their free base or free acid forms or in the form of their pharmaceutically-acceptable salts. In the practice of the present invention, compounds of the present invention in their free base or free acid forms generally will have a molecular weight of 1000 or below, most often a molecular weight of 800 or below and often a molecular weight of 600 or below.

The following preparations and schemes are illustrative of synthesis of compounds of the present invention. Abbreviations which are used throughout these schemes and in the application generally, are identified in the following table:

| ABBREVIATION | MEANING |
|---|---|
| ACN | Acetonitrile |
| Ac₂O | Acetic anhydride |
| Cbz and Z | Benzyloxycarbonyl |
| Boc and/or boc | tert-butyloxycarbonyl |
| THF | Tetrahydrofuran |
| DCM | Dichloromethane |
| DDQ | 2,3-dichloro-5,6-dicyano-1,4-benzoquinone |
| DCHA | dicyclohexylammonium |
| mCPBA | 3-chloroperbenzoic acid |
| Cbz-Cl | Benzyloxycarbonyl chloride |
| Hex | Hexanes |
| HPLC | high performance liquid chromatography |
| TLC | thin layer chromatography |
| EtOAc | ethyl acetate |
| Ph | Phenyl |
| HATU | 2-(7-Aza-1H-benzotriazole-1-yl)-1,1,3,3-tetramethyluronium hexafluorophosphate |
| Me | Methyl* |

-continued

| ABBREVIATION | MEANING |
|---|---|
| iPr | Iso-propyl |
| cPr | Cyclopropyl |
| (2R-EtOMe) and/or R-MeCHOMe | 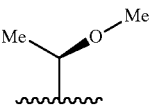 [SMILES: *[C@@H](C)OC] |
| TBAF | tetrabutyl ammonium fluoride |
| OMs | Methanesulfonyloxy |
| TBDMSCl | tert-butyl-dimethyl-silyl chloride |
| Ph₃P | Triphenylphosphine |
| n-Bu | Normal butyl |
| Swern[O] | Swern Oxidation |
| TBA-Cl | Tetra-n-butyl ammonium chloride |
| NP-HPLC | Normal phase-high performance liquid chromatography |
| EDCI | N-3-(dimethylaminopropyl)-N'-ethylcarbodiimide hydrochloride 1-Ethyl-3-(3-Dimethylaminopropyl)carbodiimide-HCl |
| Et₂O | Ethylene oxide ( 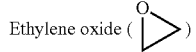 ) |
| TES | Triethylsilane |
| MeNO₂ | Nitromethane |
| EtOH | Ethanol |
| DCE, or EDC | Dichloroethane, Ethylenedichloride |
| NaHMDS | Sodium hexamethyldisilazide or sodium bis(trimethylsilyl)amide |
| Boc-Chg-OH (Boc-L-cyclohexylglcine) | 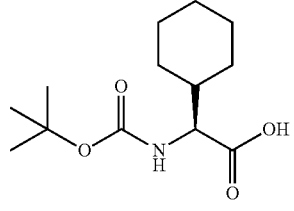 [SMILES: CC(C)(C)OC(=O)N[C@H](C(=O)O)C1CCCCC1] |
| Cbz-Chg-OH | 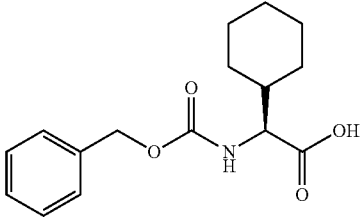 [SMILES: O=C(N[C@H](C(=O)O)C1CCCCC1)OCc1ccccc1] |
| Boc-N(Me)Ala-OH | 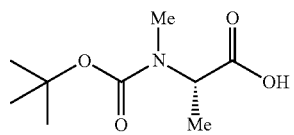 |
| Boc-Abu-OH | 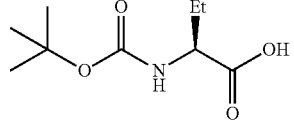 |

-continued

| ABBREVIATION | MEANING |
|---|---|
| Cbz-Tle-OH | (structure: benzyloxycarbonyl-tert-leucine) |
| Boc-Ser-OH | (structure: Boc-serine) |
| Boc-Ser(Me)-OH | (structure: Boc-O-methyl serine) |
| Boc-Thr(tBu)-OH | (structure: Boc-threonine tert-butyl ether) |
| Boc-Thr(Me)-OH | (structure: Boc-O-methyl threonine) |
| h | hour |
| NMP | N-methylpyrrolidinone |
| PhCOCl | Benzoyl chloride |
| DIAD | diisopropyl azo dicarboxylate |
| DIBAL | Diisobutylaluminum hydride |
| DMAP | 4-dimethylamino pyridine |
| DMF | Dimethylformamide |
| DMSO | dimethyl sulfoxide |
| TFA | trifluoroacetic acid |
| TFAA | trifluoroactic anhydride |
| HOAc or AcOH | acetic acid |
| DIPEA | Diisopropylethylamine |
| NMM | N-methylmorpholine |
| NCS | N-chlorosuccinimide |
| TEA (Et₃N) | Triethylamine |
| MsCl | Methane-sulfonylchloride |
| Et | Ethyl |
| tBu or tert-Bu | tert-butyl |
| cHex | Cyclohexyl |
| (2R-EtOH) and/or R-MeCHOH | (structure: Me-CH(OH)-) |
| MsCl | Methanesulfonyl chloride |
| OTs | —O—SO₂—Ph—Me |
| OTBS | tert-butyl-dimethyl-silanyloxy |
| Ac | Acetyl (—C(=O)—Me) |

-continued

| ABBREVIATION | MEANING |
|---|---|
| DMA | Dimethylamine |
| HWE | Honer-Wadsworth-Emmons reaction |
| DMS | Dimethylsulfide |
| Meldrum's Acid | 2,2-dimethyl-1,3-dioxane-4,6-dione |
| Imid. | Imidazole |
| HOBT, or HBT | Hydroxybenzotriazole |
| RT | Room temperature |
| MeOH | Methanol |
| NaOAc | Sodium acetate |
| ClCO₂Me | Ethyl chloroformate |
| TBSCl | tert-butyl-dimethyl-silanyl chloride |
| Cbz-N(Me)Ala-OH Z-N(Me)Ala-OH | (structure: Cbz-N-methyl alanine) |
| Cbz-N(Me)Ala(βF)-OH Z-N(Me)Ala(βF)-OH | (structure: Cbz-N-methyl β-fluoro alanine) |
| Boc-N(Me)Ala(βF)-OH | (structure: Boc-N-methyl β-fluoro alanine) |
| Boc-Tle-OH | (structure: Boc-tert-leucine) |
| Boc-Val-OH | (structure: Boc-valine) |
| Cbz-Val-OH | (structure: Cbz-valine) |
| Cbz-Ser(tBu)-OH | (structure: Cbz-serine tert-butyl ether) |

| ABBREVIATION | MEANING |
|---|---|
| Cbz-Thr(tBu)-OH | [structure] |
| Boc-Thr-OH | [structure] |
| PSI | Pounds per Square Inch (Gauge) |
| NaOMe | Sodium methoxide |

*As is a commonly accepted convention, depending on the context, which will be apparent to those skilled in the art, a vacant terminal bond may be used to indicate either a methyl group, or the point of attachment to another structure for a radical.

Abbreviations for NMR data reported in the following examples are as follows: s=singlet, d=doublet, t=triplet, q=quartet, m=multiplet, dd=doublet of doublets, ddd=doublet of doublet of doublets, dt=doublet of triplets, app=apparent, br=broad, δ indicates the chemical shift; J and $J_{CF}$ indicate NMR coupling constants measured in Hertz.

The binding affinities of compounds of the present invention to XIAP BIR-3 or to cIAP-1 BIR-3 (as reported below as ranges) were determined substantially as described by Nikolovska-Coleska, Z. et. al. (Analytical Biochemistry (2004), vol. 332:261-273 and incorporated herein by reference) using as the fluorogenic substrate: the fluorescently labeled peptide AbuRPF-K(5-Fam)-NH$_2$. The binding affinities of the compounds are reported as a $K_D$ value (μM). Briefly, various concentrations of test peptides were mixed with 5 nM of the fluorescently labeled peptide (i.e., a mutated N-terminal Smac peptide—AbuRPF-K(5-Fam)-NH$_2$) and 40 nM of the respective IAP BIR3 for 15 min at RT in 100 mL of 0.1M Potassium Phosphate buffer, pH 7.5 containing 100 mg/ml bovine g-globulin. Following incubation, the polarization values (mP) were measured on a Victor2V (available from PerkinElmer Life Sciences) using a 485 nm excitation filter and a 520 nm emission filter. The reported binding affinities (K$_D$ values) are supplied as ranges (A=<0.1 μM, B=0.1 μM to 1 μM, C=>1 μM to 10 μM, D=>10 μM).

Compounds of the invention also were tested for their ability to inhibit the growth of an ovarian cancer cell line, SK-OV-3. A known assay previously used for measuring cell growth (as described in Hansen, M. B., Nielsen, S. E., and Berg, K. (1989) J. Immunol. Methods 119, 203-210 and incorporated herein by reference in its entirety) was used. Briefly, SK-OV-3 cells are seeded in 96-well plates in McCoy's medium containing 10% fetal bovine serum albumin (5,000 per well) and incubated overnight at 37° C. The next day, test compounds are added at various concentrations (0.003-10 μM) and the plates are incubated at 37° C. for an additional 72 hrs. This incubation time was considered to be optimal for measuring inhibitory effects of the different compounds tested. 50 microliters of 5 mg/mL MTT reagent is added to each well and the plates are incubated at 37° C. for another three (3) hours. At the end of the three (3) hour incubation period, 50 microliters of DMSO is added to each well to dissolve cells and the optical density (OD) of the wells is measured with a microplate reader (Victor$^2$ 1420, Wallac, Finland) at 535 nm. Cell survival (CS) was calculated using the following equation:

CS=(OD treated well/mean OD control wells)×100%.

The CC$_{50}$ (reported in the following tables), is defined as the drug concentration that results in 50% cell survival (CS), and is derived by calculating the point where the dose-response curve crosses the 50% CS point using GraphPad Prism. The reported CC$_{50}$ values are supplied as ranges (A=<0.1 μM, B=0.1 μM to 1 μM, C=>1 μM to 10 μM, D=>10 μM).

Scheme I

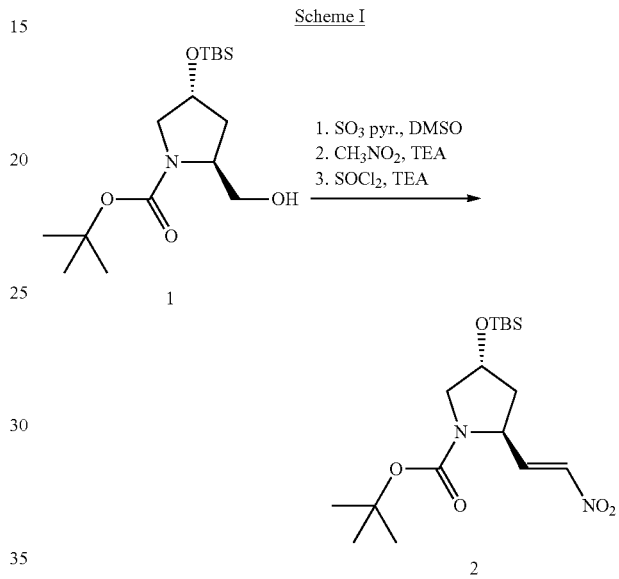

4-(tert-Butyl-dimethyl-silanyloxy)-2-(2-nitro-vinyl)-pyrrolidine-1-carboxylic acid tert-butyl ester (2): To a solution of 1 (25.8 g, 77.8 mmol; See: Rosen, T., et al. J. Med. Chem. 1988, 31, 1598-1611) in DMSO (60 mL) and CH$_2$Cl$_2$ (300 mL) at 0° C. were added Et$_3$N (54 mL, 389.1 mmol) and SO$_3$.pyridine complex (49.5 g, 311.2 mmol). The reaction mixture was then allowed to stir for 2 h at 0° C. Upon completion of the reaction, the mixture was diluted with EtOAc and washed successively with dilute aqueous HCl and brine and concentrated. The resultant residue was dissolved in 1:1 Et$_2$O/hexanes, washed successively with 1M HCl and brine to remove residual DMSO. The organic extracts were dried over anhydrous Na$_2$SO$_4$, filtered, and concentrated to afford the desired prolinal (25.4 g, 99%) as a pale yellow-colored oil which was used without further purification.

To a solution of prolinal (25.4 g, 77.1 mmol) in CH$_3$NO$_2$ (128 mL) at 0° C. was added Et$_3$N (10 mL). The reaction mixture was then stirred for an additional 17 h warming gradually to ambient temperature. The reaction mixture was concentrated and the residue was concentrated twice from toluene to remove any residual water. The crude alcohols (29.8 g, 99%) were used without further purification.

To a solution of alcohols (29.8 g, 76.4 mmol) and Et$_3$N (42.6 mL, 305.9 mmol) in CH$_2$Cl$_2$ (400 mL) at −78° C. was added dropwise a solution of SOCl$_2$ (7.2 mL, 99.4 mmol) in CH$_2$Cl$_2$ over a period of 1 h during which time the reaction mixture becomes brown and heterogeneous. The reaction mixture was then stirred for an additional 15 min, after which time it was concentrated to form a brown residue. The residue was slurried in 10% EtOAc/hexanes and purified by flash silica gel chromatography (10-15% EtOAc/hexanes) to afford 2 (15.1 g, 53%) as an orange-colored solid. ¹H NMR (300 MHz, CDCl₃): δ7.08 (dd, J=6.9, 13.5 Hz, 1H), 6.96 (d, J=13.5 Hz, 1H), 4.51 (dd, J=6.3, 35.8 Hz, 1H), 4.29 (s, 1H), 3.51-3.36 (m, 2H), 2.08 (ddd, J=3.3, 7.5, 11.4 Hz, 1H), 1.79 (s, 1H), 1.38 (s, 9H), 0.79 (s, 9H), 0.05 (s, 6H) ppm. Mass spectrum, m/z [273.1] (M-Boc)+.

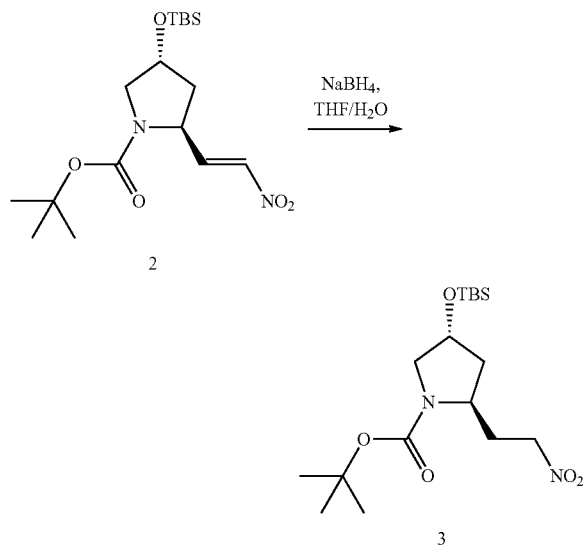

4-(tert-Butyl-dimethyl-silanyloxy)-2-(2-nitro-ethyl)-pyrrolidine-1-carboxylic acid tert-butyl ester (3): A 1 L round-bottomed flask was charged with NaBH₄ (3.2 g, 84.5 mmol) in THF (300 mL) and then cooled to −20° C. Water (50 mL) was added to the reaction mixture followed by the dropwise addition of 2 (6.3 g, 16.9 mmol) in THF (50 mL) over 1 h. After an additional 30 min, the cold reaction mixture was quenched by the careful addition of 1M HCl (60 mL). The reaction mixture was then diluted with EtOAc. The organic phase was washed successively with 1M HCl and brine, dried over anhydrous Na₂SO₄, filtered, and concentrated. The crude product was chromatographed by flash silica gel chromatography (4:1 hexanes/EtOAc) to afford 5.9 g (93%) of 3. ¹H NMR (CDCl₃, 300 MHz), mixture of rotamers: δ4.48 (m, 1H), 4.32 (m, 1H), 4.08 (m, 1H), 3.55 (m, 0.4H), 3.38 (m, 0.6H), 3.28 (app dd, J=11.7, 4.2 Hz, 1H), 2.32 (m, 1H), 2.18 (m, 1H), 2.04 (m, 2H), 1.67 (m, 1H), 1.45 (s, 9H), 0.85 (s, 9H), 0.05 (s, 6H) ppm.

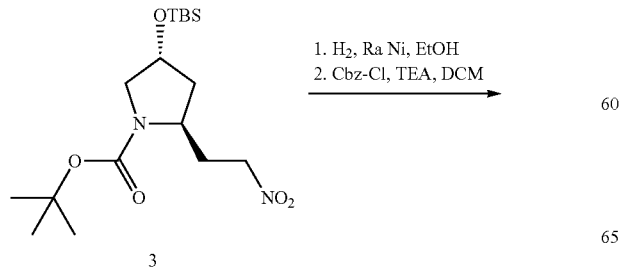

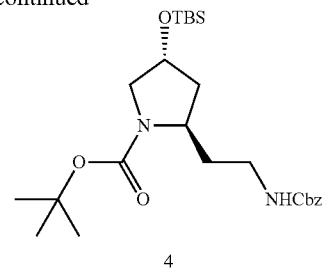

2-(2-Benzyloxycarbonylamino-ethyl)-4-(tert-butyl-dimethyl-silanyloxy)-pyrrolidine-1-carboxylic acid tert-butyl ester (4): A 500 mL Parr bottle was charged with 3 (5.9 g, 15.7 mmol) in absolute EtOH (50 mL). Raney nickel (~1 mL, 2400 Ni slurry in H₂O) was added and the heterogeneous reaction mixture was shaken at 55 PSI hydrogen pressure. After 1 h, the catalyst was removed by filtration and the solids were washed with MeOH/EtOAc/water. The filtrate was concentrated in vacuo and the residue was dissolved in EtOAc. The organic solution was washed with brine, dried over anhydrous Na₂SO₄, filtered, and concentrated to afford 5.59 g of crude amine which was used without further purification.

The crude amine was dissolved in DCM (100 mL) and cooled to 0° C. Cbz-Cl (2.95 g, 17.3 mmol) was added and the reaction mixture was slowly warmed to ambient temperature. After 16 h, the reaction mixture was diluted with DCM and washed successively with 1M HCl and brine, dried over anhydrous Na₂SO₄, filtered, and concentrated. The crude product was purified by flash silica gel chromatography (9:1 to 4:1 hexanes/EtOAc) to afford 5.9 g (78%, 2 steps) of 4. ¹H NMR (CDCl₃, 300 MHz), mixture of rotamers: δ7.32 (m, 5H), 5.85 (m, 0.5H), 5.61 (m, 0.25H), 5.08 (m, 2H), 4.87 (m, 0.25H), 4.33 (m, 1H), 4.05 (m, 0.7H), 3.89 (m, 0.3H), 3.31 (m, 3H), 3.00 (m, 1H), 2.00 (m, 2H), 1.65 (m, 2H), 1.44 (s, 9H), 0.86 (s, 9H), 0.05 (s, 6H) ppm. Mass spectrum, m/z [379.2] (M-Boc)+.

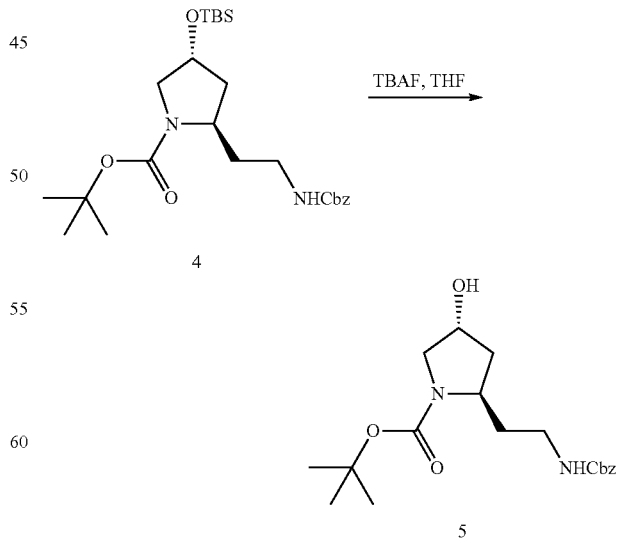

2-(2-Benzyloxycarbonylamino-ethyl)-4-hydroxy-pyrrolidine-1-carboxylic acid tert-butyl ester (5): A solution containing 4 (5.9 g, 12.5 mmol) in anhydrous THF (100 mL) was cooled to 0° C. TBAF (1M/THF, 14 mL, 14.0 mmol) was added in one portion. After 5 h, the reaction mixture was diluted with EtOAc and washed successively with 1M HCl and brine, dried over anhydrous $Na_2SO_4$, filtered, and concentrated. The crude product was purified by flash silica gel chromatography (1:1 to 1:3 hexanes/EtOAc) to afford 4.1 g (91%) of 5. $^1$H NMR ($CDCl_3$, 300 MHz): δ7.31 (m, 5H), 5.93 (m, 1H), 5.07 (m, 2H), 4.37 (m, 1H), 4.03 (m, 1H) 3.51-3.06 (m, 4H), 2.05 (m, 1H), 1.77 (m, 1H), 1.44 (s, 9H) ppm. Mass spectrum, m/z [365.2] (M+H)+.

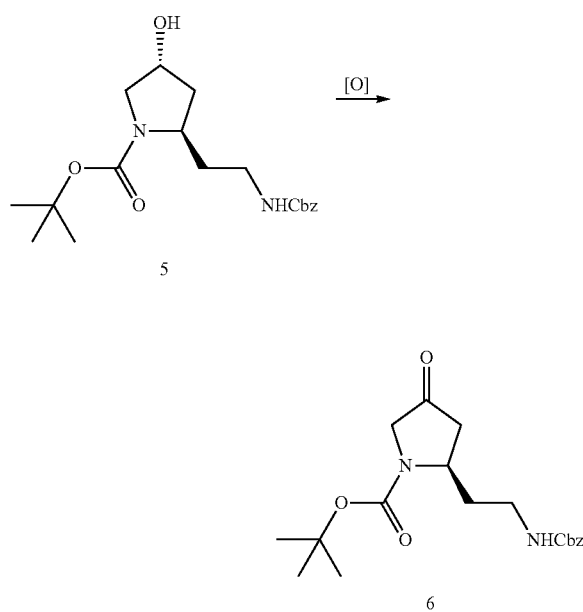

2-(2-Benzyloxycarbonylamino-ethyl)-4-oxo-pyrrolidine-1-carboxylic acid tert-butyl ester (6): A solution containing 5 (10.2 g, 28.0 mmol) in DCM (100 mL) and DMSO (20 mL) was cooled to 0° C. TEA (14.1 g, 140 mmol) and $SO_3$·pyridine complex (17.9 g, 112 mmol) were then added and the mixture stirred until homogeneous (approx. 45 min) then warmed to ambient temperature. After 3 h, the reaction mixture was diluted with water (200 mL) and diethyl ether (500 mL). The layers were separated and the organic phase was washed successively with 1N HCl, water, aqueous $NaHCO_3$, water, and brine then dried over anhydrous $Na_2SO_4$, filtered, and concentrated. The crude product was purified by flash silica gel chromatography (2:1 to 1:1 hexanes/EtOAc) to afford 9.34 g (92%) of 6 as a pale yellow-colored oil. $^1$H NMR ($CDCl_3$, 300 MHz): δ7.32 (m, 5H), 5.90 (br s, 1H), 5.09 (app dd, J=19.4, 12.2 Hz, 2H), 4.52 (m, 1H), 3.95 (br d, 1H), 3.52 (m, 2H), 2.93 (m, 1H), 2.80 (dd, J=18.3, 9.3 Hz, 1H), 2.22 (br d, 1H), 1.69 (m, 1H), 1.55 (m, 1H), 1.57 (s, 9H) ppm. Mass spectrum, m/z [363.2] (M+H)+.

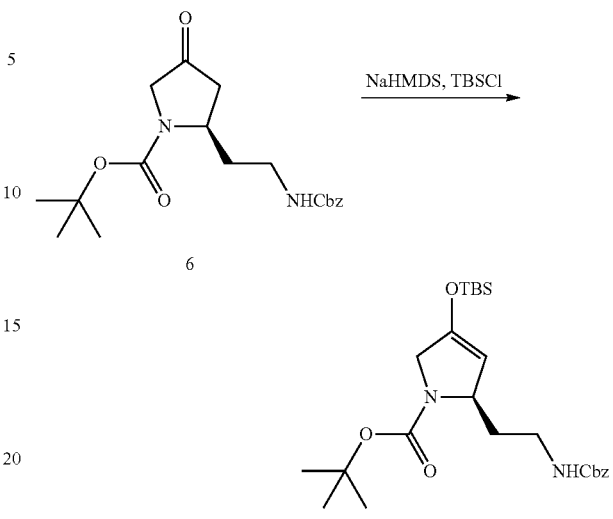

2-(2-Benzyloxycarbonylamino-ethyl)-4-(tert-butyl-dimethyl-silanyloxy)-2,5-dihydro-pyrrole-1-carboxylic acid tert-butyl ester (7): To a pre-cooled (−78° C.) solution containing 6 (400 mg, 1.10 mmol) in THF (10 mL) was added 1M NaHMDS/THF (2.43 mL) in a dropwise fashion. After 45 min, a solution containing TBSCl (348 mg, 2.31 mmol) in THF (5 mL) was added to the heterogeneous reaction mixture. After 30 min, the homogeneous reaction mixture was quenched with saturated aqueous $NH_4Cl$. The solution was diluted with EtOAc and the layers were separated. The organic phase was washed with brine then dried over anhydrous $Na_2SO_4$, filtered, and concentrated. The crude product was purified by flash silica gel chromatography (4:1 hexanes/EtOAc) to afford 440 mg (83%) of 7 as a white foam. $^1$H NMR ($CDCl_3$, 300 MHz), mixture of rotamers: δ7.26 (m, 5H), 5.87 (m, 0.25H), 5.70 (m, 0.25H), 5.48 (m, 0.5H), (app dd, J=16.4, 12.8 Hz, 2H), 4.92 (m, 0.3H), 4.55 (br s, 0.7H), 4.49 (m, 0.7H), 4.39 (m, 0.3H), 3.99 (m, 0.2H), 3.92 (m, 0.4H), 3.86 (br s, 0.4H), 3.76 (m, 1H), 3.28 (m, 0.5H), 3.13 (m, 0.5H), 3.03 (m, 0.5H), 2.92 (m, 0.5H), 1.78 (m, 1H), 1.64 (m, 1H), 1.38 (s, 9H), 0.85 (s, 9H), 0.11 (s, 6H) ppm. Mass spectrum, m/z [499.2] (M+Na)+.

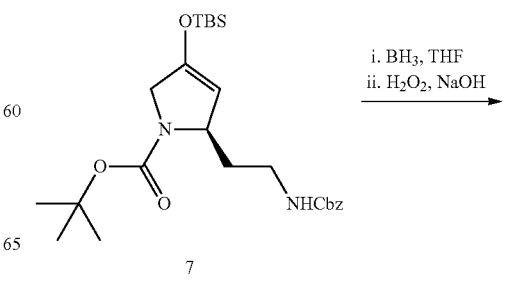

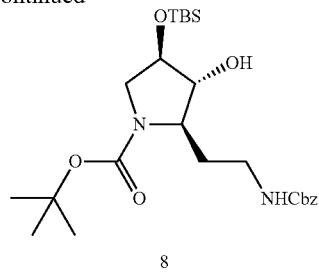

8

2-(2-Benzyloxycarbonylamino-ethyl)-4-(tert-butyl-dimethyl-silanyloxy)-3-hydroxy-pyrrolidine-1-carboxylic acid tert-butyl ester (8): A solution containing 7 (440 mg, 0.92 mmol) in anhydrous THF (15 mL) was cooled to −30° C. Borane (1M/THF, 3.68 mL) was added dropwise. After 10 min, the reaction mixture was allowed to slowly warm to 0° C. at which point TLC analysis revealed complete consumption of 7. The reaction mixture was recooled to −10° C. and 1M NaOH (2.6 mL) was added followed by the addition of 35% hydrogen peroxide (0.73 mL). The reaction mixture was then warmed to 0° C. After 1 h, the reaction mixture was quenched by the addition of saturated aqueous $Na_2S_2O_3$ and the product was extracted with EtOAc. The combined organic extracts were washed successively with water and brine, dried over anhydrous $Na_2SO_4$, filtered, and concentrated. The crude product was purified by flash silica gel chromatography (4:1 hexanes/EtOAc) to afford 250 mg (55%) of 8. $^1$H NMR ($CDCl_3$, 300 MHz), mixture of rotamers: δ7.25 (m, 5H), 6.07 (m, 0.6H), 5.93 (m, 0.2H), 5.67 (m, 0.2H), 5.00 (m, 2H), 4.03 (m, 1.5H), 3.84 (m, 0.75H), 3.75-3.63 (m, 1.5H), 3.54 (m, 1.25H), 3.37 (m, 0.6H), 3.26 (m, 0.4H), 3.13 (m, 1.5H), 2.95 (m, 0.75H), 1.90 (m, 1H), 1.67 (m, 1H), 1.36 (s, 9H), 0.80 (s, 9H), 0.00 (s, 6H) ppm. Mass spectrum, m/z [495.2] (M+H)+.

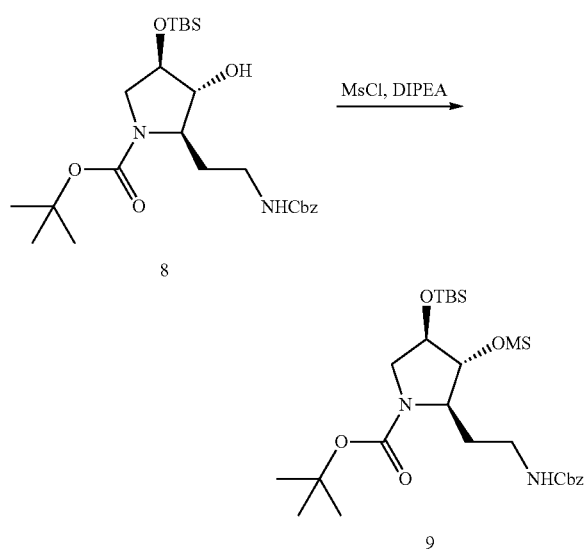

2-(2-Benzyloxycarbonylamino-ethyl)-4-(tert-butyl-dimethyl-silanyloxy)-3-methanesulfonyloxy-pyrrolidine-1-carboxylic acid tert-butyl ester (9): A solution containing crude 8 (500 mg, 1.01 mmol) in DCM (15 mL) was cooled to 0° C. DIPEA (261 mg, 2.02 mmol) was added followed by the addition of MsCl (117 mg, 1.02 mmol) and DMAP (13 mg, 0.1 mmol). After 2 h, the reaction mixture was warmed to ambient temperature, diluted with DCM, washed successively with 1M HCl and brine, dried over anhydrous $Na_2SO_4$, filtered, and concentrated to afford 578 mg (quant.) of crude 9 as a tan-colored foam which was used without further purification. $^1$H NMR ($CDCl_3$, 300 MHz), mixture of rotomers: δ7.35 (m, 5H), 5.90 (m, 1H), 5.10 (m, 2H), 4.67 (m, 1H), 4.40 (m, 1H), 4.11 (m, 2H), 3.94 (m, 0.5H), 3.80 (m, 0.5H), 3.74 (app dd, J=12.2, 5.0 Hz, 1H), 3.51 (m, 0.5H), 3.31 (m, 0.5H), 3.02 (s, 3H), 1.96 (m, 0.5H), 1.85 (m, 0.5H), 1.46 (s, 9H), 0.88 (s, 9H), 0.05 (s, 6H) ppm. Mass spectrum, m/z [595.2] (M+Na)+.

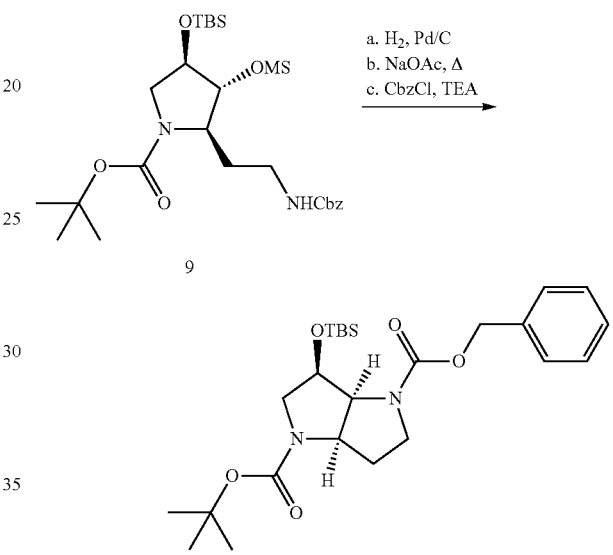

3-(tert-Butyl-dimethyl-silanyloxy)-hexahydro-pyrrolo[3,2-b]pyrrole-1,4-dicarboxylic acid 4-benzyl ester 1-tert-butyl ester (10): A 500 mL Parr bottle was charged with crude 9 (5.6 g, 9.78 mmol) and 10% Pd-on-carbon (2 g) in reagent grade MeOH (50 mL). The mixture was stirred under a balloon of $H_2$ with a slow stream of $H_2$ bubbling through the reaction mixture. After 3 h, the catalyst was removed by filtration through Celite® and the solids were washed with EtOH (100 mL).

To the above filtrate containing the crude amine was added NaOAc (1.66 g, 20 mmol) and the mixture was concentrated to remove MeOH. was immersed into a preheated (85-90° C.) oil bath. After 20 min, the reaction mixture was allowed to cool to ambient temperature and then concentrated in vacuo. The crude residue was dissolved in EtOAc (100 mL) and washed successively with aqueous $NaHCO_3$, and brine, dried over anhydrous $Na_2SO_4$, filtered, and concentrated to afford 2.4 g of the crude bicyclic amine which was used without further purification.

A solution containing the crude bicyclic amine (2.4 g, 7.12 mmol) in DCM (50 mL) was cooled to 0° C. DIPEA (1.85 g, 14.3 mmol) was added followed by Cbz-Cl (1.45 g, 8.51 mmol) and the reaction mixture was allowed to warm to ambient temperature. After 1 h, the reaction mixture was diluted with EtOAc (300 mL) and washed successively with 1N HCl, water, aqueous $NaHCO_3$, and brine, dried over anhydrous $Na_2SO_4$, filtered, and concentrated. The crude product was purified by flash silica gel chromatography (10:1 to 2:1 hexanes/EtOAc) to afford 2.9 g (63%, 3 steps) of 10 as a colorless oil. ¹H NMR (CDCl₃, 300 MHz), mixture of rotomers: δ7.33 (m, 5H), 5.28-4.96 (m, 2H), 4.36-4.15 (m, 3H), 3.70-3.44 (m, 4H), 2.38 (m, 0.5H), 2.23 (m, 0.5H), 2.05 (m, 1H), 1.46 (s, 9H), 0.85 (s, 9H), 0.01 (s, 6H) ppm. Mass spectrum, m/z [477.2] (M+H)+.

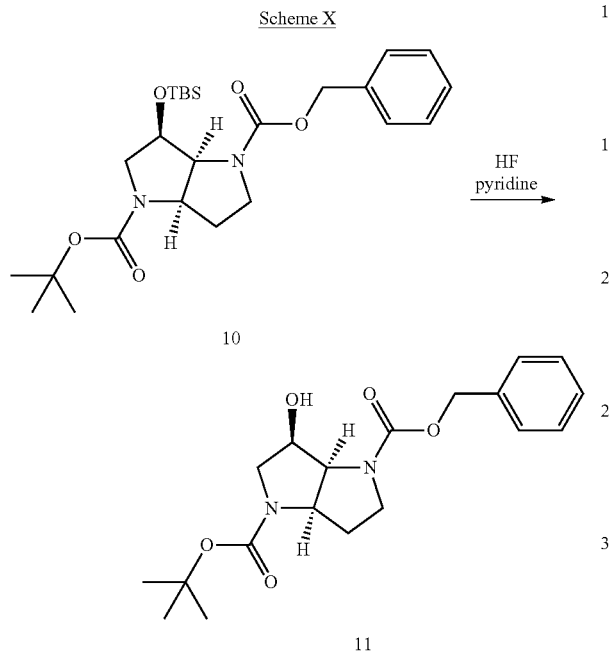

Scheme X

3-Hydroxy-hexahydro-pyrrolo[3,2-b]pyrrole-1,4-dicarboxylic acid 4-benzyl ester 1-tert-butyl ester (11): A solution containing 10 (868 mg, 1.8 mmol) in THF (10 mL) was cooled to 0° C. HF.pyridine reagent (1 mL, 36 mmol) was added and the reaction mixture was allowed to warm to ambient temperature. After 16 h, the reaction mixture was diluted with EtOAc and washed successively with water, aqueous NaHCO₃, water, and brine, dried over anhydrous Na₂SO₄, filtered, and concentrated. The crude product was purified by flash silica gel chromatography (1:1 hexanes/EtOAc) to afford 600 mg (90%) of 11. ¹H NMR (CDCl₃, 300 MHz): δ7.29 (m, 5H), 5.10 (app dd, J=22.7, 12.5 Hz, 2H), 4.32 (m, 4H), 3.71 (m, 2H), 3.58 (m, 1H), 3.38 (m, 1H), 3.17 (m, 1H), 2.14 (m, 1H), 2.02 (m, 1H), 1.42 (s, 9H) ppm. Mass spectrum, m/z [363.2] (M+H)+.

Scheme XI

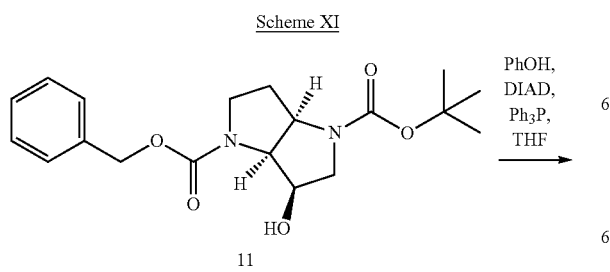

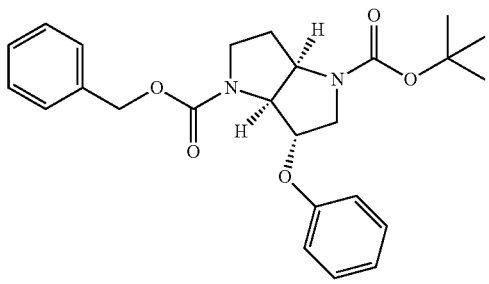

3-Phenoxy-hexahydro-pyrrolo[3,2-b]pyrrole-1,4-dicarboxylic acid 4-benzyl ester 1-tert-butyl ester (12): To a solution of 11 (600 mg, 1.65 mmol) in THF (10 mL) was added phenol (186 mg, 1.98 mmol) and Ph₃P (520 mg, 1.98 mmol). DIAD (459 mg, 2.31 mmol) was then added and the reaction mixture was immersed into a preheated (75° C.) oil bath. After 16 h, the reaction mixture was concentrated in vacuo and the residue was passed through a short column of silica gel (4:1 hexanes/EtOAc). The crude product was then purified by reverse-phase HPLC (2" Dynamax® C18, 10-70% ACN/water containing 0.1% HOAc over 30 min; Flow: 40 mL/min) to afford 340 mg (46%) of 12 as a white solid. ¹H NMR (CDCl₃, 300 MHz), mixture of rotomers: δ7.37-7.27 (m, 6H), 7.22 (m, 1H), 7.04 (m, 1H), 6.96-6.88 (m, 1H), 6.81 (d, J=8.4 Hz, 1H), 5.27-5.13 (m, 2H), 5.01 (dd, J=3.3, 6.3 Hz, 0.5H), 4.77 (d, J=2.7 Hz, 0.5H), 4.57-4.45 (m, 1H), 4.43-4.32 (m, 1H), 3.99-3.89 (m, 1H), 3.85-3.73 (m, 1H), 3.37 (m, 1H), 3.21 (dt, J=5.7, 11.7 Hz, 1H), 2.38 (m, 0.5H), 2.23 (dd, J=5.7, 13.2 Hz, 0.5H), 1.91-1.83 (m, 1H), 1.47 (m, 9H) ppm. Mass spectrum, m/z [339.2] (M−Boc)+.

Scheme XII

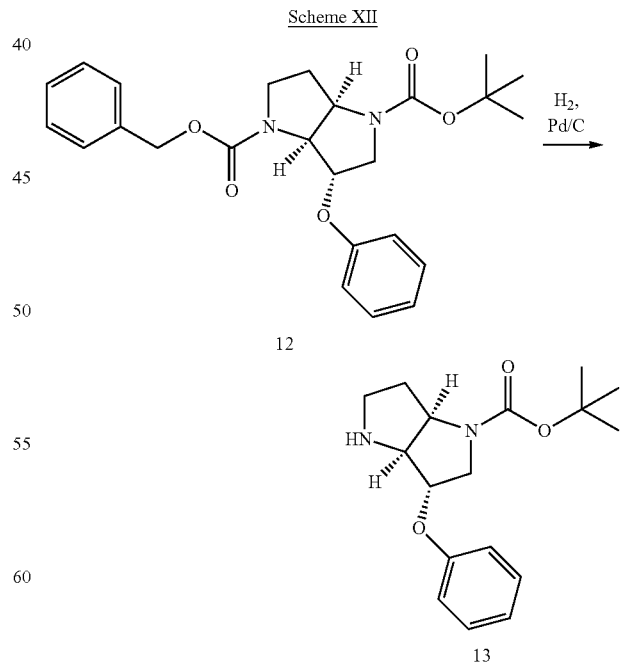

3-Phenoxy-hexahydro-pyrrolo[3,2-b]pyrrole-1-carboxylic acid tert-butyl ester (13): A 500 mL Parr bottle was charged with crude 12 (370 mg, 0.84 mmol) and 5% Pd-on-carbon (50 mg) in reagent grade MeOH (10 mL). The mixture was pressurized to 50 PSI H₂ then shaken for 1 h. The catalyst was removed by filtration through Celite® and the solids were washed with MeOH and EtOAc. The filtrate was concentrated in vacuo to afford 256 mg (quant.) of 13 which was used without further purification.

Na₂SO₄, filtered, and concentrated. The crude product was purified by flash silica gel chromatography (4:1 hexanes/EtOAc) to afford 410 mg (90%) of 14 as a white solid. ¹H NMR (CDCl₃, 300 MHz), mixture of rotamers: δ7.31 (m, 9H), 6.96 (m, 1H), 5.79 (m, 1H). 5.07 (m, 2H), 4.91 (d, J=2.7 Hz, 1H), 4.51-4.43 (m, 2H), 4.35 (t, J=7.5 Hz, 1H), 4.07-3.99 (m, 2H), 3.90 (app d, J=26.4 Hz, 0.5H), 3.77 (app d, J=27.3 Hz, 0.5H), 3.31 (m, 2H), 2.49 (m, 0.5H), 2.35 (m, 0.5H), 1.92 (m, 1H), 1.51 (m, 9H), 0.95 (m, 6H) ppm.

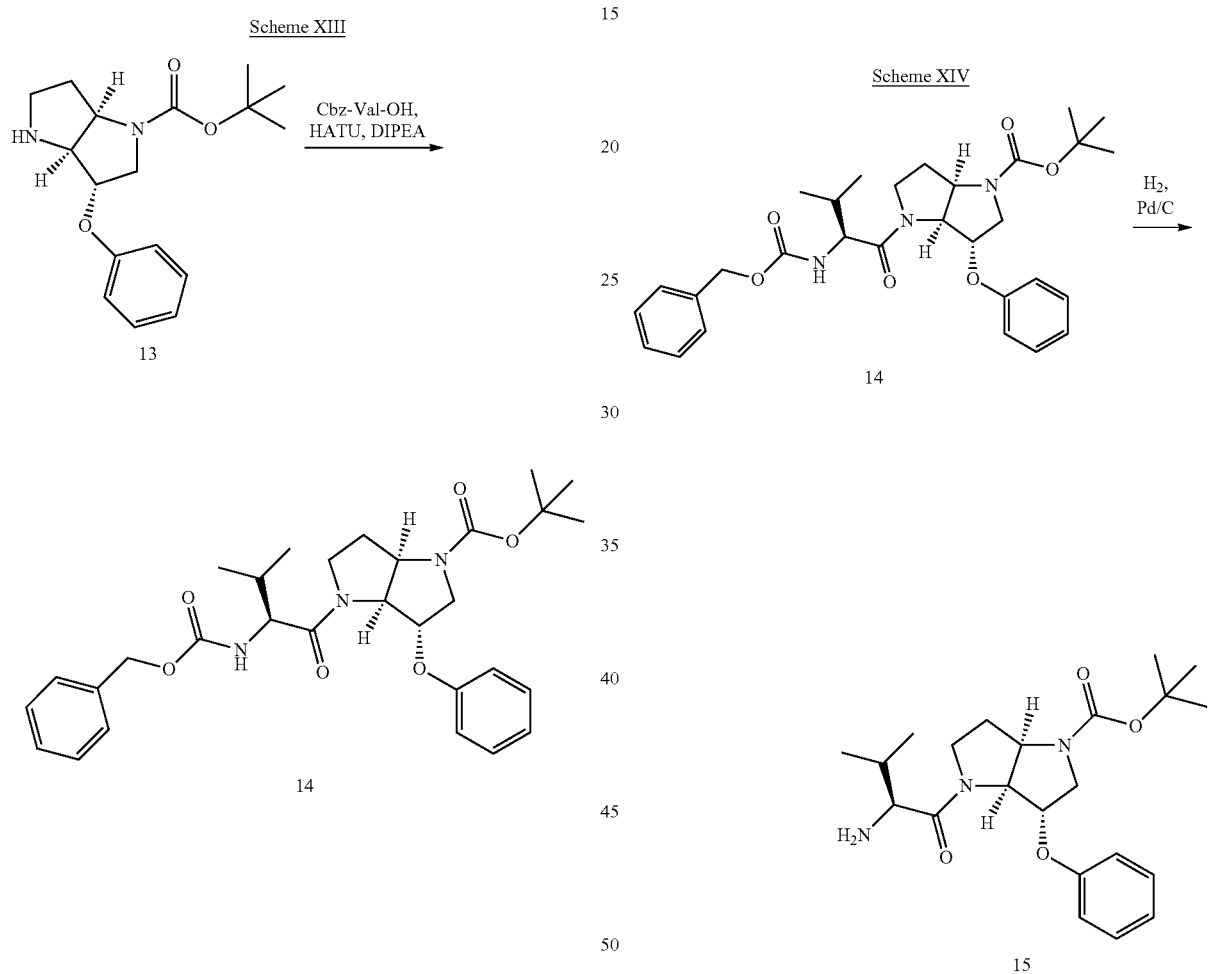

4-(2-Benzyloxycarbonylamino-3-methyl-butyryl)-3-phenoxy-hexahydro-pyrrolo[3,2-b]pyrrole-1-carboxylic acid tert-butyl ester (14): To a solution containing Cbz-Val-OH (233 mg, 0.92 mmol) and crude 13 (256 mg, 0.84 mmol) in anhydrous NMP (3 mL) was cooled to 0° C. HATU (352 mg, 0.93 mmol) and DIPEA (125 mg, 1.01 mmol) were added and the reaction mixture was slowly warmed to ambient temperature. After 16 h, the reaction mixture was diluted with diethyl ether and EtOAc (1:4) and washed successively with 1M HCl, aqueous NaHCO₃, water, and brine, dried over anhydrous 4-(2-Amino-3-methyl-butyryl)-3-phenoxy-hexahydro-pyrrolo[3,2-b]pyrrole-1-carboxylic acid tert-butyl ester (15): A 500 mL Parr bottle was charged with crude 14 (410 mg, 0.76 mmol) and 10% Pd-on-carbon (50 mg) in reagent grade MeOH (10 mL). The mixture was pressurized to 50 PSI H₂ then shaken for 2 h. The catalyst was removed by filtration through Celite® and the solids were washed with MeOH and EtOAc. The filtrate was concentrated in vacuo to afford 307 mg (quant.) of 15 which was used without further purification.

Scheme XV

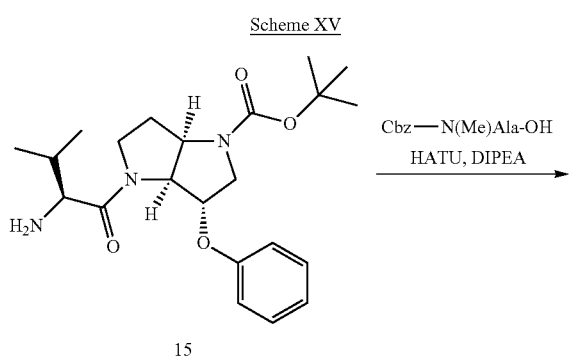

mmol) and crude 15 (307 mg, 0.76 mmol) in anhydrous NMP (3 mL) was cooled to 0° C. HATU (315 mg, 0.83 mmol) and DIPEA (118 mg, 0.91 mmol) were added and the reaction mixture was slowly warmed to ambient temperature. After 16 h, the reaction mixture was diluted with diethyl ether and EtOAc (1:4) and washed successively with 1M HCl, aqueous NaHCO$_3$, water, and brine, dried over anhydrous Na$_2$SO$_4$, filtered, and concentrated to afford 420 mg (88%) of crude 16 which was used without further purification. $^1$H NMR (CDCl$_3$, 300 MHz), mixture of rotomers: δ7.37-7.25 (m, 9H), 6.96 (m, 1H), 6.69 (br s, 1H), 5.19 (m, 2H), 4.91 (m, 1H), 4.81 (m, 1H), 4.58-4.46 (m, 2H), 4.04 (m, 2H), 3.97 (app d, J=12.6 Hz, 0.5H), 3.84 (app d, J=12.6 Hz, 0.5H), 3.40-3.25 (m, 2H), 2.88 (s, 3H), 2.48 (dd, J=5.7, 13.5 Hz, 0.5H), 2.33 (dd, J=5.4, 12.9 Hz, 0.5H), 2.06-1.82 (m, 2H), 1.51 (s, 4.5H), 1.49 (s, 4.5H), 1.36 (d, J=6.9 Hz, 3H), 0.91 (dd, J=2.7, 6.6 Hz, 3H), 0.83 (dd, J=1.8, 6.9 Hz, 3H) ppm.

Scheme XVI

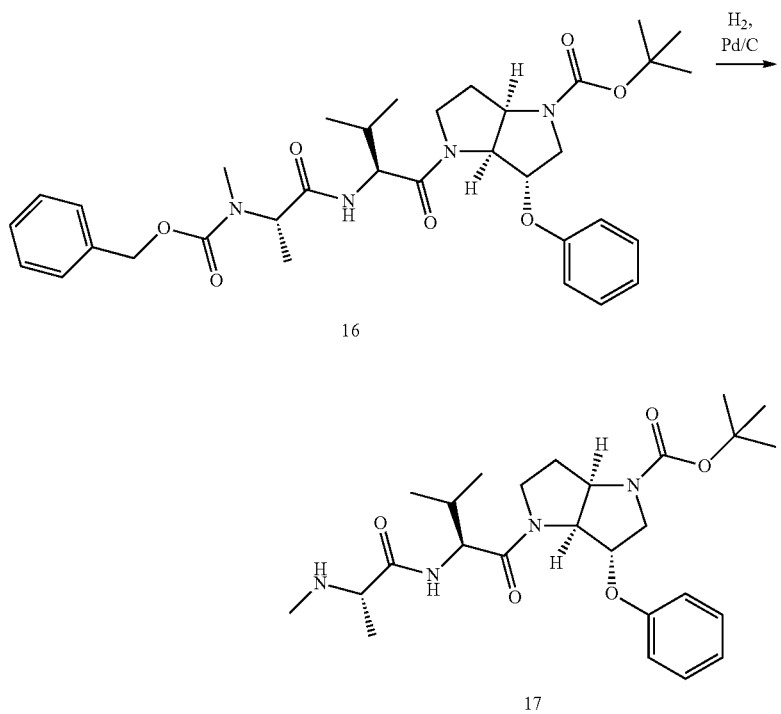

-continued

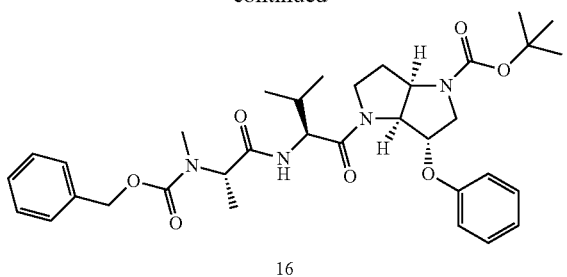

4-{2-[2-(Benzyloxycarbonyl-methyl-amino)-propionylamino]-3-methyl-butyryl}-3-phenoxy-hexahydro-pyrrolo[3,2-b]pyrrole-1-carboxylic acid tert-butyl ester (16). To a solution containing Cbz-N(Me)Ala-OH (196 mg, 0.83

4-[3-Methyl-2-(2-methylamino-propionylamino)-butyryl]-3-phenoxy-hexahydro-pyrrolo[3,2-b]pyrrole-1-carboxylic acid tert-butyl ester (17): A 500 mL Parr bottle was charged with crude 16 (50 mg, 0.08 mmol) and 10% Pd-on-carbon (50 mg) in reagent grade MeOH (3 mL). The mixture was pressurized to 50 PSI H$_2$ then shaken for 2 h. The catalyst was removed by filtration through Celite® and the solids were washed with MeOH and EtOAc. The filtrate was concentrated in vacuo. The crude product was purified by RP-HPLC (2" Dynamax® C18, 10-70% ACN/water containing 0.1% HOAc over 30 min; Flow: 40 mL/min) to afford 20 mg (51%) of 17 after lyophilization.

Scheme XVII

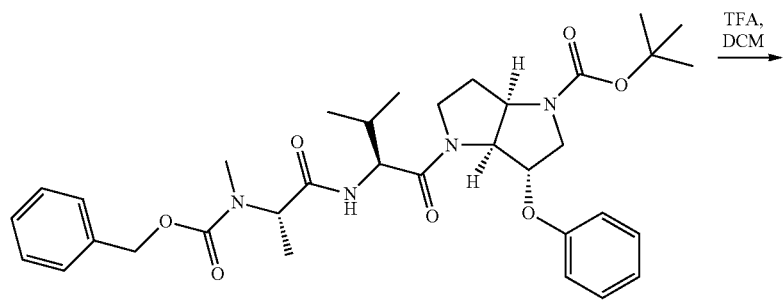

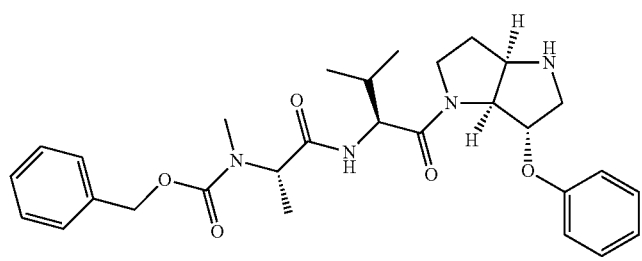

Methyl-{1-[2-methyl-1-(6-phenoxy-hexahydro-pyrrolo[3,2-b]pyrrole-1-carbonyl)-propylcarbamoyl]-ethyl}-carbamic acid benzyl ester (18): To a solution containing 16 (370 mg, 0.59 mmol) in DCM (10 mL) was added TFA (4 mL) at 0° C. After 1 h, the reaction mixture was diluted with DCM and the resultant organic solution was washed successively with saturated aqueous NaHCO₃ and brine, dried over anhydrous Na₂SO₄, filtered, and concentrated to afford crude 18 which was used without further purification.

N-[1-(4-Acetyl-6-phenoxy-hexahydro-pyrrolo[3,2-b]pyrrole-1-carbonyl)-2-methyl-propyl]-2-methylamino-propionamide (19): A solution containing 18 (150 mg, 0.28 mmol) in DCM (3 mL) was cooled to 0° C. TEA (57 mg, 0.57 mmol) and Ac₂O (34 mg, 0.36 mmol) were added followed by the addition of DMAP (4 mg, 0.03 mmol). After 30 min, the reaction mixture was diluted with DCM, washed successively with 1M HCl and brine, dried over anhydrous Na₂SO₄, fil- Scheme XVIII

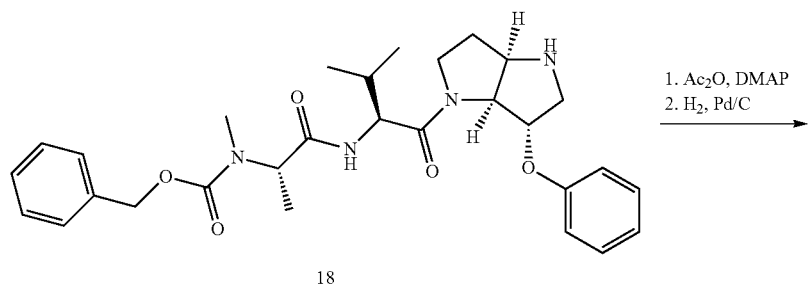

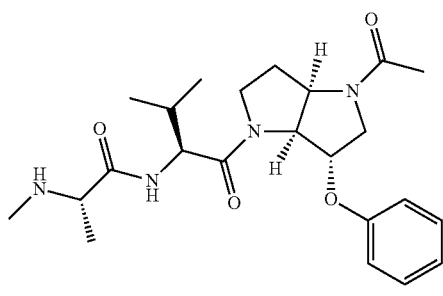

tered, and concentrated to afford crude acetamide which was used without further purification. Mass spectrum, m/z [565] (M+H)+.

A 500 mL Parr bottle was charged with the crude acetamide (0.28 mmol) and 10% Pd-on-carbon (50 mg) in reagent grade MeOH (5 mL). The mixture was pressurized to 50 PSI $H_2$ then shaken for 90 min. The catalyst was removed by filtration through Celite® and the solids were washed with MeOH and EtOAc. The filtrate was concentrated in vacuo. The crude product was purified by RP-HPLC (2" Dynamax® C18, 10-70% ACN/water containing 0.1% HOAc over 30 min; Flow: 40 mL/min) to afford 77 mg (62%) of 19 after lyophilization.

EXAMPLE 1

4-[3-Methyl-2-(2-methylamino-propionylamino)-butyryl]-3-phenoxy-hexahydro-pyrrolo[3,2-b]pyrrole-1-carboxylic acid tert-butyl ester (17)

$^1$H NMR (300 MHz, $d_6$-DMSO): δ8.05 (d, J=8.7 Hz, 1H), 7.4-7.2 (m, 3H), 6.95 (m, 1H), 4.9 (s, 1H), 4.5-5.3 (m, 3H), 4.0 (m, 1H), 3.8-3.6 (m, 1H), 3.4-3.2 (m, 3H), 3.0 (dd, J=13.5, 6.6 Hz, 1H), 2.65 (s, 1H), 2.1-1.9 (m, 2H), 1.4 (s, 9H), 1.09 (d, J=6.6 Hz, 3H), 0.89 (d, J=6.9 Hz, 3H), 0.85 (d, J=6.6 Hz, 3H) ppm; $^{13}$C NMR (75 MHz, $d_6$-DMSO): δ175.2, 171.4, 157.4, 153.9, 153.8 (rotomer), 130.2, 121.7, 116.0, 115.9 (rotomer), 79.8, 77.0, 76.3 (rotomer), 66.2, 65.2 (rotomer), 60.3, 59.6 (rotomer), 56.0, 55.9 (rotomer), 52.4, 51.9 (rotomer), 46.0, 34.8, 31.9, 31.0 (rotomer), 30.8, 28.8, 19.9, 19.7 (rotomer), 18.5 ppm. Mass spectrum, m/z [489.2] (M+H)+.

N-[1-(4-Methanesulfonyl-6-phenoxy-hexahydro-pyrrolo[3,2-b]pyrrole-1-carbonyl)-2-methyl-propyl]-2-methylamino-propionamide (20): A solution containing 18 (150 mg, 0.28 mmol) in DCM (3 mL) was cooled to 0° C. DIPEA (74 mg, 0.57 mmol) and DMAP (4 mg, 0.03 mmol) were added followed by the addition of MsCl (36 mg, 0.32 mmol). After 1 h, the reaction mixture was warmed to ambient temperature, diluted with DCM, washed successively with 1M HCl and brine, dried over anhydrous $Na_2SO_4$, filtered, and concentrated to afford the crude sulfonamide which was used without further purification. Mass spectrum, m/z [601] (M+H)+.

A 500 mL Parr bottle was charged with the crude sulfonamide (0.28 mmol) and 10% Pd-on-carbon (50 mg) in reagent grade MeOH (5 mL). The mixture was pressurized to 50 PSI $H_2$ then shaken for 1 h. The catalyst was removed by filtration through Celite® and the solids were washed with MeOH and EtOAc. The filtrate was concentrated in vacuo. The crude product was purified by RP-HPLC (2" Dynamax® C18, 10-70% ACN/water containing 0.1% HOAc over 30 min; Flow: 40 mL/min) to afford 92 mg (68%) of 20 after lyophilization.

EXAMPLE 2

N-[1-(4-Acetyl-6-phenoxy-hexahydro-pyrrolo[3,2-b]pyrrole-1-carbonyl)-2-methyl-propyl]-2-methylamino-propionamide (19)

$^1$H NMR (300 MHz, $d_6$-DMSO), mixture of rotomers: δ8.05 (d, J=8.7 Hz, 1H), 7.4-7.2 (m, 3H), 6.95 (m, 1H), 4.83 (d, J=3 Hz, 0.7H; major rotomer), 4.75 (d, J=3 Hz, 0.3H; minor rotomer), 4.6 (m, 1H), 4.42 (m, 3H), 4.01 (m, 1H), 3.71 (d, J=12.6 Hz, 1H), 3.56 (dd, J=12.3, 3.3 Hz, 1H), 3.34 (m, 1H), 3.09 (m, 1H), 2.1 (s, 3H), 1.1 (d, J=6.9 Hz, 3H), 0.88 (d, J=6.9 Hz, 3H), 0.85 (d, J=6.9 Hz, 3H) ppm; $^{13}$C NMR (75 MHz, $d_6$-DMSO), major rotomer: δ174.6, 171.3, 169.1, 157.5, 130.2, 121.8, 116.0, 77.1, 64.8, 60.0, 59.3, 56.1, 53.3, 46.0, 34.4, 30.7, 23.6, 21.8, 20.0, 19.4, 18.5 ppm. Mass spectrum, m/z [431.2] (M+H)+.

EXAMPLE 3

N-[1-(4-Methanesulfonyl-6-phenoxy-hexahydro-pyrrolo[3,2-b]pyrrole-1-carbonyl)-2-methyl-propyl]-2-methylamino-propionamide (20)

$^1$H NMR (300 MHz, $d_6$-DMSO): δ8.13 (d, J=9.0 Hz, 1H), 7.27-7.35 (m, 4H), 6.98 (m, 1H), 4.87 (d, J=2.4 Hz, 1H), 4.40-4.52 (m, 3H), 4.06 (app t, J=9.6 Hz, 1H), 3.69-3.42 (m, 4H), 3.09 (app q, J=6.6 Hz, 1H), 3.01 (s, 3H), 2.20 (s, 3H), 2.15-1.90 (m, 4H), 1.12 (d, J=6.9 Hz, 3H), 0.90 (d, J=6.6 Hz, 3H), 0.87 (d, J=6.9 Hz, 3H) ppm; $^{13}$C NMR (75 MHz, $d_6$-DMSO): δ174.8, 171.5, 157.0, 130.3, 121.9, 115.9, 77.2, 66.3, 62.8, 59.3, 56.2, 54.4, 46.3, 36.0, 34.5, 33.4, 30.7, 19.9, 19.4, 18.8 ppm. Mass spectrum, m/z [467.2] (M+H)+.

EXAMPLES 4 through 14 were prepared using the chemistries described in Schemes XI through XIX by replacing phenol with 2-phenylphenol, 5,6,7,8-tetrahydro-naphthalen-1-ol, 5,6,7,8-tetrahydro-naphthalen-2-ol, naphthalen-1-ol, naphthalen-2-ol, 4-fluorophenol, and 3,4-difluorophenol and/or Boc-Val-OH with Boc-Chg-OH, Boc-Tle-OH, and Boc-Thr(Me)-OH.

EXAMPLE 4

N-{2-[6-(Biphenyl-2-yloxy)-hexahydro-pyrrolo[3,2-b]pyrrol-1-yl]-1-cyclohexyl-2-oxo-ethyl}-2-methylamino-propionamide $^1$H NMR ($d_6$-DMSO, 300 MHz): δ8.08 (d, J=8.7 Hz, 1H), 7.55 (m, 2H), 7.45-7.27 (m, 5H), 7.06 (app t, J=7.2 Hz, 1H), 6.85 (br s, 3H), 4.72 (d, J=2.4 Hz, 1H), 4.45 (app t, J=8.1 Hz, 1H), 4.25 (d, J=5.4 Hz, 1H), 3.93 (m, 1H), 3.88 (m, 1H), 3.40 (app q, J=9.3 Hz, 1H), 3.08 (m, 1H), 2.90 (m, 2H), 2.20 (s, 3H), 1.89 (s, 6H), 1.80 (m, 2H), 1.64 (m, 5H), 1.27-0.93 (m, 4H), 1.11 (d, J=6.9 Hz, 1H) ppm; $^{13}$C NMR ($d_6$-DMSO, 75 MHz): δ173.9, 172.2, 170.2, 169.9, 154.0, 153.2, 138.1, 132.0, 130.6, 130.3, 129.3, 128.7, 127.9, 126.7, 122.1, 121.1, 117.2, 114.2, 81.4, 66.6, 59.7, 58.6, 54.7, 51.6, 46.1, 33.7, 32.8, 29.2, 28.0, 25.8, 25.5, 25.4, 21.3, 18.7 ppm. Mass spectrum, m/z [505.3] (M+H)+.

EXAMPLE 5

N-{1-Cyclohexyl-2-oxo-2-[6-(5,6,7,8-tetrahydro-naphthalen-1-yloxy)-hexahydro-pyrrolo[3,2-b]pyrrol-1-yl]-ethyl}-2-methylamino-propionamide $^1$H NMR ($d_6$-DMSO, 300 MHz): δ7.99 (d, J=8.7 Hz, 1H), 7.25 (d, J=8.1 Hz, 1H), 7.01 (t, J=7.8 Hz, 1H), 6.63 (d, J=7.8 Hz, 1H), 4.67 (d, J=2.7 Hz, 1H), 4.46 (t, J=8.1 Hz, 1H), 4.25 (d, J=5.4 Hz, 1H), 3.95 (m, 6H), 3.39 (app q, J=9.3 Hz, 1H), 3.01 (m, 2H), 2.80 (dd, J=3.3, 12.6 Hz, 1H), 2.66 (m, 2H), 2.56 (m, 2H), 2.17 (s, 3H), 1.89 (s, 2H), 1.81 (m, 2H), 1.68 (m, 8H), 1.23-0.89 (m, 4H), 1.09 (d, J=6.9 Hz, 1H) ppm; $^{13}$C NMR ($d_6$-DMSO, 75 MHz): δ174.3, 172.2, 170.2, 154.9, 137.8, 125.6, 125.4, 121.2, 109.5, 80.5, 66.6, 59.7, 59.0, 54.6, 52.0, 46.1, 34.1, 33.2, 29.2, 29.1, 28.0, 25.8, 25.5, 25.4, 22.7, 22.42, 22.38, 21.3, 19.0 ppm. Mass spectrum, m/z [483.3] (M+H)+.

EXAMPLE 6

N-{1-Cyclohexyl-2-oxo-2-[6-(5,6,7,8-tetrahydro-naphthalen-2-yloxy)-hexahydro-pyrrolo[3,2-b]pyrrol-1-yl]-ethyl}-2-methylamino-propionamide $^1$H NMR ($d_6$-DMSO, 300 MHz): δ8.00 (d, J=8.7 Hz, 1H), 6.92 (m, 3H), 4.63 (d, J=2.7 Hz, 1H), 4.40 (app t, J=8.3 Hz, 1H), 4.24 (d, J=5.1 Hz, 1H), 3.92 (m, 2H), 3.38 (app q, J=9.0 Hz, 1H), 2.99 (m, 2H), 2.80 (dd, J=3.0, 12.3 Hz, 1H), 2.64 (m, 4H), 2.18 (s, 3H), 1.89 (s, 3H), 1.80 (m, 2H), 1.68 (m, 10H), 1.23-0.89 (m, 4H), 1.10 (d, J=6.9 Hz, 1H) ppm; $^{13}$C NMR ($d_6$-DMSO, 75 MHz): δ174.3, 172.2, 170.2, 170.1, 155.0, 154.1, 137.6, 130.2, 129.7, 128.7, 118.5, 116.3, 115.5, 113.1, 84.3, 80.7, 66.5, 66.2, 62.0, 59.6, 59.0, 54.7, 54.5, 51.8, 51.4, 46.1, 34.1, 33.1, 29.2, 29.1, 28.04, 27.97, 25.8, 25.5, 25.4, 23.0, 22.9, 22.7, 21.3, 19.0 ppm. Mass spectrum, m/z [483.3] (M+H)+.

EXAMPLE 7

N-{1-Cyclohexyl-2-[6-(naphthalen-2-yloxy)-hexahydro-pyrrolo[3,2-b]pyrrol-1-yl]-2-oxo-ethyl}-2-methylamino-propionamide $^1$H NMR (CDCl$_3$, 300 MHz), mixture of rotamers: δ7.85-7.73 (m, 4H), 7.43 (app t, J=6.9 Hz, 1H), 7.33 (app t, J=6.9 Hz, 1H), 7.23 (dd, J=2.4, 9.0 Hz, 1H), 5.06 (br s, 1H), 4.62 (m, 2H), 4.17-4.09 (m, 2H), 3.52 (m, 1H), 3.35 (m, 1H), 3.17 (m, 1H), 2.92 (m, 2H), 2.45 (s, 3H), 2.17-1.99 (m, 5H), 1.76-1.68 (m, 6H), 1.34 (d, J=6.9 Hz, 3H), 1.27-1.03 (m, 4H) ppm; $^{13}$C NMR (CDCl$_3$, 75 MHz), mixture of rotamers: δ173.9, 171.2, 154.6, 134.5, 129.4, 129.1, 127.5, 127.2, 126.2, 123.8, 118.7, 109.1, 79.8, 66.4, 60.1, 59.4, 55.6, 51.8, 47.0, 40.5, 34.0, 32.7, 29.7, 28.6, 26.0, 25.9, 25.8, 18.7 ppm. Mass spectrum, m/z [479.2] (M+H)+.

EXAMPLE 8

N-{1-Cyclohexyl-2-[6-(naphthalen-1-yloxy)-hexahydro-pyrrolo[3,2-b]pyrrol-1-yl]-2-oxo-ethyl}-2-methylamino-propionamide $^1$H NMR (CDCl$_3$, 300 MHz), mixture of rotamers: δ8.18-8.15 (m, 1H), 7.81-7.78 (m, 1H), 7.70-7.62 (m, 2H), 7.49-7.41 (m, 3H), 5.14 (br s, 1H), 4.68 (d, J=5.4 Hz, 1H), 4.61 (app dd, J=8.1, 8.7 Hz, 1H), 4.21 (app t, J=5.1 Hz, 1H), 4.15 (app t, J=9.3 Hz, 1H), 3.53 (m, 1H), 3.44 (d, J=13.8 Hz, 1H), 3.13 (app q, J=7.2 Hz, 1H), 2.96 (dd, J=2.7, 13.2 Hz, 1H), 2.41 (s, 3H), 2.09-1.99 (m, 6H), 1.76 (m, 6H), 1.32 (d, J=6.9 Hz, 3H), 1.30-1.02 (m, 4H) ppm. Mass spectrum, m/z [479.2] (M+H)+.

EXAMPLE 9

N-{1-[6-(4-Fluoro-phenoxy)-4-methanesulfonyl-hexahydro-pyrrolo[3,2-b]pyrrole-1-carbonyl]-2-methyl-propyl}-2-methylamino-propionamide $^1$H NMR (CDCl$_3$, 300 MHz): δ9.61 (br s, 4H), 7.96 (m, 1H), 7.12 (m, 2H), 6.99 (m, 1H), 4.91 (br s, 1H), 4.57 (m, 2H), 4.35 (app t, J=4.4 Hz, 1H), 4.16 (app t, J=9.3 Hz, 1H), 3.75 (d, J=13.2 Hz, 1H), 3.69 (m, 1H), 3.53 (m, 1H), 3.47 (dd, J=2.3, 13.4 Hz, 1H), 2.97 (s, 3H), 2.51 (s, 3H), 2.45 (m, 1H), 2.07 (m, 2H), 2.03 (s, 9H), 1.38 (d, J=6.6 Hz, 3H), 0.95 (app dd, J=4.4, 6.8 Hz, 6H) ppm; $^{13}$C NMR (CDCl$_3$, 75 MHz): δ176.6, 172.2, 171.7, 159.5, 156.3, 152.3, 152.2, 116.5, 116.3, 116.23, 116.18, 77.0, 66.3, 62.8, 58.2, 56.7, 54.2, 46.5, 35.1, 33.4, 32.6, 31.0, 21.8, 19.4, 18.1, 17.4 ppm. Mass spectrum, m/z [485.2] (M+H)+.

EXAMPLE 10

N-{1-Cyclohexyl-2-[6-(4-fluoro-phenoxy)-4-methanesulfonyl-hexahydro-pyrrolo[3,2-b]pyrrol-1-yl]-2-oxo-ethyl}-2-methylamino-propionamide $^1$H NMR (CDCl$_3$, 300 MHz): δ7.72 (d, J=8.7 Hz, 1H), 7.17 (m, 2H), 7.01 (app t, J=8.6 Hz, 1H), 6.33 (br d, 3.6H), 4.96 (d, J=2.4 Hz, 1H), 4.56 (m, 2H), 4.35 (app t, J=4.4 Hz, 1H), 4.24 (app t, J=9.2 Hz, 1H), 3.77 (app d, J=13.2 Hz, 1H), 13.52 (m, 2H), 3.28 (m, 1H), 2.98 (s, 3H), 2.47 (m, 1H), 2.43 (s, 3H), 2.06 (br s, 5.4H), 1.75-1.60 (m, 6H), 1.33 (d, J=6.9 Hz, 1H), 1.29-1.00 (m, 5H) ppm; $^{13}$C NMR (CDCl$_3$, 75 MHz): δ176.2, 174.4, 171.9, 159.5, 156.3, 152.37, 152.34, 116.6, 116.35, 116.27, 116.24, 66.3, 63.0, 59.5, 55.8, 54.3, 46.5, 40.7, 35.1, 34.2, 33.4, 29.9, 28.9, 26.1, 25.94, 25.90, 21.5, 18.8 ppm. Mass spectrum, m/z [525.2] (M+H)+.

EXAMPLE 11

N-{1-[6-(4-Fluoro-phenoxy)-4-methanesulfonyl-hexahydro-pyrrolo[3,2-b]pyrrole-1-carbonyl]-2-methoxy-propyl}-2-methylamino-propionamide $^1$H NMR (CDCl$_3$, 300 MHz): δ7.81 (d, J=7.5 Hz, 1H), 7.14 (m, 2H), 7.00 (m, 2H), 4.90-4.85 (m, 2H), 4.61 (d, J=4.5 Hz, 1H), 4.35 (app t, J=4.4 Hz, 1H), 4.01 (app t, J=9.2 Hz, 1H), 3.77-3.56 (m, 3H), 3.49 (app dd, J=2.9, 13.4 Hz, 1H), 3.38 (m, 1H), 3.36 (s, 3H), 2.97 (s, 3H), 2.46 (s, 3H), 2.43 (m, 1H), 2.04 (br s, 5H), 1.35 (d, J=6.9 Hz, 1H), 1.15 (d, J=6.3 Hz, 1H) ppm; $^{13}$C NMR (CDCl$_3$, 75 MHz): δ176.2, 173.8, 173.7, 169.5, 159.5, 156.3, 152.3, 152.3, 116.5, 116.2, 116.2, 116.1, 66.3, 62.7, 59.1, 57.0, 54.8, 54.1, 46.7, 35.2, 33.8, 33.7, 33.5, 21.6, 18.5, 15.1 ppm. Mass spectrum, m/z [501.2] (M+H)+.

EXAMPLE 12

N-{1-[6-(3,4-Difluoro-phenoxy)-4-methanesulfonyl-hexahydro-pyrrolo[3,2-b]pyrrole-1-carbonyl]-2-methyl-propyl}-2-methylamino-propionamide $^1$H NMR (CDCl$_3$, 300 MHz): δ7.80 (app d, J=8.7 Hz, 1H), 7.18-7.05 (m, 4H), 6.96 (m, 1H), 4.91 (d, J=2.4 Hz, 1H), 4.57 (m, 2H), 4.35 (app t, J=4.4 Hz, 1H), 4.21 (app t, J=9.2 Hz, 1H), 3.76 (app d, J=13.5 Hz, 1H), 3.53 (m, 2H), 3.34 (q, J=6.9 Hz, 1H), 2.97 (s, 3H), 2.48 (m, 1H), 2.45 (s, 3H), 2.15-2.0 (m, 6H), 1.35 (d, J=6.6 Hz, 1H), 0.96 (app dd, J=3.8, 6.8 Hz, 6H) ppm; $^{13}$C NMR (CDCl$_3$, 75 MHz): δ174.2, 172.0, 152.5, 152.4, 149.0, 147.4, 147.3, 144.1, 117.9, 117.7, 110.5, 110.5, 105.3, 105.0, 66.1, 62.8, 59.4, 56.4, 54.2, 46.4, 35.2, 34.0, 33.4, 31.1, 19.5, 18.7, 18.2 ppm. Mass spectrum, m/z [503.2] (M+H)+.

EXAMPLE 13

N-{1-Cyclohexyl-2-[6-(3,4-difluoro-phenoxy)-4-methanesulfonyl-hexahydro-pyrrolo[3,2-b]pyrrol-1-yl]-2-oxo-ethyl}-2-methylamino-propionamide $^1$H NMR (CDCl$_3$, 300 MHz): δ7.73 (app d, J=8.1 Hz, 1H), 7.16 (m, 1H), 7.10 (m, 1H), 6.98 (m, 1H), 5.80 (br d, 2H), 4.93 (d, J=2.4 Hz, 1H), 4.55 (m, 2H), 4.34 (app t, J=4.5 Hz, 1H), 4.25 (app t, J=9.2 Hz, 1H), 3.76 (app d, J=13.5 Hz, 1H), 3.52 (m, 2H), 3.23 (m, 1H), 2.97 (s, 3H), 2.47 (m, 1H), 2.43 (s, 3H), 2.08 (m, 1H), 2.05 (s, 3H), 1.75-1.58 (m, 7H), 1.33 (d, J=6.9 Hz, 1H), 1.29-1.00 (m, 6H) ppm; $^{13}$C NMR (CDCl$_3$, 75 MHz): δ174.5, 172.0, 152.6, 152.5, 149.0, 147.4, 117.9, 117.7, 110.6, 105.3, 105.0, 66.1, 62.9, 59.7, 55.8, 54.2, 46.5, 40.6, 35.1, 34.3, 33.3, 29.9, 28.9, 26.1, 25.9, 25.8, 18.9 ppm. Mass spectrum, m/z [543.2] (M+H)+.

EXAMPLE 14

N-{1-[6-(3,4-Difluoro-phenoxy)-4-methanesulfonyl-hexahydro-pyrrolo[3,2-b]pyrrole-1-carbonyl]-2-methoxy-propyl}-2-methylamino-propionamide $^1$H NMR (CDCl$_3$, 300 MHz): δ7.82 (d, J=7.8 Hz, 1H), 7.18-7.05 (m, 2H), 6.99-6.95 (m, 1H), 5.52 (br s, 2H), 4.89-4.84 (m, 2H), 4.60 (d, J=4.8 Hz, 1H), 4.35 (app t, J=4.5 Hz, 1H), 4.02 (app t, J=9.5 Hz, 1H), 3.75 (app d, J=13.8 Hz, 1H), 3.69-3.57 (m, 2H), 3.51 (app dd, J=3.0, 13.5 Hz, 1H), 3.36 (s, 3H), 3.23 (app q, J=6.9 Hz, 1H), 2.97 (s, 3H), 2.47 (m, 1H), 2.44 (s, 3H), 2.10-1.98 (m, 1H), 2.05 (s, 3H), 1.33 (d, J=7.2 Hz, 1H), 1.15 (d, J=6.3 Hz, 1H) ppm; $^{13}$C NMR (CDCl$_3$, 75 MHz): δ174.6, 169.7, 152.5, 117.9, 117.7, 110.61, 110.56, 105.3, 105.0, 66.1, 62.7, 59.7, 57.0, 54.7, 54.1, 46.7, 35.3, 34.5, 33.5, 21.4, 19.0, 15.1 ppm. Mass spectrum, m/z [519.2] (M+H)+.

TABLE 1

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 1 | 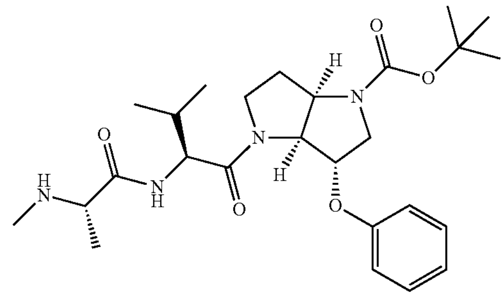 [SMILES: CN[C@@H](C)C(=O)N[C@H](C(=O)N1CC[C@@H]2[C@H]1[C@@H](Oc1ccccc1)CN2C(=O)OC(C)(C)C)C(C)C] | B | A | A | 489.2 (M + H) |

TABLE 1-continued

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 2 | 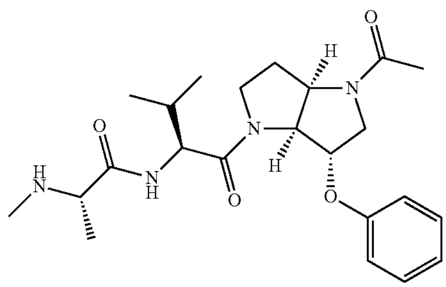 [SMILES: CN[C@@H](C)C(=O)N[C@H](C(=O)N1CC[C@@H]2[C@H]1[C@@H](Oc1ccccc1)CN2C(C)=O)C(C)C] | C | A | A | 431.2 (M + H) |
| 3 | 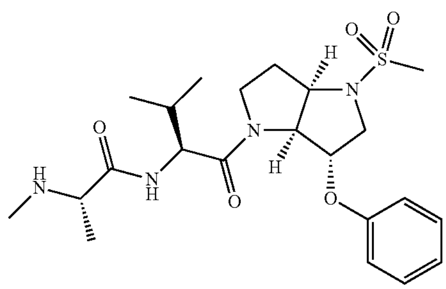 [SMILES: CN[C@@H](C)C(=O)N[C@H](C(=O)N1CC[C@@H]2[C@H]1[C@@H](Oc1ccccc1)CN2S(C)(=O)=O)C(C)C] | A | A | A | 467.2 (M + H) |
| 4 | 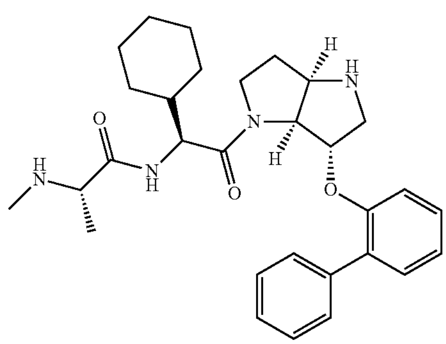 [SMILES: CN[C@@H](C)C(=O)N[C@H](C(=O)N1CC[C@H]2NC[C@H](Oc3ccccc3-c3ccccc3)[C@H]21)C1CCCCC1] | B | A | B | 505.3 (M + H) |
| 5 | 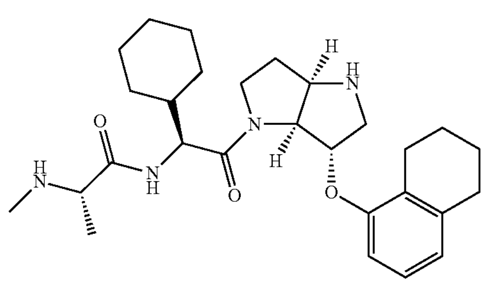 [SMILES: CN[C@@H](C)C(=O)N[C@H](C(=O)N1CC[C@H]2NC[C@H](Oc3cccc4c3CCCC4)[C@H]21)C1CCCCC1] | B | A | B | 483.3 (M + H) |
| 6 | 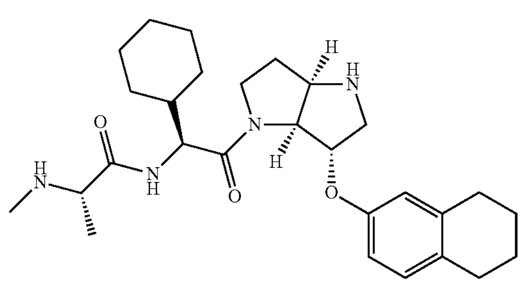 [SMILES: CN[C@@H](C)C(=O)N[C@H](C(=O)N1CC[C@H]2NC[C@H](Oc3ccc4c(c3)CCCC4)[C@H]21)C1CCCCC1] | A | A | A | 483.3 (M + H) |

TABLE 1-continued
| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 7 | 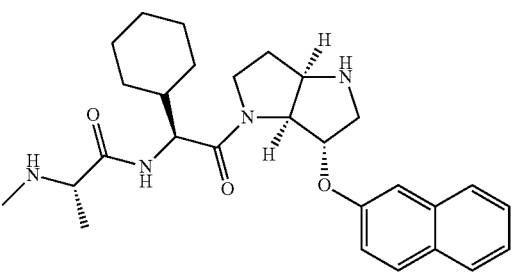 [SMILES: CN[C@@H](C)C(=O)N[C@H](C(=O)N1CC[C@H]2NC[C@H](Oc3ccc4ccccc4c3)[C@H]21)C1CCCCC1] | A | A | A | 479.2 (M + H) |
| 8 | 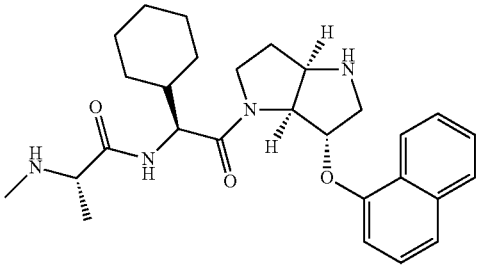 [SMILES: CN[C@@H](C)C(=O)N[C@H](C(=O)N1CC[C@H]2NC[C@H](Oc3cccc4ccccc34)[C@H]21)C1CCCCC1] | A | A | B | 479.2 (M + H) |
| 9 | 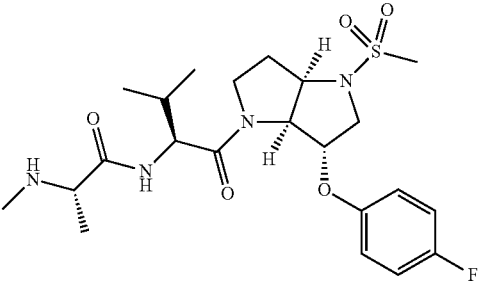 [SMILES: CN[C@@H](C)C(=O)N[C@H](C(=O)N1CC[C@@H]2[C@H]1[C@@H](Oc1ccc(F)cc1)CN2S(C)(=O)=O)C(C)C] | A | A | A | 485.2 (M + H) |
| 10 | 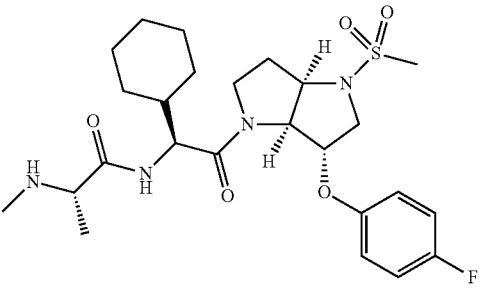 [SMILES: CN[C@@H](C)C(=O)N[C@H](C(=O)N1CC[C@@H]2[C@H]1[C@@H](Oc1ccc(F)cc1)CN2S(C)(=O)=O)C1CCCCC1] | A | A | A | 525.3 (M + H) |
| 11 | 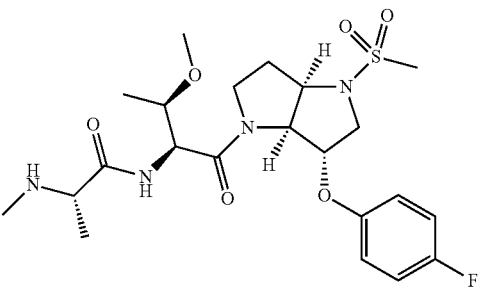 [SMILES: CN[C@@H](C)C(=O)N[C@H](C(=O)N1CC[C@@H]2[C@H]1[C@@H](Oc1ccc(F)cc1)CN2S(C)(=O)=O)[C@@H](C)OC] | A | A | A | 501.2 (M + H) |

TABLE 1-continued

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 12 | 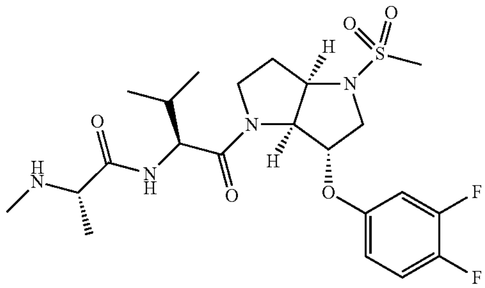 [SMILES: CN[C@@H](C)C(=O)N[C@H](C(=O)N1CC[C@@H]2[C@H]1[C@@H](Oc1ccc(F)c(F)c1)CN2S(C)(=O)=O)C(C)C] | A | A | A | 503.2 (M + H) |
| 13 | 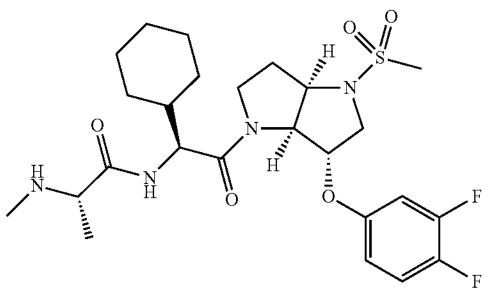 [SMILES: CN[C@@H](C)C(=O)N[C@H](C(=O)N1CC[C@@H]2[C@H]1[C@@H](Oc1ccc(F)c(F)c1)CN2S(C)(=O)=O)C1CCCCC1] | A | A | A | 543.2 (M + H) |
| 14 | 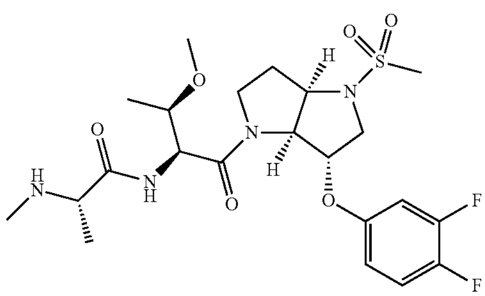 [SMILES: CN[C@@H](C)C(=O)N[C@H](C(=O)N1CC[C@@H]2[C@H]1[C@@H](Oc1ccc(F)c(F)c1)CN2S(C)(=O)=O)[C@@H](C)OC] | A | A | A | 519.2 (M + H) |

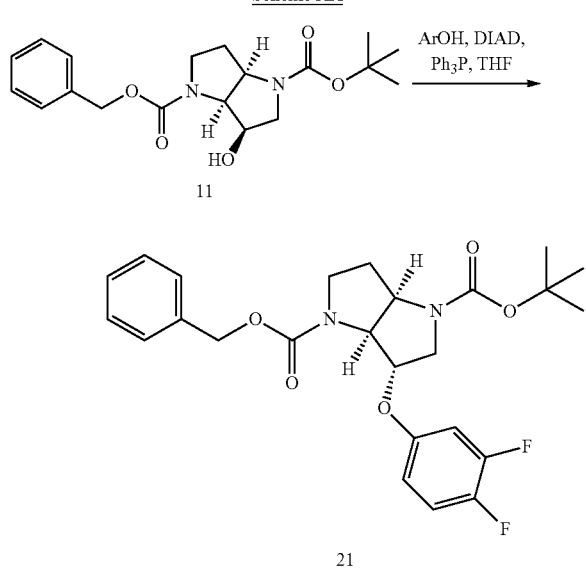

Scheme XX 3-(3,4-Difluoro-phenoxy)-hexahydro-pyrrolo[3,2-b]pyrrole-1,4-dicarboxylic acid 4-benzyl ester 1-tert-butyl ester (21): To a stirred solution of bicyclic alcohol 11 (300 mg, 0.83 mmol) in benzene (5 mL) at ambient temperature was added Ph$_3$P (440 mg, 1.66 mmol) and 3,4-difluorophenol (215 mg, 1.66 mmol). Neat DIAD (350 μL, 1.66 mmol) was added dropwise via syringe over 1 min, which was slightly exothermic and resulted in an increase of the solution temperature to ~40° C. The flask was placed in a preheated 70° C. oil bath and stirred for 1 h. TLC analysis (1:1 hexanes/EtOAc) indicated the complete consumption of starting material and conversion to product which has the same R$_f$ as the phenol and the elimination side product in this TLC system. The reaction was diluted with hexanes and applied directly to a silica column for flash silica gel chromatography (1:1 hexanes/EtOAc). The desired product was only partially purified and 600 mg of yellow oil was obtained that contained a mixture of DIAD, reduced DIAD, and a small amount of the side product derived from elimination of the hydroxyl group in 10. A more sophisticated TLC analysis (4:1 toluene/Et$_2$O, eluted 2×) provided clean separation of these compounds for analysis. However, the crude material was purified by reverse-phase HPLC (2" Dynamax C18, 50-100% ACN/water containing 0.1% HOAc over 25 min; Flow: 40 mL/min). After concentrating the product-containing fractions in vacuo, the residue was dissolved in Et₂O and washed successively with NaHCO₃, water, and brine. The organic extract was dried over anhydrous Na₂SO₄, filtered, and concentrated to afford 260 mg (69%) of 21 as a light yellow-colored oil. $^1$H NMR (300 MHz, CDCl₃), mixture of rotamers: δ 7.36 (m, 5H), 7.16-7.00 (m, 2H), 6.72 (m, 0.7H), 6.50 (m, 0.3H), 5.30-5.13 (m, 2H), 4.90 (m, 0.6H), 4.64 (m, 0.4H), 4.54-4.48 (m, 1H), 4.38-4.30 (m, 1H), 3.98-3.74 (m, 2H), 3.44-3.31 (m, 1H), 3.20 (dt, J=11.3, 6.0 Hz, 1H), 2.40 (m, 0.5H), 2.24 (m, 0.5H), 1.88 (m, 1H), 1.48 (s, 9H) ppm; $^{13}$C NMR (CDCl₃, 75 MHz): δ 155.0, 154.2, 153.4, 152.3, 136.3, 128.9, 128.6, 128.3, 128.0, 117.5, 117.3, 110.8, 105.8, 105.6, 105.3, 80.3, 79.2, 78.8, 67.8, 67.3, 65.7, 65.4, 64.8, 64.4, 61.7, 60.7, 51.8, 51.5, 51.4, 51.0, 45.8, 45.6, 45.2, 45.0, 31.7, 31.5, 31.1, 30.4, 30.1, 28.6, 28.5 ppm. Mass spectrum, m/z [375.2] (M-Boc)+.

Scheme XXI

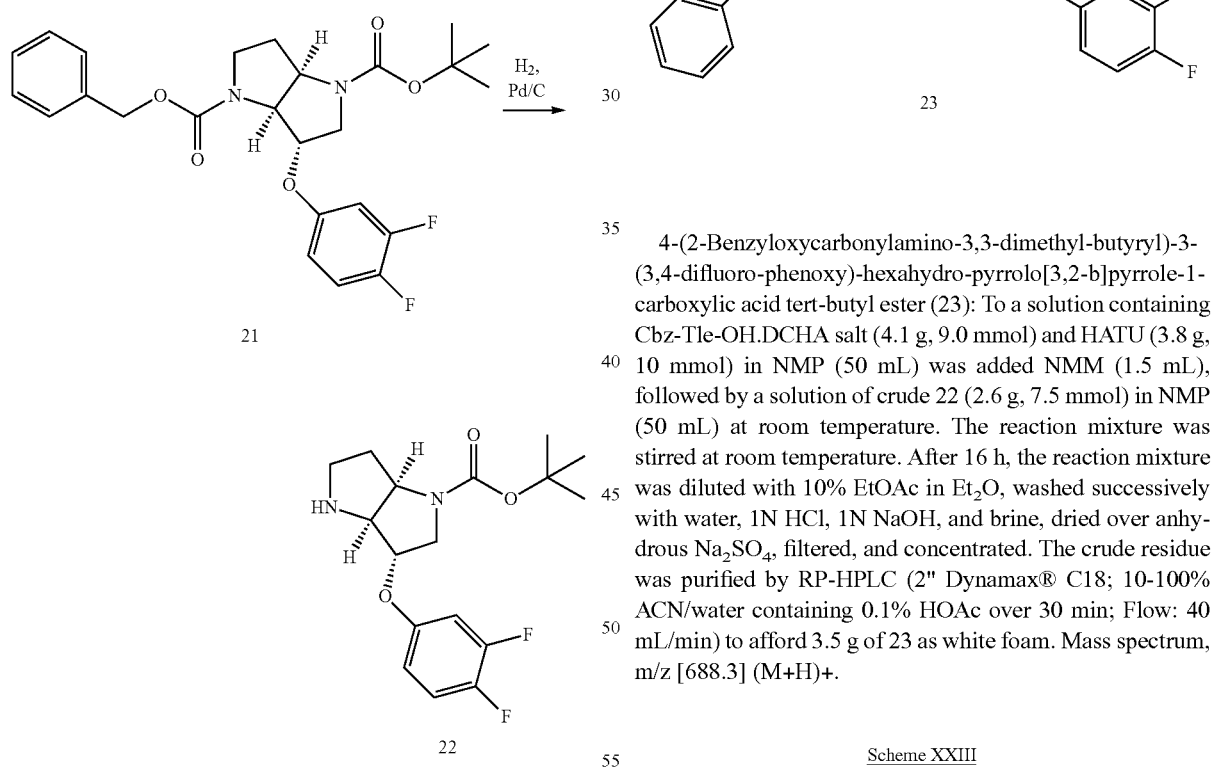

3-(3,4-Difluoro-phenoxy)-hexahydro-pyrrolo[3,2-b]pyrrole-1-carboxylic acid tert-butyl ester (22): A mixture of compound 21 (3.8 g, 8.0 mmol) and 10% Pd-on-carbon (wet, 500 mg) in MeOH/EtOAc (1:1, 100 mL) was pressurized to 50 PSI H₂ and shaken for 3 h using a Parr apparatus. The reaction mixture was filtered through a pad of celite and the solids were washed with EtOAc. The clarified filtrate was concentrated in vacuo to give 22 (2.8 g, 100%). The crude product was used without further purification. Mass spectrum, m/z [341.1] (M+H)+.

Scheme XXII

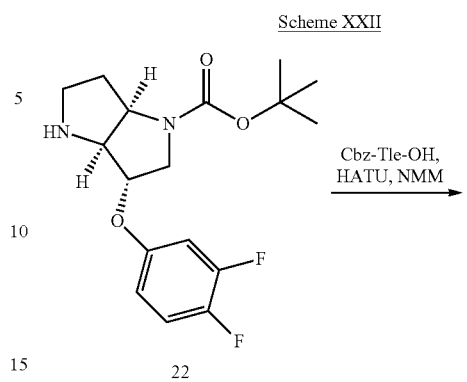

4-(2-Benzyloxycarbonylamino-3,3-dimethyl-butyryl)-3-(3,4-difluoro-phenoxy)-hexahydro-pyrrolo[3,2-b]pyrrole-1-carboxylic acid tert-butyl ester (23): To a solution containing Cbz-Tle-OH.DCHA salt (4.1 g, 9.0 mmol) and HATU (3.8 g, 10 mmol) in NMP (50 mL) was added NMM (1.5 mL), followed by a solution of crude 22 (2.6 g, 7.5 mmol) in NMP (50 mL) at room temperature. The reaction mixture was stirred at room temperature. After 16 h, the reaction mixture was diluted with 10% EtOAc in Et₂O, washed successively with water, 1N HCl, 1N NaOH, and brine, dried over anhydrous Na₂SO₄, filtered, and concentrated. The crude residue was purified by RP-HPLC (2" Dynamax® C18; 10-100% ACN/water containing 0.1% HOAc over 30 min; Flow: 40 mL/min) to afford 3.5 g of 23 as white foam. Mass spectrum, m/z [688.3] (M+H)+.

Scheme XXIII

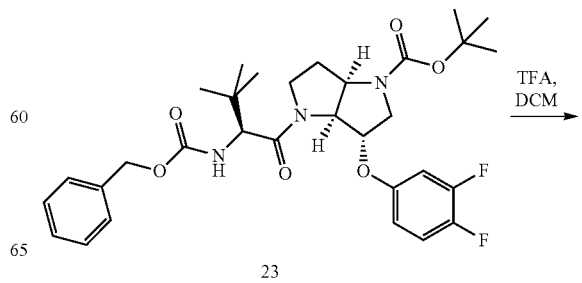

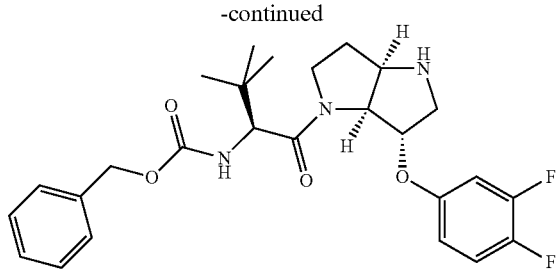

24

{1-[6-(3,4-Difluoro-phenoxy)-hexahydro-pyrrolo[3,2-b] pyrrole-1-carbonyl]-2,2-dimethyl-propyl}-carbamic acid benzyl ester (24): The Boc-containing compound 23 (1.0 g, 1.70 mmol) was dissolved in DCM (4 mL) and cooled to 0° C. before TFA (2 mL) was added and the reaction stirred at 0° C. for 1 h. TLC analysis (10:1 DCM/MeOH) indicated the starting material had all been consumed and the product had formed. The reaction mixture was concentrated at low pressure on the rotary evaporator. The crude residue was dissolved in DCM and washed successively with saturated aqueous NaHCO₃ (3×), and brine. The organic layer was dried over anhydrous Na₂SO₄, filtered, and concentrated to afford 845 mg of 24 as a white foam. Mass spectrum, m/z [488.3] (M+H)+.

Scheme XXIV

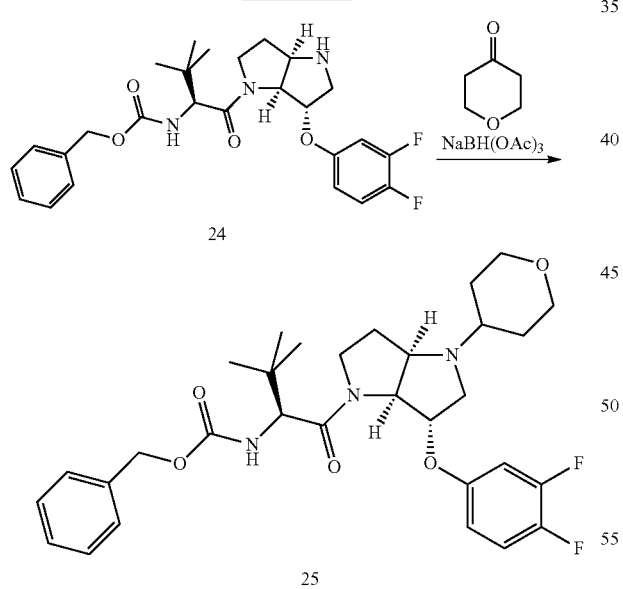

{1-[6-(3,4-Difluoro-phenoxy)-4-(tetrahydro-pyran-4-yl)-hexahydro-pyrrolo[3,2-b]pyrrole-1-carbonyl]-2,2-dimethyl-propyl}-carbamic acid benzyl ester (25): Secondary amine 24 (200 mg, 0.41 mmol) was dissolved in 1,2-dichloroethane (4 mL) at ambient temperature and tetrahydro-4H-pyran-4-one (84 μL, 0.90 mmol), HOAc (50 μL, 0.82 mmol), and sodium triacetoxyborohydride (172 mg, 0.78 mmol) were added. After 12 h, the reaction mixture was diluted with EtOAc, washed successively with saturated aqueous NaHCO₃ (3×), and brine, dried over anhydrous Na₂SO₄, filtered, and concentrated. The crude orange mixture was purified by reverse-phase HPLC (2" Dynamax® C18, 10-100% ACN/water containing 0.1% HOAc over 25 min; Flow: 40 mL/min) to give 100 mg of 24 and 90 mg of 25 as a colorless oil. Mass spectrum, m/z [572.0] (M+H)+.

Scheme XXV

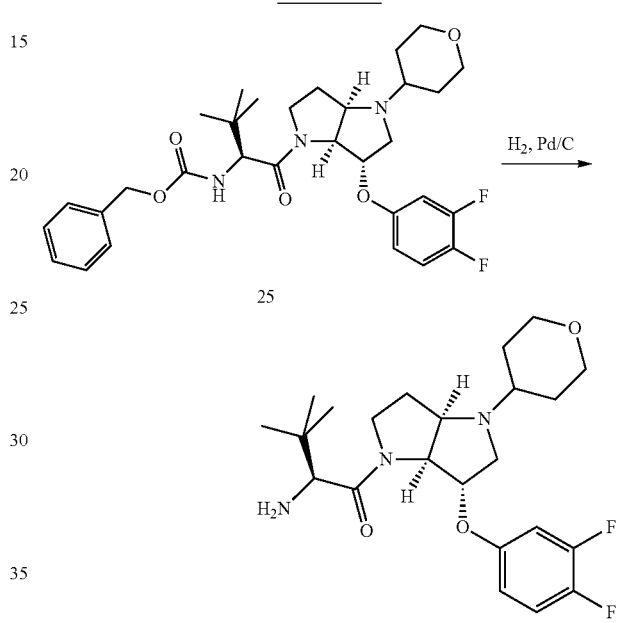

2-Amino-1-[6-(3,4-difluoro-phenoxy)-4-(tetrahydro-pyran-4-yl)-hexahydro-pyrrolo[3,2-b]pyrrol-1-yl]-3,3-dimethyl-butan-1-one (26): A mixture of carbamate 25 (170 mg, 0.30 mmol) and 10% Pd-on-carbon (wet, 100 mg, 0.09 mmol) in MeOH (20 mL) was stirred vigorously under 1 atm H₂ for 2.5 h. The catalyst was removed by filtration with an Acrodisc® 0.45 μm nylon membrane syringe filter and the solvent was removed in vacuo to afford 125 mg (96%) of 26 as an oil which was carried on without further purification. Mass spectrum, m/z [437.9] (M+H)+.

Scheme XXVI

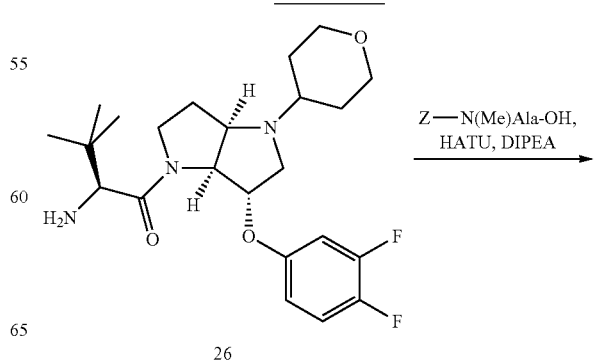

-continued

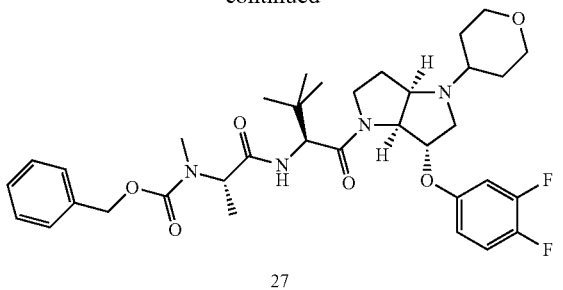

27

(1-{1-[6-(3,4-Difluoro-phenoxy)-4-(tetrahydro-pyran-4-yl)-hexahydro-pyrrolo[3,2-b]pyrrole-1-carbonyl]-2,2-dimethyl-propylcarbamoyl}-ethyl)-methyl-carbamic acid benzyl ester (27): HATU (126 mg, 0.33 mmol) and Cbz-N(Me)Ala-OH (79 mg, 0.33 mmol) were dissolved in NMP (0.5 mL) and DIPEA (70 μL, 0.39 mmol) was added. The reaction mixture was cooled to 0° C. and a solution of 26 (125 mg, 0.30 mmol) in NMP (2 mL) was added. The reaction mixture was warmed to ambient temperature. After 12 h, the reaction mixture was quenched with 1N NaOH (0.5 mL) and diluted with water. The product was extracted with 10:1 Et₂O/EtOAc, and the combined organic extracts were washed successively with water, saturated aqueous NaHCO₃, and brine, dried over anhydrous Na₂SO₄, filtered, and concentrated to afford 160 mg of 27 as a beige-colored foam that was used without further purification. Mass spectrum, m/z [657.2] (M+H)+.

N-{1-[6-(3,4-Difluoro-phenoxy)-4-(tetrahydro-pyran-4-yl)-hexahydro-pyrrolo[3,2-b]pyrrole-1-carbonyl]-2,2-dimethyl-propyl}-2-methylamino-propionamide (28): The Cbz-protected intermediate 27 (160 mg, 0.24 mmol) was stirred vigorously with 10% Pd-on-carbon (wet, 100 mg, 0.09 mmol) in MeOH (20 mL) under 1 atm H₂. After 4 h, the catalyst was removed by filtration with an Acrodisc® 0.45 μm nylon membrane syringe filter and the solvent was removed in vacuo. The crude product was purified by reverse-phase HPLC (2″ Dynamax® C18, 10-55% ACN/water containing 0.1% HOAc over 20 min; Flow: 40 mL/min) to afford 70 mg of 28 (45%, 3 steps) as a flocculent, white solid following lyophilization.

EXAMPLE 15

N-{1-[6-(3,4-Difluoro-phenoxy)-4-(tetrahydro-pyran-4-yl)-hexahydro-pyrrolo[3,2-b]pyrrole-1-carbonyl]-2,2-dimethyl-propyl}-2-methylamino-propionamide (28)

$^1$H NMR (CDCl₃, 300 MHz): δ7.81 (d, J=9.6 Hz, 1H), 7.02 (m, 2H), 6.87 (m, 1H), 6.30 (br d, 1H), 4.67 (br s, 2H), 4.41 (d, J=5.1 Hz, 1H), 3.99 (m, 3H), 3.79 (t, J=4.5 Hz, 1H), 3.57 (app td, J=10.3, 3.6 Hz, 1H), 3.38 (m, 2H), 3.23 (m, 2H), 2.96 (app d, J=11.4 Hz, 1H), 2.79 (m, 1H), 2.41 (s, 3H), 2.04 (s, 3H), 1.91 (m, 2H), 1.71 (m, 2H), 1.59 (m, 2H), 1.32 (d, J=6.6 Hz, Scheme XXVII

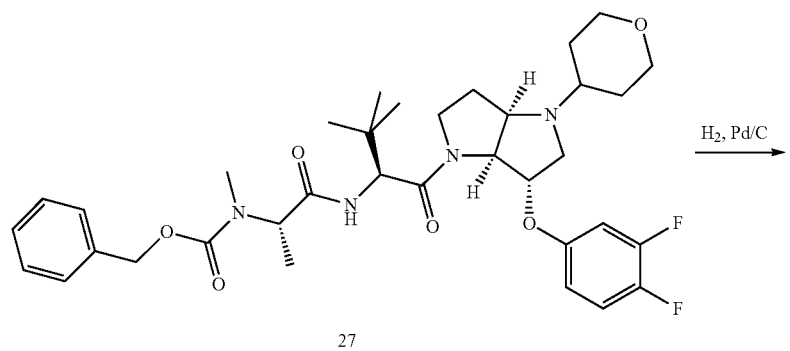

27

H₂, Pd/C

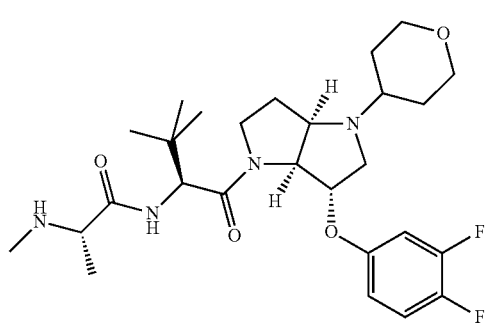 [SMILES: CN[C@@H](C)C(=O)N[C@H](C(=O)N1CC[C@@H]2[C@H]1[C@@H](Oc1ccc(F)c(F)c1)CN2C1CCOCC1)C(C)(C)C]

28

1H), 1.00 (s, 9H) ppm; $^{13}$C NMR (CDCl$_3$, 75 MHz): δ175.8, 174.0, 173.4, 170.7, 170.0, 153.9, 153.8, 152.3, 152.1, 149.0, 148.8, 147.0, 146.8, 143.8, 143.7, 117.4, 117.2, 112.0, 111.1, 111.0, 111.0, 111.0, 106.6, 106.3, 105.7, 105.4, 81.7, 80.1, 67.5, 67.3, 67.1, 67.0, 64.0, 62.2, 59.5, 57.6, 57.4, 57.3, 54.0, 52.6, 47.5, 45.3, 35.8, 34.1, 34.0, 32.7, 31.8, 29.8, 28.4, 26.7, 21.6, 18.9 ppm. Mass spectrum, m/z [523.0] (M+H)+.

EXAMPLE 17

N-{1-[4-Cyclopentyl-6-(3,4-difluoro-phenoxy)-hexahydro-pyrrolo[3,2-b]pyrrole-1-carbonyl]-2,2-dimethyl-propyl}-2-methylamino-propionamide Mass spectrum, m/z [506.9] (M+H)+.

TABLE 2

| Example | Structure | K$_D$ (XIAP BIR3) µM | K$_D$ (c-IAP-1 BIR3) µM | CC$_{50}$ (SK-OV-3) µM | Mass spectrum, m/z |
|---|---|---|---|---|---|
| 15 | [structure] | B | A | A | 522.9 (M + H) |
| 16 | [structure] | A | A | B | 466.8 (M + H) |
| 17 | [structure] | B | A | A | 506.9 (M + H) |

EXAMPLES 16 and 17 were prepared using the chemistries described in Schemes XXIV through XXVII by replacing tetrahydro-pyran-4-one with acetaldehyde and cyclopentanone.

EXAMPLE 16

N-{1-[6-(3,4-Difluoro-phenoxy)-4-ethyl-hexahydro-pyrrolo[3,2-b]pyrrole-1-carbonyl]-2,2-dimethyl-propyl}-2-methylamino-propionamide Mass spectrum, m/z [466.8] (M+H)+.

Scheme XXVIII

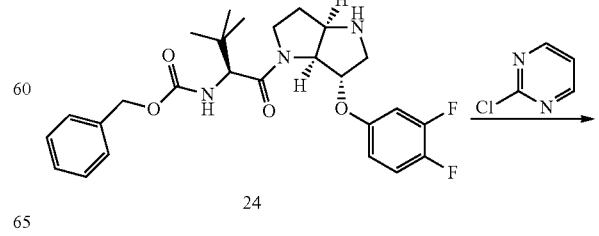

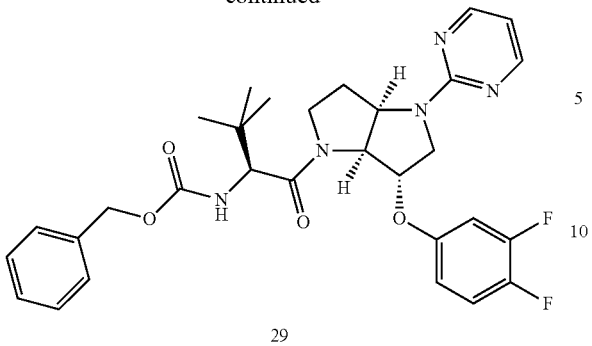

29

{1-[6-(3,4-Difluoro-phenoxy)-4-pyrimidin-2-yl-hexahydro-pyrrolo[3,2-b]pyrrole-1-carbonyl]-2,2-dimethyl-propyl}-carbamic acid benzyl ester (29): Secondary amine 24 (200 mg, 0.41 mmol), DIPEA (110 µL, 0.62 mmol), and 2-chloro-pyrimidine (62 mg, 0.53 mmol) were dissolved in DMF (4 mL) and stirred at 80° C. After 12 h, the reaction mixture was cooled to ambient temperature, diluted with water, and extracted with EtOAc. The combined organic extracts were washed with brine and dried over anhydrous Na$_2$SO$_4$, filtered, and concentrated. The crude product was purified by flash silica gel chromatography (1:1 hexanes/EtOAc) to afford 140 mg (60%) of 29 as a colorless oil. Mass spectrum, m/z [566.0] (M+H)+.

1-one (30): A mixture of carbamate 29 (140 mg, 0.25 mmol) and 10% Pd-on-carbon (wet, 100 mg, 0.09 mmol) in MeOH (20 mL) was stirred vigorously under 1 atm H$_2$. After 3 h, the catalyst was removed by filtration with an Acrodisc® 0.45 µm nylon membrane syringe filter and the solvent was removed in vacuo to afford 106 mg (100%) of 30 as a white solid which was used without further purification. Mass spectrum, m/z [431.8] (M+H)+.

Scheme XXX

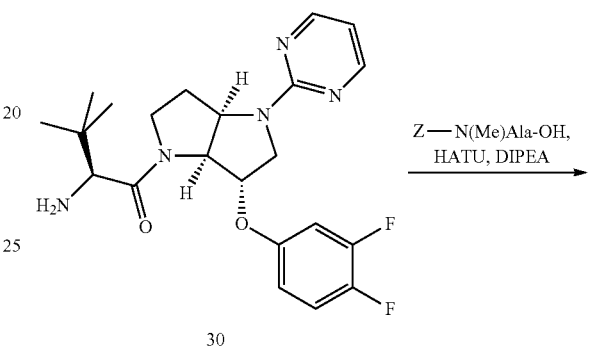

30

Scheme XXIX

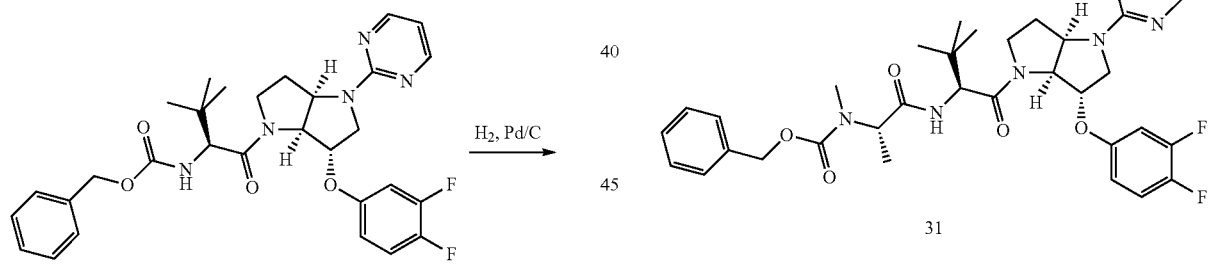

2-Amino-1-[6-(3,4-difluoro-phenoxy)-4-pyrimidin-2-yl-hexahydro-pyrrolo[3,2-b]pyrrol-1-yl]-3,3-dimethyl-butan- (1-{1-[6-(3,4-Difluoro-phenoxy)-4-(tetrahydro-pyran-4-yl)-hexahydro-pyrrolo[3,2-b]pyrrole-1-carbonyl]-2,2-dimethyl-propylcarbamoyl}-ethyl)-methyl-carbamic acid benzyl ester (31): HATU (105 mg, 0.28 mmol) and Cbz-N(Me)Ala-OH (65 mg, 0.28 mmol) were dissolved in NMP (0.5 mL) and DIPEA (65 µL, 0.36 mmol) was added. The reaction mixture was cooled to 0° C. and a solution of 30 (106 mg, 0.25 mmol) in NMP (2 mL) was added. The reaction mixture was warmed to ambient temperature. After 12 h, the reaction mixture was quenched with 1N NaOH (0.5 mL) and diluted with water, extracted with 10:1 Et$_2$O/EtOAc. The combined organic extracts were washed successively with water, saturated aqueous NaHCO₃, and brine, dried over anhydrous Na₂SO₄, filtered, and concentrated to afford 180 mg (100%) of 31 as a beige-colored foam which was used without further purification. Mass spectrum, m/z [651.2] (M+H)+.

Scheme XXXI

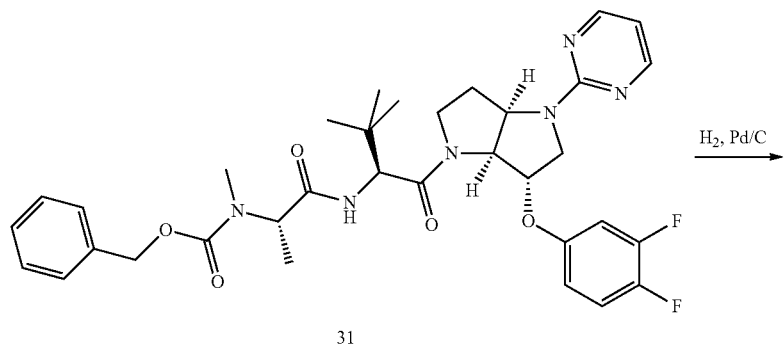

31

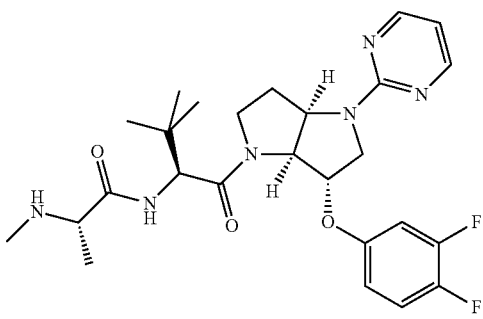

32

N-{1-[6-(3,4-Difluoro-phenoxy)-4-pyrimidin-2-yl-hexahydro-pyrrolo[3,2-b]pyrrole-1-carbonyl]-2,2-dimethyl-propyl}-2-methylamino-propionamide (32): The Cbz-protected intermediate 31 (180 mg, 0.27 mmol) was stirred vigorously with 10% Pd-on-carbon (wet, 100 mg, 0.09 mmol) in MeOH (20 mL) under 1 atm H₂. After 4 h, the catalyst was removed by filtration with an Acrodisc® 0.45 µm nylon membrane syringe filter and the solvent was removed in vacuo. The crude product was purified by reverse-phase HPLC (2" Dynamax® C18, 10-55% ACN/water containing 0.1% HOAc over 20 min; Flow: 40 mL/min) to afford 45 mg of 32 (32%, 3 steps) as a flocculent, white solid following lyophilization.

EXAMPLE 18

N-{1-[6-(3,4-Difluoro-phenoxy)-4-pyrimidin-2-yl-hexahydro-pyrrolo[3,2-b]pyrrole-1-carbonyl]-2,2-dimethyl-propyl}-2-methylamino-propionamide (32)

¹H NMR (CDCl₃, 300 MHz): δ8.35 (d, J=5.1 Hz, 2H), 7.74 (d, J=9.0 Hz, 1H), 7.07 (m, 2H), 6.96 (m, 1H), 6.60 (t, J=4.8 Hz, 1H), 6.00 (br s, 3H), 4.89 (app d, J=3.3 Hz, 1H), 4.81 (m, 1H), 4.73 (d, J=9.3 Hz, 1H), 4.67 (m, 1H), 4.25 (app d, J=12.6 Hz, 1H), 4.03 (app t, J=9.3 Hz, 1H), 3.81 (m, 1H), (app dd, J=3.5, 13.1 Hz, 1H), 3.38 (m, 1H), 2.68 (s, 3H), 2.56 (app dd, J=5.3, 13.4 Hz, 1H), 2.09 (s, 3H), 1.47 (d, J=6.6 Hz, 3H), 1.01 (s, 9H) ppm; ¹³C NMR (CDCl₃, 75 MHz): δ170.5, 170.2, 159.9, 158.0, 153.4, 153.3, 152.3, 152.1, 149.0, 148.9, 147.2, 147.1, 144.1, 117.6, 117.4, 111.0, 110.7, 105.7, 105.5, 66.1, 60.5, 59.0, 58.2, 52.6, 47.5, 36.2, 33.4, 30.6, 26.6, 17.0 ppm. Mass spectrum, m/z [517.0] (M+H)+.

TABLE 3

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 18 | 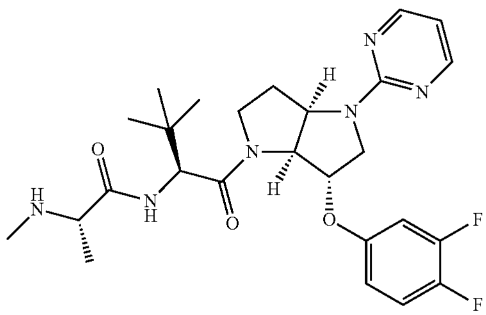 [SMILES: CN[C@@H](C)C(=O)N[C@H](C(=O)N1CC[C@@H]2[C@H]1[C@@H](Oc1ccc(F)c(F)c1)CN2c1ncccn1)C(C)(C)C] | A | A | A | 516.9 (M + H) |

Scheme XXXII

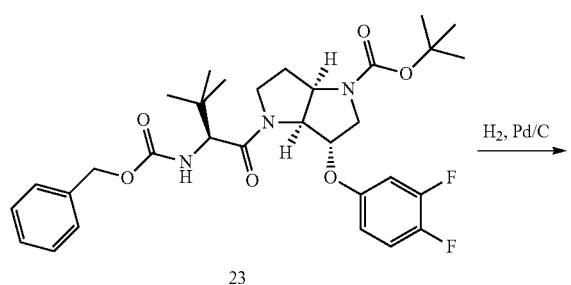

Scheme XXXIII

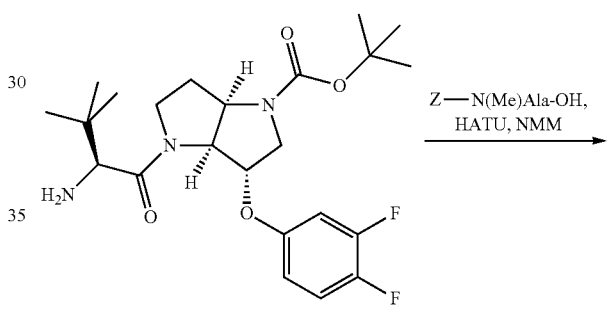

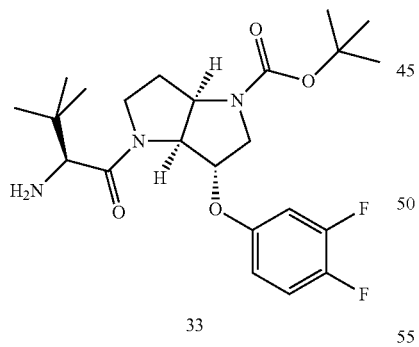

4-(2-Amino-3,3-dimethyl-butyryl)-3-(3,4-difluoro-phenoxy)-hexahydro-pyrrolo[3,2-b]pyrrole-1-carboxylic acid tert-butyl ester (33): A mixture of compound 23 (2.4 g, 4.1 mmol) and 10% Pd-on-carbon (wet, 500 mg) in MeOH/EtOAc (1:1, 100 mL) was pressurized to 50 PSI $H_2$ and shaken for 3 h using a Parr apparatus. The reaction mixture was filtered through a pad of celite and the solids were washed with EtOAc. The clarified filtrate was concentrated in vacuo to give 33 as a white solid (1.84 g, 100%). The crude product was used without further purification. Mass spectrum, m/z [454.2] (M+H)+.

4-{2-[2-(Benzyloxycarbonyl-methyl-amino)-propionylamino]-3,3-dimethyl-butyryl}-3-(3,4-difluoro-phenoxy)-hexahydro-pyrrolo[3,2-b]pyrrole-1-carboxylic acid tert-butyl ester (34): To a solution Cbz-N(Me)-Ala-OH (1.2 g, 4.8 mmol) and HATU (2.0 g, 5.3 mmol) in NMP (30 mL) was added NMM (0.7 mL) followed by a solution of compound 33 (1.8 g, 4.0 mmol crude) in NMP (30 mL) at ambient temperature. After 16 h, the reaction mixture was diluted with 10% EtOAc in $Et_2O$, washed successively with water, 1N HCl, 1N NaOH, and brine, dried over anhydrous $Na_2SO_4$, filtered, and concentrated. The crude residue was purified by RP-HPLC (2" Dynamax® C18; 10-100% ACN/water containing 0.1% HOAc over 30 min; Flow: 40 mL/min) to afford 2.4 g of compound 34 as white solid. Mass spectrum, m/z [673.0] (M+H)+.

Scheme XXXIV

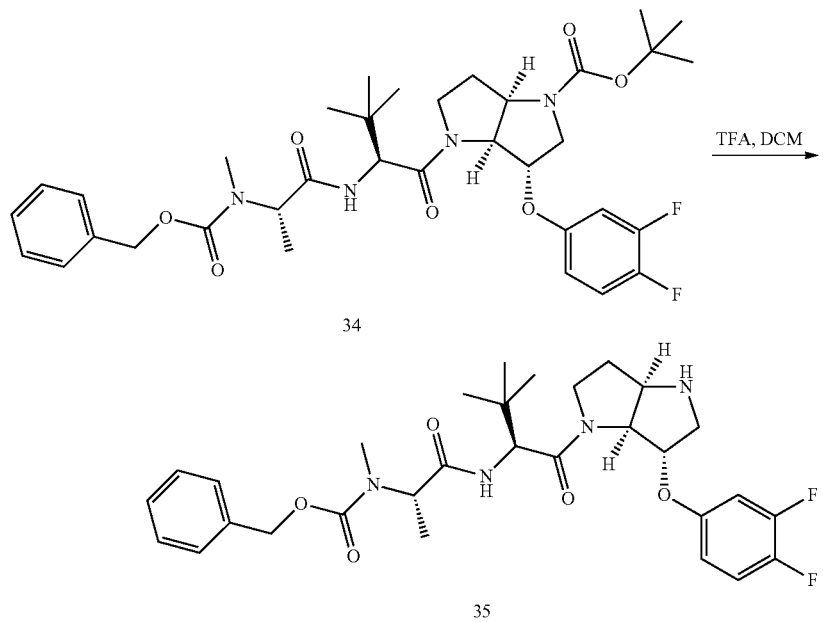

(1-{1-[6-(3,4-Difluoro-phenoxy)-hexahydro-pyrrolo[3,2-b]pyrrole-1-carbonyl]-2,2-dimethyl-propylcarbamoyl}-ethyl)-methyl-carbamic acid benzyl ester (35): The Boc-containing compound 34 (2.0 g, 3.0 mmol) was dissolved in DCM (30 mL) and cooled to 0° C. TFA (10 mL) was added and the reaction mixture was slowly warmed to ambient temperature. After 2 h, the reaction mixture was concentrated in vacuo and the crude residue was dissolved in EtOAc and washed successively with saturated aqueous NaHCO$_3$ and brine. The organic extract was dried over anhydrous Na$_2$SO$_4$, filtered, and concentrated to afford 1.75 g of compound 35 as a white solid. Mass spectrum, m/z [573.1] (M+H)+.

Scheme XXXV

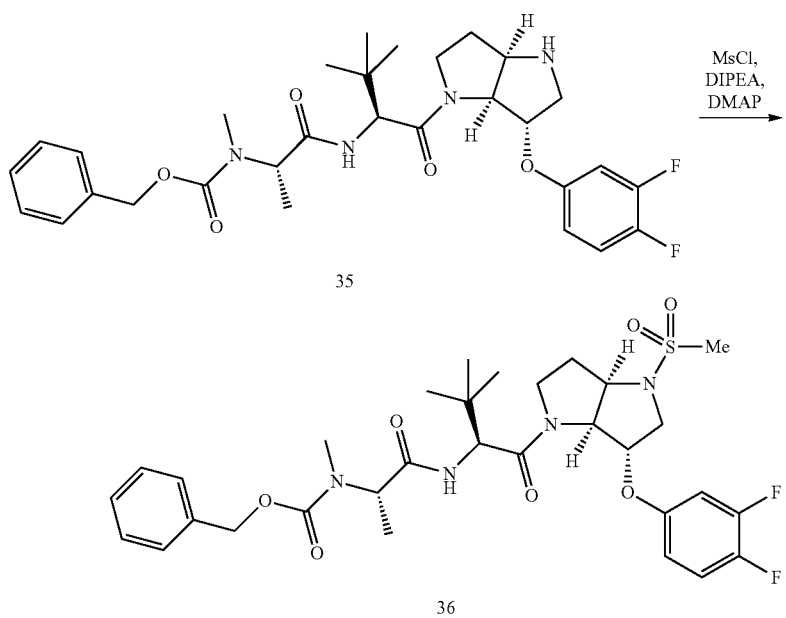

(1-{1-[6-(3,4-Difluoro-phenoxy)-4-methanesulfonyl-hexahydro-pyrrolo[3,2-b]pyrrole-1-carbonyl]-2,2-dimethyl-propylcarbamoyl}-ethyl)-methyl-carbamic acid benzyl ester (36): A solution containing 35 (228 mg, 0.4 mmol), DIPEA (104 mg, 0.8 mmol) and DMAP (cat) in DCM (5 mL) was cooled to 0° C. Methanesulfonyl chloride (55 mg, 0.48 mmol) was added. After 1 h, the reaction mixture was warmed to ambient temperature, diluted with DCM, washed successively with saturated aqueous NaHCO₃, 1N HCl, and brine, dried over anhydrous Na₂SO₄, filtered, and concentrated. The crude product was purified by RP-HPLC (2" Dynamax® C18; 10-100% ACN/water containing 0.1% HOAc over 30 min; Flow: 40 mL/min) to afford compound 36 (190 mg) as a white solid. Mass spectrum, m/z [651.1] (M+H)+.

(dd, J=5.4, 13.2 Hz, 1H), 2.08 (m, 1H), 2.02 (s, 3H), 1.48 (d, J=6.9 Hz, 3H), 1.04 (s, 9H) ppm; ¹³C NMR (CDCl₃, 75 MHz): δ176.3, 171.2, 171.1, 152.7, 152.6, 152.5, 152.5, 152.3, 149.2, 149.0, 147.5, 147.3, 144.3, 144.1, 118.0, 117.8, 110.9, 110.8, 110.7, 105.4, 105.1, 77.7, 66.3, 63.0, 58.7, 58.5, 54.3, 47.3, 35.5, 35.3, 33.5, 32.4, 26.9, 21.8, 17.2 ppm. Mass spectrum, m/z [517.0] (M+H)+.

Scheme XXXVI

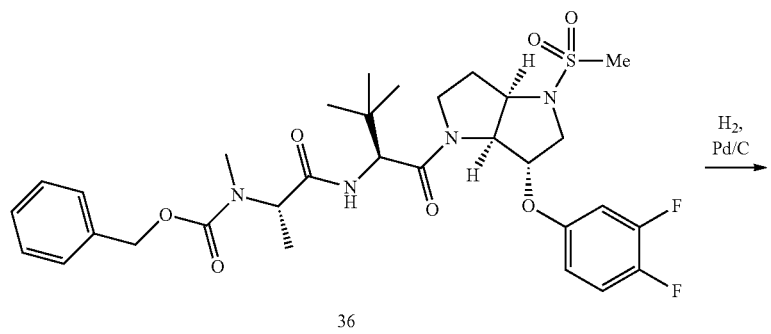

36

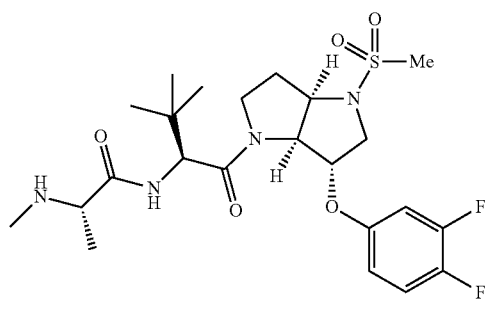

37

N-{1-[6-(3,4-Difluoro-phenoxy)-4-methanesulfonyl-hexahydro-pyrrolo[3,2-b]pyrrole-1-carbonyl]-2,2-dimethyl-propyl}-2-methylamino-propionamide (37): A 500 mL Parr bottle was charged with the sulfonamide 36 (190 mg, 0.29 mmol) and 10% Pd-on-carbon (wet, 50 mg) in MeOH (15 mL). The mixture was pressurized to 50 PSI H₂ then shaken for 3 h. The catalyst was removed by filtration with an Acrodisc® 0.45 μm nylon membrane syringe filter and the solvent was removed in vacuo. The crude product was purified by RP-HPLC (2" Dynamax® C18; 10-100% ACN/water containing 0.1% HOAc over 30 min; Flow: 40 mL/min) to afford 140 mg of compound 37 as a white solid following lyophilization.

EXAMPLE 19

N-{1-[6-(3,4-Difluoro-phenoxy)-4-methanesulfonyl-hexahydro-pyrrolo[3,2-b]pyrrole-1-carbonyl]-2,2-dimethyl-propyl}-2-methylamino-propionamide (37)

¹H NMR (CDCl₃, 300 MHz, δppm): δ8.04 (d, J=8.4 Hz, 1H), 7.71 (br s, 2H), 7.12 (m, 1H), 7.07 (dd, J=9.60, 18.9 Hz, 1H), 6.93 (m, 1H), 4.84 (d, J=1.8 Hz, 1H), 4.59 (d, J=4.20 Hz, 1H), 4.56 (s, 1H), 4.33 (dd, J=4.5, 4.5 Hz, 1H), 4.17 (dd, J=9.0, 9.0 Hz, 1H), 3.81 (dd, J=6.6, 13.5 Hz, 1H), 3.74 (d, J=13.5 Hz, 1H), 3.51 (m, 2H), 2.85 (s, 3H), 2.58 (s, 3H), 2.42

EXAMPLE 20 was prepared using the chemistries described in Schemes XXXV and XXXVI by replacing methanesulfonyl chloride with 2-methyl-propane-1-sulfonyl chloride.

EXAMPLE 20

N-{1-[6-(3,4-Difluoro-phenoxy)-4-(2-methyl-propane-1-sulfonyl)-hexahydro-pyrrolo[3,2-b]pyrrole-1-carbonyl]-2,2-dimethyl-propyl}-2-methylamino-propionamide ¹H NMR (CDCl₃, 300 MHz): δ ppm): δ7.87 (d, J=9.0 Hz, 1H), 7.06-7.20 (2H), 6.96 (m, 1H), 4.87 (d, J=2.7, 1H), 4.59 (s, 1H), 4.57 (d, J=4.8 Hz, 1H), 4.39 (dd, J=4.5, 4.5 Hz, 1H), 4.24 (dd, J=9.3, 9.5 Hz, 1H), 3.76 (d, J=12.9 Hz, 1H), 3.55 (m, 2H), 3.51 (dd, J=2.7, 13.2 Hz, 1H), 3.32 (dd, J=7.5, 14.4 Hz, 1H), 2.95 (d, J=6.6 Hz, 2H), 2.49 (s, 3H), 2.38 (m, 2H), 2.62 (m, 1H), 1.40 (d, J=6.6 Hz, 3H), 1.17 (d, J=6.9 Hz, 3H), 1.16 (d, J=6.9 Hz, 3H), 1.06 (s, 9H) ppm; ¹³C NMR (CDCl₃, 75 MHz, δppm): δ173.8, 171.3, 152.7, 152.7, 152.6, 152.6, 152.5, 152.3, 149.2, 149.1, 147.5, 147.3, 144.3, 144.1, 118.0, 117.8, 110.7, 105.4, 105.1, 77.6, 66.2, 62.7, 59.9, 57.8, 56.0, 54.0, 47.2, 35.5, 34.3, 33.6, 26.9, 24.8, 23.0, 22.9, 18.7 ppm. Mass spectrum, m/z [559.1] (M+H)+.

TABLE 4

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 19 | 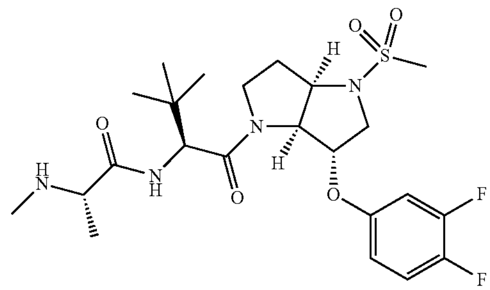 [SMILES: CN[C@@H](C)C(=O)N[C@H](C(=O)N1CC[C@@H]2[C@H]1[C@@H](Oc1ccc(F)c(F)c1)CN2S(C)(=O)=O)C(C)(C)C] | A | A | A | 516.9 (M + H) |
| 20 | 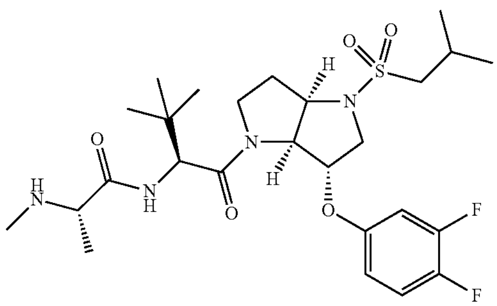 [SMILES: CN[C@@H](C)C(=O)N[C@H](C(=O)N1CC[C@@H]2[C@H]1[C@@H](Oc1ccc(F)c(F)c1)CN2S(=O)(=O)CC(C)C)C(C)(C)C] | A | A | A | 559.1 (M + H) |

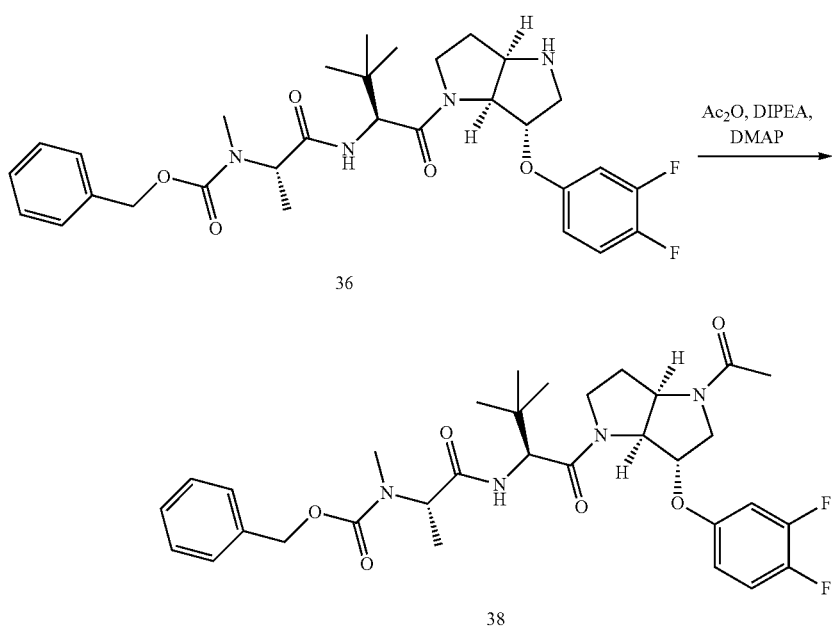

(1-{1-[4-Acetyl-6-(3,4-difluoro-phenoxy)-hexahydro-pyrrolo[3,2-b]pyrrole-1-carbonyl]-2,2-dimethyl-propylcarbamoyl}-ethyl)-methyl-carbamic acid benzyl ester (38): A solution containing 35 (228 mg, 0.4 mmol), DIPEA (104 mg, 0.8 mmol) and DMAP (cat) in DCM (5 mL) was cooled to 0° C., followed by the addition of Ac₂O (50 mg, 0.48 mmol). After 1 h, the reaction mixture was warmed to ambient temperature, diluted with DCM, washed successively with saturated aqueous NaHCO₃, 1N HCl, and brine, dried over anhydrous Na₂SO₄, filtered, and concentrated to afford crude 38 which was used without further purification. Mass spectrum, m/z [615.1] (M+H)+.

Scheme XXXVIII

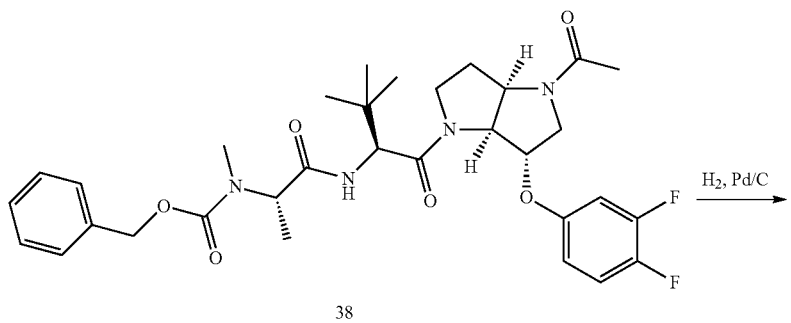

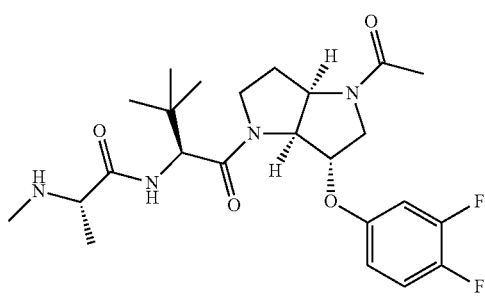

N-{1-[4-Acetyl-6-(3,4-difluoro-phenoxy)-hexahydro-pyrrolo[3,2-b]pyrrole-1-carbonyl]-2,2-dimethyl-propyl}-2-methylamino-propionamide (39): A 500 mL Parr bottle was charged with the crude 38 and 10% Pd-on-carbon (wet, 50 mg) in 1:1 MeOH/EtOAc (20 mL). The mixture was pressurized to 50 PSI H$_2$ then shaken for 3 h. The catalyst was removed by filtration with an Acrodisc® 0.45 µm nylon membrane syringe filter and the solvent was removed in vacuo. The crude product was purified by RP-HPLC (2" Dynamax® C18; 10-100% ACN/water containing 0.1% HOAc over 30 min; Flow: 40 mL/min) to afford 135 mg of 39 as a white solid following lyophilization.

EXAMPLE 21

N-{1-[4-Acetyl-6-(3,4-difluoro-phenoxy)-hexahydro-pyrrolo[3,2-b]pyrrole-1-carbonyl]-2,2-dimethyl-propyl}-2-methylamino-propionamide (39)

$^1$H NMR (CDCl$_3$, 300 MHz), mixture of rotomers: δ8.07 (d, J=8.4 Hz, 1H), 7.78 (br s, 2H), 7.14-7.28 (m, 1H), 7.02-7.14 (m, 1H), 6.90-7.02 (m, 1H), 4.77 (d, J=3.0 Hz, 1H), 4.50-4.72 (2H), 4.10-4.30 (m, 1H), 3.86-4.00 (1H), 3.81 (d, J=12.0 Hz, 1H), 3.54 (dd, J=3.30, 12.0 Hz, 1H), 3.24-3.48 (2H), 2.64 (s, 3H), 2.53 (dd, J=5.4, 13.2 Hz, 1H), 2.21 (m, 1H), 2.15 (s, 3H), 1.55 (d, J=6.9 Hz, 3H), 1.08 (m, 1H), 1.07 (s, 9H) ppm; $^{13}$C NMR (CDCl$_3$, 75 MHz): δ175.8, 170.9, 170.8, 170.6, 170.3, 169.9, 153.4, 153.2, 153.1, 153.0, 152.4, 152.2, 149.1, 148.9, 147.3, 147.1, 144.1, 144.0, 117.8, 117.5, 111.2, 105.7, 105.6, 105.4, 105.3, 66.7, 64.8, 60.6, 60.2, 58.7, 58.6, 58.5, 58.4, 53.5, 51.6, 47.3, 46.9, 35.6, 33.0, 32.3, 32.2, 30.7, 27.0, 23.4, 22.1, 21.7, 17.1 ppm. Mass spectrum, m/z [480.9] (M+H)+.

EXAMPLE 22 was prepared using the chemistries described in Schemes XXXVII and XXXVIII by replacing acetyl chloride with 3-methyl-butyryl chloride.

EXAMPLE 22

N-{1-[6-(3,4-Difluoro-phenoxy)-4-(3-methyl-butyryl)-hexahydro-pyrrolo[3,2-b]pyrrole-1-carbonyl]-2,2-dimethyl-propyl}-2-methylamino-propionamide $^1$H NMR (CDCl$_3$, 300 MHz): δ8.01 (d, J=8.4 Hz, 1H), 6.80-7.20 (m, 4H), 4.64 (m, 1H), 4.56 (m, 1H), 4.49 (d, J=5.4 Hz, 1H), 4.17 (m, 1H), 3.62-3.82 (m, 2H), 3.43 (dd, J=3.0, 12.0 Hz, 1H), 3.24 (m, 1H), 2.54 (s, 3H), 2.58 (s, 3H), 2.43 (dd, J=6.0, 14.4 Hz, 1H), 2.14 (m, 1H), 1.45 (d, J=6.9 Hz, 3H), 1.04 (s, 9H), 0.93 (m, 6H) ppm; $^{13}$C NMR (CDCl$_3$, 75 MHz): δ175.9, 172.4, 172.0, 171.6, 171.4, 170.9, 170.8, 153.3, 153.2, 153.1, 153.0, 152.3, 152.1, 149.1, 148.9, 147.3, 147.1, 144.1, 143.9, 117.7, 117.5, 111.2, 111.1, 105.7, 105.6, 105.4, 105.3, 76.6, 66.5, 64.5, 60.2, 60.0, 58.8, 58.7, 58.4, 52.9, 51.4, 47.3, 47.0, 44.3, 44.0, 43.0, 35.5, 35.5, 33.5, 32.8, 32.7, 30.8, 26.9, 26.3, 26.0, 23.1, 22.8, 22.7, 22.6, 22.4, 21.9, 17.5, 17.4 ppm. Mass spectrum, m/z [522.9] (M+H)+.

TABLE 5

| Example | Structure | $K_D$ (XIAP BIR3) µM | $K_D$ (c-IAP-1 BIR3) µM | $CC_{50}$ (SK-OV-3) µM | Mass spectrum, m/z |
|---|---|---|---|---|---|
| 21 | 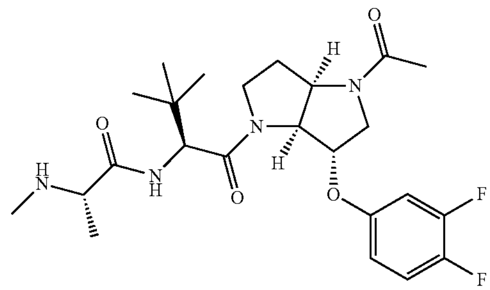 [SMILES: CN[C@@H](C)C(=O)N[C@H](C(=O)N1CC[C@@H]2[C@H]1[C@@H](Oc1ccc(F)c(F)c1)CN2C(C)=O)C(C)(C)C] | B | A | A | 480.9 (M + H) |
| 22 | 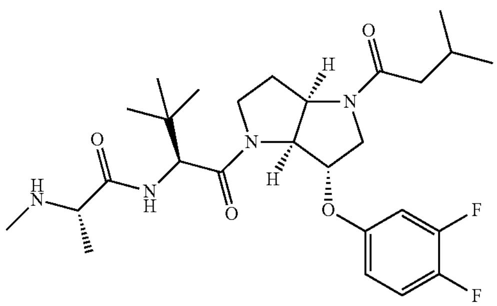 [SMILES: CN[C@@H](C)C(=O)N[C@H](C(=O)N1CC[C@@H]2[C@H]1[C@@H](Oc1ccc(F)c(F)c1)CN2C(=O)CC(C)C)C(C)(C)C] | A | A | A | 522.9 (M + H) |

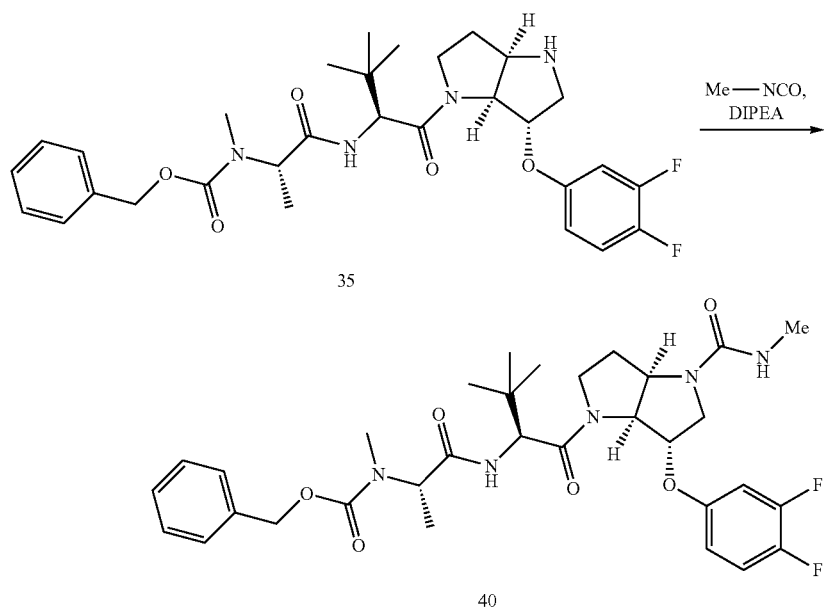

Scheme XXXIX

35

40

(1-{1-[6-(3,4-Difluoro-phenoxy)-4-methylcarbamoyl-hexahydro-pyrrolo[3,2-b]pyrrole-1-carbonyl]-2,2-dimethyl-propylcarbamoyl}-ethyl)-methyl-carbamic acid benzyl ester (40): A solution containing 35 (228 mg, 0.4 mmol), DIPEA (104 mg, 0.8 mmol) in DCM (5 mL) was cooled to 0° C. Methyl isocyanate (35 mg, 0.6 mmol) was added. After 3 h, the reaction mixture was warmed to ambient temperature, diluted with DCM, washed successively with saturated aqueous NaHCO₃, 1N HCl, and brine, dried over anhydrous Na₂SO₄, filtered, and concentrated to afford the crude 40 (230 mg) which was used without further purification. Mass spectrum, m/z [630.1] (M+H)+.

Scheme XL

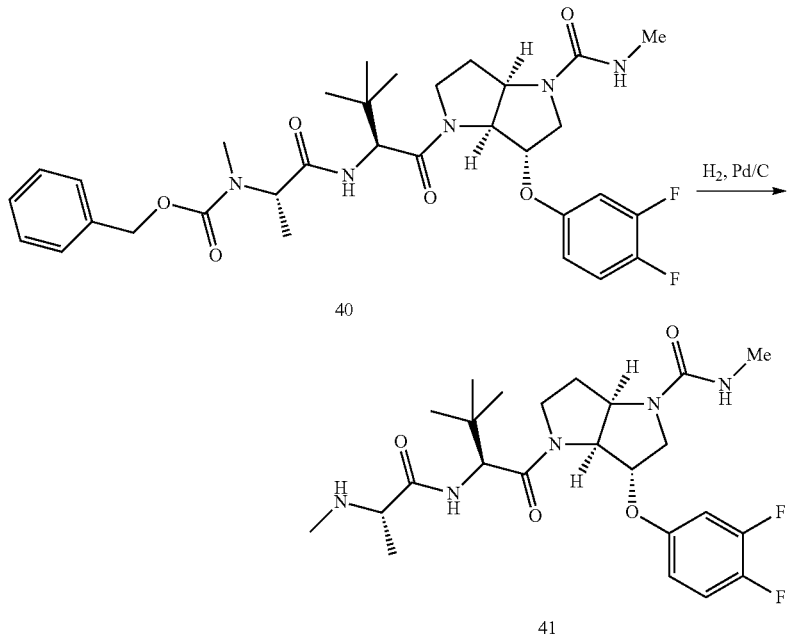

3-(3,4-Difluoro-phenoxy)-4-[3,3-dimethyl-2-(2-methylamino-propionylamino)-butyryl]-hexahydro-pyrrolo[3,2-b]pyrrole-1-carboxylic acid methylamide (41): A 500 mL Parr bottle was charged with the crude 40 and 10% Pd-on-carbon (wet, 50 mg) in 1:1 MeOH/EtOAc (20 mL). The mixture was pressurized to 50 PSI $H_2$, and shaken for 3 h. The catalyst was removed by filtration with an Acrodisc® 0.45 μm nylon membrane syringe filter and the solvent was removed in vacuo. The crude product was purified by RP-HPLC (2" Dynamax® C18; 10-100% ACN/water containing 0.1% HOAc over 30 min; Flow: 40 mL/min) to afford 160 mg of 41 as a white solid following lyophilization.

EXAMPLE 23

3-(3,4-Difluoro-phenoxy)-4-[3,3-dimethyl-2-(2-methylamino-propionylamino)-butyryl]-hexahydro-pyrrolo[3,2-b]pyrrole-1-carboxylic acid methylamide (41)

$^1$H NMR (CDCl$_3$, 300 MHz): δ7.94 (d, J=9.60 Hz, 1H), 7.18 (ddd, J=3.0, 6.3, 12.1 Hz, 1H), 7.08 (dd, J=9.2, 18.5 Hz, 1H), 6.99 (m, 1H), 5.08 (br s, 1H), 4.84 (d, J=3.3 Hz, 1H), 4.45-4.65 (m, 3H), 4.15 (m, 1H), 3.80 (d, J=11.7 Hz, 1H), 3.38 (m, 2H), 2.86 (d, J=4.2 Hz, 3H), 2.48 (s, 3H), 2.42 (m, 1H), 2.00 (m, 1H), 1.41 (d, J=6.6 Hz, 3H), 1.04 (s, 9H) ppm; $^{13}$C NMR (CDCl$_3$, 75 MHz): δ171.5, 170.7, 157.6, 153.3, 153.2, 152.2, 152.1, 149.0, 148.8, 147.1, 147.0, 143.9, 143.8, 117.5, 117.7, 117.3, 111.3, 111.2, 105.4, 105.1, 65.7, 59.7, 47.1, 35.5, 32.7, 31.2, 26.6, 17.5 ppm. Mass spectrum, m/z [495.9] (M+H)+.

EXAMPLES 24 through 29 were prepared using the chemistries described in Schemes XX, XXI, XXII, XXXII, XXXIII, XXXIV, XXXIX and XL by replacing methyl isocyanate with isopropyl isocyanate and dimethylcarbamyl chloride and/or Cbz-Tle-OH with Cbz-Chg-OH and/or 3,4-difluorophenol with 4-fluorophenol.

EXAMPLE 24

3-(3,4-Difluoro-phenoxy)-4-[3,3-dimethyl-2-(2-methylamino-propionylamino)-butyryl]-hexahydro-pyrrolo[3,2-b]pyrrole-1-carboxylic acid isopropylamide $^1$H NMR (CDCl$_3$, 300 MHz): δ8.19 (d, J=8.4 Hz, 1H), 7.96 (br s, 2H), 7.19 (ddd, J=3.0, 6.5, 12.1 Hz, 1H), 7.06 (dd, J=9.0, 18.5 Hz, 1H), 6.99 (m, 1H), 4.80 (d, J=2.1, 1H), 4.62 (d, J=8.4 Hz, 1H), 4.56 (br s, 1H), 4.33 (d, J=7.2, 4.5 Hz, 1H), 4.14 (dd, J=8.7, 9.0 Hz, 1H), 3.98 (m, 2H), 3.79 (d, J=10.2 Hz, 1H), 3.30-3.50 (m, 2H), 2.64 (s, 3H), 2.40 (m, 1H), 2.06 (s, 1H), 2.02 (m, 1H), 1.55 (d, J=6.6 Hz, 3H), 1.20 (d, J=6.6 Hz, 6H), 1.12 (d, J=6.6 Hz, 1H), 1.07 (s, 9H) ppm; $^{13}$C NMR (CDCl$_3$, 75 MHz): δ175.6, 170.8, 170.5, 157.8, 155.8, 153.4, 153.3, 152.3, 152.1, 149.0, 148.8, 147.2, 147.0, 144.0, 143.8, 117.6, 117.4, 111.2, 105.6, 105.4, 65.8, 59.7, 58.7, 58.4, 52.0, 47.2, 42.8, 42.2, 35.5, 32.3, 31.4, 26.9, 23.7, 23.6, 21.8, 17.1 ppm. Mass spectrum, m/z [524.0] (M+H)+.

EXAMPLE 25

3-(3,4-Difluoro-phenoxy)-4-[3,3-dimethyl-2-(2-methylamino-propionylamino)-butyryl]-hexahydro-pyrrolo[3,2-b]pyrrole-1-carboxylic acid dimethylamide $^1$H NMR (CDCl$_3$, 300 MHz): δ8.10 (d, J=8.4 Hz, 1H), 7.32 (br s, 2H), 7.21 (ddd, J=3.0, 6.6, 12.2 Hz, 1H), 7.06 (dd, J=9.3, 18.5 Hz, 1H), 6.99 (m, 1H), 4.87 (m, 1H), 4.84 (s, 1H), 4.62 (d, J=8.7 Hz, 1H), 4.47 (d, J=5.4 Hz, 1H), 4.13 (dd, J=9.0, 9.0 Hz, 1H), 3.91 (dd, J=6.9, 13.8 Hz, 1H), 3.57 (s, 2H), 3.39 (m, 1H), 2.88 (s, 6H), 2.64 (s, 3H), 2.08 (m, 1H), 1.55 (d, J=6.9 Hz, 3H), 1.08 (s, 9H) ppm; $^{13}$C NMR (CDCl$_3$, 75 MHz): δ175.6, 171.0, 162.4, 153.3, 153.3, 153.2, 153.2, 152.3, 152.1, 149.0, 148.8, 147.2, 147.0, 144.0, 143.8, 117.6, 117.4, 111.2, 105.6, 105.4, 77.6, 64.8, 60.8, 58.7, 58.5, 55.2, 47.5, 38.4, 35.6, 32.4, 31.7, 27.0, 21.7, 17.2 ppm. Mass spectrum, m/z [510.0] (M+H)+.

EXAMPLE 26

4-[2-Cyclohexyl-2-(2-methylamino-propionylamino)-acetyl]-3-(4-fluoro-phenoxy)-hexahydropyrrolo[3,2-b]pyrrole-1-carboxylic acid methylamide $^1$H NMR (CDCl$_3$/d$_4$-MeOH, 300 MHz): δ7.11 (m, 2H), 6.91 (m, 2H), 4.82 (app d, J=3.0 Hz, 1H), 4.49 (m, 2H), 4.41 (app d, J=8.1 Hz, 1H), 4.04 (app t, J=9.0 Hz, 1H), 3.76 (m, 2H), 3.48 (br s, 6H, obscured by d$_1$-water), 3.31 (m, 2H), 2.76 (s, 3H), 2.55 (s, 3H), 2.36 (m, 1H), 1.93 (m, 1H), 1.72-1.53 (m, 6H), 1.46 (d, J=6.9 Hz, 1H), 1.28-0.92 (m, 5H) ppm; $^{13}$C NMR (CDCl$_3$/d$_4$-MeOH, 75 MHz): δ170.9, 169.3, 157.4, 152.9, 116.8, 116.7, 116.1, 115.8, 65.8, 59.7, 57.5, 56.6, 51.7, 46.4, 40.0, 31.8, 31.1, 29.6, 28.9, 27.2, 25.9, 25.7, 16.5 ppm. Mass spectrum, m/z [504.3] (M+H)+.

EXAMPLE 27

4-[3,3-Dimethyl-2-(2-methylamino-propionylamino)-butyryl]-3-(4-fluoro-phenoxy)-hexahydropyrrolo[3,2-b]pyrrole-1-carboxylic acid methylamide $^1$H NMR (CDCl$_3$/d$_4$-MeOH, 300 MHz): δ7.10 (m, 2H), 6.90 (m, 2H), 4.76 (app d, J=3.6 Hz, 1H), 4.50 (m, 3H), 4.00 (app t, J=9.2 Hz, 1H), 3.88 (app q, J=6.9 Hz, 1H), 3.60 (br m, 8H, obscured by d$_1$-water), 3.30 (m, 2H), 2.74 (s, 3H), 2.55 (s, 3H), 2.34 (m, 1H), 1.94 (m, 1H), 1.46 (d, J=6.9 Hz, 1H), 0.98 (s, 9H) ppm; $^{13}$C NMR (CDCl$_3$/d$_4$-MeOH, 75 MHz): δ174.3, 170.3, 169.0, 168.9, 159.3, 157.4, 156.1, 152.8, 152.8, 119.5, 119.4, 116.7, 116.6, 116.4, 116.1, 115.8, 80.5, 65.9, 61.8, 59.7, 47.1, 35.3, 31.6, 31.1, 27.3, 27.1, 26.6, 26.4, 20.8, 16.3 ppm. Mass spectrum, m/z [478.5] (M+H)+.

EXAMPLE 28

4-[2-Cyclohexyl-2-(2-methylamino-propionylamino)-acetyl]-3-(4-fluoro-phenoxy)-hexahydropyrrolo[3,2-b]pyrrole-1-carboxylic acid isopropylamide $^1$H NMR (CDCl$_3$, 300 MHz): δ7.72 (app d, J=9.0 Hz, 1H), 7.20 (m, 2H), 6.97 (m, 2H), 6.25 (br s, 1H), 4.89 (app d, J=3.6, Hz, 1H), 4.53 (m, 3H), 4.15 (app t, J=9.5 Hz, 1H), 4.02 (m, 2H), 3.75 (app d, J=11.4 Hz, 1H), 3.36 (m, 2H), 3.23 (m, 1H), 2.41 (s, 3H), 2.40 (m, 1H), 2.04 (s, 3H), 1.97 (m, 1H), 1.69 (m, 5H), 1.32 (d, J=6.6 Hz, 1H), 1.28-0.93 (m, 6H), 1.19 (s, 3H), 1.17 (s, 3H), ppm; $^{13}$C NMR (CDCl$_3$, 75 MHz): δ175.3, 174.4, 174.1, 173.8, 171.6, 171.4, 169.2, 159.3, 156.2, 155.7, 153.0, 153.0, 120.1, 120.0, 116.9, 116.8, 116.4, 116.2, 115.9, 81.0, 76.5, 76.0, 67.1, 65.8, 65.5, 65.2, 62.3, 61.9, 60.6, 60.0, 59.8, 59.6, 57.3, 55.7, 51.9, 51.8, 46.6, 46.4, 42.7, 41.0, 40.7, 38.7, 36.8, 36.1, 34.3, 31.2, 30.0, 29.9, 29.7, 29.0, 28.8, 26.1, 25.9, 23.7, 23.6, 21.4, 18.9, 15.0, 10.5 ppm. Mass spectrum, m/z [532.6] (M+H)+.

EXAMPLE 29

4-[3,3-Dimethyl-2-(2-methylamino-propionylamino)-butyryl]-3-(4-fluoro-phenoxy)-hexahydropyrrolo[3,2-b]pyrrole-1-carboxylic acid isopropylamide $^1$H NMR (CDCl$_3$, 300 MHz): δ7.83 (app d, J=9.3 Hz, 1H), 7.70 (app d, J=9.3 Hz, 1H), 7.19 (m, 2H), 6.96 (m, 2H), 4.84 (app dd, J=3.5, 8.0 Hz, 1H), 4.55 (m, 3H), 4.15 (app t, J=9.2 Hz, 1H), 4.01 (m, 2H), 3.74 (app d, J=11.4 Hz, 1H), 3.35 (m, 2H), 3.26 (m, 0.5H), 3.08 (app q, J=6.9 Hz, 1H), 2.96 (br s, 1H), 2.40 (m, 1H), 2.38 (2 s, 3H), 2.03 (s, 0.5H), 1.94 (m, 1H), 1.30 (d, J=6.9 Hz, 1.5H), 1.23 (d, J=6.9 Hz, 1.5H), 1.19 (s, 3H), 1.17 (s, 3H), 1.01 (s, 9H) ppm; $^{13}$C NMR (CDCl$_3$, 75 MHz): δ175.1, 173.6, 171.0, 170.9, 159.3, 159.2, 156.1, 155.6, 153.1, 116.9, 116.8, 116.4, 116.2, 116.1, 115.9, 115.8, 77.1, 65.8, 61.3, 60.2, 59.8, 57.5, 57.1, 51.9, 47.0, 42.7, 42.2, 35.6, 35.5, 35.1, 31.2, 26.7, 26.7, 23.7, 23.6, 19.5, 10.9 ppm. Mass spectrum, m/z [506.5] (M+H)+.

TABLE 6

| Example | Structure | K$_D$ (XIAP BIR3) µM | K$_D$ (c-IAP-1 BIR3) µM | CC$_{50}$ (SK-OV-3) µM | Mass spectrum, m/z |
|---|---|---|---|---|---|
| 23 | 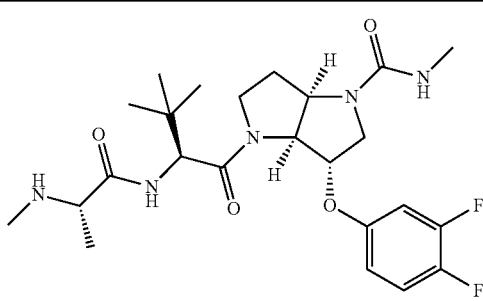 | A | A | A | 494.9 (M + H) |

TABLE 6-continued

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 24 | 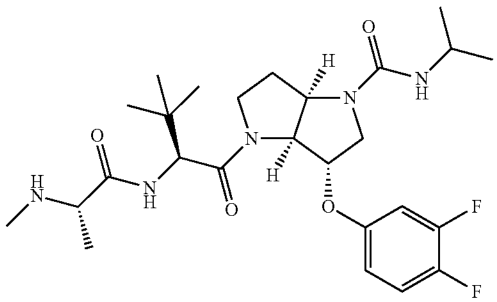 [SMILES: CN[C@@H](C)C(=O)N[C@H](C(=O)N1CC[C@@H]2[C@H]1[C@@H](Oc1ccc(F)c(F)c1)CN2C(=O)NC(C)C)C(C)(C)C] | A | A | A | 523.9 (M + H) |
| 25 | 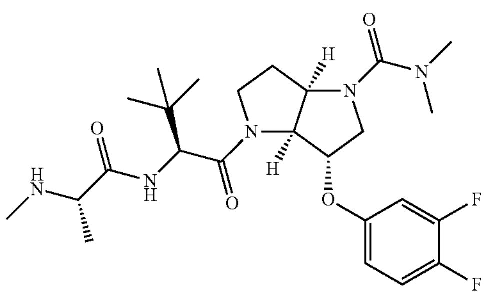 [SMILES: CN[C@@H](C)C(=O)N[C@H](C(=O)N1CC[C@@H]2[C@H]1[C@@H](Oc1ccc(F)c(F)c1)CN2C(=O)N(C)C)C(C)(C)C] | A | A | A | 509.9 (M + H) |
| 26 | 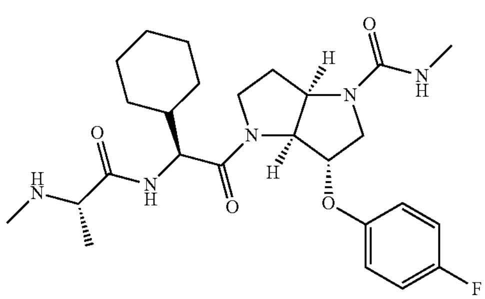 [SMILES: CNC(=O)N1C[C@H](Oc2ccc(F)cc2)[C@@H]2[C@H]1CCN2C(=O)[C@@H](NC(=O)[C@H](C)NC)C1CCCCC1] | A | A | A | 504.3 (M + H) |
| 27 | 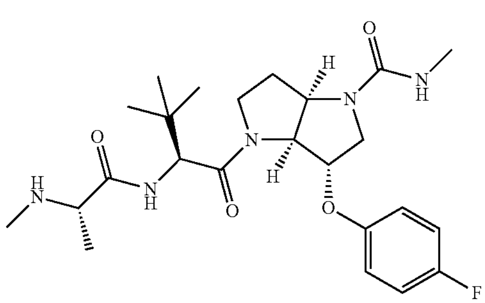 [SMILES: CNC(=O)N1C[C@H](Oc2ccc(F)cc2)[C@@H]2[C@H]1CCN2C(=O)[C@@H](NC(=O)[C@H](C)NC)C(C)(C)C] | A | A | A | 478.5 (M + H) |

TABLE 6-continued

| Example | Structure | $K_D$ (XIAP BIR3) µM | $K_D$ (c-IAP-1 BIR3) µM | $CC_{50}$ (SK-OV-3) µM | Mass spectrum, m/z |
|---|---|---|---|---|---|
| 28 | 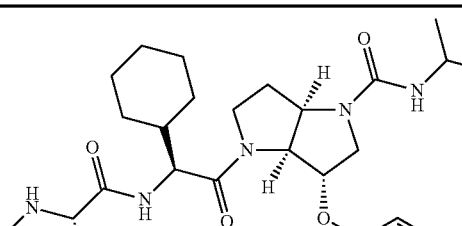 | A | A | A | 532.6 (M + H) |
| 29 | 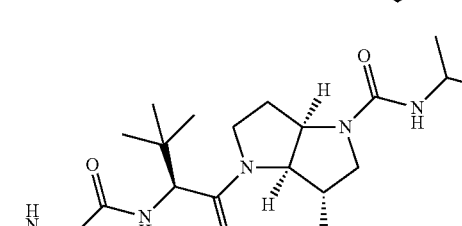 | A | A | A | 506.5 (M + H) |

Scheme XLI

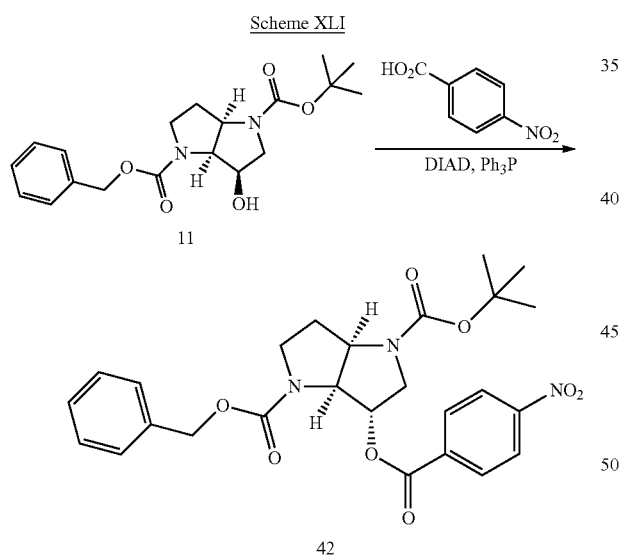

Scheme XLII

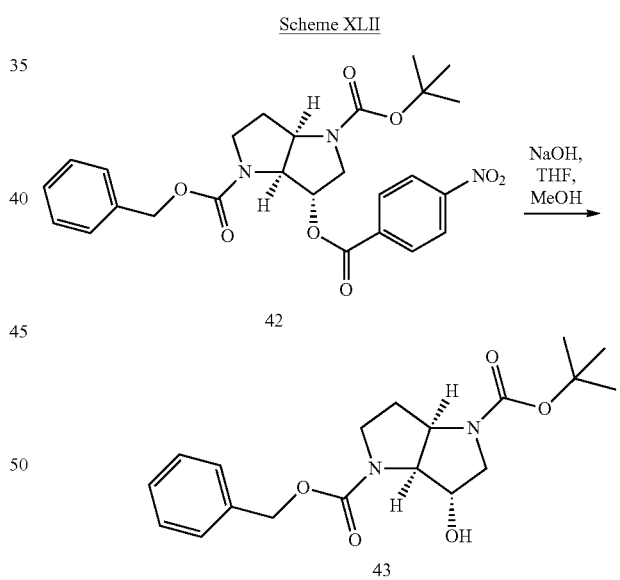

3-(4-Nitro-benzoyloxy)-hexahydro-pyrrolo[3,2-b]pyrrole-1,4-dicarboxylic acid 4-benzyl ester 1-tert-butyl ester (42): To a solution of bicyclic alcohol 11 (4.0 g, 11.0 mmol) in benzene (55 mL) at ambient temperature was added Ph$_3$P (5.8 mg, 22.1 mmol) and p-nitrobenzoic acid (3.7 g, 22.1 mmol). DIAD (4.6 mL, 22.1 mmol) was added dropwise via syringe over 1 h, keeping the temperature below 25° C. After 12 h, the reaction mixture was concentrated in vacuo and the residue was purified by flash silica gel chromatography (3:1 to 1:1 hexanes/EtOAc). The partially-purified product (42) was used without further purification. Mass spectrum, m/z [511.9] (M+H)+.

3-Hydroxy-hexahydro-pyrrolo[3,2-b]pyrrole-1,4-dicarboxylic acid 4-benzyl ester 1-tert-butyl ester (43): The crude ester (42, 11.7 g crude, ~11.0 mmol) was dissolved in 1:1 THF/MeOH (75 mL) and cooled to 0° C. and 1M NaOH (45 mL) was added in one portion. After 45 min, the reaction mixture was quenched with glacial HOAc (10 mL) and concentrated in vacuo. The residue was dissolved in EtOAc and the organic solution was washed successively with aqueous NaHCO$_3$ (5×) and brine, dried over anhydrous Na$_2$SO$_4$, filtered, and concentrated. The crude product was absorbed onto silica gel and purified by flash silica gel chromatography (2:1 to 1:2 hexanes/EtOAc) to provide 43 as a white foam (3.5 g, 88%, 2 steps): $^1$H NMR (300 MHz, CDCl$_3$): δ7.39 (m, 5H), 5.15 (m, 2H), 4.40 (m, 2H), 4.13 (m, 1H), 3.54 (m, 3H), 3.35 (m, 1H), 2.83 (m, 1H), 2.11 (m, 2H), 1.49 (s, 9H) ppm. Mass spectrum, m/z [306.6] (M−t-Bu)+.

Scheme XLIII

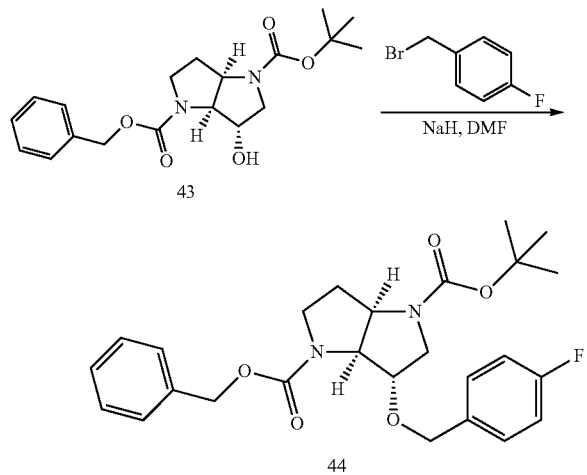

3-(4-Fluoro-benzyloxy)-hexahydro-pyrrolo[3,2-b]pyrrole-1,4-dicarboxylic acid 4-benzyl ester 1-tert-butyl ester (44): Bicyclic alcohol 43 (4.2 g, 11.59 mmol) and 4-fluorobenzyl bromide (2.2 mL, 17.4 mmol) were dissolved in DMF (115 mL) and cooled to 0° C. Sodium hydride (930 mg, 23.2 mmol) was added and, after ~5 min, the ice bath was removed. After 15 min, the reaction mixture was diluted with toluene (250 mL) and saturated aqueous NH$_4$Cl (500 mL) and extracted with 1:1 Et$_2$O/hexanes (600 mL). The organic layer was washed successively with 1N HCl, water, saturated aqueous NaHCO$_3$, water, and brine, dried over anhydrous Na$_2$SO$_4$, filtered, and concentrated. The crude product was purified by flash silica gel chromatography (10:1 to 1:1 hexanes/EtOAc) to afford 5.15 g of 44 as a viscous oil (94%): $^1$H NMR (300 MHz, CDCl$_3$): δ7.36 (m, 6H), 7.07-6.92 (m, 3H), 5.15 (m, 2H), 4.63 (m, 1H), 4.50 (m, 1H), 4.32 (m, 1H), 4.19 (m, 1H), 3.97 (m, 1H), 3.87-3.64 (m, 2H), 3.25-3.08 (m, 2H), 2.35 (m, 0.5H), 2.17 (m, 0.5H), 1.88 (m, 1H), 1.46 (s, 9H) ppm. Mass spectrum, m/z [414.7] (M−t-Bu)+.

Scheme XLIV

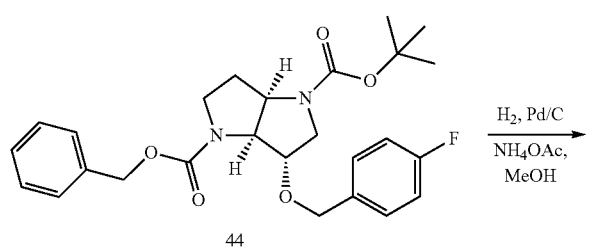

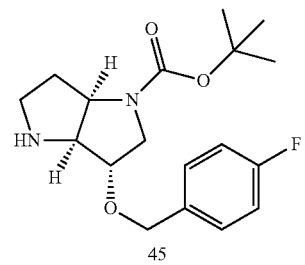

3-(4-Fluoro-benzyloxy)-hexahydro-pyrrolo[3,2-b]pyrrole-1-carboxylic acid tert-butyl ester (45): To a solution of 44 (3.40 g, 7.22 mmol) in MeOH (70 mL) was added NH$_4$OAc (280 mg, 3.61 mmol) and 10% Pd-on-carbon (wet, 770 mg, 0.70 mmol). The reaction flask was evacuated and backfilled with hydrogen (4×) and then maintained under a balloon of hydrogen gas. After 90 min, the catalyst was removed by filtration and the filtrate was concentrated in vacuo. The residue was dissolved in Et$_2$O and washed successively with saturated aqueous NaHCO$_3$, and brine, dried over anhydrous Na$_2$SO$_4$, filtered and concentrated to afford 3.0 g of 45 as a colorless oil which was used in the next step without further purification. Mass spectrum, m/z [336.7] (M+H)+.

Scheme XLV

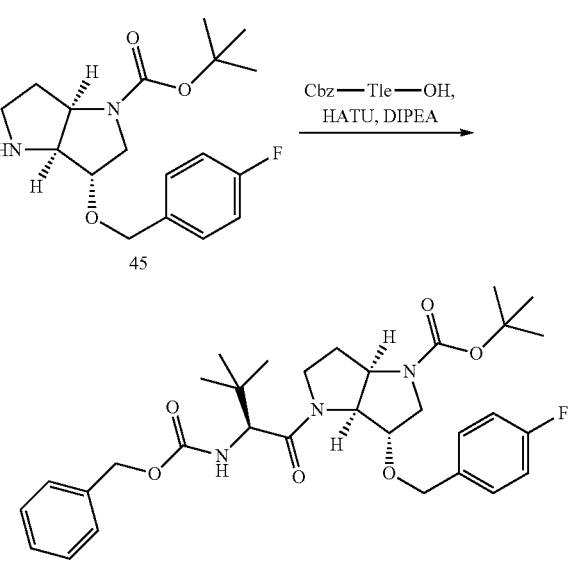

4-(2-Benzyloxycarbonylamino-3,3-dimethyl-butyryl)-3-(4-fluoro-benzyloxy)-hexahydro-pyrrolo[3,2-b]pyrrole-1-carboxylic acid tert-butyl ester (46): A solution of Cbz-Tle-OH dicyclohexylamine salt (3.55 g, 7.94 mmol), HATU (3.03 g, 7.94 mmol), and DIPEA (1.65 mL, 9.38 mmol) in NMP (25 mL) was cooled to 0° C. and bicyclic amine 45 (7.22 mmol)

in NMP (50 mL) was added. The solution was allowed to warm to ambient temperature. After 10 h, the reaction mixture was cooled to 0° C. and 1N NaOH was added (10 mL), and the solution was stirred for 10 min before further diluting with water (200 mL). The aqueous mixture was extracted with 10:1 Et₂O/EtOAc (750 mL) and the combined organic extracts were washed successively with water, 1N HCl, 10% H₃PO₄, water, aqueous NaHCO₃, water, and brine. The organic layer was dried over anhydrous Na₂SO₄, filtered, and concentrated to afford 4.2 g (98%, 2 steps) of 46 as a white foam that was used without further purification. Mass spectrum, m/z [584.1] (M+H)+.

(1:1 hexanes/EtOAc) indicated the reaction was complete. The catalyst was removed by filtration and the solvent was concentrated in vacuo. The residue was dissolved in Et₂O and washed successively with saturated aqueous NaHCO₃ and brine, dried over anhydrous Na₂SO₄, filtered, and concentrated to provide 3.30 g of 47 as colorless oil which was used without further purification. Mass spectrum, m/z [449.9] (M+H)+.

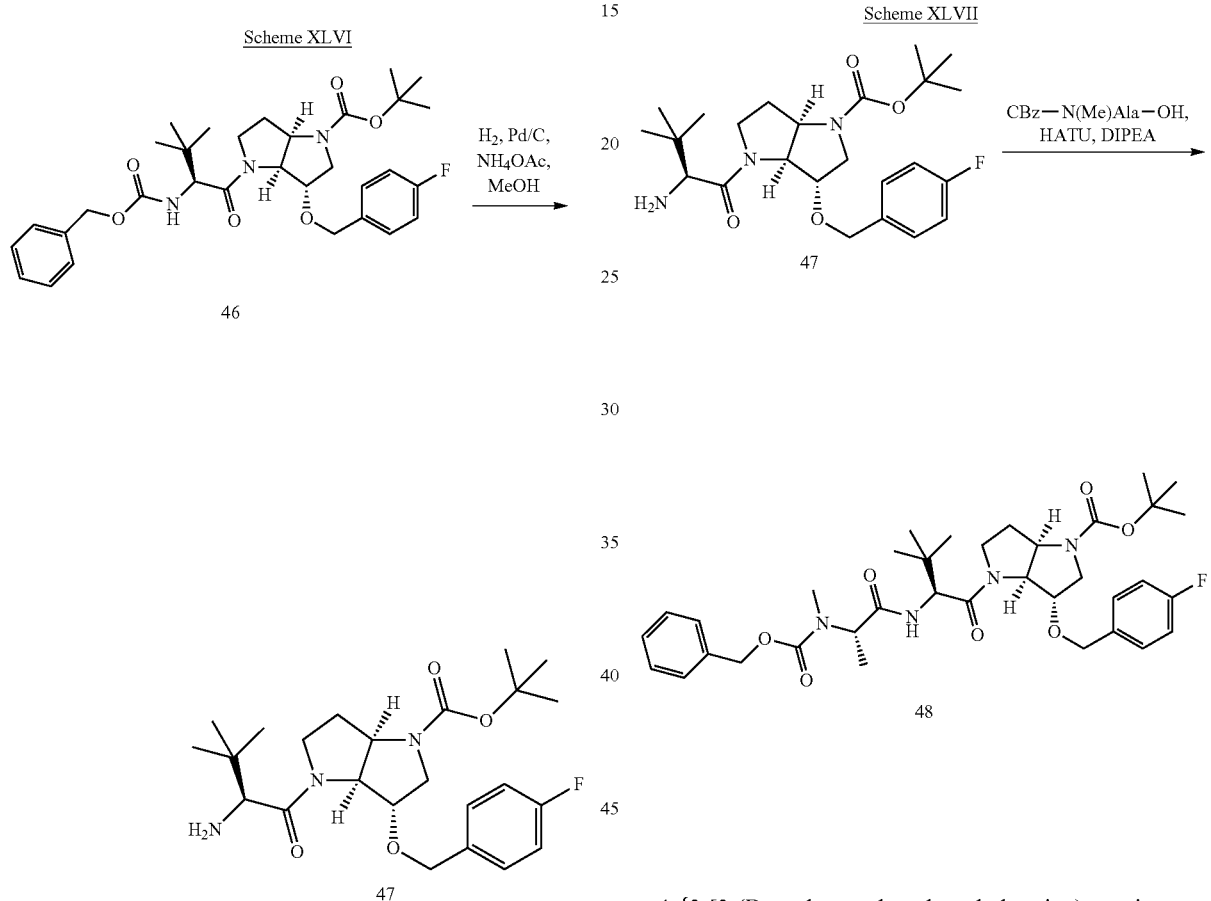

4-(2-Amino-3,3-dimethyl-butyryl)-3-(4-fluoro-benzyloxy)-hexahydro-pyrrolo[3,2-b]pyrrole-1-carboxylic acid tert-butyl ester (47): A solution containing 46 (4.10 g, 7.02 mmol) and NH₄OAc (275 mg, 3.50 mmol) in MeOH (70 mL) was treated with 10% Pd-on-carbon (wet, 745 mg, 0.70 mmol) and the stirred mixture was purged with hydrogen. After 3 h stirring under a balloon of hydrogen, TLC analysis 4-{2-[2-(Benzyloxycarbonyl-methyl-amino)-propionylamino]-3,3-dimethyl-butyryl}-3-(4-fluoro-benzyloxy)-hexahydro-pyrrolo[3,2-b]pyrrole-1-carboxylic acid tert-butyl ester (48): A stirred solution of Cbz-N(Me)Ala-OH (7.85 g, 7.70 mmol), HATU (2.95 g, 7.70 mmol), and DIPEA (1.60 mL, 9.10 mmol) in NMP (20 mL) was cooled to 0° C. and amine 47 (7.02 mmol) in NMP (20 mL) was added. The solution was allowed to warm to ambient temperature. After 13 h, the reaction mixture was cooled to 0° C. and 1N NaOH (10 mL) was added. The reaction mixture was diluted with water and extracted with Et₂O. The combined organic extracts were washed successively with water, 1N HCl, 10% H₃PO₄, water, NaHCO₃, water, and brine. The organic layer was dried over anhydrous Na₂SO₄, filtered, and concentrated to afford 4.5 g (96%, 2 steps) of 48 as a white foam which was used without further purification. Mass spectrum, m/z [691.2] (M+Na)+.

Scheme XLVIII

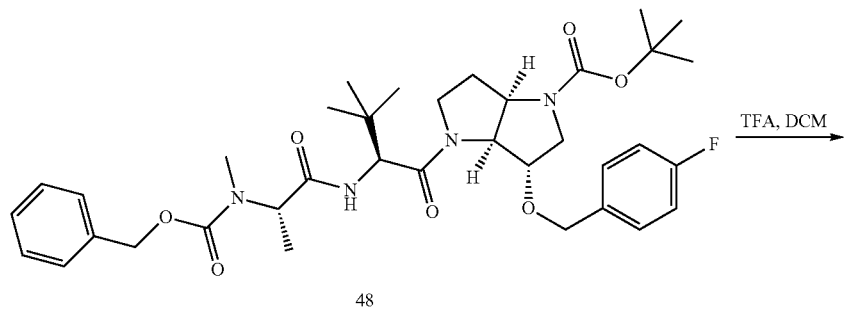

(1-{1-[6-(4-Fluoro-benzyloxy)-hexahydro-pyrrolo[3,2-b]pyrrole-1-carbonyl]-2,2-dimethyl-propylcarbamoyl}-ethyl)-methyl-carbamic acid benzyl ester (49): A solution containing 48 (4.0 g, 5.98 mmol) in DCM (20 mL) was cooled to 0° C. and TFA (10 mL) was added. After 2.5 h, the reaction mixture was concentrated in vacuo and the residue was dissolved in EtOAc. The organic solution was washed successively with aqueous NaHCO$_3$, water, and brine, dried over anhydrous Na$_2$SO$_4$, filtered, and concentrated to afford 3.3 g of 49 as a beige-colored foam which was used directly in the next reaction. Mass spectrum, m/z [569.1] (M+Na)+.

(1-{1-[4-Benzylcarbamoyl-6-(4-fluoro-benzyloxy)-hexahydro-pyrrolo[3,2-b]pyrrole-1-carbonyl]-2,2-dimethyl-propylcarbamoyl}-ethyl)-methyl-carbamic acid benzyl ester (50): Bicyclic amine 49 (300 mg, 0.53 mmol) and TEA (150 µL) were dissolved in DCM (5 mL) at ambient temperature and benzyl isocyanate (135 µL, 1.06 mmol) was added. After 3 h, MeOH (20 mL) and 30% NH$_4$OH (1 mL) were added and the solution was stirred for 15 min before being concentrated in vacuo. The residue was dissolved in EtOAc and washed successively with 1N HCl, water, aqueous NaHCO$_3$, water, and brine. The organic layer was dried over anhydrous

Scheme XLIX

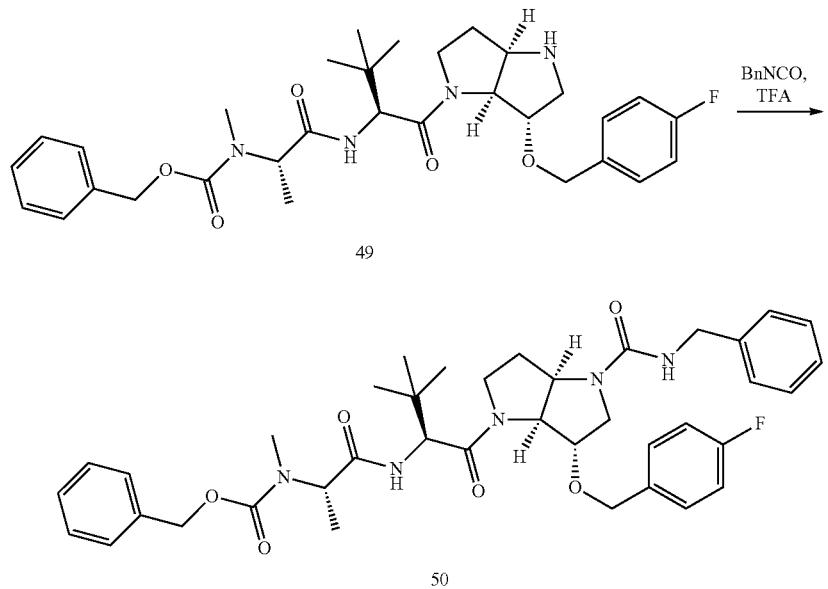

Na₂SO₄, filtered, and concentrated to afford 450 mg of 50 as an amorphous solid which was used without further purification. Mass spectrum, m/z [702.3] (M+Na)+.

Scheme L

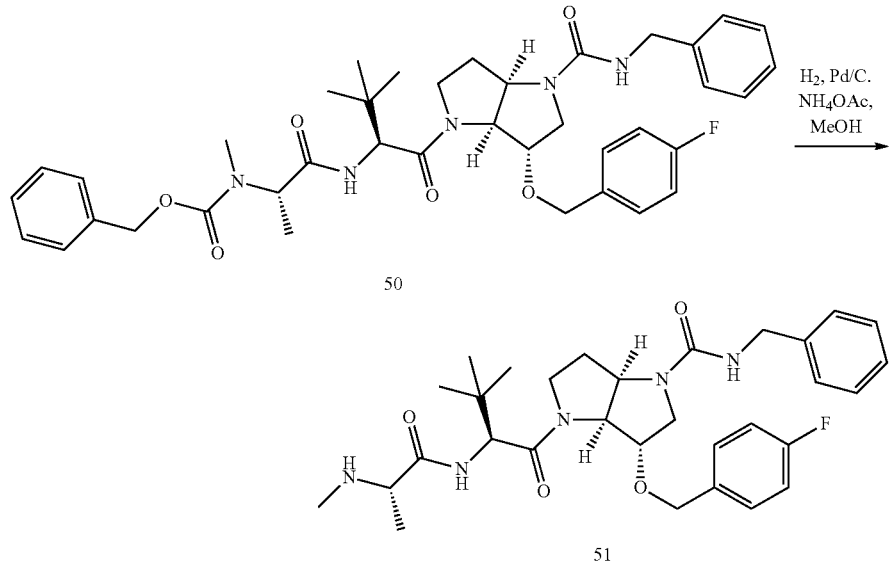

4-[3,3-Dimethyl-2-(2-methylamino-propionylamino)-butyryl]-3-(4-fluoro-benzyloxy)-hexahydro-pyrrolo[3,2-b]pyrrole-1-carboxylic acid benzylamide (51): A solution containing 50 (0.53 mmol) and NH₄OAc (25 mg, 0.27 mmol) in MeOH (10 mL) was treated with 10% Pd-on-carbon (wet, 60 mg, 0.05 mmol) and the stirred mixture was purged with hydrogen. After 1 h stirring under a balloon of hydrogen, TLC analysis (10:1 DCM/MeOH) indicated the reaction was complete. The catalyst was removed by filtration with an Acrodisc® 0.45 μm nylon membrane syringe filter and the solvent was removed in vacuo. The crude product was purified by reverse-phase HPLC (2" Dynamax® C18, 10-60% ACN/water containing 0.1% HOAc over 25 min; Flow: 40 mL/min). Fractions containing pure product were combined, frozen, and lyophilized to provide 251 mg (84%, 2 steps) of 51 as a floculent white powder.

EXAMPLE 30

4-[3,3-Dimethyl-2-(2-methylamino-propionylamino)-butyryl]-3-(4-fluoro-benzyloxy)-hexahydro-pyrrolo[3,2-b]pyrrole-1-carboxylic acid benzylamide (51)

¹H NMR (CDCl₃, 300 MHz): δ7.86 (d, J=9.6 Hz, 1H), 7.31 (m, 7H), 7.00 (t, J=8.7 Hz, 1H), 4.74 (app d, J=11.7 Hz, 1H), 4.59 (m, 5H), 4.43 (m, 2H), 4.13 (m, 2H), 3.66 (d, J=11.1 Hz, 3H), 3.29 (m, 2H), 3.11 (q, J=6.9 Hz, 1H), 2.85 (br s, 2H), 2.40 (s, 3H), 2.39 (m, 1H), 2.01 (m, 1H), 1.32 (d, J=6.9 Hz, 3H), 0.98 (s, 9H) ppm; ¹³C NMR (CDCl₃, 75 MHz): δ174.8, 170.3, 164.1, 160.8, 156.1, 139.3, 133.7, 133.6, 129.8, 129.7, 128.8, 127.9, 127.8, 127.5, 115.4, 115.1, 79.2, 70.5, 65.8, 60.2, 59.7, 56.9, 52.1, 46.8, 44.9, 35.6, 35.0, 31.7, 26.6, 19.4 ppm. Mass spectrum, m/z [568.1] (M+H)+.

EXAMPLES 31 through 45 were prepared using the general chemistries described in Schemes XXIV→XXVII, XXVIII→XXXI, XXXV→XXXVI, XXXVII→XXXVIII, XXXIX→XL, and XLIV→L by replacing 4-fluoro-benzyl bromide with benzyl bromide and/or Boc-Tle-OH with Cbz-Tle-OH, Boc-Chg-OH, or Cbz-Chg-OH and/or Boc-N(Me)Ala-OH with Cbz-N(Me)Ala-OH, Boc-N(Me)Ala(β-F)—OH, or Cbz-N(Me)Ala(β-F)—OH [See: Hoveyda, H. R.; Pinault, J.-F. Org. Lett. 2006, 8, 5849-5852] and/or benzyl isocyanate with methyl isocyanate, isopropyl isocyanate, dimethylcarbamyl chloride, 2-methyl-propane-1-sulfonyl chloride, methanesulfonyl chloride, acetyl chloride, 3-methyl-butyryl chloride, 2-oxo-propionyl chloride, tetrahydro-4H-pyran-4-one, cyclopentanone, and 2-chloropyrimidine.

EXAMPLE 31

(S)—N—((S)-2-((3aR,6S,6aS)-6-(benzyloxy)hexahydropyrrolo[3,2-b]pyrrol-1(2H)-yl)-1-cyclohexyl-2-oxoethyl)-2-(methylamino)propanamide ¹H NMR (d₆-DMSO, 300 MHz): δ8.06 (m, 1H), 7.32 (m, 5H), 4.64 (m, 2H), 4.41 (app t, J=8.0 Hz, 1H), 4.26 (d, J=6.0 Hz, 1H), 3.91 (m, 1H), 3.86 (m, 2H), 3.39 (m, 1H), 3.10 (m, 2H), 2.87 (m, 1H), 2.77 (m, 1H), 2.21 (s, 3H), 1.89 (s, 9H), 1.82 (m, 2H), 1.65 (m, 6H), 1.16-0.90 (m, 4H), 1.12 (d, J=6.9 Hz, 1H) ppm; ¹³C NMR (d₆-DMSO, 75 MHz): δ173.5, 172.2, 169.9, 169.6, 138.7, 128.2, 128.1, 128.0, 127.6, 127.5, 127.3, 86.3, 83.4, 70.5, 70.0, 67.4, 66.7, 62.1, 59.8, 58.7, 54.6, 54.2, 51.7, 51.3, 45.9, 45.0, 40.6, 33.7, 32.4, 30.4, 29.3, 29.1, 28.2, 28.0, 25.8, 25.6, 25.5, 21.3, 18.7 ppm. Mass spectrum, m/z [443.3] (M+H)+.

EXAMPLE 32

3-Benzyloxy-4-[2-cyclohexyl-2-(3-fluoro-2-methylamino-propionylamino)-acetyl]-hexahydro-pyrrolo[3,2-b]pyrrole-1-carboxylic acid tert-butyl ester ¹H NMR (CDCl₃, 300 MHz), mixture of rotamers: δ7.95 (m, 1H), 7.31-7.24 (m, 4H), 4.83-4.53 (m, 4H), 4.57 (m, 1H), 4.15 (m, 1H), 4.02 (m, 1H), 3.87 (d, J=13.2 Hz, 1H), 3.71 (d, J=12.6 Hz, 1H), 3.30 (m, 2H), 3.23-3.17 (m, 3H), 2.49 (s, 3H), 2.41 (m, 1H), 2.38 (m, 1H), 1.79-1.50 (m, 8H), 1.48 (s, 9H), 1.27-0.93 (m, 4H) ppm. Mass spectrum, m/z [561.3] (M+H)+.

EXAMPLE 33

N-[2-(6-Benzyloxy-hexahydro-pyrrolo[3,2-b]pyrrol-1-yl)-1-cyclohexyl-2-oxo-ethyl]-3-fluoro-2-methylamino-propionamide $^1$H NMR (CDCl$_3$, 300 MHz), mixture of rotomers: δ7.93 (d, J=9.3 Hz, 1H), 7.38-7.29 (m, 4H), 4.82-4.58 (m, 4H), 4.50 (t, J=8.1 Hz, 1H), 4.31 (m, 1H), 4.23 (m, 1H), 4.13 (m, 1H), 3.55 (m, 1H), 3.28 (m, 2H), 3.22 (m, 1H), 2.98 (m, 1H), 2.49 (s, 3H), 2.27 (m, 1H), 2.12 (m, 1H), 1.79-1.50 (m, 10H), 1.27-0.95 (m, 4H) ppm. Mass spectrum, m/z [461.2] (M+H)+.

EXAMPLE 34

4-[3,3-Dimethyl-2-(2-methylamino-propionylamino)-butyryl]-3-(4-fluoro-benzyloxy)-hexahydro-pyrrolo[3,2-b]pyrrole-1-carboxylic acid tert-butyl ester $^1$H NMR (CDCl$_3$, 300 MHz): δ7.83 (m, 1H), 7.33 (dd, J=5.7, 8.1 Hz, 1H), 7.00 (t, J=8.6 Hz, 1H), 4.78-4.51 (m, 4H), 4.43 (app t, J=4.7 Hz, 1H), 4.08 (m, 2H), 3.82 (d, J=12.9 Hz, 0.6H), 3.65 (d, J=12.6 Hz, 0.4H), 3.30 (m, 1H), 3.21 (m, 1H), 3.09 (q, J=6.9 Hz, 1H), 2.50 (br s, 0.6H), 2.45 (m, 1H), 2.39 (s, 2.4H), 2.26 (dd, J=5.4, 13.5 Hz, 1H), 1.97 (m, 1H), 1.46 (2 s, 9H), 1.31 (d, J=6.6 Hz, 3H), 0.97 (s, 9H) ppm; $^{13}$C NMR (CDCl$_3$, 75 MHz): δ174.9, 174.5, 170.3, 170.0, 164.1, 160.8, 154.2, 133.9, 133.8, 129.8, 129.7, 115.4, 115.2, 80.3, 80.1, 79.5, 78.7, 70.9, 70.6, 70.5, 67.5, 66.3, 65.1, 60.5, 60.3, 59.9, 57.0, 52.6, 51.8, 46.8, 46.7, 36.1, 35.7, 35.2, 35.1, 32.1, 31.4, 28.6, 28.5, 26.7, 26.6, 19.8, 19.6 ppm. Mass spectrum, m/z [535.0] (M+H)+.

EXAMPLE 35

N-{1-[6-(4-Fluoro-benzyloxy)-hexahydro-pyrrolo[3,2-b]pyrrole-1-carbonyl]-2,2-dimethyl-propyl}-2-methylamino-propionamide ester $^1$H NMR (CDCl$_3$, 300 MHz): δ7.81 (d, J=9.3 Hz, 1H), 7.33 (dd, J=5.6, 8.3 Hz, 1H), 7.00 (t, J=8.7 Hz, 1H), 6.57 (m, 4H), 4.74 (app d, J=11.7 Hz, 1H), 4.61 (d, J=10.2 Hz, 1H), 4.57 (t, J=6.3 Hz, 1H), 4.16 (app t, J=5.7 Hz, 1H), 4.04 (m, 2H), 3.49 (dt, J=7.0, 10.4 Hz, 1H), 3.26 (app q, J=6.9 Hz, 1H), 3.13 (d, J=12.9 Hz, 1H), 2.86 (app dd, J=12.8, 3.8 Hz, 1H), 2.41 (s, 3H), 2.11 (m, 2H), 1.99 (s, 6H), 1.32 (d, J=6.6 Hz, 3H), 0.97 (s, 9H) ppm; $^{13}$C NMR (CDCl$_3$, 75 MHz): δ176.2, 174.0, 170.3, 164.1, 160.8, 133.8, 129.9, 129.8, 129.7, 115.4, 115.2, 82.5, 70.5, 66.5, 60.1, 59.9, 59.6, 57.1, 51.8, 47.5, 36.1, 35.7, 34.2, 32.1, 26.6, 22.0, 18.9 ppm. Mass spectrum, m/z [434.8] (M+H)+.

EXAMPLE 36

4-[3,3-Dimethyl-2-(2-methylamino-propionylamino)-butyryl]-3-(4-fluoro-benzyloxy)-hexahydro-pyrrolo[3,2-b]pyrrole-1-carboxylic acid methylamide $^1$H NMR (CDCl$_3$, 300 MHz): δ7.85 (d, J=9.9 Hz, 1H), 7.31 (app dd, J=5.6, 8.6 Hz, 1H), 6.99 (t, J=8.7 Hz, 1H), 4.72 (d, J=11.7 Hz, 1H), 4.57 (m, 4H), 4.24 (m, 1H), 4.12 (m, 2H), 3.62 (d, J=11.4 Hz, 1H), 3.27 (m, 2H), 3.08 (q, J=6.9 Hz, 1H), 2.80 (d, J=4.8 Hz, 1H), 2.39 (s, 3H), 2.38 (m, 1H), 1.98 (m, 1H), 1.30 (d, J=6.9 Hz, 1H), 0.97 (s, 9H) ppm; $^{13}$C NMR (CDCl$_3$, 75 MHz): δ174.9, 170.4, 164.1, 160.8, 156.9, 133.7, 133.7, 129.8, 129.7, 115.4, 115.2, 79.2, 71.0, 70.5, 65.7, 60.5, 60.3, 59.7, 56.9, 52.1, 46.8, 36.0, 35.6, 35.1, 31.7, 27.5, 26.7, 19.8, 19.5 ppm. Mass spectrum, m/z [492.0] (M+H)+.

EXAMPLE 37

4-[3,3-Dimethyl-2-(2-methylamino-propionylamino)-butyryl]-3-(4-fluoro-benzyloxy)-hexahydro-pyrrolo[3,2-b]pyrrole-1-carboxylic acid isopropylamide $^1$H NMR (CDCl$_3$/d$_4$-MeOH, 300 MHz): δ7.19 (m, 2H), 6.85 (m, 2H), 4.64-4.38 (m, 3H, obscured by d$_1$-H$_2$O), 3.93 (m, 2H), 3.76 (m, 1H), 3.47 (app d, J=11.7 Hz, 1H), 3.39 (app q, J=6.9 Hz, 1H), 3.15 (m, 1H), 3.09 (dd, J=4.2, 11.7 Hz, 1H), 2.32 (s, 3H), 2.18 (dd, J=5.6, 13.4 Hz, 1H), 1.86 (m, 1H), 1.83 (s, 3H), 1.23 (d, J=6.6 Hz, 3H), 0.99 (d, J=6.6 Hz, 6H), 0.83 (s, 9H) ppm; $^{13}$C NMR (CDCl$_3$/d$_4$-MeOH, 75 MHz): δ177.0, 172.0, 169.8, 163.8, 160.6, 155.8, 155.8, 133.3, 133.3, 129.6, 129.5, 115.1, 114.8, 78.7, 70.1, 65.5, 59.1, 58.0, 57.7, 57.6, 51.6, 46.6, 42.3, 42.2, 35.1, 32.5, 31.3, 26.2, 23.0, 22.9, 22.8, 22.2, 17.3 ppm. Mass spectrum, m/z [520.0] (M+H)+.

EXAMPLE 38

N-{1-[6-(4-Fluoro-benzyloxy)-4-(2-methyl-propane-1-sulfonyl)-hexahydro-pyrrolo[3,2-b]pyrrole-1-carbonyl]-2,2-dimethyl-propyl}-2-methylamino-propionamide $^1$H NMR (CDCl$_3$, 300 MHz): δ7.88 (d, J=9.3 Hz, 1H), 7.30 (app dd, J=5.4, 8.7 Hz, 2H), 7.02 (t, J=8.6 Hz, 1H), 4.75 (app d, J=11.4 Hz, 1H), 4.58 (m, 3H), 4.37 (t, J=4.8 Hz, 1H), 4.19 (m, 2H), 3.62 (app d, J=13.2 Hz, 1H), 3.48 (app dt, J=5.7, 11.1 Hz, 1H), 3.35 (app dd, J=3.5, 13.4 Hz, 1H), 3.11 (q, J=6.9 Hz, 1H), 2.80 (d, J=6.9 Hz, 2H), 2.42 (s, 3H), 2.40 (m, 1H), 2.27 (sept, J=6.6 Hz, 1H), 2.08 (m, 2H), 1.33 (d, J=7.2 Hz, 3H), 1.03 (s, 6H), 1.00 (s, 9H) ppm; $^{13}$C NMR (CDCl$_3$, 75 MHz): δ174.8, 170.6, 164.1, 160.8, 133.4, 133.4, 129.5, 129.4, 115.5, 115.2, 82.4, 79.6, 70.6, 66.2, 62.4, 60.5, 60.2, 57.0, 55.6, 54.2, 46.9, 35.5, 35.1, 33.9, 26.6, 24.5, 22.7, 22.6, 19.4 ppm. Mass spectrum, m/z [555.0] (M+H)+.

EXAMPLE 39

N-{1-[6-(4-Fluoro-benzyloxy)-4-(3-methyl-butyryl)-hexahydro-pyrrolo[3,2-b]pyrrole-1-carbonyl]-2,2-dimethyl-propyl}-2-methylamino-propionamide $^1$H NMR (CDCl$_3$, 300 MHz): δ7.86 (app t, J=8.9 Hz, 1H), 7.30 (m, 2H), 7.00 (m, 2H), 4.71 (m, 2H), 4.59 (m, 3H), 4.12 (m, 2H), 3.66 (app d, J=12.0 Hz, 0.5H), 3.34 (dd, J=3.9, 12.0 Hz, 1H), 3.21 (m, 0.5H), 3.08 (m, 1H), 2.43 (app dd, J=5.7, 8.1 Hz, 1H), 2.39 (s, 3H), 2.12 (m, 6H), 1.30 (d, J=6.9 Hz, 3H), 0.99-0.92 (s, 15H) ppm; $^{13}$C NMR (CDCl$_3$, 75 MHz): δ175.1, 174.9, 172.0, 171.5, 170.4, 170.2, 164.1, 160.8, 133.8, 133.7, 129.7, 129.6, 129.6, 129.5, 115.4, 115.4, 115.1, 115.1, 79.4, 78.2, 70.5, 70.3, 66.7, 64.3, 60.3, 59.9, 59.7, 57.0, 56.8, 53.3, 51.0, 46.9, 46.6, 44.2, 43.0, 36.0, 35.6, 35.6, 35.1, 33.7, 31.2, 26.6, 26.0, 25.8, 23.0, 22.8, 22.7, 22.5, 19.5 ppm. Mass spectrum, m/z [519.0] (M+H)+.

EXAMPLE 40

N-{1-[4-Acetyl-6-(4-fluoro-benzyloxy)-hexahydropyrrolo[3,2-b]pyrrole-1-carbonyl]-2,2-dimethylpropyl}-2-methylamino-propionamide $^1$H NMR (CDCl$_3$, 300 MHz): δ7.84 (m, 1H), 7.31 (m, 2H), 7.00 (m, 2H), 5.42 (m, 3H), 4.76 (app d, J=11.7 Hz, 1H), 4.68 (m, 1H), 4.58 (m, 3H), 4.10 (m, 2H), 3.59 (app d, J=12.0 Hz, 3H), 3.37 (app dd, J=4.4, 12.2 Hz, 1H), 3.23 (m, 2H), 2.45 (m, 1H), 2.40 (s, 3H), 2.12 (s, 1H), 2.03 (s, 5H), 1.31 (d, J=6.9 Hz, 3H), 0.97 (s, 9H) ppm; $^{13}$C NMR (CDCl$_3$, 75 MHz): δ178.2, 177.1, 175.5, 174.2, 170.3, 170.2, 169.9, 169.6, 164.1, 160.9, 133.6, 129.9, 129.8, 115.5, 115.2, 79.2, 70.5, 66.8, 65.7, 64.6, 61.8, 60.3, 59.9, 59.6, 57.2, 57.1, 53.9, 51.3, 46.9, 46.6, 35.6, 35.5, 34.4, 34.3, 33.3, 31.1, 26.6, 26.5, 23.2, 22.0, 21.6, 19.0 ppm. Mass spectrum, m/z [477.0] (M+H)+.

EXAMPLE 41

(3S,3aS,6aR)-4-((S)-3,3-dimethyl-2((S)-2-(methylamino) propanamido)butanoyl)-3-(4-fluorobenzyloxy)-N,N-dimethylhexahydropyrrolo[3,2-b]pyrrole-1(2H)-carboxamide $^1$H NMR (CDCl$_3$, 300 MHz): δ7.87 (app d, J=9.0 Hz, 1H), 7.30 (m, 2H), 6.99 (t, J=8.9 Hz, 2H), 5.09 (br s, 2H), 4.85 (app t, J=4.7 Hz, 1H), 4.71 (app d, J=12.3 Hz, 1H), 4.56 (m, 2H), 4.11 (br s, 1H), 4.06 (app t, J=9.2 Hz, 1H), 3.39 (app d, J=1.8 Hz, 1H), 3.32 (m, 3H), 2.81 (s, 6H), 2.44 (s, 3H), 2.03 (s, 3H), 1.99 (m, 2H), 1.36 (d, J=6.6 Hz, 3H), 0.98 (s, 9H) ppm; $^{13}$C NMR (CDCl$_3$, 75 MHz): δ175.5, 173.5, 170.4, 164.1, 162.3, 160.8, 133.9, 133.8, 129.7, 129.6, 129.4, 115.4, 115.1, 79.3, 70.4, 64.9, 60.5, 59.5, 57.4, 55.4, 47.3, 38.3, 36.0, 35.7, 34.0, 32.0, 26.7, 26.6, 21.5, 18.7 ppm. Mass spectrum, m/z [505.9] (M+H)+.

EXAMPLE 42

N-{1-[6-(4-Fluoro-benzyloxy)-4-(2-oxo-propionyl)-hexahydro-pyrrolo[3,2-b]pyrrole-1-carbonyl]-2,2-dimethyl-propyl}-2-methylamino-propionamide $^1$H NMR (CDCl$_3$, 300 MHz): δ7.85 (app d, J=9.3 Hz, 1H), 7.30 (m, 2H), 7.00 (t, J=8.7 Hz, 2H), 4.76-4.53 (m, 5H), 4.13 (m, 2H), 3.81 (app d, J=13.5 Hz, 1H), 3.54 (app dd, J=3.9, 13.2 Hz, 1H), 3.27 (m, 1H), 3.15 (dd, J=6.9, 13.5 Hz, 1H), 2.84 (br s, 2H), 2.44 (s, 3H), 2.41 (s, 3H), 2.29-2.07 (m, 1H), 1.32 (d, J=6.9 Hz, 3H), 0.98 (s, 9H) ppm; $^{13}$C NMR (CDCl$_3$, 75 MHz): δ198.2, 174.6, 170.5, 164.2, 162.5, 160.9, 133.5, 129.9, 129.8, 115.5, 115.5, 115.2, 115.2, 79.7, 70.6, 70.5, 66.6, 63.6, 60.9, 60.1, 57.1, 54.0, 53.0, 52.5, 46.8, 35.6, 35.5, 35.6, 34.9, 34.6, 30.9, 27.6, 27.0, 26.7, 19.3 ppm. Mass spectrum, m/z [505.0] (M+H)+.

EXAMPLE 43

(S)—N—((S)-1-((3aR,6S,6aS)-6-(4-fluorobenzyloxy)-4-(tetrahydro-2H-pyran-4-yl)hexahydropyrrolo[3,2-b]pyrrol-1(2H)-yl)-3,3-dimethyl-1-oxobutan-2-yl)-2-(methylamino)propanamide $^1$H NMR (CDCl$_3$, 300 MHz): δ7.80 (d, J=9.3 Hz, 1H), 7.33 (app dd, J=5.7, 8.1 Hz, 2H), 6.98 (app t, J=8.7 Hz, 2H), 5.90 (br d, 2H), 4.78 (m, 1H), 4.63 (m, 2H), 4.43 (d, J=6.3 Hz, 1H), 3.97 (m, 3H), 3.83 (app t, J=5.1 Hz, 1H), 3.68 (app t, J=5.4 Hz, 1H), 3.48 (m, 1H), 3.35 (m, 2H), 3.25 (m, 1H), 3.15 (m, 1H) 2.65 (m, 2H), 2.40 (s, 3H), 2.02 (s, 3H), 1.92 (m, 1H), 1.82-1.51 (m, 6H), 1.31 (d, J=6.6 Hz, 3H), 0.97 (s, 9H) ppm; $^{13}$C NMR (CDCl$_3$, 75 MHz): δ175.6, 174.0, 169.8, 168.6, 163.9, 160.7, 150.0, 134.4, 129.7, 129.6, 115.3, 115.0, 83.7, 82.1, 70.9, 68.4, 67.6, 67.4, 67.2, 62.2, 59.6, 56.9, 56.8, 54.6, 53.6, 47.2, 35.9, 34.3, 32.9, 32.7, 30.3, 28.5, 26.8, 26.7, 21.7, 19.0 ppm. Mass spectrum, m/z [519.0] (M+H)+.

EXAMPLE 44

(S)—N—((S)-1-((3aR,6S,6aS)-4-cyclopentyl-6-(4-fluorobenzyloxy) hexahydropyrrolo[3,2-b]pyrrol-1 (2H)-yl)-3,3-dimethyl-1-oxobutan-2-yl)-2-(methylamino) propanamide $^1$H NMR (CDCl$_3$, 300 MHz): δ8.73 (m, 3H), 7.86 (d, J=9.3 Hz, 1H), 7.31 (app dd, J=5.6, 8.6 Hz, 2H), 6.97 (app t, J=8.6 Hz, 2H), 4.77 (m, 1H), 4.60 (m, 2H), 4.47 (m, 1H), 3.91 (m, 1H), 3.84 (m, 1H), 3.60 (m, 1H), 3.53 (m, 1H), 3.43 (m, 1H), 3.27 (app dd, J=6.0, 10.8 Hz, 1H), 2.96 (m, 1H), 2.65 (app dd, J=4.7, 11.0 Hz, 1H), 2.43 (s, 3H), 2.12 (m, 1H), 1.99 (s, 6H), 1.87-1.64 (m, 5H), 1.49 (m, 4H), 1.32 (d, J=6.9 Hz, 3H), 0.95 (s, 9H) ppm; $^{13}$C NMR (CDCl$_3$, 75 MHz): δ176.0, 172.8, 169.8, 163.9, 160.7, 134.3, 129.7, 129.6, 115.3, 115.0, 83.9, 82.2, 71.0, 67.6, 66.0, 65.3, 58.9, 57.2, 47.4, 36.1, 35.8, 33.4, 31.7, 29.9, 29.3, 26.7, 26.6, 24.0, 23.5, 21.9, 18.2 ppm. Mass spectrum, m/z [503.0] (M+H)+.

EXAMPLE 45

(S)—N—((S)-1-((3aR,6S,6aS)-6-(4-fluorobenzyloxy)-4-(pyrimidin-2-yl)hexahydropyrrolo[3,2-b]pyrrol-1(2H)-yl)-3,3-dimethyl-1-oxobutan-2-yl)-2-(methylamino)propanamide $^1$H NMR (CDCl$_3$, 300 MHz): δ8.33 (d, J=4.8 Hz, 2H), 7.84 (app d, J=9.3 Hz, 1H), 7.32 (app dd, J=5.6, 8.3 Hz, 2H), 6.98 (app t, J=8.9 Hz, 2H), 6.55 (app t, J=5.0 Hz, 1H), 4.80 (app dd, J=4.8, 9.6 Hz, 1H), 4.76-4.60 (m, 3H), 4.22 (d, J=4.20 Hz, 1H), 4.13-4.08 (m, 3H), 3.44 (dd, J=4.5, 12.9 Hz, 1H), 3.31 (m, 1H), 3.15 (dd, J=7.2, 13.8 Hz, 1H), 2.49 (app dd, J=5.6, 13.4 Hz, 1H), 2.42 (s, 3H), 2.10 (m, 1H), 2.06 (s, 1.5H), 1.32 (app d, J=7.2 Hz, 1H), 0.99 (s, 9H) ppm; $^{13}$C NMR (CDCl$_3$, 75 MHz): δ174.7, 170.4, 164.1, 160.8, 159.9, 157.9, 133.9, 133.9, 129.8, 129.7, 115.4, 115.1, 110.3, 79.1, 70.6, 65.8, 60.3, 60.1, 57.0, 52.9, 47.0, 35.8, 34.9, 31.2, 26.7, 19.4 ppm. Mass spectrum, m/z [513.0] (M+H)+.

TABLE 7

| Example | Structure | K_D (XIAP BIR3) μM | K_D (c-IAP-1 BIR3) μM | CC₅₀ (SK-OV-3) μM | Mass spectrum, m/z |
|---|---|---|---|---|---|
| 30 | 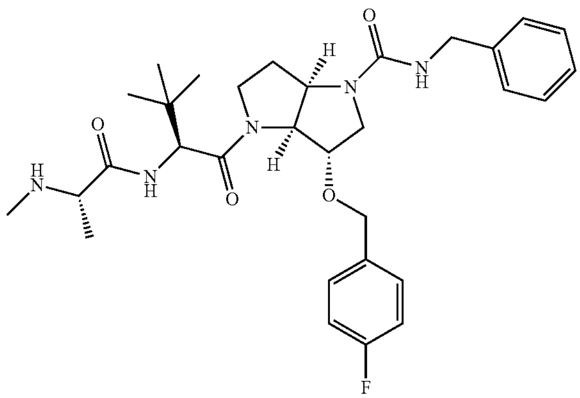 [SMILES: CN[C@@H](C)C(=O)N[C@H](C(=O)N1CC[C@@H]2[C@H]1[C@@H](OCc1ccc(F)cc1)CN2C(=O)NCc1ccccc1)C(C)(C)C] | A | A | A | 568.1 (M + H) |
| 31 | 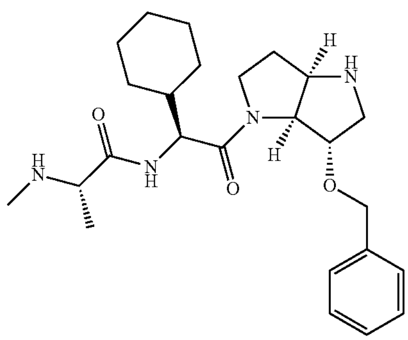 [SMILES: CN[C@@H](C)C(=O)N[C@H](C(=O)N1CC[C@H]2NC[C@H](OCc3ccccc3)[C@H]21)C1CCCCC1] | B | A | B | 443.3 (M + H) |
| 32 | 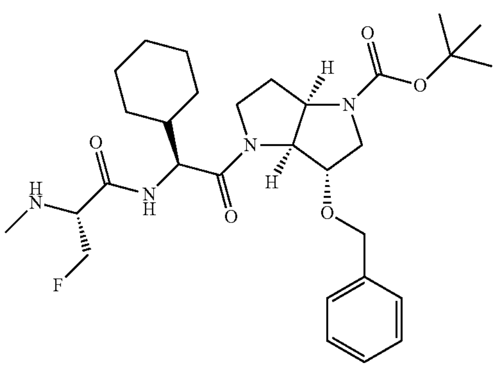 [SMILES: CN[C@@H](CF)C(=O)N[C@H](C(=O)N1CC[C@@H]2[C@H]1[C@@H](OCc1ccccc1)CN2C(=O)OC(C)(C)C)C1CCCCC1] | A | A | B | 561.3 (M + H) |
| 33 | 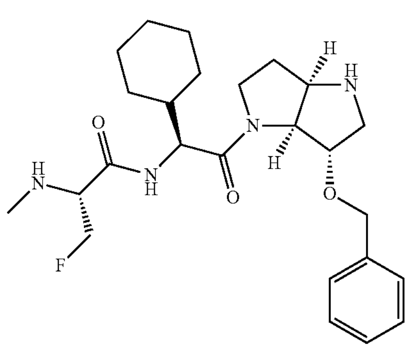 [SMILES: CN[C@@H](CF)C(=O)N[C@H](C(=O)N1CC[C@H]2NC[C@H](OCc3ccccc3)[C@H]21)C1CCCCC1] | B | A | D | 461.2 (M + H) |

TABLE 7-continued

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 34 | 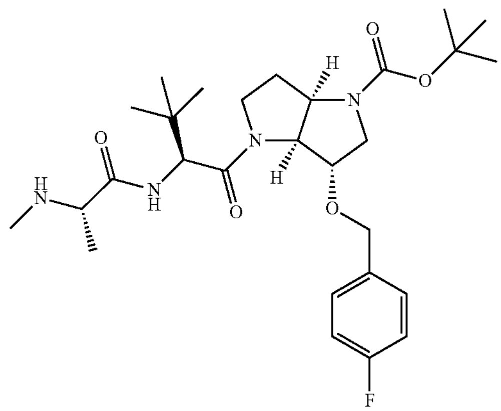 [SMILES: CN[C@@H](C)C(=O)N[C@H](C(=O)N1CC[C@@H]2[C@H]1[C@@H](OCc1ccc(F)cc1)CN2C(=O)OC(C)(C)C)C(C)(C)C] | A | A | A | 535.0 (M + H) |
| 35 | 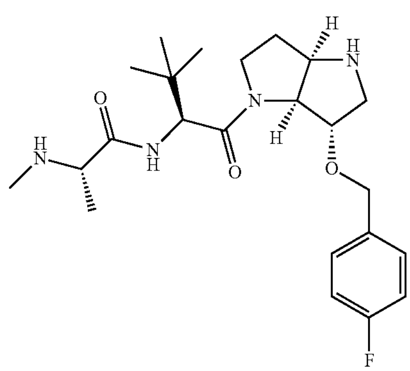 [SMILES: CN[C@@H](C)C(=O)N[C@H](C(=O)N1CC[C@H]2NC[C@H](OCc3ccc(F)cc3)[C@H]21)C(C)(C)C] | B | A | A | 434.8 (M + H) |
| 36 | 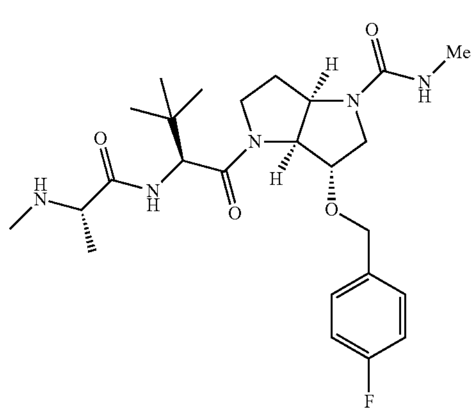 [SMILES: CNC(=O)N1C[C@H](OCc2ccc(F)cc2)[C@@H]2[C@H]1CCN2C(=O)[C@@H](NC(=O)[C@H](C)NC)C(C)(C)C] | B | A | A | 491.9 (M + H) |

TABLE 7-continued

| Example | Structure | $K_D$ (XIAP BIR3) µM | $K_D$ (c-IAP-1 BIR3) µM | $CC_{50}$ (SK-OV-3) µM | Mass spectrum, m/z |
|---|---|---|---|---|---|
| 37 | 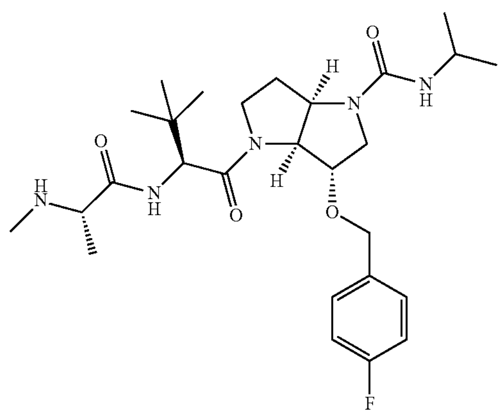 [SMILES: CN[C@@H](C)C(=O)N[C@H](C(=O)N1CC[C@@H]2[C@H]1[C@@H](OCc1ccc(F)cc1)CN2C(=O)NC(C)C)C(C)(C)C] | A | A | A | 520.0 (M + H) |
| 38 | 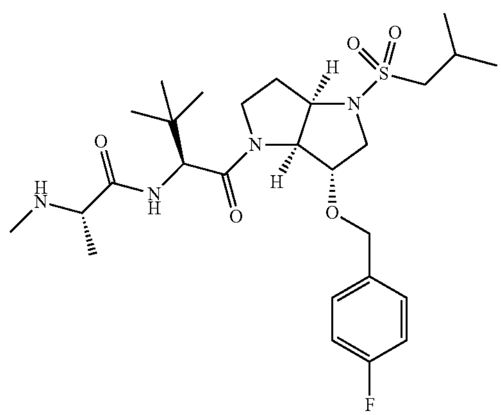 [SMILES: CN[C@@H](C)C(=O)N[C@H](C(=O)N1CC[C@@H]2[C@H]1[C@@H](OCc1ccc(F)cc1)CN2S(=O)(=O)CC(C)C)C(C)(C)C] | A | A | A | 555.0 (M + H) |
| 39 | 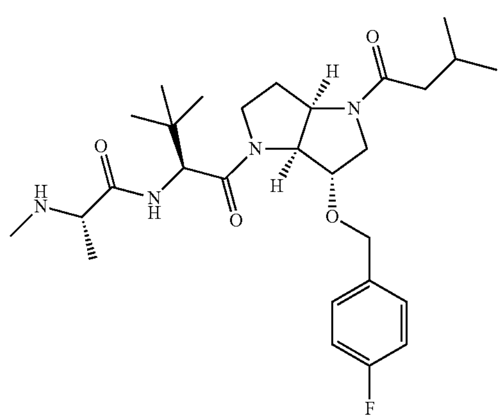 [SMILES: CN[C@@H](C)C(=O)N[C@H](C(=O)N1CC[C@@H]2[C@H]1[C@@H](OCc1ccc(F)cc1)CN2C(=O)CC(C)C)C(C)(C)C] | A | A | A | 519.0 (M + H) |

TABLE 7-continued

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 40 | 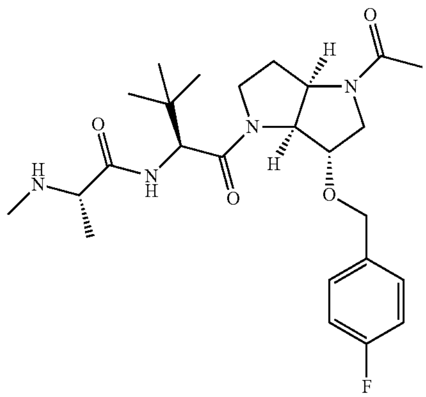 [SMILES: CN[C@@H](C)C(=O)N[C@H](C(=O)N1CC[C@@H]2[C@H]1[C@@H](OCc1ccc(F)cc1)CN2C(C)=O)C(C)(C)C] | A | A | A | 476.9 (M + H) |
| 41 | 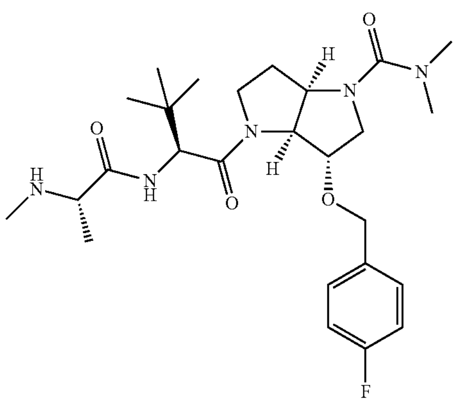 | A | A | A | 505.9 (M + H) |
| 42 | 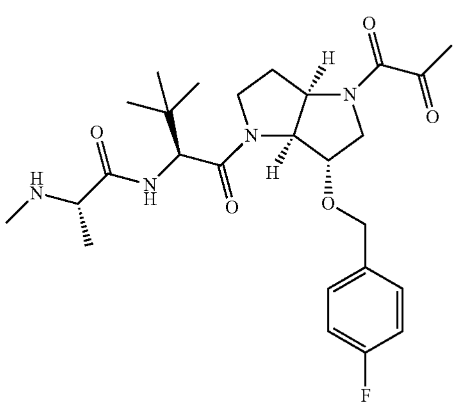 [SMILES: CN[C@@H](C)C(=O)N[C@H](C(=O)N1CC[C@@H]2[C@H]1[C@@H](OCc1ccc(F)cc1)CN2C(=O)C(C)=O)C(C)(C)C] | A | A | A | 504.9 (M + H) |

TABLE 7-continued

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 43 | 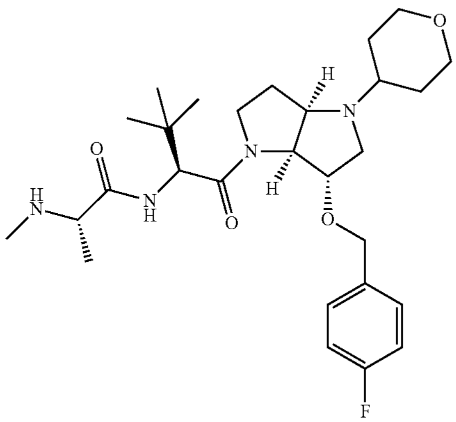 [SMILES: CN[C@@H](C)C(=O)N[C@H](C(=O)N1CC[C@@H]2[C@H]1[C@@H](OCc1ccc(F)cc1)CN2C1CCOCC1)C(C)(C)C] | B | A | A | 519.0 (M + H) |
| 44 | 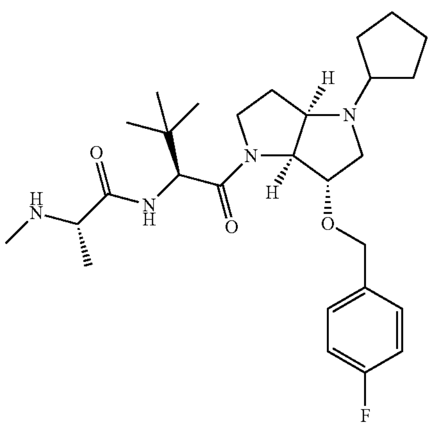 [SMILES: CN[C@@H](C)C(=O)N[C@H](C(=O)N1CC[C@@H]2[C@H]1[C@@H](OCc1ccc(F)cc1)CN2C1CCCC1)C(C)(C)C] | B | A | A | 503.0 (M + H) |
| 45 | 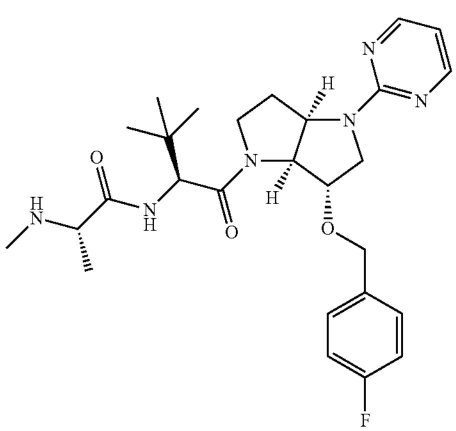 [SMILES: CN[C@@H](C)C(=O)N[C@H](C(=O)N1CC[C@@H]2[C@H]1[C@@H](OCc1ccc(F)cc1)CN2c1ncccn1)C(C)(C)C] | B | A | A | 513.0 (M + H) |

Scheme LI

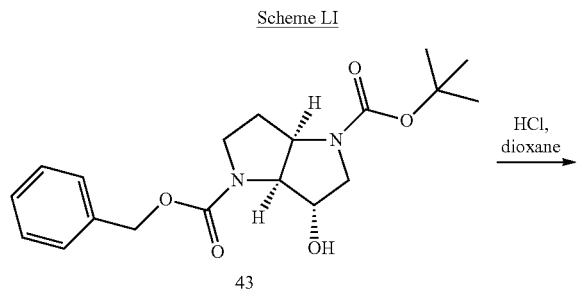

6-Hydroxy-hexahydro-pyrrolo[3,2-b]pyrrole-1-carboxylic acid benzyl ester hydrochloride salt (52): To a solution of bicyclic alcohol 43 (6.5 g, 17.9 mmol) in DCM (20 mL) at 0° C. was added 4N HCl/1,4-dioxane (20 mL, 80 mmol) and the reaction mixture was slowly warming to ambient temperature. After 90 min, an additional portion of 4N HCl/1,4-dioxane (20 mL) was added. After 3 h, the reaction mixture was diluted with toluene and concentrated in vacuo. The crude 52 (HCl salt) was used in the next step without further purification. Mass spectrum, m/z [262.5] (M+H)+.

Scheme LII

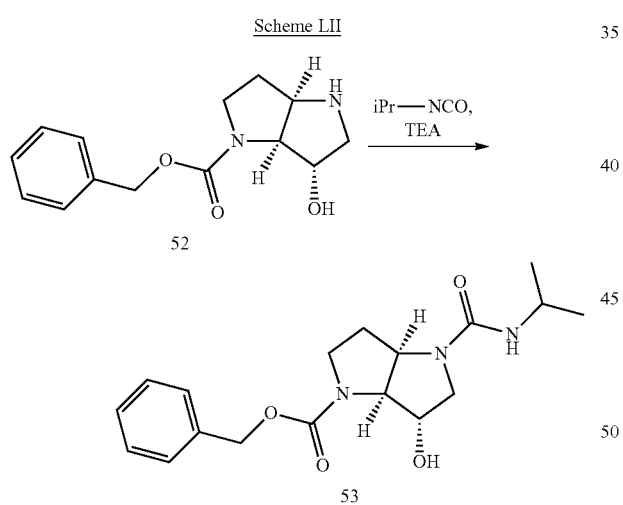

6-Hydroxy-4-isopropylcarbamoyl-hexahydro-pyrrolo[3,2-b]pyrrole-1-carboxylic acid benzyl ester (53): A suspension of the crude 52.HCl salt (~5.3 g, 17.9 mmol) and Et₃N (7.5 mL, 54 mmol) in DCM (200 mL) was stirred at 0° C. Isopropyl isocyanate (1.8 mL, 17.9 mmol) was added dropwise over 2 min. After 30 min, aqueous NH₄OH (30%, 10 mL) and MeOH (100 mL) were added and the solution was concentrated in vacuo. The residue was partitioned between DCM and 1N HCl, the organic layer was separated and dried over anhydrous Na₂SO₄, filtered, and concentrated to afford crude 53 as a beige-colored foam (6.5 g) which was used without further purification. Mass spectrum, m/z [347.7] (M+H)+.

Scheme LIII

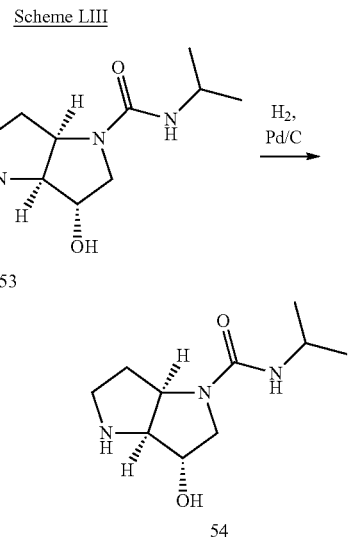

3-Hydroxy-hexahydro-pyrrolo[3,2-b]pyrrole-1-carboxylic acid isopropylamide (54): A mixture containing crude 53 (~6.2 g, 17.9 mmol) and 10% Pd-on-carbon (wet, 1.9 g, 1.8 mmol) in MeOH (200 mL) was stirred vigorously under an atmosphere of H₂. After 3 h, the catalyst was removed by filtration and the filtrate was concentrated in vacuo to afford 4.5 g of 54 as a colorless oil which was used without further purification.

Scheme LIV

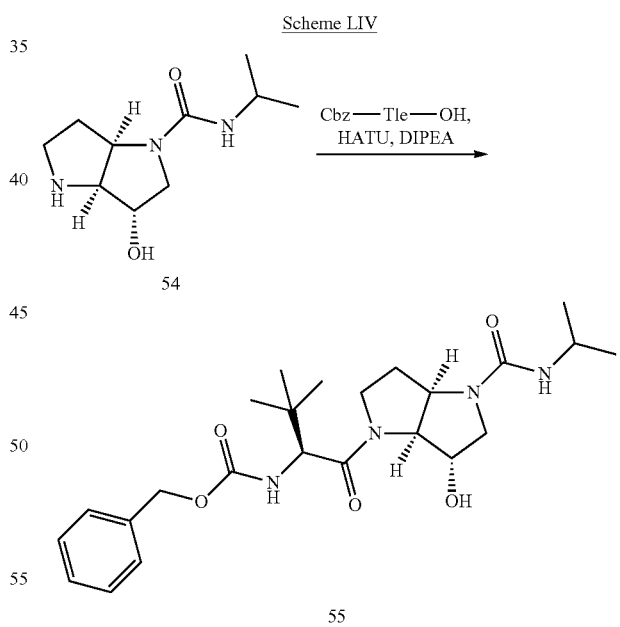

[1-(6-Hydroxy-4-isopropylcarbamoyl-hexahydro-pyrrolo[3,2-b]pyrrole-1-carbonyl)-2,2-dimethyl-propyl]-carbamic acid benzyl ester (55): A solution containing crude 54 (~3.8 g, 17.9 mmol) and DIPEA (4.1 mL, 23.3 mmol) in NMP (50 mL) was cooled to 0° C. In a separate flask, Cbz-Tle-OH dicyclohexylamine salt (8.8 g, 19.7 mmol), HATU (7.5 g, 19.7 mmol), and DIPEA (4.1 mL, 23.3 mmol) were dissolved in NMP (130 mL) at 0° C. A portion of the HATU/Cbz-Tle-OH solution (117 mL, ~1.0 equiv) was added to the solution containing 54. After 30 min, the reaction mixture was diluted with water and extracted with 1:1 Et₂O/EtOAc. The combined organic extracts were washed successively with 10% H₃PO₄, water, saturated aqueous NaHCO₃, water, and brine, dried over anhydrous Na₂SO₄, filtered, and concentrated to afford 7.2 g of 55 as a beige-colored foam (88%, 4 steps) which was used without further purification. Mass spectrum, m/z [460.9] (M+H)+.

off-white-colored foam which was used without further purification. Mass spectrum, m/z [326.7] (M+H)+.

Scheme LVI

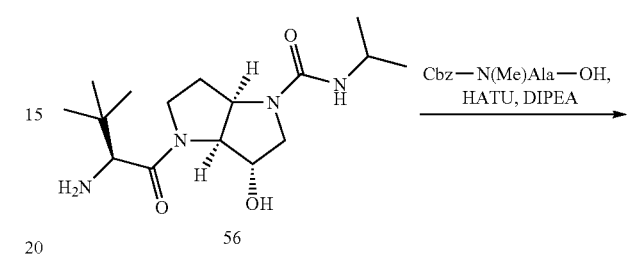

Scheme LV

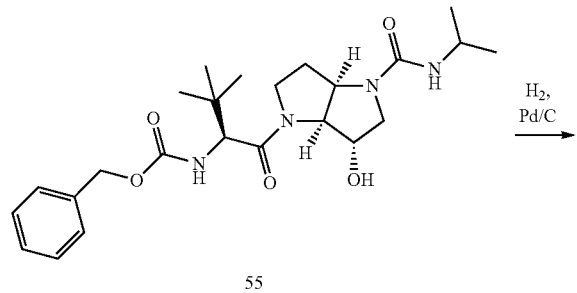

55

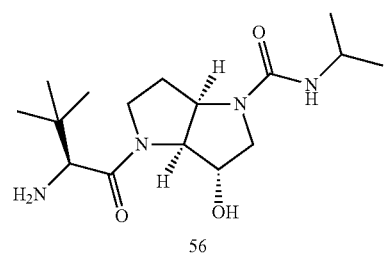

56

4-(2-Amino-3,3-dimethyl-butyryl)-3-hydroxy-hexahydro-pyrrolo[3,2-b]pyrrole-1-carboxylic acid isopropylamide (56): A mixture containing 55 (7.2 g, 15.6 mmol) and 10% Pd-on-carbon (wet, 1.7 g, 1.5 mmol) in MeOH (200 mL) were stirred vigorously under an atmosphere of H₂. After 2 h, the was removed by filtration and the filtrate was diluted with toluene and concentrated in vacuo to afford 6.1 g of 56 as an {1-[1-(6-Hydroxy-4-isopropylcarbamoyl-hexahydro-pyrrolo[3,2-b]pyrrole-1-carbonyl)-2,2-dimethyl-propylcarbamoyl]-ethyl}-methyl-carbamic acid benzyl ester (57): A solution containing 56 (5.10 g, 15.6 mmol) and DIPEA (3.6 mL, 20.3 mmol) in NMP (20 mL) was cooled to 0° C. In a separate flask at 0° C., Cbz-N(Me)Ala-OH (4.1 g, 17.2 mmol), HATU (6.6 g, 17.2 mmol), and DIPEA (3.6 mL, 20.3 mmol) were dissolved in NMP (80 mL). A portion of the HATU/Cbz-N(Me)Ala-OH solution (72 mL, ~1.0 equiv) was then added to the cooled solution of 56. After 45 min, the reaction mixture was diluted with water and extracted with EtOAc. The combined organic extracts were washed successively with 10% H₃PO₄, water, saturated aqueous NaHCO₃, water, and brine, dried over anhydrous Na₂SO₄, filtered, and concentrated to afford 7.0 g (82%, 2 steps) of 57 as a white foam. Mass spectrum, m/z [546.0] (M+H)+.

Scheme LVII

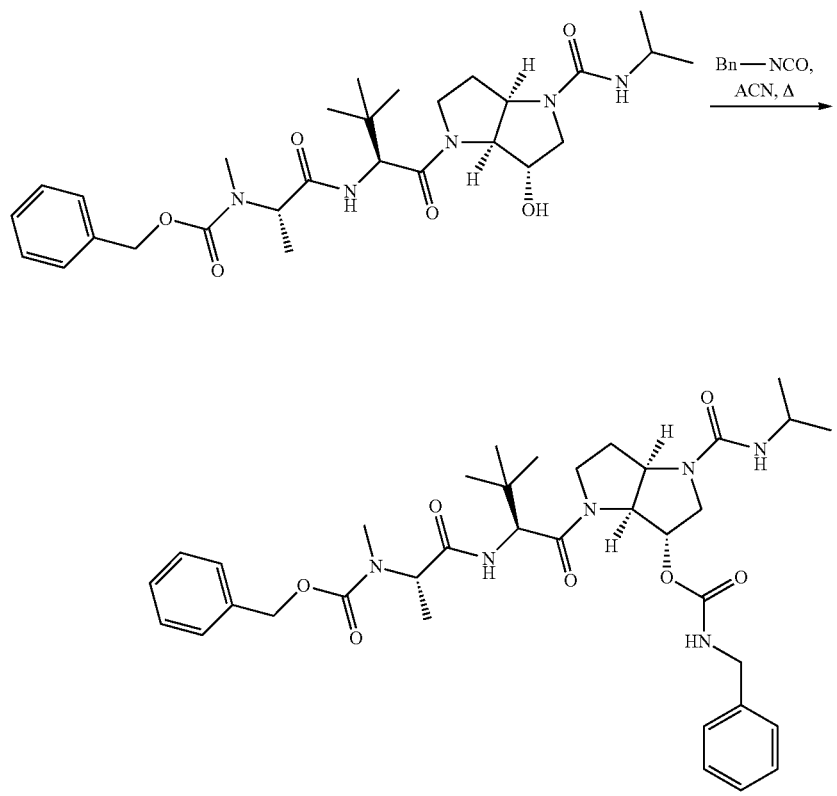

58

{1-[1-(6-Benzylcarbamoyloxy-4-isopropylcarbamoyl-hexahydro-pyrrolo[3,2-b]pyrrole-1-carbonyl)-2,2-dimethyl-propylcarbamoyl]-ethyl}-methyl-carbamic acid benzyl ester (58): A solution containing 57 (280 mg, 0.51 mmol) and benzyl isocyanate (350 μL, 2.83 mmol) in acetonitrile (500 μL) was warmed to reflux. After 12 h, the reaction mixture was cooled to ambient temperature, diluted with MeOH, and treated with aqueous $NH_4OH$ (30%, 5 mL). The solution was concentrated in vacuo and the residue was dissolved in EtOAc, washed successively with 1N HCl, water, aqueous $NaHCO_3$, and brine, dried over anhydrous $Na_2SO_4$, filtered, and concentrated. The crude product was purified by reverse-phase HPLC (2" Dynamax® C18, 50-100% MeOH/water containing 0.1% HOAc over 20 min; Flow: 40 mL/min). The pure fractions were combined and concentrated to afford 58 as a white solid (250 mg, 72%). Mass spectrum, m/z [679.3] (M+H)+.

Scheme LVIII

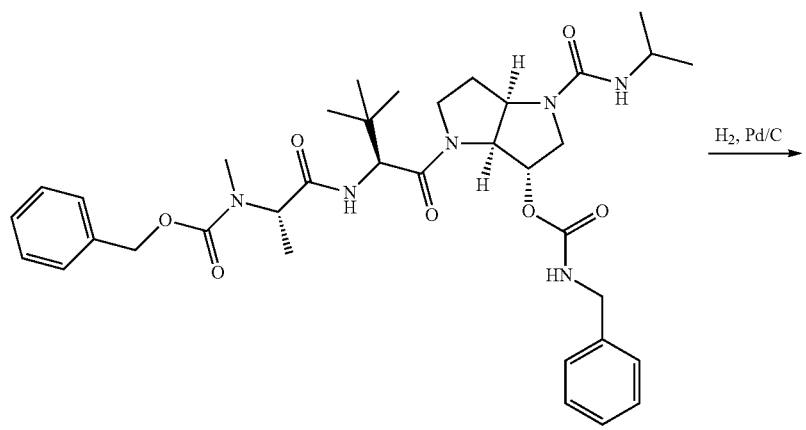

58

-continued

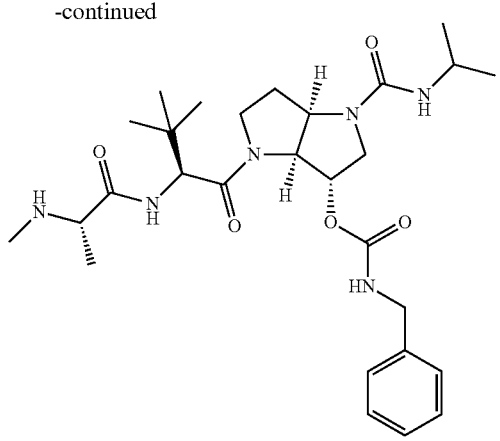

59

Benzyl-carbamic acid 4-[3,3-dimethyl-2-(2-methylamino-propionylamino)-butyryl]-1-isopropylcarbamoyl-octahydro-pyrrolo[3,2-b]pyrrol-3-yl ester (59): A mixture of 58 (250 mg, 0.37 mmol) and 10% Pd-on-carbon (wet, 100 mg, 0.10 mmol) in MeOH (10 mL) was stirred vigorously under an atmosphere of $H_2$. After 3.5 h, the catalyst was removed by filtration with an Acrodisc® 0.45 µm nylon membrane syringe filter and the solvent was removed in vacuo. The crude product was purified by reverse-phase HPLC (2" Dynamax® C18, 20-80% MeOH/water containing 0.1% HOAc over 25 min; Flow: 40 mL/min). The product-containing fractions were combined and lyophilized to provide 59 (130 mg, 65%) as a flocculent white powder.

EXAMPLE 46

Benzyl-carbamic acid 4-[3,3-dimethyl-2-(2-methylamino-propionylamino)-butyryl]-1-isopropylcarbamoyl-octahydro-pyrrolo[3,2-b]pyrrol-3-yl ester (59)

$^1$H NMR (CDCl$_3$, 300 MHz), mixture of rotomers: δ7.82 (m, 1.3H), 7.28 (m, 5.5H), 6.62 (m, 0.2H), 5.27 (m, 0.9H), 5.16 (m, 0.9H), 5.07 (m, 0.1H), 4.96 (m, 0.1H), 4.63 (m, 0.3H), 4.56 (m, 1.7H), 4.47 (m, 1H), 4.34 (m, 1.5H), 4.21 (m, 0.5H), 4.10 (m, 1H), 4.01-3.73 (m, 5H), 3.62 (m, 1H), 3.33 (m, 2H), 3.11 (q, J=6.9 Hz, 0.7H), 2.77 (q, J=6.9 Hz, 0.3H), 2.41 (m, 1H), 2.37 (s, 2H), 2.27 (s, 1H), 2.03 (s, 2H), 1.97 (m, 1H), 1.29 (d, J=6.6 Hz, 3H), 1.15 (3 s, 6H), 0.98 (2 s, 9H) ppm; $^{13}$C NMR (CDCl$_3$, 75 MHz): δ174.8, 170.6, 155.7, 155.6, 115.3, 138.1, 128.8, 128.7, 127.9, 127.7, 127.7, 127.6, 75.1, 65.8, 64.0, 60.2, 60.1, 57.1, 56.7, 52.2, 46.9, 45.2, 42.7, 36.5, 35.6, 34.9, 31.7, 26.7, 26.6, 23.7, 23.5, 19.5 ppm. Mass spectrum, m/z [545.1] (M+H)+.

EXAMPLES 47 through 61 were prepared using the general chemistries described in Schemes LVII and LVIII by replacing benzyl isocyanate with phenyl isocyanate, N,N-diphenylcarbamoyl chloride, 1-naphthyl isocyanate, N-methyl-N-phenylcarbamoyl chloride, 2-naphthyl isocyanate, ethyl isocyanate, n-propyl isocyanate, isopropyl isocyanate, tert-butyl isocyanate, cyclopentyl isocyanate, cyclohexyl isocyanate, 1-pyrrolidinecarbonyl chloride, 1-piperidinecarbonyl chloride, and 4-morpholinecarbonyl chloride.

EXAMPLE 47

Phenyl-carbamic acid 4-[3,3-dimethyl-2-(2-methylamino-propionylamino)-butyryl]-1-isopropylcarbamoyl-octahydro-pyrrolo[3,2-b]pyrrol-3-yl ester $^1$H NMR (CDCl$_3$, 300 MHz), mixture of rotomers: δ8.62 (br s, 0.3H), 8.04 (d, J=9.6 Hz, 0.3H), 7.90 (d, J=9.6 Hz, 0.7H), 7.56 (s, 1H), 7.51 (m, 0.3H), 7.42 (m, 1.4H), 7.29 (m, 2.3H), 7.05 (m, 1H), 5.27 (d, J=3.3 Hz, 0.7H), 5.16 (d, J=9.3 Hz, 0.3H), 5.01 (m, 0.25H), 4.72 (t, J=7.1 Hz, 0.25H), 4.64-4.53 (m, 2.5H), 4.19-4.10 (m, 2H), 3.97 (m, 1H), 3.81 (m, 0.3H), 3.68 (br d, 0.7H), 3.48 (br s, 1H), 3.40 (dd, J=12.0, 3.6 Hz, 1H), 3.33 (m, 1H), 3.16-3.02 (m, 1H), 2.42 (m, 1H), 2.35 (2 s, 3H), 2.00 (m, 1H), 1.31 (3 s, 3H), 1.15 (4 s, 6H), 1.02 (2 s, 9H) ppm; $^{13}$C NMR (CDCl$_3$, 75 MHz): δ175.3, 174.8, 170.7, 169.7, 155.7, 155.6, 153.0, 152.5, 138.2, 137.7, 129.0, 123.7, 123.3, 119.0, 118.4, 76.2, 75.1, 65.7, 63.8, 60.4, 60.1, 58.3, 57.1, 56.7, 52.1, 50.1, 46.8, 45.1, 42.7, 42.6, 36.6, 35.5, 34.9, 31.6, 30.6, 26.6, 26.5, 23.60, 23.5, 23.4, 19.5 ppm. Mass spectrum, m/z [531.1] (M+H)+.

EXAMPLE 48

Diphenyl-carbamic acid 4-[3,3-dimethyl-2-(2-methylamino-propionylamino)-butyryl]-1-isopropylcarbamoyl-octahydro-pyrrolo[3,2-b]pyrrol-3-yl ester $^1$H NMR (CDCl$_3$, 300 MHz): δ7.80 (d, J=9.6 Hz, 1H), 7.30 (m, 5H), 7.19 (m, 5H), 5.22 (d, J=3.0 Hz, 1H), 4.54 (d, J=9.3 Hz, 1H), 4.32 (m, 1H), 4.22 (m, 1H), 4.13-3.90 (m, 8H), 3.80 (d, J=12.3 Hz, 1H), 3.35-3.24 (m, 2H), 3.13-3.03 (m, 1H), 2.37 (s, 3H), 2.29 (m, 1H), 2.08 (s, 3H), 1.91 (m, 1H), 1.29 (d, J=6.9 Hz, 3H), 1.19 (3 s, 6H), 0.99 (s, 9H) ppm; $^{13}$C NMR (CDCl$_3$, 75 MHz): δ174.9, 170.7, 155.6, 153.6, 142.2, 129.1, 126.8, 126.4, 75.8, 65.5, 60.3, 60.0, 57.1, 51.9, 46.9, 42.8, 35.5, 35.0, 31.6, 26.7, 23.8, 23.6, 23.1, 19.6 ppm. Mass spectrum, m/z [607.2] (M+H)+.

EXAMPLE 49

Naphthalen-1-yl-carbamic acid 4-[3,3-dimethyl-2-(2-methylamino-propionylamino)-butyryl]-1-isopropylcarbamoyl-octahydro-pyrrolo[3,2-b]pyrrol-3-yl ester $^1$H NMR (CDCl$_3$, 300 MHz), mixture of rotomers: δ8.59 (s, 0.25H), 8.21 (m, 0.25H), 7.94-7.7.84 (m, 3.5H), 7.66 (m, 1H), 7.56-7.42 (m, 3H), 7.21 (s, 1H), 5.30 (d, J=3.3 Hz, 0.75H), 5.22 (d, J=9.6 Hz, 0.25H), 5.15 (m, 0.25H), 4.79 (m, 0.25H), 4.59 (m, 2.5H), 4.13 (m, 1H), 4.06-3.95 (m, 2H), 3.83 (m, 0.25H), 3.74 (m, 0.75H), 3.45-2.96 (m, 6H), 2.42 (m, 1H), 2.38 (s, 3H), 2.03 (s, 2.5H), 1.30 (d, J=6.9 Hz, 2.25H), 1.21-1.15 (5 s, 6.75H), 1.01 (s, 9H) ppm; $^{13}$C NMR (CDCl$_3$, 75 MHz), mixture of rotomers: δ175.1, 174.9, 170.7, 170.0, 155.7, 155.6, 154.3, 153.4, 134.2, 134.1, 132.9, 132.1, 128.8, 128.6, 126.5, 126.2, 126.1, 126.10, 125.8, 125.6, 125.2, 121.8, 120.8, 75.5, 65.8, 64.1, 60.2, 60.1, 57.1, 56.6, 52.2, 50.4, 46.9, 45.1, 42.7, 42.6, 36.4, 35.6, 35.0, 34.9, 31.7, 30.6, 26.7, 26.6, 23.7, 23.6, 19.6, 19.4 ppm. Mass spectrum, m/z [581.2] (M+H)+.

EXAMPLE 50

Methyl-phenyl-carbamic acid 4-[3,3-dimethyl-2-(2-methylamino-propionylamino)-butyryl]-1-isopropyl-carbamoyl-octahydro-pyrrolo[3,2-b]pyrrol-3-yl ester $^1$H NMR (CDCl$_3$, 300 MHz), mixture of rotomers: δ7.81 (m, 1H), 7.31 (m, 2H), 7.18 (m, 3H), 5.14 (d, J=3.3 Hz, 1H), 4.53 (d, J=9.3 Hz, 1H), 4.09 (m, 1H), 3.97 (m, 2H), 3.70 (m, 1H), 3.31 (m, 2H), 3.28 (s, 3H), 3.05 (m, 1H), 2.58 (s, 3H), 2.39 (m, 1H), 2.36 (s, 3H), 2.02 (s, 0.8H), 1.93 (br s, 1H), 1.28 (d, J=7.2 Hz, 3H), 1.16 (d, J=6.0 Hz, 6H), 0.98 (s, 9H) ppm; $^{13}$C NMR (CDCl$_3$, 75 MHz), mixture of rotomers: δ175.0, 170.6, 155.6, 154.4, 142.9, 128.9, 126.4, 125.7, 75.7, 65.7, 60.3, 60.0, 57.0, 52.1, 46.8, 42.7, 37.8, 35.5, 35.1, 31.6, 26.6, 23.7, 23.5, 19.7 ppm. Mass spectrum, m/z [545.1] (M+H)+.

EXAMPLE 51

Naphthalen-2-yl-carbamic acid 4-[3,3-dimethyl-2-(2-methylamino-propionylamino)-butyryl]-1-isopropylcarbamoyl-octahydro-pyrrolo[3,2-b]pyrrol-3-yl ester $^1$H NMR (CDCl$_3$, 300 MHz), mixture of rotomers: δ8.82 (s, 0.25H), 8.06-7.90 (m, 2.75H), 7.70 (m, 3H), 7.54 (m, 0.25H), 7.44-7.32 (m, 2.75H), 5.30 (d, J=3.3 Hz, 0.75H), 5.16 (d, J=9.3 Hz, 0.25H), 5.01 (m, 0.25H), 4.72 (m, 0.25H), 4.63 (m, 0.75H), 4.56 (m, 1.75H), 4.15 (m, 2H), 3.96 (m, 1H), 3.81-3.68 (m, 1H), 3.45-3.28 (m, 5H), 3.20-3.04 (m, 1H), 2.40 (m, 1H), 2.35 (s, 3H), 2.01 (m, 1H), 2.00 (s, 1H), 1.33 (d, J=6.9 Hz, 1H), 1.28 (d, J=6.9 Hz, 2H), 1.15 (d, J=6.6 Hz, 3H), 1.12 (d, J=6.6 Hz, 3H), 1.01 (s, 9H) ppm; $^{13}$C NMR (CDCl$_3$, 75 MHz), mixture of rotomers: δ175.3, 174.6, 170.7, 169.7, 155.7, 155.6, 153.2, 152.7, 135.7, 135.3, 134.0, 133.9, 130.3, 130.2, 128.8, 127.6, 127.5, 126.5, 124.8, 124.7, 119.4, 119.1, 115.2, 114.5, 76.3, 75.1, 65.8, 63.8, 60.4, 60.1, 59.9, 58.4, 57.2, 56.8, 52.1, 50.2, 46.9, 45.2, 42.7, 42.6, 36.7, 35.5, 34.8, 34.6, 31.6, 30.6, 26.7, 26.6, 23.6, 23.5, 23.5, 21.8, 19.3 ppm. Mass spectrum, m/z [581.2] (M+H)+.

EXAMPLE 52

Ethyl-carbamic acid 4-[3,3-dimethyl-2-(2-methylamino-propionylamino)-butyryl]-1-isopropylcarbamoyl-octahydro-pyrrolo[3,2-b]pyrrol-3-yl ester $^1$H NMR (CDCl$_3$, 300 MHz), mixture of rotomers: δ7.85 (m, 1H), 5.09-4.96 (m, 2H), 4.61-4.32 (m, 3H), 4.12-3.73 (m, 3H), 3.58 (m, 1H), 3.34-2.95 (m, 5H), 2.56 (br s, 3H), 2.38 (m, 1H), 2.35 (s, 3H), 2.00 (s, 0.6H), 1.97 (m, 1H), 1.27 (s, 3H), 1.13 (m, 9H), 0.97 (s, 9H) ppm; $^{13}$C NMR (CDCl$_3$, 75 MHz), mixture of rotomers: δ174.9, 170.6, 155.6, 155.2, 79.0, 76.0, 74.8, 65.8, 64.1, 60.6, 60.3, 60.1, 58.9, 57.0, 56.7, 52.2, 50.5, 46.8, 45.2, 42.6, 42.5, 36.5, 36.0, 35.8, 35.5, 35.1, 31.7, 30.5, 26.6, 23.6, 23.5, 19.6, 19.5, 15.2 ppm. Mass spectrum, m/z [483.0] (M+H)+.

EXAMPLE 53

Butyl-carbamic acid 4-[3,3-dimethyl-2-(2-methylamino-propionylamino)-butyryl]-1-isopropylcarbamoyl-octahydro-pyrrolo[3,2-b]pyrrol-3-yl ester $^1$H NMR (CDCl$_3$, 300 MHz), mixture of rotomers: δ7.91-7.72 (m, 0.8H), 7.59 (m, 0.2H), 6.09 (m, 0.2H), 5.78 (m, 0.2H), 5.12-4.90 (m, 1.8H), 4.62-4.35 (m, 2.8H), 4.09 (m, 1H), 3.98 (m, 2H), 3.80 (m, 0.2H), 3.60 (m, 0.8H), 3.34 (m, 2H), 3.10 (m, 3H), 2.92 (s, 3H), 2.44-2.33 (m, 1H), 2.38 (s, 3H), 2.04 (s, 0.9H), 2.00 (m, 1H), 1.48 (m, 2H), 1.35 (m, 2H), 1.31 (d, J=6.9 Hz, 2.25H), 1.17 (s, 6.75H), 1.00 (s, 9H), 0.92 (t, J=7.1 Hz, 3H) ppm; $^{13}$C NMR (CDCl$_3$, 75 MHz), mixture of rotomers: δ174.8, 174.7, 173.4, 170.5, 170.4, 169.9, 156.0, 155.5, 155.4, 155.2, 75.9, 75.1, 74.8, 65.7, 65.1, 64.0, 60.4, 60.2, 60.0, 58.7, 56.9, 56.6, 52.1, 50.4, 46.7, 45.1, 42.5, 42.4, 40.8, 36.4, 36.0, 35.4, 35.0, 34.9, 31.8, 31.7, 31.5, 30.4, 27.4, 26.6, 23.6, 23.4, 19.9, 19.8, 19.5, 19.4, 13.7 ppm. Mass spectrum, m/z [511.1] (M+H)+.

EXAMPLE 54

Isopropyl-carbamic acid 4-[3,3-dimethyl-2-(2-methylamino-propionylamino)-butyryl]-1-isopropylcarbamoyl-octahydro-pyrrolo[3,2-b]pyrrol-3-yl ester $^1$H NMR (CDCl$_3$, 300 MHz), mixture of rotomers: δ7.87 (m, 1H), 5.06 (m, 1H), 4.82 (m, 1H), 4.54 (m, 2H), 4.42 (m, 1H), 4.11-3.87 (m, 3H), 3.76 (m, 1H), 3.57 (m, 1H), 3.47 (br s, 2H), 3.33-3.23 (m, 2H), 3.05 (m, 1H), 2.38 (m, 1H), 2.34 (s, 3H), 1.98 (s, 0.9H), 1.94 (m, 1H), 1.28 (m, 3H), 1.12 (m, 12H), 0.96 (s, 9H) ppm; $^{13}$C NMR (CDCl$_3$, 75 MHz), mixture of rotomers: δ174.8, 174.6, 173.4, 170.6, 169.9, 155.7, 155.6, 155.2, 154.4, 75.8, 74.6, 65.8, 64.0, 60.5, 60.2, 60.1, 58.6, 57.0, 56.6, 52.2, 50.4, 46.8, 45.1, 43.3, 43.0, 42.5, 42.5, 36.5, 35.5, 35.0, 31.6, 30.5, 27.4, 26.6, 26.5, 23.6, 23.5, 23.0, 22.9, 21.5, 19.6, 19.5 ppm. Mass spectrum, m/z [497.1] (M+H)+.

EXAMPLE 55 tert-Butyl-carbamic acid 4-[3,3-dimethyl-2-(2-methylamino-propionylamino)-butyryl]-1-isopropylcarbamoyl-octahydro-pyrrolo[3,2-b]pyrrol-3-yl ester $^1$H NMR (CDCl$_3$, 300 MHz), mixture of rotomers: δ7.88 (m, 0.5H), 7.67 (m, 0.5H), 5.05 (m, 1H), 4.93-4.71 (m, 1H), 4.54 (m, 2H), 4.41 (m, 1H), 4.10 (m, 1H), 3.97 (m, 2H), 3.56

(m, 1H), 3.37-3.23 (m, 3H), 3.08-2.90 (m, 2H), 2.45-2.23 (m, 4H), 2.04 (br s, 0.6H), 1.98 (m, 1H), 1.33 (m, 1H), 1.28 (s, 9H), 1.20 (m, 2H), 1.14 (s, 6H), 0.98 (s, 9H) ppm; $^{13}$C NMR (CDCl$_3$, 75 MHz), mixture of rotomers: δ175.0, 174.7, 174.3, 173.4, 172.9, 170.6, 170.5, 169.9, 155.7, 153.5, 78.3, 75.6, 74.3, 74.2, 65.8, 65.5, 64.6, 63.9, 61.9, 61.4, 61.0, 60.7, 60.4, 60.2, 60.1, 58.4, 57.2, 57.0, 56.7, 56.5, 52.3, 50.7, 50.4, 46.8, 45.2, 45.0, 42.6, 42.5, 42.3, 36.6, 35.5, 35.5, 35.5, 35.3, 35.2, 35.1, 31.7, 30.6, 29.0, 27.5, 26.7, 23.7, 23.6, 19.7, 19.6, 10.6, 10.3, 10.1 ppm. Mass spectrum, m/z [511.1] (M+H)+.

EXAMPLE 56

Cyclopentyl-carbamic acid 4-[3,3-dimethyl-2-(2-methylamino-propionylamino)-butyryl]-1-isopropyl-carbamoyl-octahydro-pyrrolo[3,2-b]pyrrol-3-yl ester $^1$H NMR (CDCl$_3$, 300 MHz), mixture of rotomers: δ7.87 (m, 1H), 5.11-4.79 (m, 2H), 4.59-4.39 (m, 2H), 4.05 (m, 1.5H), 3.97-3.69 (m, 2.5H), 3.57 (m, 1H), 3.44 (m, 1.5H), 3.32-3.16 (m, 2H), 3.09-2.94 (m, 1H), 2.37 (m, 1H), 2.33 (s, 3H), 1.97 (s, 0.9H), 1.87 (m, 3H), 1.65-1.50 (m, 4H), 1.37 (m, 2H), 1.26 (s, 3H), 1.11 (s, 6H), 0.95 (s, 9H) ppm; $^{13}$C NMR (CDCl$_3$, 75 MHz), mixture of rotomers: δ174.8, 174.6, 170.6, 169.8, 155.7, 155.6, 154.7, 75.8, 74.7, 65.8, 63.9, 60.5, 60.2, 60.0, 58.5, 57.0, 56.5, 52.9, 52.6, 52.2, 50.4, 46.8, 45.0, 42.5, 42.4, 36.5, 35.4, 34.9, 33.2, 33.0, 31.6, 30.5, 26.6, 26.5, 23.70, 23.6, 23.5, 23.5, 23.4, 21.5, 19.6, 19.5 ppm. Mass spectrum, m/z [523.1] (M+H)+.

EXAMPLE 57

Cyclohexyl-carbamic acid 4-[3,3-dimethyl-2-(2-methylamino-propionylamino)-butyryl]-1-isopropyl-carbamoyl-octahydro-pyrrolo[3,2-b]pyrrol-3-yl ester $^1$H NMR (CDCl$_3$, 300 MHz), mixture of rotomers: δ7.86 (m, 1H), 5.05 (m, 1H), 4.89 (m, 1H), 4.59-4.40 (m, 3H), 4.06 (m, 1.7H), 3.92 (m, 1.3H), 3.56 (m, 1H), 3.40 (m, 1H), 3.28 (m, 2H), 3.08-2.97 (m, 4H), 2.37 (m, 1H), 2.34 (s, 3H), 1.98 (s, 0.6H), 1.95 (m, 1H), 1.86 (m, 2H), 1.66 (m, 2H), 1.55 (m, 1H), 1.26 (m, 5H), 1.11 (m, 9H), 0.96 (s, 9H) ppm; $^{13}$C NMR (CDCl$_3$, 75 MHz), mixture of rotomers: δ174.9, 174.8, 174.7, 170.7, 170.1, 155.9, 155.8, 155.3, 154.5, 75.9, 74.8, 65.9, 64.2, 60.6, 60.3, 60.2, 58.9, 57.2, 56.7, 52.3, 50.6, 50.2, 50.1, 46.9, 45.2, 42.7, 42.6, 36.6, 35.6, 35.1, 33.5, 33.4, 31.8, 30.6, 26.8, 26.7, 25.6, 25.0, 24.9, 23.7, 23.6, 21.7, 19.7, 19.6 ppm. Mass spectrum, m/z [537.1] (M+H)+.

EXAMPLE 58

Pyrrolidine-1-carboxylic acid 4-[3,3-dimethyl-2-(2-methylamino-propionylamino)-butyryl]-1-isopropyl-carbamoyl-octahydro-pyrrolo[3,2-b]pyrrol-3-yl ester $^1$H NMR (CDCl$_3$, 300 MHz), mixture of rotomers: δ7.99-7.31 (m, 2H), 5.06 (m, 1H), 4.59-4.46 (m, 3H), 4.30 (m, 4.10-3.89 (m, 6H), 3.56 (m, 1H), 3.29 (m, 8H), 3.10 (m, 1H), 2.39 (m, 1H), 2.35 (s, 3H), 2.27 (m, 1H), 1.98 (m, 2H), 1.80 (m, 6H), 1.27 (d, J=6.3 Hz, 3H), 1.24 (m, 2H), 1.12 (d, J=6.3 Hz, 6H), 1.00 (m, 2H), 0.96 (s, 9H) ppm; $^{13}$C NMR (CDCl$_3$, 75 MHz), mixture of rotomers: δ174.7, 170.5, 156.3, 156.1, 155.7, 153.8, 75.2, 65.8, 60.4, 60.2, 60.1, 57.0, 52.3, 49.7, 47.2, 46.8, 46.2, 45.9, 42.6, 35.6, 35.5, 35.4, 34.8, 31.6, 26.6, 25.7, 25.4, 24.9, 23.6, 23.5, 22.6, 20.0, 19.5, 19.1 ppm. Mass spectrum, m/z [509.1] (M+H)+.

EXAMPLE 59

Piperidine-1-carboxylic acid 4-[3,3-dimethyl-2-(2-methylamino-propionylamino)-butyryl]-1-isopropyl-carbamoyl-octahydro-pyrrolo[3,2-b]pyrrol-3-yl ester $^1$H NMR (CDCl$_3$, 300 MHz), mixture of rotomers: δ7.83-7.65 (m, 2H), 5.05 (m, 1H), 4.59-4.45 (m, 3H), 4.11-3.86 (m, 3H), 3.55 (m, 1H), 3.30 (m, 7H), 3.05 (m, 1H), 2.94 (br s, 2H), 2.38 (m, 1H), 2.34 (s, 3H), 1.98 (s, 0.8H), 1.95 (m, 1H), 1.51 (m, 7H), 1.26 (d, J=6.9 Hz, 3H), 1.12 (s, 6H), 0.95 (s, 9H) ppm; $^{13}$C NMR (CDCl$_3$, 75 MHz), mixture of rotomers: δ174.7, 173.3, 170.5, 155.7, 154.2, 75.3, 65.7, 61.4, 60.3, 60.2, 57.0, 52.2, 46.7, 44.8, 42.5, 35.5, 35.4, 35.0, 31.6, 26.6, 25.6, 24.2, 23.6, 23.5, 19.6, 10.2 ppm. Mass spectrum, m/z [523.1] (M+H)+.

EXAMPLE 60

Morpholine-4-carboxylic acid 4-[3,3-dimethyl-2-(2-methylamino-propionylamino)-butyryl]-1-isopropyl-carbamoyl-octahydro-pyrrolo[3,2-b]pyrrol-3-yl ester $^1$H NMR (CDCl$_3$, 300 MHz), mixture of rotomers: δ7.83 (m, 1H), 5.15 (m, 1H), 4.70-4.37 (m, 6H), 4.13 (m, 1H), 4.06-3.94 (m, 2H), 3.64 (m, 4.2H), 3.41-3.27 (m, 7H), 3.17 (m, 0.8H), 2.43 (m, 1H), 2.41 (s, 3H), 2.03 (s, 3H), 2.00 (m, 1H), 1.32 (d, J=6.9 Hz, 3H), 1.22 (m, 2H), 1.17 (s, 6H), 1.05 (m, 2H), 1.01 (s, 9H) ppm; $^{13}$C NMR (CDCl$_3$, 75 MHz), mixture of rotomers: δ175.1, 174.7, 173.6, 170.8, 156.0, 155.8, 154.3, 75.8, 66.7, 66.5, 65.8, 65.7, 61.5, 60.3, 60.1, 57.4, 57.3, 52.3, 46.9, 44.5, 44.0, 42.8, 42.7, 35.6, 35.5, 34.8, 31.8, 27.6, 26.8, 26.6, 23.8, 23.6, 21.6, 19.5, 10.5 ppm. Mass spectrum, m/z [525.1] (M+H)+.

EXAMPLE 61

4-[3,3-Dimethyl-2-(2-methylamino-propionylamino)-butyryl]-3-hydroxy-hexahydro-pyrrolo[3,2-b]pyrrole-1-carboxylic acid isopropylamide $^1$H NMR (CDCl$_3$, 300 MHz), mixture of rotomers: δ8.05 (d, J=9.3 Hz, 0.25H), 7.86 (d, J=9.3 Hz, 0.75H), 4.69-4.33 (m, 7H), 4.11 (m, 1H), 3.95 (m, 2H), 3.72-3.14 (m, 5H), 2.38 (s, 3H), 2.27 (m, 1H), 2.04 (m, 1H), 1.97 (s, 0.5H), 1.29 (d, J=6.9 Hz, 3H), 1.13 (d, J=6.6 Hz, 6H), 0.96 (s, 9H) ppm; $^{13}$C NMR (CDCl$_3$, 75 MHz), mixture of rotomers: δ175.7, 174.2, 170.8, 169.6, 155.9, 155.8, 75.4, 72.7, 69.1, 68.6, 61.2, 59.9, 59.5, 59.4, 57.3, 57.0, 53.6, 52.7, 47.4, 45.3, 42.5, 42.49, 35.6, 35.3, 34.8, 34.3, 31.8, 30.7, 27.4, 26.7, 26.5, 23.7, 26.5, 23.7, 23.6, 23.5, 22.1, 19.3, 19.0 ppm. Mass spectrum, m/z [411.9] (M+H)+.

TABLE 8
| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 46 | 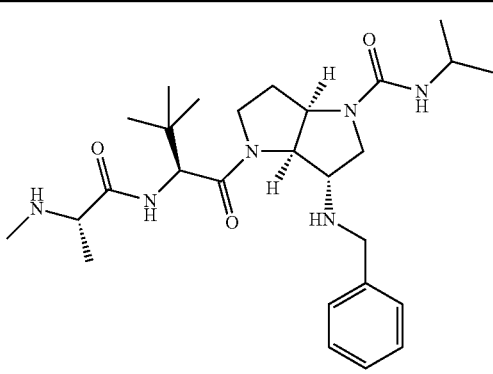 | B | A | A | 545.1 (M + H) |
| 47 | 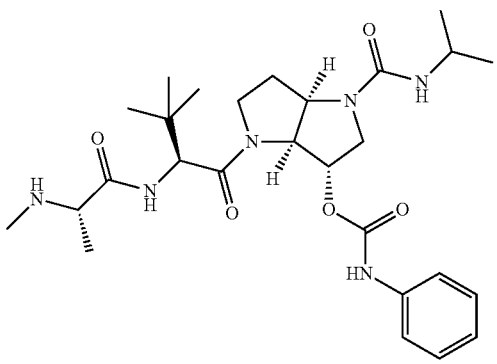 [SMILES: CN[C@@H](C)C(=O)N[C@H](C(=O)N1CC[C@@H]2[C@H]1[C@@H](OC(=O)Nc1ccccc1)CN2C(=O)NC(C)C)C(C)(C)C] | B | A | A | 531.1 (M + H) |
| 48 | 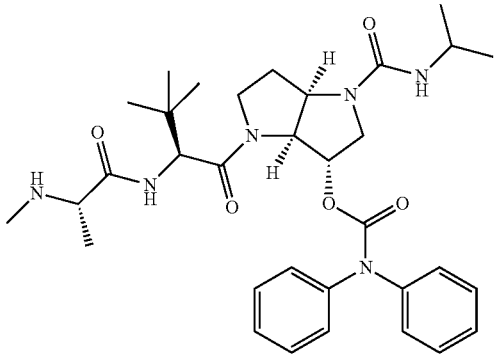 [SMILES: CN[C@@H](C)C(=O)N[C@H](C(=O)N1CC[C@@H]2[C@H]1[C@@H](OC(=O)N(c1ccccc1)c1ccccc1)CN2C(=O)NC(C)C)C(C)(C)C] | B | A | B | 607.2 (M + H) |
| 49 | 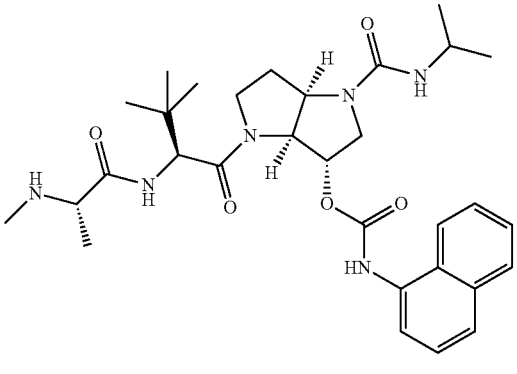 [SMILES: CN[C@@H](C)C(=O)N[C@H](C(=O)N1CC[C@@H]2[C@H]1[C@@H](OC(=O)Nc1cccc3ccccc13)CN2C(=O)NC(C)C)C(C)(C)C] | B | A | A | 581.2 (M + H) |

TABLE 8-continued
| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 50 | 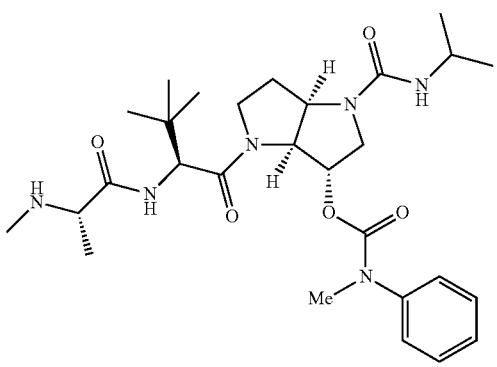 [SMILES: CN[C@@H](C)C(=O)N[C@H](C(=O)N1CC[C@@H]2[C@H]1[C@@H](OC(=O)N(C)c1ccccc1)CN2C(=O)NC(C)C)C(C)(C)C] | B | A | B | 545.1 (M + H) |
| 51 | 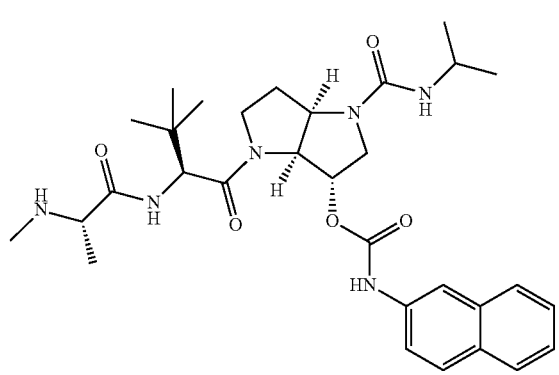 [SMILES: CN[C@@H](C)C(=O)N[C@H](C(=O)N1CC[C@@H]2[C@H]1[C@@H](OC(=O)Nc1ccc3ccccc3c1)CN2C(=O)NC(C)C)C(C)(C)C] | B | A | C | 581.2 (M + H) |
| 52 | 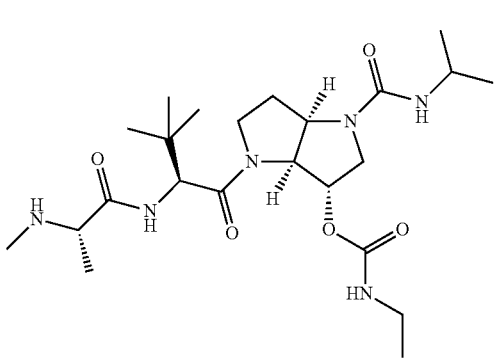 [SMILES: CCNC(=O)O[C@H]1CN(C(=O)NC(C)C)[C@@H]2CCN(C(=O)[C@@H](NC(=O)[C@H](C)NC)C(C)(C)C)[C@H]12] | C | A | C | 483.0 (M + H) |
| 53 | 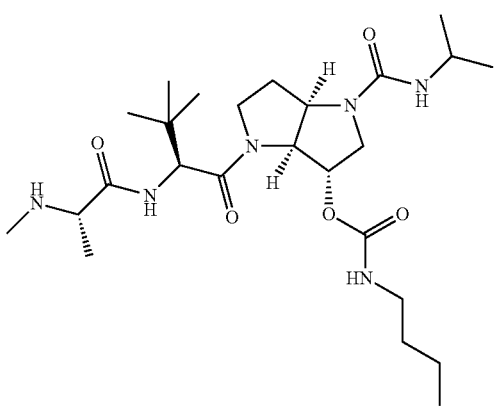 [SMILES: CCCCNC(=O)O[C@H]1CN(C(=O)NC(C)C)[C@@H]2CCN(C(=O)[C@@H](NC(=O)[C@H](C)NC)C(C)(C)C)[C@H]12] | B | A | B | 511.1 (M + H) |

TABLE 8-continued

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 54 | 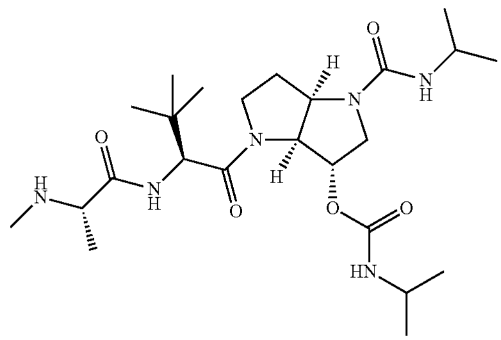 [SMILES: CN[C@@H](C)C(=O)N[C@H](C(=O)N1CC[C@@H]2[C@H]1[C@@H](OC(=O)NC(C)C)CN2C(=O)NC(C)C)C(C)(C)C] | C | A | C | 497.1 (M + H) |
| 55 | 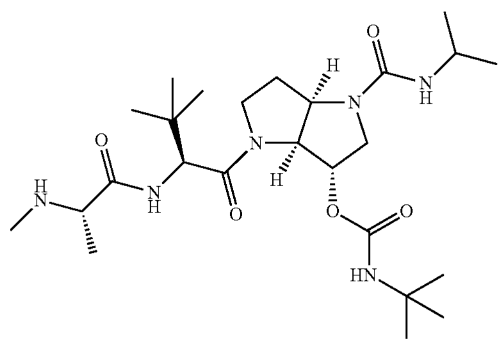 [SMILES: CN[C@@H](C)C(=O)N[C@H](C(=O)N1CC[C@@H]2[C@H]1[C@@H](OC(=O)NC(C)(C)C)CN2C(=O)NC(C)C)C(C)(C)C] | C | A | B | 511.1 (M + H) |
| 56 | 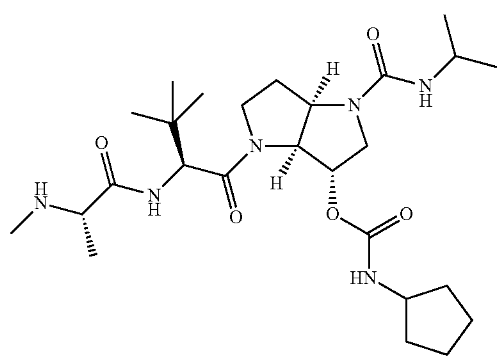 [SMILES: CN[C@@H](C)C(=O)N[C@H](C(=O)N1CC[C@@H]2[C@H]1[C@@H](OC(=O)NC1CCCC1)CN2C(=O)NC(C)C)C(C)(C)C] | B | A | B | 523.1 (M + H) |
| 57 | 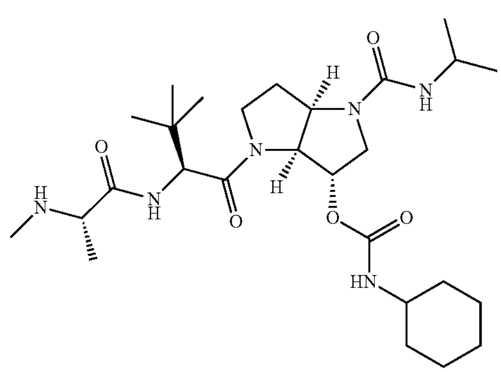 [SMILES: CN[C@@H](C)C(=O)N[C@H](C(=O)N1CC[C@@H]2[C@H]1[C@@H](OC(=O)NC1CCCCC1)CN2C(=O)NC(C)C)C(C)(C)C] | B | A | A | 537.1 (M + H) |

TABLE 8-continued

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 58 | 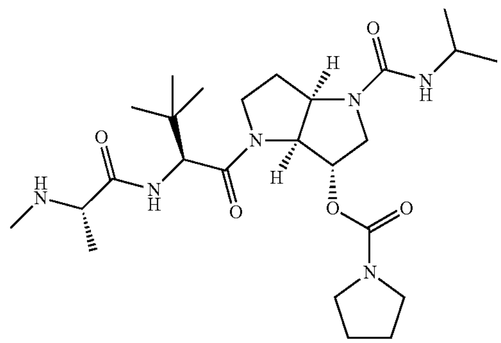 [SMILES: CN[C@@H](C)C(=O)N[C@H](C(=O)N1CC[C@@H]2[C@H]1[C@@H](OC(=O)N1CCCC1)CN2C(=O)NC(C)C)C(C)(C)C] | C | B | C | 509.1 (M + H) |
| 59 | 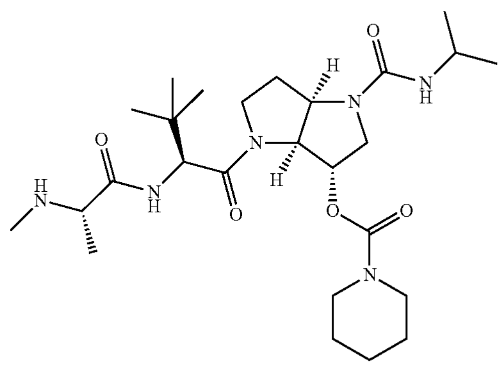 [SMILES: CN[C@@H](C)C(=O)N[C@H](C(=O)N1CC[C@@H]2[C@H]1[C@@H](OC(=O)N1CCCCC1)CN2C(=O)NC(C)C)C(C)(C)C] | C | A | C | 523.1 (M + H) |
| 60 | 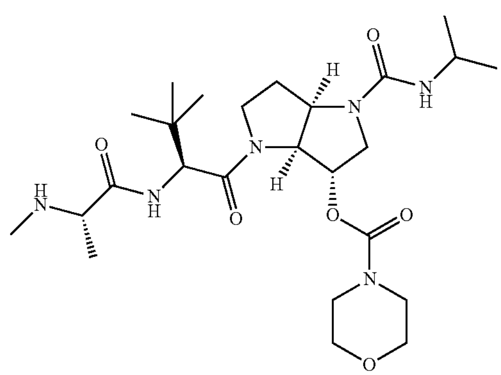 [SMILES: CN[C@@H](C)C(=O)N[C@H](C(=O)N1CC[C@@H]2[C@H]1[C@@H](OC(=O)N1CCOCC1)CN2C(=O)NC(C)C)C(C)(C)C] | C | A | C | 525.1 (M + H) |
| 61 | 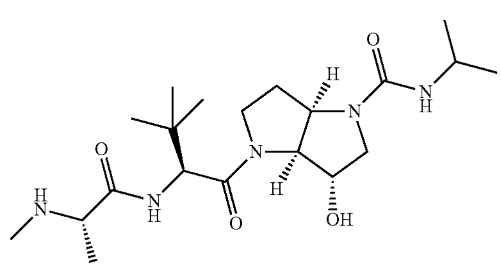 [SMILES: CN[C@@H](C)C(=O)N[C@H](C(=O)N1CC[C@@H]2[C@H]1[C@@H](O)CN2C(=O)NC(C)C)C(C)(C)C] | D | B | C | 411.9 (M + H) |

Scheme LIX

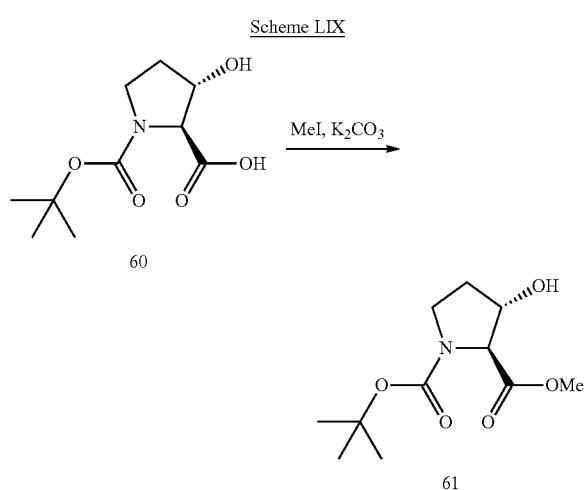

3-Hydroxy-pyrrolidine-1,2-dicarboxylic acid 1-tert-butyl ester 2-methyl ester (61): A solution containing 3-hydroxy-pyrrolidine-1,2-dicarboxylic acid 1-tert-butyl ester (60, 16 g, 71 mmol. See: Hodges, J. A.; Raines, R. T. *J. Am. Chem. Soc.* 2005, 45, 15923) in DMF (100 mL) was cooled to 0° C. To this solution was added K$_2$CO$_3$ (16 g, 116 mmol) followed by iodomethane (5.4 mL, 87 mmol). The reaction mixture was slowly warmed to ambient temperature over 1 h at which time it became a yellow heterogeneous solution. This mixture was heated at 90° C. for 1 h and then cooled to ambient temperature. The solution was diluted with brine, extracted with diethyl ether, dried over anhydrous Na$_2$SO$_4$, filtered, and concentrated to afford 14.8 g (87%) of 3-hydroxypyrrolidine-1,2-dicarboxylic acid 1-tert-butyl ester 2-methyl ester (61) as a yellow oil (See: Demange, L.; Cluzeau, J.; Menez, A.; Dugave, C. *Tetrahedron Lett.* 2001, 42, 651).

Scheme LX

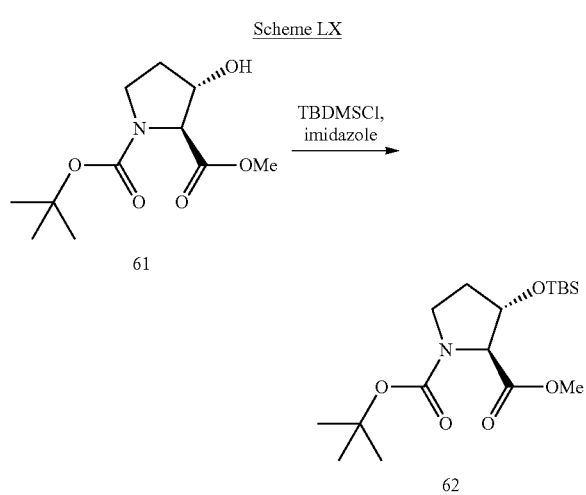

3-(tert-Butyl-dimethyl-silanyloxy)-pyrrolidine-1,2-dicarboxylic acid 1-tert-butyl ester 2-methyl ester (62): A solution containing 3-hydroxypyrrolidine-1,2-dicarboxylic acid 1-tert-butyl ester 2-methyl ester (61, 14.8 g, 60 mmol) in DCM (150 mL) was cooled to 0° C. To this solution was added imidazole (5.4 g, 79 mmol) followed by t-butyl-dimethylsilyl-chloride (10 g, 66 mmol) in two portions. The reaction mixture was warmed to ambient temperature over 1 h. After 5 h, the reaction mixture was diluted with 1M HCl and extracted twice with DCM. The combined organic extracts were dried over anhydrous Na$_2$SO$_4$, filtered, and concentrated to afford 21.2 g (99%) of 3-(tert-butyldimethylsilanyloxy)pyrrolidine-1,2-dicarboxylic acid 1-tert-butyl ester 2-methyl ester (62) as a yellow oil. $^1$H NMR (CDCl$_3$, 300 MHz): δ4.38-4.34 (m, 1H), 4.18 (br s, rotomers, 0.5H), 4.04 (app d, J=2.1 Hz, rotomers, 0.5H), 3.74 (s, 3H), 3.62-3.50 (m, 2H), 2.04-1.96 (m, 1H), 1.85-1.78 (m, 1H), 1.46 (s, minor rotomer), 1.41 (s, 9H), 0.92 (s, minor rotomer), 0.86 (s, 9H), 0.11 (s, 6H), 0.09 (s, minor rotomer) ppm.

Scheme LXI

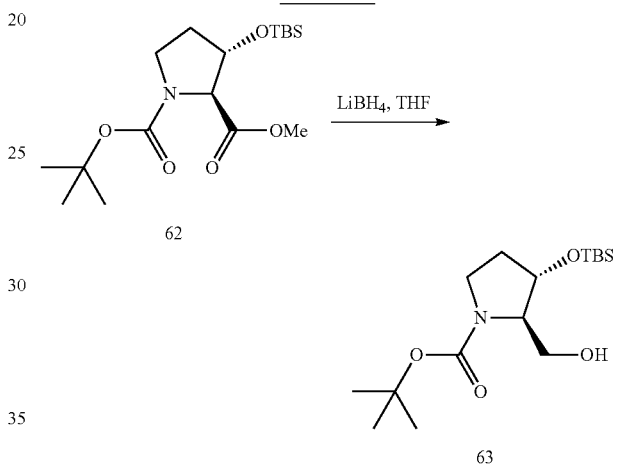

3-(tert-Butyl-dimethyl-silanyloxy)-2-hydroxymethyl-pyrrolidine-1-carboxylic acid tert-butyl ester (63): A solution containing 3-(tert-Butyldimethylsilanyloxy)pyrrolidine-1,2-dicarboxylic acid 1-tert-butyl ester 2-methyl ester (62, 12 g, 33 mmol) in THF (50 mL) was cooled to 0° C. LiBH$_4$ in THF (2M, 20 mL) was added in a dropwise fashion. After 1 h, the solution was warmed to ambient temperature. After 2 h, the solution was diluted with MeOH, then H$_2$O, and concentrated. The residue was extracted with EtOAc, washed with 1M HCl, saturated aqueous NaHCO$_3$, brine, dried over anhydrous Na$_2$SO$_4$, filtered, and concentrated to afford 9.5 g (87%) of 3-(tert-Butyldimethylsilanyloxy)-2-hydroxymethylpyrrolidine-1-carboxylic acid tert-butyl ester (63) as a colorless oil (See: Herdeis, C.; Hubmann, H. P.; Lotter, H. *Tetrahedron: Asymmetry*, 1994, 5, 119).

Scheme LXII

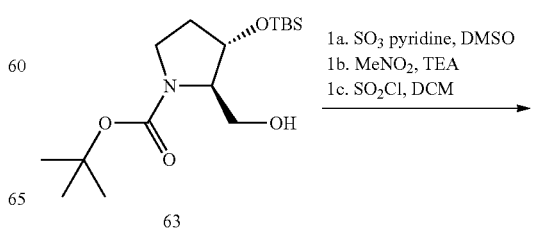

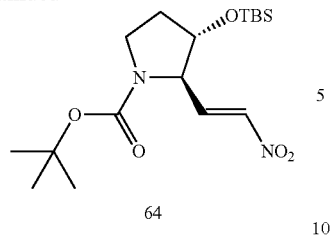

64

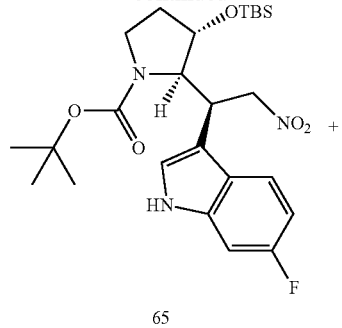

65

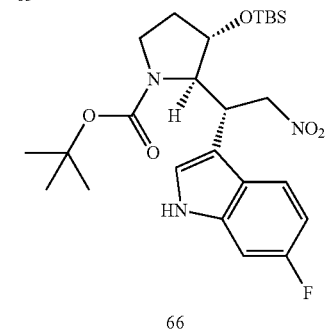

66

3S-(tert-Butyl-dimethyl-silanyloxy)-2R-(2-nitro-vinyl)-pyrrolidine-1-carboxylic acid tert-butyl ester (64): To a stirred solution containing alcohol 63 (5.7 g, 17.2 mmol) in DCM (60 mL) was added at ambient temperature Et$_3$N (14 mL, 103 mmol) and DMSO (50 mL). The reaction mixture was cooled to 0° C. and a solution of SO$_3$.pyridine (11.0 g, 69 mmol) in DMSO (50 mL) was added in a dropwise fashion. After 1 h, the reaction was warmed to ambient temperature. After 1 h, the reaction mixture was poured onto a 30% citric acid/ice mixture. The aqueous layer was extracted with DCM (3×250 mL) and the combined organic extracts were washed with brine (400 mL), dried over anhydrous Na$_2$SO$_4$, filtered, and concentrated to afford 5.6 g (99%) of crude N-Boc-(3S-OTBS)-2R-prolinal as a yellow-colored oil.

To a stirred solution containing crude N-Boc-(3S-OTBS)-2R-prolinal (5.6 g, 17 mmol) in nitromethane (30 mL) was added Et$_3$N (1.5 mL). After 12 h, the reaction mixture was concentrated in vacuo to afford 6.6 g (99%) of the intermediate carbinol as a yellow-colored oil.

To a solution containing crude carbinol (6.6 g, 17 mmol) at −78° C. in DCM (30 mL) was added thionyl chloride (2.60 g, 21.9 mmol) in CH$_2$Cl$_2$ (15 mL). After 1 h, TEA (6.96 mL, 68.8 mmol) was added and, after an additional 1 h at −78° C., the reaction mixture was quenched with MeOH (15 mL), H$_2$O (20 mL), and saturated aqueous NaHCO$_3$ (20 mL) followed by warming to 0° C. After 1 h, the reaction mixture was concentrated in vacuo and extracted with EtOAc (3×200 mL). The combined organic extracts were washed with brine (300 mL), dried over anhydrous Na$_2$SO$_4$, filtered, and concentrated to afford 6.1 g (98%) of 64 as an orange-colored oil. $^1$H NMR (CDCl$_3$, 300 MHz): δ7.04 (dd, J=13.2, 6.5 Hz, 1H), 6.91 (d, J=13.2 Hz, 1H), 4.08 (m, 1H), 3.54 (m, 2H), 3.37 (m, 1H), 1.80 (m, 2H), 1.35 (d, J=13.2 Hz, 6H), 0.80 (s, 9H), 0.00 (s, 9H) ppm. Mass spectrum, m/z calcd for C$_{12}$H$_{24}$NO$_3$Si [M+H]$^+$ 272.53. Found 272.84.

Scheme LXIII

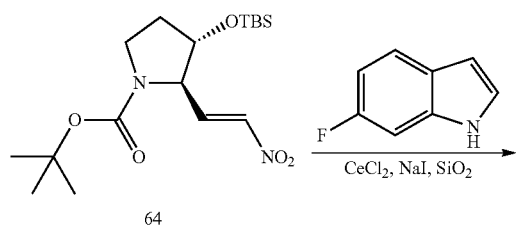

64

3S-(tert-Butyl-dimethyl-silanyloxy)-2R-[1S-(6-F-indol-3-yl)-2-nitro-ethyl]-pyrrolidine-1-carboxylic acid tert-butyl ester (65) and 3S-(tert-Butyl-dimethyl-silanyloxy)-2R-[1R-(6-F-indol-3-yl)-2-nitro-ethyl]-pyrrolidine-1-carboxylic acid tert-butyl ester (66): (See: Bartoli, G.; et al. *J. Org. Chem.* 2005, 70, 1941) A 1 L round-bottomed flask was charged with CeCl$_3$.7H$_2$O (10.3 g, 27.7 mmol), NaI (4.2 g, 27.7 mmol), and reagent grade MeOH (200 mL). To the clear, water-white solution was added silica gel (Fisher Grade 60, 230-400 mesh, 45 g) and the white, heterogeneous mixture was concentrated in vacuo (rotovap bath temp: 40° C.). To the white, free-flowing CeCl$_2$/NaI/SiO$_2$ was added 64 (25.8 g, 69.2 mmol) and 6-F-indole (11.2 g, 83.1 mmol) in anhydrous ACN (160 mL) and the pale orange mixture was concentrated under high vacuum (bath temp: 40° C.). The orange-brown solid was allowed to stand at ambient temperature. After 16 h, the solid residue was poured atop a short column of silica gel and the products were eluted (20% EtOAc/hexanes to 40% EtOAc/hexanes). The diastereomers were separated by normal phase HPLC (2" Dynamax® SiO$_2$; 10-50% EtOAc/hexanes over 30 min; Flow: 40 mL/min) to afford 12 g (34%) of isomer 65, and 10 g (28%) of isomer 66 together with some recovered 64 [TLC analysis, SiO$_2$, 4:1 hexanes/EtOAc; R$_f$(64)=0.6; R$_f$(65)=0.48; R$_f$(66)=0.45].

65: $^1$H NMR (CDCl$_3$, 300 MHz), ~3:2 mixture of carbamate rotamers: δ8.86 (br s, 0.4H, minor rotamer), 8.83 (br s, 0.6H, major rotamer), 8.15 (dd, J=5.1, 8.7 Hz, 0.6H, major rotamer), 8.04 (dd, J=5.4, 9.0 Hz, 0.4H, minor rotamer), 7.55 (d, J=2.4 Hz, 0.6H, major rotamer), 7.53 (br s, 1H), 7.50 (d, J=2.1 Hz, 0.4H, minor rotamer), 7.40 (app t, J=8.7 Hz, 0.6H, major rotamer), 7.39 (app t, J=9.3 Hz, 0.4H, minor rotamer), 5.74-5.35 (m, 1H), 5.29-5.20 (m, 1H), 4.68 (app t, J=11.4 Hz, 1H), 4.43 (m, 1H), 4.24-3.95 (m, 2H), 3.82 (t, J=9.6 Hz, 1H), 2.61 (m, 1H), 2.28 (m, 1H), 2.08 (s, 3H, minor rotamer), 1.99 (s, 6H, major rotamer), 1.14 (s, 9H), 0.10 (s, 1H, minor rotamer), 0.09 (s, 2H, major rotamer), 0.01 (s, 2H, major rotamer), 0.00 (s, 1H, minor rotamer) ppm; $^{13}$C NMR (300 MHz, CDCl$_3$), ~3:2 mixture of carbamate rotamers: δ171.2, 161.3, 157.5 (d, J$_{CF}$=102.4 Hz), 157.1 (d, J$_{CF}$=164.2 Hz), 136.7 (d, J$_{CF}$=11.1 Hz), 136.5 (d, J$_{CF}$=12.3 Hz), 123.3 (d, J$_{CF}$=18.3 Hz), 122.3 (d, J$_{CF}$=18.9 Hz), 119.3 (d, J$_{CF}$=30.9 Hz), 111.3 (d, J$_{CF}$=37.2 Hz), 108.3 (d, J$_{CF}$=25.5 Hz), 98.1 (d, J$_{CF}$=23.1 Hz), 97.8 (d, J$_{CF}$=24.6 Hz), 80.8, 79.4, 74.2, 73.8, 68.9, 68.8, 60.3, 45.2, 44.9, 40.4, 39.9, 32.0, 31.1, 28.3, 28.2, 25.2, 20.7, 17.5, 13.9, −5.6, −5.7 ppm. Mass spectrum, m/z [408.2] (M-Boc)+.

66: $^1$H NMR (CDCl$_3$, 300 MHz), ~3:2 mixture of carbamate rotomers: δ9.03 (br s, 0.4H, minor rotomer), 8.92 (br s, 0.6H, major rotomer), 8.03 (m, 1H), 7.52-7.44 (m, 2H), 7.36 (app t, J=8.4 Hz, 1H), 5.42-5.19 (m, 2H), 4.79 (m, 1H), 4.63 (m, 2H), 4.07-3.86 (m, 1H), 3.63-3.46 (m, 1H), 2.06 (s, 3H, minor rotomer), 1.99 (s, 6H, major rotomer), 1.95 (m, 1H), 1.65 (m, 1H), 1.27 (s, 6H, major rotomer), 1.20 (s, 3H, minor rotomer), 0.38-0.25 (m, 6H) ppm; $^{13}$C NMR (300 MHz, CDCl$_3$), ~3:2 mixture of carbamate rotomers: δ171.4, 161.5, 157.3 (d, J$_{CF}$=151.9 Hz), 157.1 (d, J$_{CF}$=186.9 Hz), 136.2 (d, J$_{CF}$=12.3 Hz), 123.2, 122.5 (d, J$_{CF}$=24.9 Hz), 119.5 (d, J$_{CF}$=36.0 Hz), 110.8, 108.5 (d, J$_{CF}$=24.3 Hz), 97.8 (d, J$_{CF}$=28.9 Hz), 81.2, 79.9, 78.0, 75.1, 68.8, 60.4, 46.3, 38.8, 37.9, 33.2, 32.5, 28.4, 25.5, 25.4, 20.9, 17.7, 14.1, −5.1, −5.4 ppm. Mass spectrum, m/z [408.2] (M-Boc)+.

was concentrated and the residue was dissolved in EtOAc, washed with saturated NaHCO$_3$, brine, dried over anhydrous Na$_2$SO$_4$, filtered and concentrated to give 67 (10.7, 95%) as a yellow foam. $^1$H NMR (CDCl$_3$, 300 MHz), mixture of carbamate rotomers: δ9.30 (br s, 0.5H), 9.07 (br s, 0.5H), 7.86-7.75 (m, 1H), 7.24 (app t, J=6.6 Hz, 1H), 7.15 (s, 1H), 7.08 (ap t, J=9.0 Hz, 1H), 4.38-4.30 (m, 3H), 3.86-3.61 (m, 2H), 3.44-3.28 (m, 3H), 1.71 (s, 9H), 0.96 (s, 9H), 0.06 (s, 3H), 0.001 (s, 3H) ppm; $^{13}$C NMR (CDCl$_3$, 75 MHz), mixture of carbamate rotomers: δ166.5 & 163.4, 161.3 (J$_{CF}$=13.5 Hz), 141.7 (J$_{CF}$=12.1 Hz), 129.4, 127.6 & 127.3, 125.1 (J$_{CF}$=10.4 Hz) & 124.8 (J$_{CF}$=10.4 Hz), 119.1 & 118.5, 113.2 & 112.9, 102.8 (J$_{CF}$=17.6 Hz) & 102.5 (J$_{CF}$=16.6 Hz), 85.1 & 84.4, 80.4 & 80.1, 74.7 & 74.1, 51.4 & 51.1, 48.5, 38.5 & 37.7, 33.6 & 30.7, 22.9, 0.09 ppm. Mass spectrum, m/z [478.3] (M+H)+.

Scheme LXV

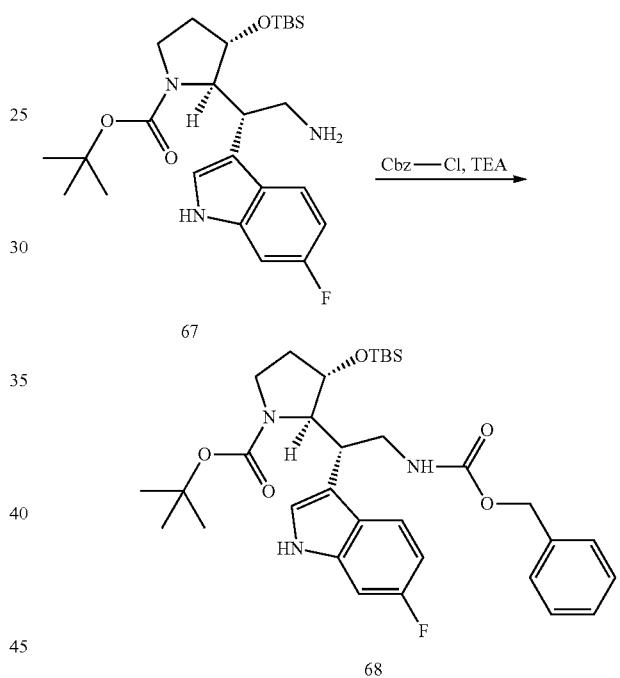

Scheme LXIV

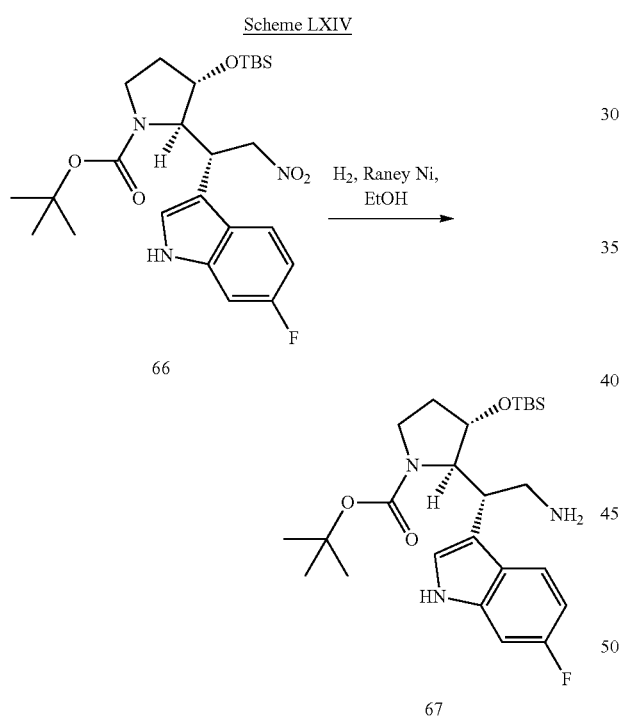

2R-[2-Amino-1S-(6-F-indol-3-yl)-ethyl]-3S-(tert-butyl-dimethyl-silanyloxy)-pyrrolidine-1-carboxylic acid tert-butyl ester (67). A Parr bottle was charged with 66 (12 g, 23.7 mmol) and Raney Ni (20 mL, 2400 Ni slurry in H$_2$O) in EtOH (120 mL) and subjected to 50 PSI H$_2$ pressure (379.2 KPa). Rapid absorption of H$_2$ was observed and the reaction was twice recharged to 50 PSI H$_2$ (379.2 KPa). After 1.5 h, the reaction mixture was filtered through diatomaceous earth (Celite®) and the solids were washed with EtOH. The filtrate 2R-[2-Benzyloxycarbonylamino-1S-(6-fluoro-1H-indol-3-yl)-ethyl]-3S-(tert-butyl-dimethyl-silanyloxy)-pyrrolidine-1-carboxylic acid tert-butyl ester (68): To a solution of DCM (10 mL) containing crude 67 (10.7 g, 22.4 mmol) at 0° C. was added TEA (4.8 mL, 34.5 mmol) followed by Cbz-Cl (3.5 mL, 25 mmol). After 1 h, the reaction was warmed to room temperature. After 1.5 h, the reaction mixture was diluted with DCM, washed successively with 1N HCl and brine, dried over anhydrous Na$_2$SO$_4$, filtered, and concentrated to afford 68 (13.5 g, 98%). $^1$H NMR (CDCl$_3$, 300 MHz): δ8.73 (br s, 1H), 7.57 (app q, J=5.1 Hz, 1H), 7.48-7.32 (m, 5H), 7.10 (m, 1H), 6.91 (m, 1H), 6.45 (br s, 1H), 5.20 (s, 2H), 4.24-4.09 (m, 2H), 3.65-3.40 (m, 4H), 3.02 (app t, J=9.6 Hz, 1H), 1.57 (s, 9H), 0.87 (s, 9H), 0.00 (s, 6H) ppm. Mass spectrum, m/z [612.4] (M+H)+.

Scheme LXVI

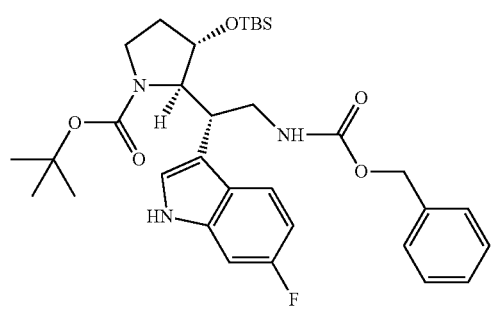

68

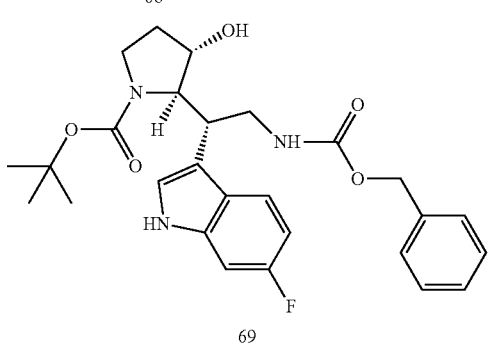

69

2R-[2-Benzyloxycarbonylamino-1S-(6-fluoro-1H-indol-3-yl)-ethyl]-3S-hydroxy-pyrrolidine-1-carboxylic acid tert-butyl ester (69): A solution of 68 (13.5 g, 22.0 mmol) in THF (60 mL) was treated with TBAF (45 mL, 1M in THF, 45 mmol) at ambient temperature. After 5 h, the reaction mixture was warmed for 1 h at 45° C. and then diluted with EtOAc, washed successively with 1N HCl and brine, dried over anhydrous Na$_2$SO$_4$, filtered, and concentrated to afford crude 10 which was purified by flash silica gel chromatography (1:2 hexanes/EtOAc) to afford 10.1 g (93%) of 69 as light peach-colored foam. $^1$H NMR (CDCl$_3$, 300 MHz): δ8.88 (s, 1H), 7.40-7.31 (m, 5H), 6.94 (app d, J=9.6 Hz, 1H), 6.81-6.75 (m, 1H), 6.67 (s, 1H), 6.45 (m, 1H), 5.12 (app q, J=11.7 Hz, 2H), 4.18-4.03 (m, 2H), 3.51-3.34 (m, 4H), 2.92 (app t, J=9.9 Hz, 1H), 2.33 (br s, 1H), 1.48 (s, 9H), 0.91-0.86 (m, 1H) ppm; $^{13}$C NMR (CDCl$_3$, 75 MHz) δ158.5, 157.2, 157.0, 136.9, 136.5, 136.3, 128.7, 128.3, 123.7, 122.8, 120.6, 113.6, 108.7, 108.4, 98.0, 97.7, 80.1, 75.7, 67.3, 66.9, 46.5, 43.4, 41.1, 32.3, 28.7 ppm. Mass spectrum, m/z [498.2] (M+H)+.

Scheme LXVII

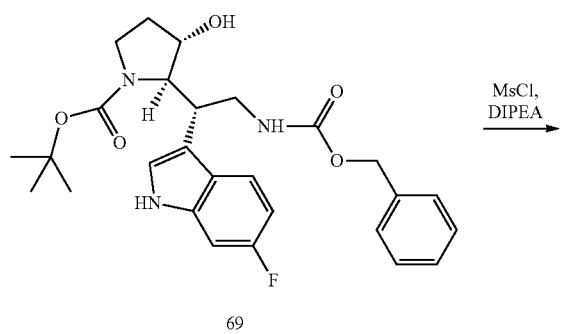

69

-continued

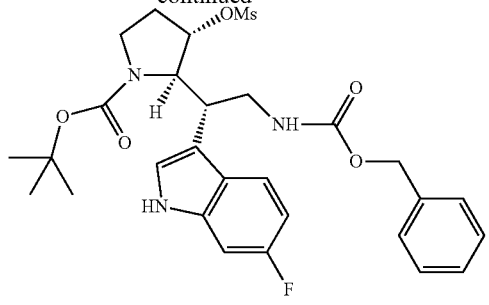

70

2R-[2-Benzyloxycarbonylamino-1S-(6-fluoro-1H-indol-3-yl)-ethyl]-3S-methanesulfonyloxy-pyrrolidine-1-carboxylic acid tert-butyl ester (70): A solution of 69 (10.0 g, 20.1 mmol) in DCM (100 mL) was cooled to 0° C. A solution of MsCl (1.5 mL, 19.4 mmol) in DCM (3 mL) was added dropwise followed by the addition of DMAP (250 mg, 2.0 mmol). After 3 h at 0° C., the reaction mixture was diluted with DCM, washed successively with 1N HCl, water, and brine, dried over anhydrous Na$_2$SO$_4$, filtered, and concentrated to afford 70 (10.4 g, 90%) as a light peach colored foam. $^1$H NMR (CDCl$_3$, 300 MHz): δ8.71 (s, 1H), 7.50 (app q, J=5.4 Hz, 1H), 7.38-7.32 (m, 5H), 7.00 (app d, J=8.4 Hz, 1H), 6.89-6.81 (m, 2H), 6.29 (br s, 1H), 5.14 (s, 2H), 4.92 (app d, J=3.9 Hz, 1H), 4.52 (s, 1H), 3.55-3.39 (m, 4H), 3.04 (app t, J=9.9 Hz, 1H), 2.79 (s, 3H), 1.82 (app q, J=7.5 Hz, 1H), 1.52 (s, 9H), 1.14 (m, 1H) ppm. Mass spectrum, m/z [576.3] (M+H)+.

Scheme LXVIII

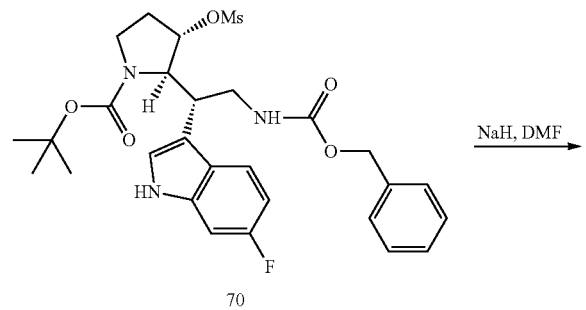

70

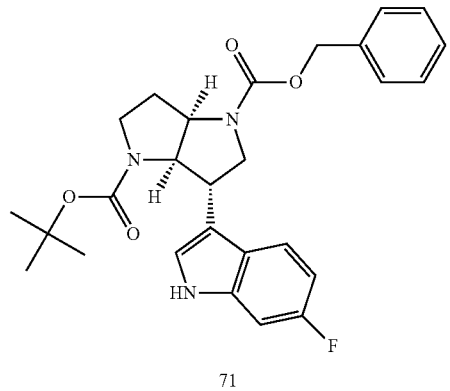

71

(3aR,6aR)-6S-(6-fluoro-1H-Indol-3-yl)-hexahydro-pyrrolo[3,2-b]pyrrole-1-carboxylic acid tert-butyl ester (71): A solution of 70 (10.4 g, 18 mmol) in DMF (30 mL) was added to a suspension of NaH (1.9 g, 60%, 46 mmol) in DMF (100 mL) at 0° C. After 1 h, the reaction mixture was diluted with H₂O, extracted with diethyl ether, washed with brine, dried over anhydrous Na₂SO₄, filtered, and concentrated to give 71 (8.3 g, 97%) as a light tan colored solid. ¹H NMR (CDCl₃, 300 MHz), mixture of carbamate rotomers: δ 8.25 (br s, 0.5H), 8.16 (s, 0.5H), 8.04 (dd, J=8.4, 14.1 Hz, 0.5H), 7.95 (dd, J=7.8, 13.5 Hz, 0.5H), 7.71 (m, 0.5H), 7.64 (m, 0.5H), 7.34 (m, 4H), 6.99 (app t, J=13.2 Hz, 1H), 6.91-6.84 (m, 1H), 6.81-6.76 (m, 0.5H), 6.68-6.61 (m, 0.5H), 5.24-5.15 (m, 2H), 4.46-4.31 (m, 2H), 4.20-4.02 (m, 1H), 3.96 (m, 1H), 3.84-3.68 (m, 1H), 3.63 (app q, J=5.7 Hz, 1H), 3.25 (m, 1H), 2.31 (dd, J=6.0, 13.5 Hz, 0.5H), 2.14 (dd, J=5.7, 13.5 Hz, 0.5H), 1.94-1.84 (m, 1H), 1.52 (s, 7H), 1.31-1.26 (m, 2H), 0.91-0.83 (m, 2H) ppm.

Scheme LXX

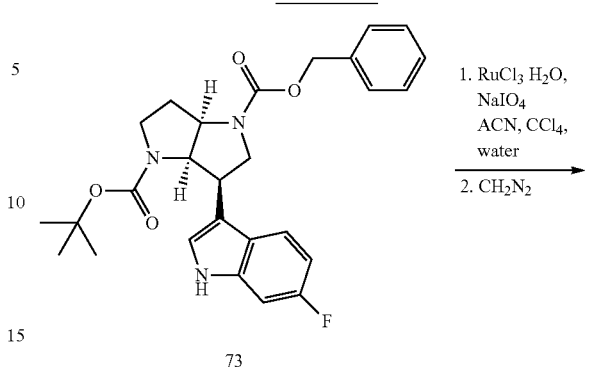

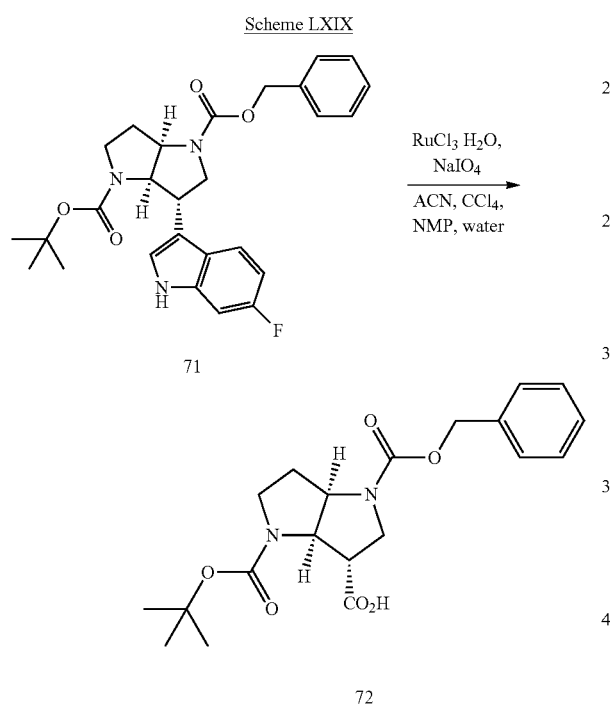

Hexahydro-pyrrolo[3,2-b]pyrrole-1,3,4-tricarboxylic acid 1-benzyl ester 4-tert-butyl ester 3-methyl ester (74): Indole 73 (0.5 g, 1.1 mmol) [prepared from compound 65 using the procedures described in Schemes LXIV through LXVIII] was dissolved in ACN (5 mL), CCl₄ (5 mL), and H₂O (10 mL). To this biphasic solution was added NaIO₄ (3.4 g, 16 mmol). After 10 min, RuCl₃.hydrate (23 mg, 0.14 mmol) was added and the solution immediately turned dark orange. Precipitation was observed after about 10 min. After 3.5 h, the solution was diluted with EtOAc and washed with brine (2×). The combined organic extracts were dried over anhydrous Na₂SO₄, filtered and concentrated to give the crude acid as a dark brown oil (460 mg) which was diluted with EtOAc (10 mL) and treated with DMSO (0.10 mL) and stirred at ambient temperature overnight. The solution was then concentrated and used without further purification.

To a solution of the crude acid (0.47 g) in Et₂O (5 mL) was added an ethereal solution of diazomethane that was prepared by treatment of N-nitroso-N-methyl urea (0.6 g) in Et₂O (10 mL) with 1M KOH (10 mL). After consumption of starting material (monitored by TLC), the reaction mixture was diluted with HOAc (5 mL). The solution was extracted with EtOAc, washed with saturated NaHCO₃, brine, dried over anhydrous Na₂SO₄, filtered and concentrated to give a dark oil that was purified by HPLC (2" Dynamax® SiO₂, 10% EtOAc/hexane to 100% EtOAc over 30 min) to give 74 (0.15 g) as a yellow-colored oil. ¹H NMR (CDCl₃, 300 MHz): δ 7.35 (m, 5H), 5.19-5.08 (m, 2H), 4.69 (m, 1H), 4.53-4.49 (m, 1H), 3.92-3.84 (m, 2H), 3.69 (s, 3H), 3.25-3.08 (m, 2H), 2.22-1.95 (m, 2H), 1.42 (s, 9H) ppm. Mass spectrum, m/z [405.2] (M+H)+.

Hexahydro-pyrrolo[3,2-b]pyrrole-1,3,4-tricarboxylic acid 1-benzyl ester 4-tert-butyl ester (72): A solution of 71 (0.5 g, 1.1 mmol) was dissolved in NMP (5 mL). To this solution was added ACN (10 mL), CCl₄ (10 mL), and H₂O (20 mL). To this biphasic solution was added NaIO₄ (3.4 g, 16 mmol). After 10 min, RuCl₃.hydrate (29 mg, 0.14 mmol) was added and the solution immediately turned dark orange. Precipitation was observed after about 10 min. After 3.5 h, the solution was diluted with EtOAc and washed with brine (2×). The combined organic extracts were dried over anhydrous Na₂SO₄, filtered and concentrated to give crude 72 as a dark brown-colored oil (470 mg) which was diluted with EtOAc (10 mL) and treated with DMSO (0.15 mL) and stirred at ambient temperature overnight. The solution was then concentrated and used without further purification. ¹H NMR (CDCl₃, 300 MHz): δ 7.36-7.29 (m, 5H), 5.14 (m, 2H), 4.55 (m, 2H), 3.75-3.53 (m, 1H), 3.32-3.17 (m, 1H), 2.38 (app t, J=8.4 Hz, 1H), 1.47 (s, 9H) ppm. Mass spectrum, m/z [391.2] (M+H)+.

Scheme LXXI

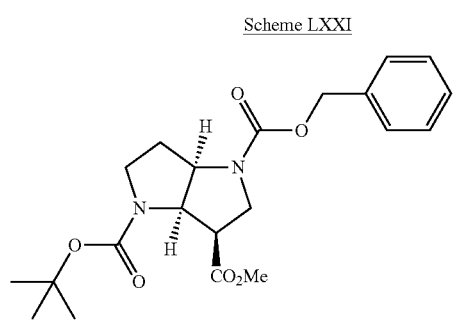

74

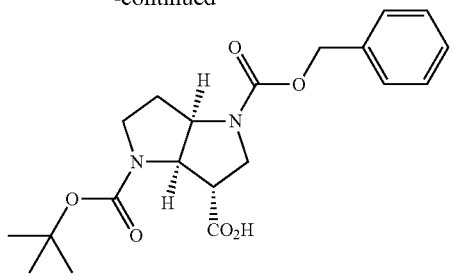

72

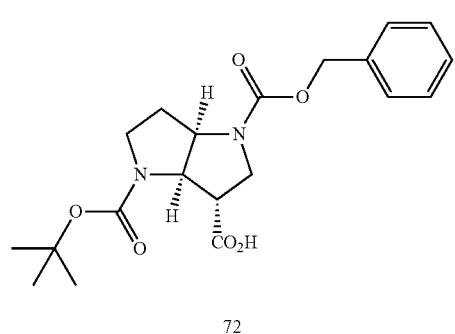

72

Hexahydro-pyrrolo[3,2-b]pyrrole-1,3,4-tricarboxylic acid 1-benzyl ester 4-tert-butyl ester (72): A solution of 74 (1.4 g, 3.5 mmol) in MeOH (20 mL) was added to a solution of NaOMe (0.34 g, 6.3 mmol) in MeOH at ambient temperature. The reaction mixture was stirred for 16 h and then concentrated. The residue was diluted with EtOAc, washed successively with 1M HCl, brine, dried over anhydrous Na$_2$SO$_4$, filtered and concentrated to afford 72 as an orange-colored foam (1.39 g) that was used without further purification.

Scheme LXXII

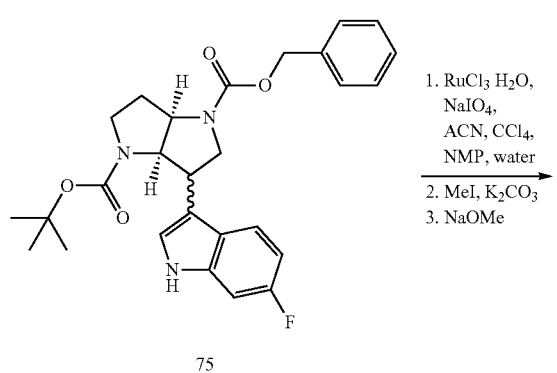

75

Hexahydro-pyrrolo[3,2-b]pyrrole-1,3,4-tricarboxylic acid 1-benzyl ester 4-tert-butyl ester (72): A solution of 75 (mixture of diastereomers, 1.5 g, 3.1 mmol) [The mixture of diastereomers was prepared from the mixture of diastereomers (65 and 66) generated in Scheme LXIII using the procedures described in Schemes LXIV through LXVIII on the diastereomeric mixture produced in each step] in NMP (5 mL), MeCN (10 mL), CCl$_4$ (10 mL) and H$_2$O (20 mL) was treated with NaIO$_4$ (9.3 g, 44 mmol) in one portion. After 10 min, RuCl$_3$.H$_2$O (57 mg, 0.28 mmol) was added and the solution immediately turned dark orange. After ~10 min, the reaction mixture became warm and precipitation was observed. After 7.5 h, the solution was diluted with EtOAc and 1M HCl and filtered through Celite®, and rinsed with EtOAc. The filtrate was extracted with EtOAc, washed successively with 1M HCl, 10% Na$_2$S$_2$O$_3$, brine, dried over anhydrous Na$_2$SO$_4$, filtered and concentrated to give a mixture of crude acids as a dark brown oil (1.4 g) which was used without further purification.

A solution of crude acids (1.4 g, 3.6 mmol) in DMF (20 mL) was cooled to 0° C. and treated with K$_2$CO$_3$ (2.5 g, 18.1 mmol). After 10 min, this suspension was treated with CH$_3$I (0.65 mL, 10.4 mmol) and the reaction mixture was allowed to warm to ambient temperature. After consumption of starting material (approximately 2 h, monitored by TLC), the reaction mixture was diluted with EtOAc, and 1M HCl. The layers were separated and the aqueous phase was extracted with EtOAc. The combined organic extracts were washed successively with 1M HCl, 10% Na$_2$S$_2$O$_3$, brine, dried over anhydrous Na$_2$SO$_4$, filtered and concentrated to give a dark brown residue. The dark residue was absorbed onto SiO$_2$ and purified by flash chromatography (1:1 hexane/EtOAc) to afford 0.69 g of a mixture of methyl esters (55%, 2 steps) as a yellow-colored foam.

To a suspension of NaOMe (2.0 g, 37 mmol) in MeOH (20 mL) was added a solution of methyl esters (1.3 g, 3.2 mmol) in a dropwise fashion at ambient temperature. The reaction mixture was stirred for 16 h and then concentrated. The residue was diluted with EtOAc, washed successively with 1M HCl, and brine, dried over anhydrous Na$_2$SO$_4$, filtered and concentrated to afford 72 as an orange-colored foam (1.1 g) that was used without further purification.

Scheme LXXIII

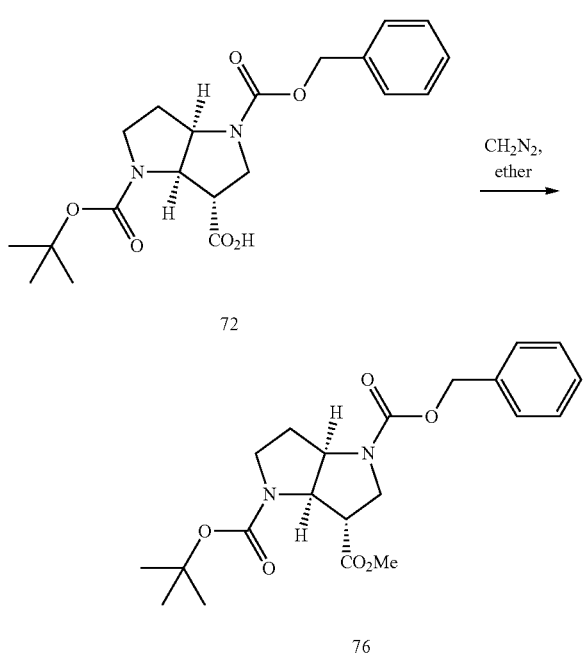

Hexahydro-pyrrolo[3,2-b]pyrrole-1,3,4-tricarboxylic acid 1-benzyl ester 4-tert-butyl ester 3-methyl ester (76): To a solution of crude 72 (0.47 g) in EtOAc (10 mL) and Et$_2$O (10 mL) was added an ethereal solution of diazomethane that was prepared by treatment of N-nitroso-N-methyl urea (0.5 g) in Et$_2$O (10 mL) with 1M KOH (10 mL). After consumption of starting material (monitored by TLC), the reaction mixture was diluted with HOAc. The solution was extracted with EtOAc, washed with saturated NaHCO$_3$, brine, dried over anhydrous Na$_2$SO$_4$, filtered and concentrated to give a dark oil that was purified by HPLC (2" Dynamax® SiO$_2$, 10% EtOAc/hexane to 100% EtOAc over 30 min) to give 76 (0.19 g) as a yellow-colored oil. $^1$H NMR (CDCl$_3$, 300 MHz): δ7.40-7.29 (m, 5H), 5.23-5.09 (m, 2H), 4.56-4.52 (m, 2H), 4.11-4.04 (m, 1H), 3.69 (s, 3H), 3.45-3.42 (m, 1H), 3.22-3.12 (m, 1H), 2.27-2.10 (m, 1H), 1.96 (m, 1H), 1.47 (s, 9H) ppm. Mass spectrum, m/z [405.2] (M+H)+.

Scheme LXXIV

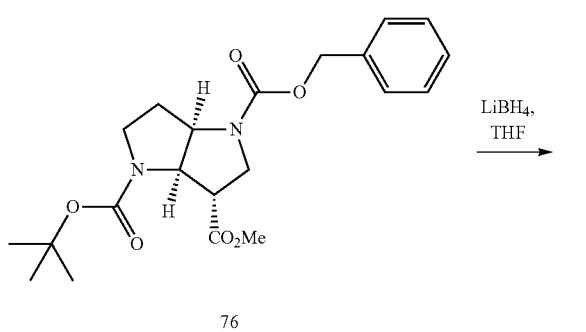

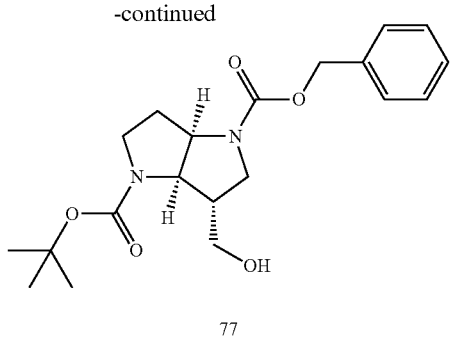

3-Hydroxymethyl-hexahydro-pyrrolo[3,2-b]pyrrole-1,4-dicarboxylic acid 1-benzyl ester 4-tert-butyl ester (77): A solution of ester 76 (2.7 g, 6.7 mmol) in THF (15 mL) was cooled to 0° C. and treated with LiBH$_4$ (10 mL, 2M in THF). After 3 h, the solution was slowly treated with MeOH followed by H$_2$O. The solution was then concentrated and diluted with EtOAc. The solution was slowly treated with 1M HCl until gas generation ceased. The solution was extracted with EtOAc, washed with brine, dried over anhydrous Na$_2$SO$_4$, filtered and concentrated. The residue was absorbed onto SiO$_2$ and purified by flash chromatography (1:1 hexane/EtOAc to 1:2 hexane/EtOAc) to afford alcohol 77 (1.9 g, 75%) as a light yellow-colored oil. $^1$H NMR (CDCl$_3$, 300 MHz): δ7.39-7.27 (m, 5H), 5.13-5.09 (m, 2H), 4.43-4.41 (m, 1H), 4.13-4.08 (m, 2H), 3.70-3.29 (m, 6H), 2.48-2.46 (m, 1H), 2.53-2.05 (m, 1H), 2.03-1.99 (m, 1H), 1.48 (s, 9H) ppm. Mass spectrum, m/z [377.5] (M+H)+.

Scheme LXXV

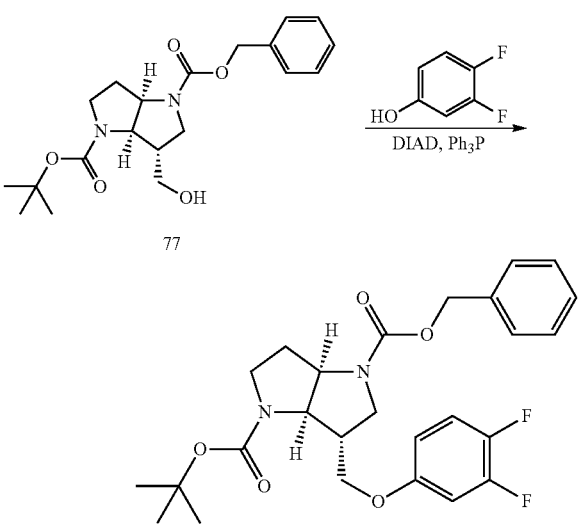

3-(3,4-Difluoro-phenoxymethyl)-hexahydro-pyrrolo[3,2-b]pyrrole-1,4-dicarboxylic acid 1-benzyl ester 4-tert-butyl ester (78): A solution of alcohol 77 (0.84 g, 2.2 mmol) in benzene (15 mL) was treated with 3,4-difluoro-phenol (402 mg, 3.1 mmol) and triphenylphosphine (864 mg, 3.3 mmol). To this solution was added DIAD (0.65 mL, 3.3 mmol) and the reaction mixture was stirred at ambient temperature. After 16 h, the solution was concentrated, diluted with DCM, washed with 1M NaOH, dried over anhydrous Na$_2$SO$_4$, filtered and concentrated. The aqueous phase was back-extracted with Et$_2$O and the combined organic extracts were absorbed on SiO$_2$ and purified by flash chromatography (3:1 hexane/EtOAc to 1:1 hexane/EtOAc) to afford 78 (0.86 g) which was contaminated with DIAD-related impurities and used without further purification.

Scheme LXXVI

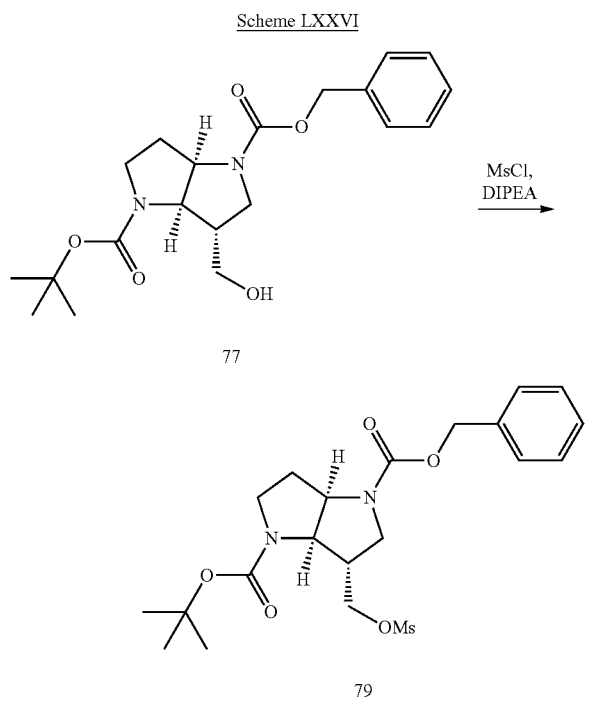

Scheme LXXVII

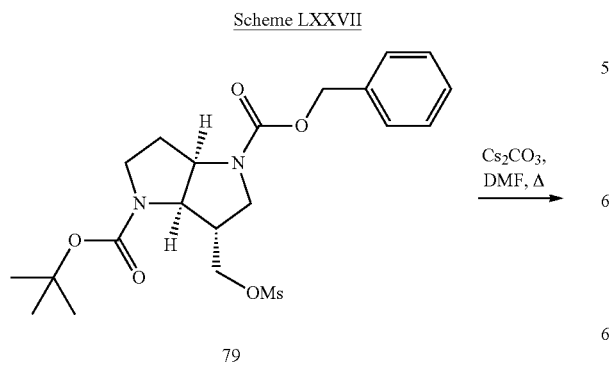

6-Methanesulfonyloxymethyl-hexahydro-pyrrolo[3,2-b]pyrrole-1-carboxylic acid tert-butyl ester (79): A solution of alcohol 77 (0.78 g, 2.1 mmol) in DCM (12 mL) was cooled to 0° C. and treated with DIPEA (0.55 mL, 3.2 mmol) followed by methanesulfonyl chloride (0.22 mL, 2.8 mmol). After 1 h, the solution was diluted with DCM, washed successively with 1M HCl, and brine, dried over anhydrous Na$_2$SO$_4$, filtered and concentrated to afford mesylate 79 as a light yellow-colored foam which was used without further purification. $^1$H NMR (CDCl$_3$, 300 MHz): δ7.36-7.31 (m, 5H), 5.19-5.09 (m, 2H), 4.45 (m, 1H), 4.29-4.04 (m, 3H), 3.71-3.44 (m, 4H), 3.22-3.12 (m, 1H), 2.96 (s, 3H), 2.85-2.70 (m, 1H), 2.21-1.99 (m, 2H), 1.49 (s, 9H) ppm.

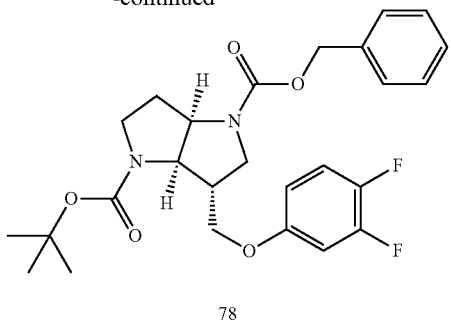

3-(3,4-Difluoro-phenoxymethyl)-hexahydro-pyrrolo[3,2-b]pyrrole-1,4-dicarboxylic acid 1-benzyl ester 4-tert-butyl ester (78): A solution of 3,4-difluoro-phenol (342 mg, 2.6 mmol) in DMF (5 mL) was treated with Cs$_2$CO$_3$ (1.0 g, 3.1 mmol). After 20 min, the yellow solution was treated with mesylate 79 (610 mg, 1.3 mmol) in DMF (5 mL). The reaction mixture was stirred at ambient temperature. After 16 h, the reaction mixture was heated at 60° C. for 3.5 h and then cooled to ambient temperature. The reaction mixture was diluted with Et$_2$O and water. The layers were separated and the aqueous phase was extracted with Et$_2$O. The combined organic extracts were washed with brine, dried over anhydrous Na$_2$SO$_4$, filtered and concentrated. The residue was purified by HPLC (2" Dynamax® SiO$_2$, 10% EtOAc/hexane to 100% EtOAc, 30 min; Flow: 40 mL/min) to afford the 78 (422 mg, 67%) as a light yellow-colored oil. $^1$H NMR (CDCl$_3$, 300 MHz): δ7.37-7.28 (m, 5H), 7.05-7.03 (m, 1H), 6.66-6.64 (m, 1H), 6.54-6.51 (m, 1H), 5.18-5.09 (m, 2H), 4.49-4.47 (m, 1H), 4.24-4.16 (m, 1H), 3.99 (m, 0.5H), 3.81-3.69 (m, 3H), 3.62 (m, 0.5H), 3.55-3.49 (m, 1H), 3.25-3.16 (m, 1H), 2.87-2.74 (m, 1H), 2.26-2.12 (m, 1H), 1.99 (m, 1H), 1.49 (s, 9H) ppm.

Scheme LXXVIII

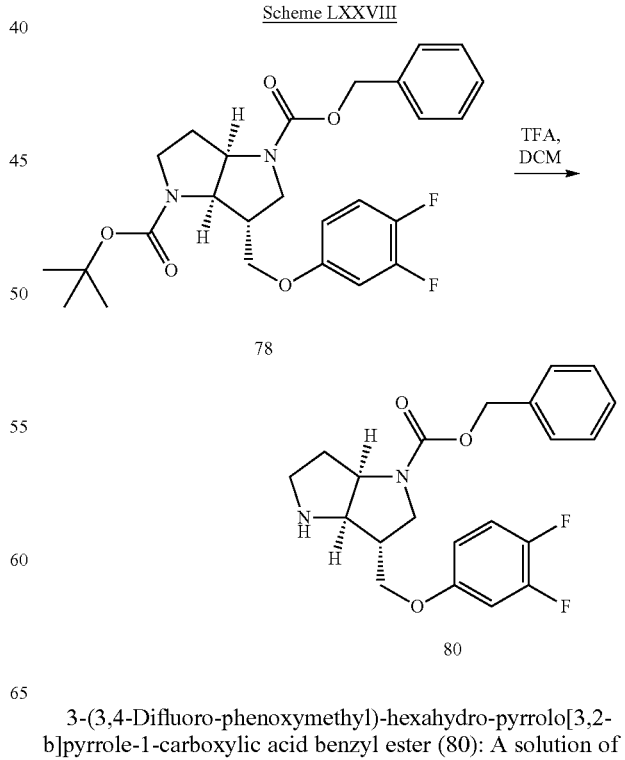

3-(3,4-Difluoro-phenoxymethyl)-hexahydro-pyrrolo[3,2-b]pyrrole-1-carboxylic acid benzyl ester (80): A solution of phenol-ether 78 (0.86 g, 1.8 mmol) in DCM (10 mL) was treated with TFA (3 mL) at 0° C. After 20 min, the reaction was warmed to ambient temperature. After 1 h, the solution was concentrated, diluted with EtOAc, washed successively with saturated aqueous NaHCO$_3$, and brine, dried over anhydrous Na$_2$SO$_4$, filtered and concentrated. The aqueous phase was back-extracted with DCM and the combined organic extracts were concentrated to give amine 80 as an orange-colored oil that was used without further purification. Mass spectrum, m/z [389.5] (M+H)+.

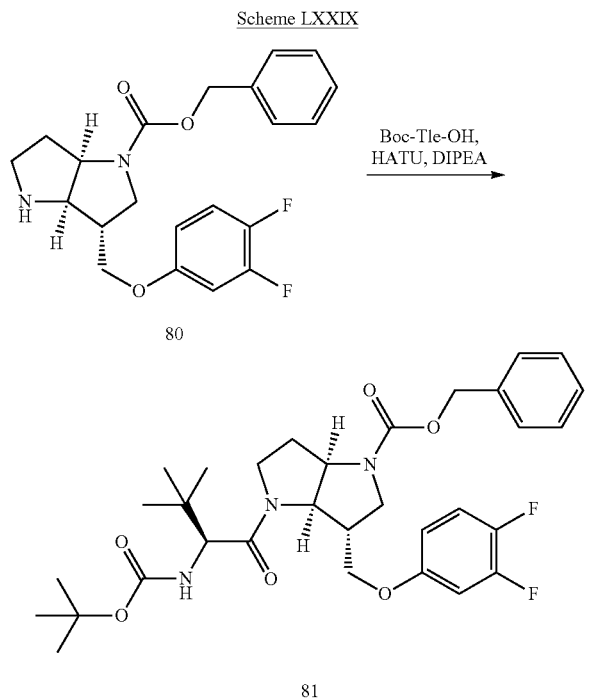

4-(2-tert-Butoxycarbonylamino-3,3-dimethyl-butyryl)-3-(3,4-difluoro-phenoxymethyl)-hexahydro-pyrrolo [3,2-b] pyrrole-1-carboxylic acid benzyl ester (81): A solution of Boc-Tle-OH (463 mg, 2.0 mmol) in NMP (6 mL) was cooled to 0° C. and treated with HATU (758 mg, 2.0 mmol) and DIPEA (0.45 mL, 2.5 mmol). After 10 min, amine 80 (772 mg, 2.0 mmol) in NMP (6 mL) was added. The reaction mixture was allowed to warm to ambient temperature. After 16 h, the solution was diluted with EtOAc, washed successively with 1M HCl, saturated aqueous NaHCO$_3$, and brine, dried over anhydrous Na$_2$SO$_4$, filtered and concentrated. The residue was diluted with ACN/water and purified by RP-HPLC (2" Dynamax® C18, 20% ACN/water to 100% ACN over 30 min; Flow: 40 mL/min). The product-containing fractions were combined, concentrated, and extracted with EtOAc. The organic extract was washed successively with saturated aqueous NaHCO$_3$, and brine, dried over anhydrous Na$_2$SO$_4$, and filtered. The aqueous phase was back-extracted with DCM and the combined organic extracts were concentrated to afford 81 (269 mg) as an off-white foam. $^1$H NMR (CDCl$_3$, 300 MHz): δ7.37-7.28 (m, 5H), 7.02 (app q, J=9.0 Hz, 1H), 6.66 (m, 1H), 6.52 (m, 1H), 5.28 (d, J=9.6 Hz, 1H), 5.19-5.13 (m, 2H), 4.46 (m, 2H), 4.31 (d, J=9.9 Hz, 1H), 4.01-3.98 (m, 2H), 3.85-3.76 (m, 2H), 3.46-3.37 (m, 2H), 2.81 (app q, J=5.7 Hz, 1H), 2.43 (m, 1H), 2.26 (m, 1H), 1.43 (s, 9H), 0.99 (s, 9H) ppm. Mass spectrum, m/z [602.8] (M+H)+.

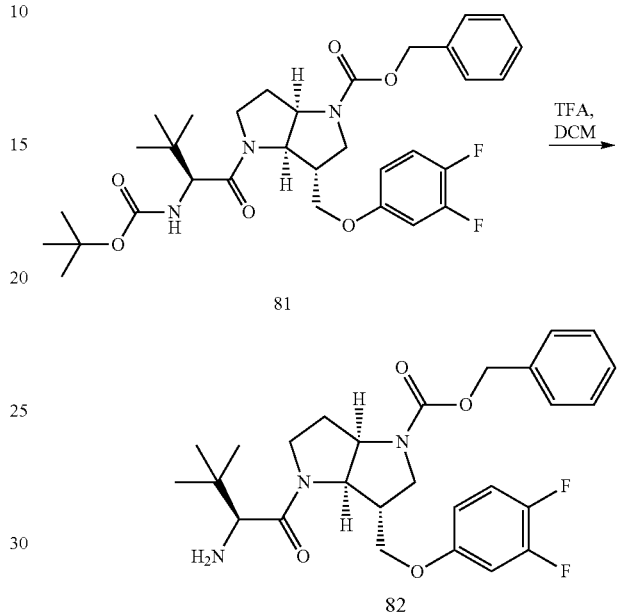

4-(2-Amino-3,3-dimethyl-butyryl)-3-(3,4-difluoro-phenoxymethyl)-hexahydro-pyrrolo[3,2-b]pyrrole-1-carboxylic acid benzyl ester (82): A solution of carbamate 81 (542 g, 0.90 mmol) in DCM (10 mL) was treated with TFA (3 mL) at 0° C. After 20 min, the reaction mixture was warmed to ambient temperature. After 1 h, the solution was concentrated, diluted with EtOAc, washed successively with saturated aqueous NaHCO$_3$, and brine, dried over anhydrous Na$_2$SO$_4$, and filtered. The aqueous phase was back-extracted with DCM and the combined organic extracts were concentrated to afford 82 (401 mg, 89%) as a light yellow-colored foam was used without further purification. $^1$H NMR (CDCl$_3$, 300 MHz): δ7.31-7.26 (m, 5H), 7.00-6.95 (m, 1H), 6.65-6.60 (m, 1H), 6.49-6.47 (m, 1H), 5.14-5.08 (m, 2H), 4.41 (m, 2H), 3.95-3.92 (m, 1H), 3.83-3.72 (m, 2H), 3.40-3.29 (m, 2H), 2.79 (app q, J=5.4 Hz, 1H), 2.34-2.19 (m, 1H), 1.66 (m, 2H), 0.94 (s, 9H) ppm. Mass spectrum, m/z [502.6] (M+H)+.

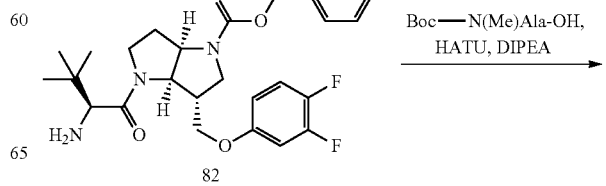

-continued

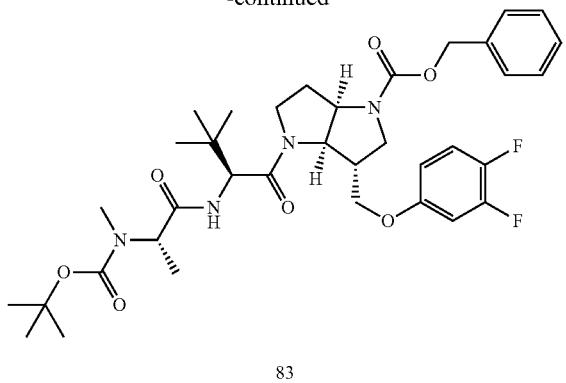

83

4-{2-[2-(tert-Butoxycarbonyl-methyl-amino)-propionylamino]-3,3-dimethyl-butyryl}-3-(3,4-difluoro-phenoxymethyl)-hexahydro-pyrrolo[3,2-b]pyrrole-1-carboxylic acid benzyl ester (83): A solution of Boc-N(Me)Ala-OH (181 mg, 0.89 mmol) in NMP (6 mL) was cooled to 0° C. and treated with HATU (345 mg, 0.91 mmol) and DIPEA (0.20 mL, 1.2 mmol). After 10 min, amine 82 (400 mg, 0.80 mmol) in NMP (5 mL) was added and the reaction mixture was allowed to warm to ambient temperature. After 16 h, the solution was diluted with EtOAc, washed successively with 1M HCl, saturated aqueous NaHCO$_3$, and brine, dried over anhydrous Na$_2$SO$_4$, filtered and concentrated to give 83 (546 mg) as an off-white foam that was used without further purification. $^1$H NMR (CDCl$_3$, 300 MHz): δ7.37-7.29 (m, 5H), 7.01 (app q, J=9.3 Hz, 1H), 6.66 (m, 1H), 6.53 (m, 1H), 5.19-5.09 (m, 2H), 4.69 (m, 1H), 4.62 (d, J=9.0 Hz, 1H), 4.49-4.44 (m, 2H), 4.05-3.97 (m, 1H), 3.84-3.77 (m, 1H), 3.48-3.36 (m, 1H), 2.79 (s, 3H), 1.50 (s, 9H), 1.32 (d, J=6.9 Hz, 3H), 0.98 (s, 9H) ppm. Mass spectrum, m/z [687.9] (M+H)+.

Scheme LXXXII

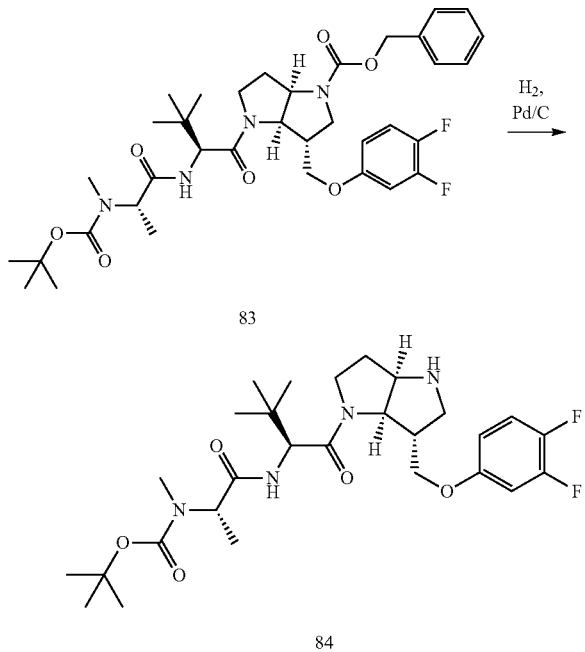

(1-{1-[6-(3,4-Difluoro-phenoxymethyl)-hexahydro-pyrrolo[3,2-b]pyrrole-1-carbonyl]-2,2-dimethyl-propylcarbamoyl}-ethyl)-methyl-carbamic acid tert-butyl ester (84): A solution of carbamate 83 (546 mg, 0.8 mmol) in MeOH (15 mL) was treated with 10% Pd/C (wet, 208 mg) and subjected to H$_2$ (50 psi) using a Parr apparatus. After 2.5 h, the reaction mixture was filtered through a filter disc (Acrodisc®, PSF—0.45 µM) with MeOH and concentrated to afford amine 84 (443 mg) as a light yellow-colored foam which was used without further purification. $^1$H NMR (CDCl$_3$, 300 MHz): δ7.07 (app q, J=9.6 Hz, 1H), 6.89-6.82 (m, 1H), 6.72-6.68 (m, 1H), 4.72-4.69 (m, 1H), 4.56 (d, J=9.3 Hz, 1H), 4.45 (dd, J=2.1, 6.0 Hz, 1H), 4.25-4.11 (m, 4H), 3.90-3.81 (m, 1H), 3.47-3.36 (m, 1H), 3.30-3.24 (m, 1H), 2.79 (s, 3H), 2.46-2.38 (m, 1H), 2.26-2.17 (m, 1H), 1.48 (s, 9H), 1.30 (d, J=6.9 Hz, 3H), 0.99 (s, 9H) ppm. Mass spectrum, m/z [553.7] (M+H)+.

Scheme LXXXIII

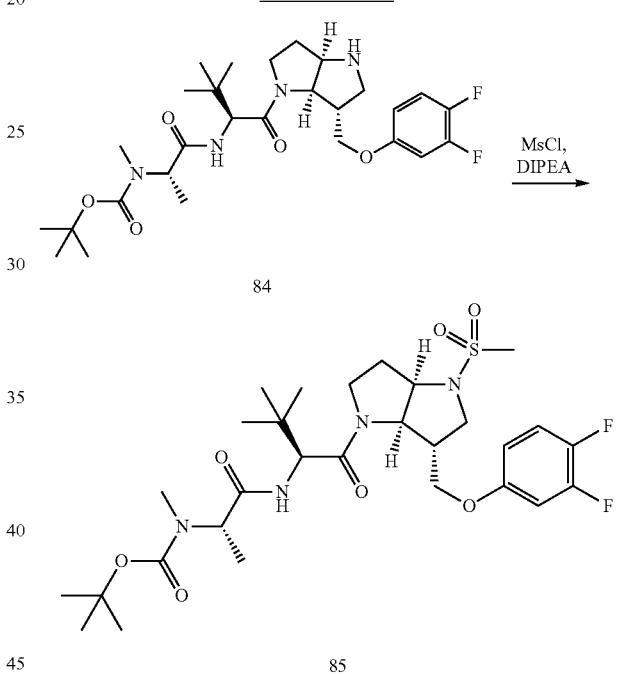

(1-{1-[6-(3,4-Difluoro-phenoxymethyl)-4-methanesulfonyl-hexahydro-pyrrolo[3,2-b]pyrrole-1-carbonyl]-2,2-dimethylpropylcarbamoyl}-ethyl)-methyl-carbamic acid tert-butyl ester (85): A solution of amine 84 (220 mg, 0.4 mmol) in DCM (10 mL) was cooled to 0° C. and treated with DIPEA (0.21 mL, 1.2 mmol) followed by methanesulfonyl chloride (0.03 mL, 0.42 mmol) and DMAP (5 mg, 0.04 mmol). After 2.5 h, the reaction mixture was diluted with DCM, washed successively with 1M HCl, and brine, dried over anhydrous Na$_2$SO$_4$, filtered and concentrated to afford 85 (271 mg, 100%) as a yellow-colored foam that was used without further purification. $^1$H NMR (CDCl$_3$, 300 MHz): δ7.08 (q, J=9.3, 18.9 Hz, 1H), 6.86 (br, 1H), 6.76-6.69 (m, 1H), 6.63-6.58 (m, 1H), 4.73-4.65 (m, 1H), 4.60 (d, J=9.6 Hz, 1H), 4.47 (d, J=6.3 Hz, 1H), 4.33-4.29 (m, 1H), 4.16-4.07 (m, 2H), 4.01-3.96 (m, 1H), 3.68-3.53 (m, 3H), 2.93-2.79 (m, 6H), 2.57-2.50 (m, 1H), 2.12-2.06 (m, 1H), 1.61 (s, 1.5H), 1.49 (s, 7.5H), 1.31 (d, J=6.9 Hz, 3H), 0.99 (s, 9H) ppm.

Scheme LXXXIV

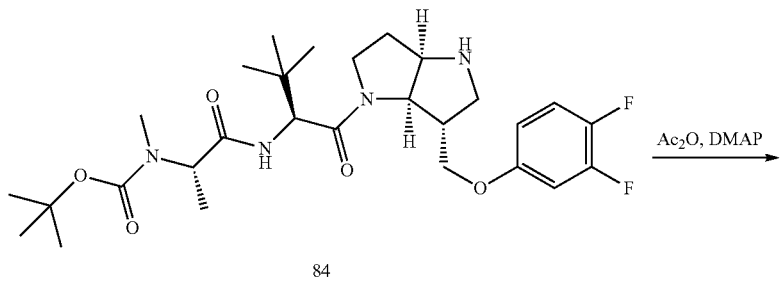

84

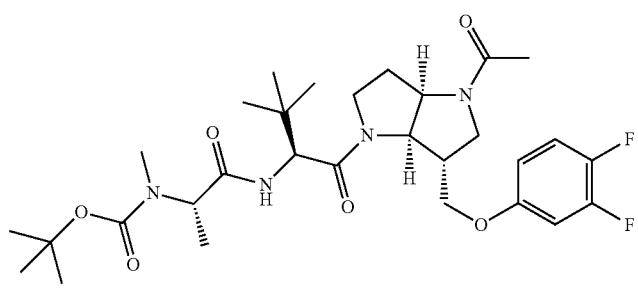

86

(1-{1-[4-Acetyl-6-(3,4-Difluoro-phenoxymethyl)-hexahydro-pyrrolo[3,2-b]pyrrole-1-carbonyl]-2,2-dimethyl-propylcarbamoyl}-ethyl)-methyl-carbamic acid tert-butyl ester (86): A solution of amine 84 (480 mg, 0.87 mmol) in DCM (8 mL) was treated with acetic anhydride (0.12 mL, 1.3 mmol) followed by DMAP (11 mg, 0.087 mmol). After 18 h, the solution was diluted with DCM, washed successively with 1M HCl, and brine, dried over anhydrous $Na_2SO_4$, filtered and concentrated to afford 86 (537 mg, 100%) as a white foam that was used without further purification. $^1$H NMR (CDCl$_3$, 300 MHz): δ 7.11-6.99 (m, 1H), 6.89 (br s, 1H), 6.74-6.67 (m, 1H), 6.61-6.56 (m, 1H), 4.77-4.69 (m, 1H), 4.63-4.57 (m, 2H), 4.39 (d, J=6.3 Hz, 1H), 4.10-3.95 (m, 2H), 3.82-3.67 (m, 2H), 3.54-3.48 (m, 1H), 3.45-3.36 (m, 1H), 2.87-2.79 (m, 4H), 2.44-2.38 (m, 1H), 2.23-2.08 (m, 6H), 1.65 (s, 1H), 1.49 (s, 9H), 1.32 (d, J=6.9 Hz, 3H), 0.99 (s, 9H) ppm.

Scheme LXXXV

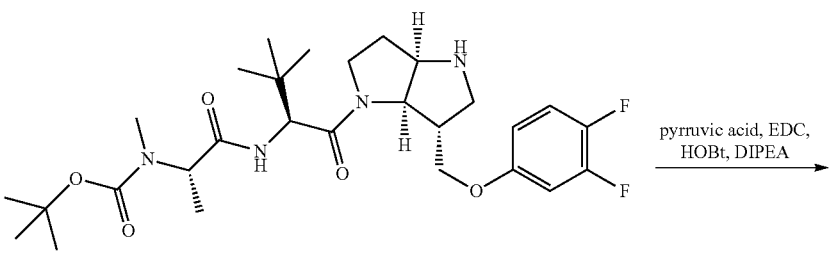

84

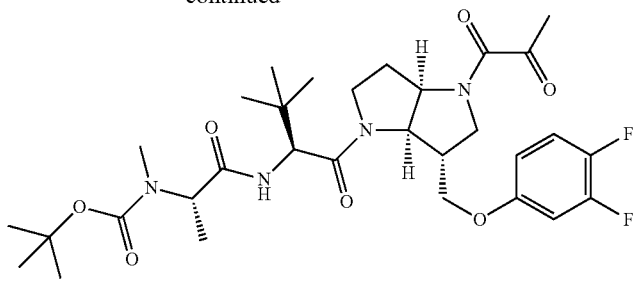

87

(1-{1-[6-(3,4-Difluoro-phenoxymethyl)-4-(2-oxo-propionyl)-hexahydro-pyrrolo[3,2-b]pyrrole-1-carbonyl]-2,2-dimethylpropylcarbamoyl}-ethyl)-methyl-carbamic acid tert-butyl ester (87): A solution of amine 84 (480 mg, 0.87 mmol) in DCM (8 mL) was cooled to 0° C. and treated with pyruvic acid (0.06 mL, 0.91 mmol), EDC (200 mg, 1.04 mmol), HOBt (141 mg, 1.04 mmol), and DIPEA (0.47 mL, 2.69 mmol). The reaction mixture was allowed to warm to ambient temperature. After 16 h, the reaction mixture was diluted with DCM, washed successively with 1M HCl, saturated aqueous NaHCO$_3$, and brine, dried over anhydrous Na$_2$SO$_4$, filtered and concentrated to afford 87 (529 mg, 97%) as a white foam that was used without further purification. $^1$H NMR (CDCl$_3$, 300 MHz): δ7.10-7.01 (m, 1H), 6.88 (br s, 1H), 6.71-6.64 (m, 1H), 6.56-6.53 (m, 1H), 4.72-4.68 (m, 1H), 4.62-4.53 (m, 2H), 4.44 (d, J=6.3 Hz, 1H), 4.15-3.97 (m, 2H), 3.89-3.81 (m, 1H), 3.72-3.61 (m, 1H), 3.53-3.36 (m, 1H), 2.88-2.79 (m, 4H), 2.49-2.00 (m, 5H), 1.49 (s, 9H), 1.32 (d, J=6.9 Hz, 3H), 0.98 (s, 9H) ppm.

Scheme LXXXVI

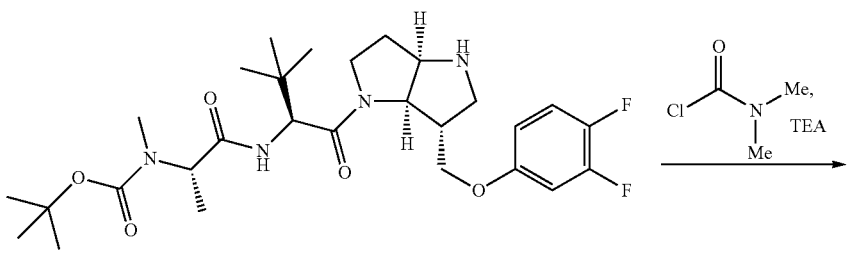

84

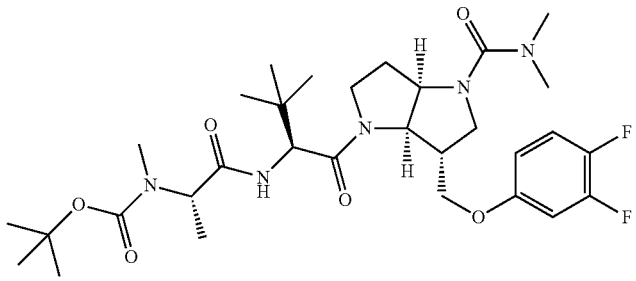

88

(1-{1-[6-(3,4-Difluoro-phenoxymethyl)-4-dimethylcarbamoyl-hexahydro-pyrrolo[3,2-b]pyrrole-1-carbonyl]-2,2-dimethylpropylcarbamoyl}-ethyl)-methyl-carbamic acid tert-butyl ester (88): A solution of amine 84 (480 mg, 0.87 mmol) in DCM (10 mL) was cooled to 0° C. and treated with TEA (0.18 mL, 1.30 mmol) followed by dimethylcarbamyl chloride (0.10 mL, 1.04 mmol). The reaction mixture was allowed to warm to ambient temperature. After 6 h, the reaction mixture was diluted with DCM, washed successively with 1M HCl, and brine, dried over anhydrous Na$_2$SO$_4$, filtered and concentrated to afford 88 (612 mg, 100%) as a white foam that was used without further purification. $^1$H NMR (CDCl$_3$, 300 MHz): δ7.04 (q, J=9.0, 18.3 Hz, 1H), 6.88 (br s, 1H), 6.75-6.67 (m, 1H), 6.61-6.56 (m, 1H), 4.79-4.51 (m, 2H), 4.31 (d, J=5.7 Hz, 1H), 4.08-4.01 (m, 1H), 3.99-3.94 (m, 1H), 3.81-3.72 (m, 1H), 3.54-3.49 (m, 1H), 3.41-3.25 (m, 2H), 2.85-2.79 (m, 9H), 2.05-2.03 (m, 2H), 1.49-1.42 (m, 9H), 1.31 (d, J=6.9 Hz, 3H), 0.99 (s, 9H) ppm.

Scheme LXXXVII

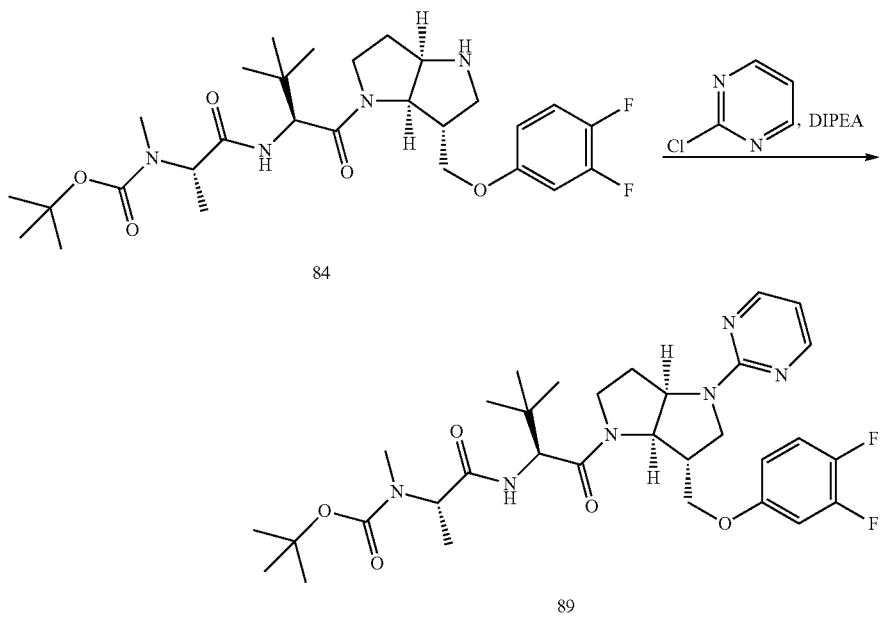

(1-{1-[6-(3,4-Difluoro-phenoxymethyl)-4-pyrimidin-2-yl-hexahydro-pyrrolo[3,2-b]pyrrole-1-carbonyl]-2,2-dimethylpropylcarbamoyl}-ethyl)-methyl-carbamic acid tert-butyl ester (89): A solution of amine 84 (325 mg, 0.59 mmol) in DMF (8 mL) was treated with 2-chloropyrimidine (88 mg, 0.76 mmol) and DIPEA (0.15 mL, 0.88 mmol) and heated to 80° C. in an oil bath. After 18 h, the reaction mixture was cooled to ambient temperature, diluted with water, and extracted with Et$_2$O (3×). The combined organic extracts were washed successively with water (3×), and brine, dried over anhydrous Na$_2$SO$_4$, filtered and concentrated to afford 89 (341 mg, 92%) as an orange-colored solid that was used without further purification. $^1$H NMR (CDCl$_3$, 300 MHz): δ8.67 (d, J=4.8 Hz, 1H), 8.35 (d, J=5.1 Hz, 1H), 7.30 (t, J=4.8 Hz, 1H), 7.08-6.87 (m, 1H), 6.86 (br s, 1H), 6.79-6.72 (m, 1H), 6.67-6.49 (m, 2H), 4.74-4.53 (m, 3H), 4.40-4.36 (m, 0.5H), 4.19-4.17 (m, 0.5H), 4.08-3.93 (m, 3H), 3.86-3.80 (m, 1H), 3.68-3.54 (m, 1H), 3.49-3.99 (m, 1H), 3.27-2.89 (m, 2H), 2.79 (s, 3H), 2.48-2.44 (m, 1.5H), 2.21-2.11 (m, 0.5H), 2.01-1.84 (m, 2H), 1.50-1.48 (m, 9H), 1.34-1.30 (m, 3H), 1.03-0.95 (m, 9H) ppm.

Scheme LXXXVIII

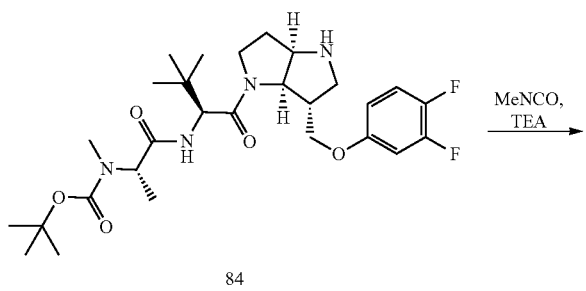

-continued

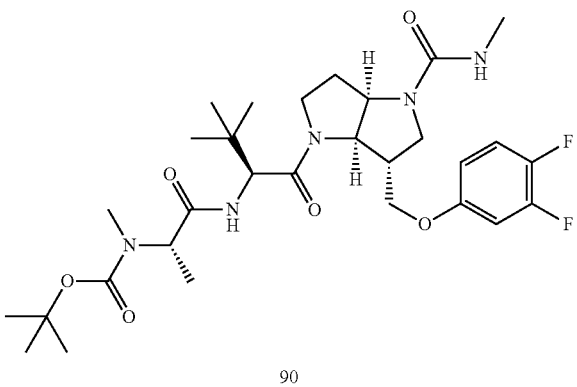

(1-{1-[6-(3,4-Difluoro-phenoxymethyl)-4-methylcarbamoyl-hexahydro-pyrrolo[3,2-b]pyrrole-1-carbonyl]-2,2-dimethylpropylcarbamoyl}-ethyl)-methyl-carbamic acid tert-butyl ester (90): A solution of amine 84 (220 mg, 0.4 mmol) in DCM (10 mL) was treated with TEA (0.11 mL, 0.78 mmol) followed by methyl isocyanate (0.05 mL, 0.78 mmol). After 2.5 h, the reaction mixture was quenched with MeOH (5 mL) followed by NH$_4$OH (15M, 10 drops). After 10 min, the solution was diluted with DCM, washed successively with 1M HCl, saturated aqueous NaHCO$_3$, and brine, dried over anhydrous Na$_2$SO$_4$, filtered and concentrated to afford 90 as a pale, yellow-colored foam (175 mg, 72%) that was used without further purification. $^1$H NMR (CDCl$_3$, 300 MHz): δ7.05 (q, J=9.0, 18.3 Hz, 1H), 6.89 (br s, 1H), 6.74-6.67 (m, 1H), 6.60-6.54 (m, 1H), 4.68 (br s, 1H), 4.61 (d, J=9.3 Hz, 1H), 4.51-4.48 (m, 1H), 4.40 (d, J=6.0 Hz, 1H), 4.25-4.22 (m, 1H), 4.08-3.99 (m, 2H), 3.79 (t, J=9.0 Hz, 1H), 3.58-3.55 (m, 1H), 3.47-3.34 (m, 2H), 2.84-2.79 (m, 7H), 2.42-2.36 (m, 1H), 2.13-2.00 (m, 1H), 1.70 (br s, 1H), 1.49 (s, 9H), 1.32 (d, J=6.9 Hz, 3H), 0.98 (s, 9H) ppm.

Scheme LXXXIX

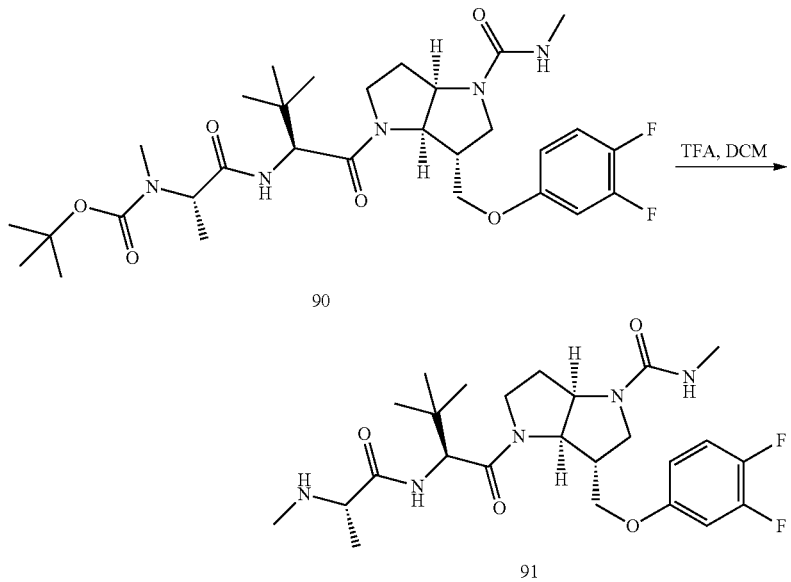

3-(3,4-Difluoro-phenoxymethyl)-4-[3,3-dimethyl-2-(2-methylamino-propionylamino)-butyryl]-hexahydro-pyrrolo[3,2-b]pyrrole-1-carboxylic acid methylamide (91): A solution of carbamate 90 (175 mg, 0.29 mmol) in DCM (10 mL) was treated with TFA (4 mL) at 0° C. After 1.5 h, the reaction mixture was concentrated, diluted with EtOAc, washed successively with saturated aqueous NaHCO$_3$, and brine dried over anhydrous Na$_2$SO$_4$, filtered and concentrated. The crude residue was purified by reverse phase HPLC (2" Dynamax® C18; 10% ACN/water to 70% ACN/water containing 0.1% HOAc, 30 min; Flow: 40 mL/min). The product-containing fractions were combined, frozen, and lyophilized to afford 91 (80 mg, 55%) as a white flocculent solid.

EXAMPLE 62

3-(3,4-Difluoro-phenoxymethyl)-4-[3,3-dimethyl-2-(2-methylamino-propionylamino)-butyryl]-hexahydro-pyrrolo[3,2-b]pyrrole-1-carboxylic acid methylamide (91)

$^1$H NMR (CDCl$_3$, 300 MHz): δ7.87 (d, J=9.3 Hz, 1H), 7.04 (q, J=9.0, 18 Hz, 1H), 6.73-6.66 (m, 1H), 6.59-6.54 (m, 1H), 4.58 (d, J=9.6 Hz, 1H), 4.51-4.48 (m, 1H), 4.41 (d, J=6 Hz, 1H), 4.14-4.02 (m, 2H), 3.79 (t, J=8.7 Hz, 1H), 3.58 (d, J=10.2 Hz, 1H), 3.48-3.36 (m, 2H), 3.07 (dd, J=7.2, 14.1 Hz, 1H), 2.88-2.83 (m, 4H), 2.42-2.36 (m, 4H), 2.14-2.03 (m, 1H), 1.64 (br s, 2H), 1.31 (d, J=6.9 Hz, 3H), 1.04-1.02 (m, 9H) ppm; $^{13}$C NMR (CDCl$_3$, 75 MHz): δ174.8, 170.1, 157.0 154.8, 154.7, 154.6, 152.2, 152.0, 148.9, 148.7, 146.9, 146.7, 143.7, 143.5, 117.4, 117.1, 109.8, 109.7, 109.6, 109.5, 104.4, 104.1, 68.9, 64.2, 60.3, 56.6, 48.4, 46.9, 43.2, 35.5, 35.1, 31.9, 27.4, 26.6, 26.5, 19.6 ppm. Mass spectrum, m/z [510.7] (M+H)+.

EXAMPLES 63 through 72 were prepared using the general chemistries described in Schemes LXXXIII→LXXXIX by replacing methanesulfonyl chloride, acetic anhydride, pyruvic acid, dimethylcarbamyl chloride, 2-chloropyrimidine, or methyl isocyanate with isopropyl isocyanate, cyclopropylcarbonyl chloride, or methyl chloroformate.

EXAMPLE 63

N-{1-[6-(3,4-Difluoro-phenoxymethyl)-4-methanesulfonyl-hexahydro-pyrrolo[3,2-b]pyrrole-1-carbonyl]-2,2-dimethyl-propyl}-2-methylamino propionamide $^1$H NMR (CDCl$_3$, 300 MHz): δ7.84 (d, J=9.0 Hz, 1H), 7.07 (q, J=9.3, 18 Hz, 1H), 6.75-6.68 (m, 1H), 6.62-6.57 (m, 1H), 4.58 (d, J=9.0 Hz, 1H), 4.49 (d, J=5.7 Hz, 1H), 4.32 (t, J=5.4 Hz, 1H), 4.16-4.11 (m, 2H), 4.01-3.96 (m, 1H), 3.68-3.50 (m, 4H), 3.30-3.23 (m, 2H), 2.93-2.89 (m, 3H), 2.82 (br s, 1H), 2.54 (dd, J=5.4, 12.9 Hz, 1H), 2.45 (s, 3H), 2.11-2.07 (m, 1H), 1.37 (d, J=7.2 Hz, 3H), 1.03 (s, 9H) ppm; $^{13}$C NMR (CDCl$_3$, 75 MHz): δ173.5, 170.2, 154.5, 154.4, 152.2, 152.1, 148.9, 148.8, 147.1, 146.9, 143.9, 143.7, 117.6, 117.4, 109.9, 109.8, 109.7, 104.4, 104.1, 69.4, 65.7, 63.4, 59.8, 57.0, 51.4, 46.5, 43.1, 35.9, 35.4, 34.3, 32.8, 26.6, 18.8, ppm. Mass spectrum, m/z [531.7] (M+H)+.

EXAMPLE 64

N-{1-[6-(3,4-Difluoro-phenoxymethyl)-hexahydro-pyrrolo[3,2-b]pyrrole-1-carbonyl]-2,2-dimethyl-propyl}-2-methylamino propionamide $^1$H NMR (CDCl$_3$, 300 MHz): δ7.81 (d, J=9.6 Hz, 1H), 7.09-7.01 (m, 5H), 6.81-6.74 (m, 1H), 6.64-6.60 (m, 1H), 4.61 (d, J=9.6 Hz, 1H), 4.36 (dd, J=2.1, 6.0 Hz, 1H), 4.27 (dd, J=3.6, 9.0 Hz, 1H), 4.14-4.04 (m, 3H), 3.76-3.67 (m, 1H), 3.36-3.30 (m, 1H), 3.24-3.17 (m, 1H), 3.12-3.06 (m, 1H), 2.62-2.59 (m, 1H), 2.40 (s, 3H), 2.16-2.09 (m, 1H), 2.02 (s, 6H), 1.32 (d, J=6.9 Hz, 3H), 1.02 (s, 9H) ppm; $^{13}$C NMR (CDCl$_3$, 75 MHz): δ176.3, 174.2, 154.9, 154.8, 154.7, 152.0, 148.9, 148.7, 146.8, 146.6, 143.6, 143.5, 117.3, 117.0, 109.9, 109.8, 109.7, 104.4, 104.2, 69.4, 65.0, 61.5, 59.7, 56.7, 49.3, 46.7, 46.3, 35.6, 34.4, 30.5, 26.5, 21.8, 18.9, ppm. Mass spectrum, m/z [268.5] (M+H)+.

EXAMPLE 65

N-{1-[4-Acetyl-6-(3,4-difluoro-phenoxymethyl)-hexahydro-pyrrolo[3,2-b]pyrrole-1-carbonyl]-2,2-dimethyl-propyl}-2-methylamino propionamide $^1$H NMR (CDCl$_3$, 300 MHz): δ7.89-7.84 (m, 1H), 7.10-7.01 (m, 1H), 6.74-6.63 (m, 1H), 6.60-6.52 (m, 1H), 4.64-4.54 (m, 2H), 4.40 (d, J=6.0 Hz, 1H), 4.22-3.97 (m, 2H), 3.88-3.61 (m, 2H), 3.56-3.48 (m, 1H), 3.42-3.36 (m, 1H), 3.08 (dd, J=6.6, 13.8 Hz, 1H), 2.89-2.84 (m, 1H), 2.45-2.34 (m, 6H), 2.20-2.06 (m, 5H), 1.31 (d, J=6.9 Hz, 3H), 1.02 (s, 9H) ppm; $^{13}$C NMR (CDCl$_3$, 75 MHz): δ175.0, 174.9, 170.2, 169.5, 169.4, 154.7, 154.6, 152.2, 152.0, 148.9, 148.7, 146.8, 143.8, 143.6, 117.5, 117.2, 117.1, 109.6, 109.5, 104.3, 104.1, 69.4, 68.7, 65.2, 63.6, 60.9, 60.3, 56.6, 56.5, 49.9, 48.4, 47.2, 46.9, 43.4, 42.3, 35.5, 35.4, 35.1, 33.2, 31.2, 26.5, 23.1, 22.0, 19.6, ppm. Mass spectrum, m/z [495.7] (M+H)+.

EXAMPLE 66

N-{1-[6-(3,4-Difluoro-phenoxymethyl)-4-(2-oxo-propionyl)-hexahydro-pyrrolo[3,2-b]pyrrole-1-carbonyl]-2,2-dimethyl-propyl}-2-methylamino propionamide $^1$H NMR (CDCl$_3$, 300 MHz): mixture of rotomers, δ7.96 (d, J=8.4 Hz, 1H), 7.10-6.99 (m, 1H), 6.71-6.63 (m, 1H), 6.56-6.51 (m, 1H), 4.97-4.94 (m, 0.5H), 4.70 (t, J=7.5 Hz, 1H), 4.62-4.54 (m, 1.5H), 4.45 (d, J=6.0 Hz, 0.5H), 4.19-4.13 (m, 1H), 4.06-3.99 (m, 1.5H), 3.90-3.77 (m, 2H), 3.72-3.66 (m, 1H), 3.54-3.37 (m, 1.5H), 3.23 (br s, 1.5H), 2.87-2.80 (m, 1.5H), 2.50-2.32 (m, 7H), 2.20 (br s, 1.5H), 2.05-1.95 (m, 1H), 1.34 (d, J=7.2 Hz, 3H), 1.02 (s, 9H) ppm; $^{13}$C NMR (CDCl$_3$, 75 MHz): mixture of rotomers, δ198.0, 197.7, 174.2, 170.2, 169.6, 162.8, 162.2, 154.6, 154.5, 152.2, 152.0, 148.9, 148.7, 147.0, 146.8, 143.8, 143.6, 117.5, 117.4, 117.3, 117.2, 109.7, 109.6, 109.5, 104.3, 104.2, 104.0, 103.9, 69.3, 69.0, 65.4, 63.2, 61.5, 61.1, 59.8, 56.8, 50.2, 49.4, 47.1, 46.8, 43.7, 41.7, 35.4, 34.2, 31.0, 27.4, 26.9, 26.6, 19.0 ppm. Mass spectrum, m/z [523.7] (M+H)+.

EXAMPLE 67

3-(3,4-Difluoro-phenoxymethyl)-4-[3.3-dimethyl-2-(2-methylaminopropionylamino)-butyryl]-hexahydro-pyrrolo[3,2-b]pyrrole-1-carboxylic acid isopropylamide $^1$H NMR (CDCl$_3$, 300 MHz): δ0.87 (d, J=9.3 Hz, 1H), 7.04 (q, J=9.0, 18.6 Hz, 1H), 6.74-6.67 (m, 1H), 6.59-6.56 (m, 1H), 4.58 (d, J=9.6 Hz, 1H), 4.49-4.41 (m, 2H), 4.13-3.93 (m, 4H), 3.82 (t, J=9.0 Hz, 1H), 3.55 (dd, J=1.8, 10.8 Hz, 1H), 3.50-3.36 (m, 2H), 3.07 (dd, J=6.9, 13.8 Hz, 1H), 2.86-2.84 (m, 1H), 2.39 (s, 3H), 2.35-2.31 (m, 1H), 2.14-2.05 (m, 1H), 1.72 (s, 2H), 1.31 (d, J=6.6 Hz, 3H), 1.17 (t, J=6.3 Hz, 6H), 1.02 (s, 9H) ppm; $^{13}$C NMR (CDCl$_3$, 75 MHz): δ175.1, 170.4, 169.9, 160.0, 155.0, 154.9, 152.4, 152.2, 149.1, 148.9, 147.1, 146.9, 143.9, 143.8, 117.6, 117.3, 109.9, 109.8, 104.7, 104.4, 69.7, 69.4, 64.5, 64.4, 60.6, 60.4, 56.7, 56.6, 48.7, 47.2, 43.4, 42.7, 35.7, 35.4, 32.1, 26.8, 23.8, 23.7, 19.8 ppm. Mass spectrum, m/z [538.7] (M+H)+.

EXAMPLE 68

3-(3,4-Difluoro-phenoxymethyl)-4-[3.3-dimethyl-2-(2-methylaminopropionylamino)-butyryl]-hexahydro-pyrrolo[3,2-b]pyrrole-1-carboxylic acid dimethylamide $^1$H NMR (CDCl$_3$, 300 MHz): δ7.84 (d, J=9.6 Hz, 1H), 7.04 (q, J=9.0, 18.0 Hz, 1H), 6.74-6.67 (m, 1H), 6.60-6.55 (m, 1H), 4.80-4.74 (m, 1H), 4.62 (d, J=9.6 Hz, 1H), 4.32 (d, J=5.7 Hz, 1H), 4.14-4.08 (m, 1H), 4.01-3.96 (m, 1H), 3.79 (t, J=8.4 Hz, 1H), 3.56-3.50 (m, 1H), 3.45-3.38 (m, 2H), 3.14-3.07 (m, 1H), 2.91-2.84 (m, 9H), 2.42-2.39 (m, 3H), 2.06-2.04 (m, 3H), 1.32 (d, J=6.9 Hz, 3H), 1.03 (s, 9H) ppm; $^{13}$C NMR (CDCl$_3$, 75 MHz): δ174.9, 170.3, 162.7, 155.0, 154.9, 152.3, 152.1, 149.0, 148.8, 147.0, 146.8, 143.8, 143.6, 117.4, 117.2, 109.8, 109.7, 104.5, 104.3, 69.1, 64.1, 61.1, 60.3, 56.8, 52.1, 47.3, 45.7, 45.6, 43.5, 38.3, 35.7, 35.1, 32.4, 26.7, 19.6 ppm. Mass spectrum, m/z [524.7] (M+H)+.

EXAMPLE 69

N-{1-[4-Cyclopropanecarbonyl-6-(3,4-difluoro-phenoxymethyl)-hexahydro-pyrrolo[3,2-b]pyrrole-1-carbonyl]-2,2-dimethyl-propyl}-2-methylamino propionamide $^1$H NMR (CDCl$_3$, 300 MHz): δ7.88 (t, J=8.7 Hz, 1H), 7.10-6.99 (m, 1H), 6.74-6.64 (m, 1H), 6.59-6.54 (m, 1H), 4.71-4.69 (m, 0.5H), 4.65-4.56 (m, 2H), 4.40 (d, J=5.7 Hz, 0.5H), 4.23-4.06 (m, 2H), 4.01-3.95 (m, 1H), 3.92-3.76 (m, 1H), 3.69-3.63 (m, 0.5H), 3.56-3.37 (m, 1.5H), 3.07 (dd, J=7.2, 21 Hz, 1H), 2.92-2.82 (m, 1H), 2.40-2.23 (m, 4H), 2.18-2.05 (m, 1H), 1.88 (br s, 2H), 1.69-1.57 (m, 1H), 1.31 (d, J=6.6 Hz, 3H), 1.15-1.02 (m, 9H), 0.91-0.76 (m, 3H) ppm; $^{13}$C NMR (CDCl$_3$, 75 MHz): δ175.0, 174.8, 172.4, 170.2, 170.1, 154.8, 152.2, 152.0, 148.9, 146.9, 146.8, 143.8, 143.6, 117.4, 117.3, 117.2, 117.1, 109.7, 109.6, 104.4, 104.3, 104.1, 104.0, 69.3, 68.9, 65.4, 63.4, 60.5, 60.3, 56.7, 56.5, 49.2, 48.7, 47.2, 46.9, 43.4, 42.0, 35.5, 35.4, 35.1, 33.5, 31.4, 26.6, 19.6, 12.9, 12.6, 8.6, 8.0, 7.9, 7.6 ppm. Mass spectrum, m/z [521.2] (M+H)+.

EXAMPLE 70

3-(3,4-Difluoro-phenoxymethyl)-4-[3.3-dimethyl-2-(2-methylaminopropionylamino)-butyryl]-hexahydro-pyrrolo[3,2-b]pyrrole-1-carboxylic acid methyl ester $^1$H NMR (CDCl$_3$, 300 MHz): δ7.84 (d, J=9.3 Hz, 1H), 7.05 (dd, J=9.0, 18.9 Hz, 1H), 6.71-6.62 (m, 1H), 6.58-6.54 (m, 1H), 4.60 (d, J=9.9 Hz, 1H), 4.43 (br s, 2H), 4.12 (t, J=9.3 Hz, 1H), 4.02-3.98 (m, 1H), 3.82 (t, J=8.4 Hz, 1H), 3.71 (br s, 3H), 3.45-3.38 (m, 2H), 3.09 (dd, J=6.6, 13.8 Hz, 1H), 2.85 (br s, 3H), 2.39 (m, 3H), 2.37-2.23 (br s, 1H), 2.07-2.04 (m, 2H), 1.31 (d, J=6.6 Hz, 3H), 1.04-1.02 (m, 9H) ppm; $^{13}$C NMR (CDCl$_3$, 75 MHz): δ175.1, 170.3, 155.5, 455.0, 154.9, 152.2, 149.1, 148.9, 147.1, 146.9, 143.9, 143.7, 117.5, 117.3, 109.9, 104.6, 104.3, 69.3, 65.3, 64.4, 61.1, 60.4, 56.9, 52.8, 49.3, 48.9, 47.1, 43.1, 42.5, 35.7, 35.2, 32.4, 31.5, 26.8, 21.0, 19.8 ppm. Mass spectrum, m/z [511.1] (M+H)+.

EXAMPLE 71

N-{1-[6-(3,4-Difluoro-phenoxymethyl)-4-(3-methyl-butyryl)-hexahydro-pyrrolo[3,2-b]pyrrole-1-carbonyl]-2,2-dimethyl-propyl}-2-methylamino propionamide $^1$H NMR (CDCl$_3$, 300 MHz): δ7.84 (d, J=9.3 Hz, 1H), 7.10-7.00 (m, 1H), 6.73-6.66 (m, 1H), 6.59-6.53 (m, 1H), 4.66-4.50 (m, 2H), 4.09 (d, J=6.3 Hz, 0.5H), 4.19-3.97 (m, 2H), 3.78-3.72 (m, 1.5H), 3.52-3.34 (m, 2H), 3.11 (dd, J=6.6, 20.7 Hz, 1H), 2.88-2.78 (m, 2H), 2.48-2.36 (m, 6H), 2.23-2.06 (m, 4H), 1.32 (d, J=6.6 Hz, 3H), 1.02-0.92 (m, 15H) ppm; $^{13}$C NMR (CDCl$_3$, 75 MHz): δ174.6, 171.6, 170.2, 154.7, 154.6, 152.2, 152.0, 148.9, 148.7, 146.9, 146.8, 143.8, 143.6, 117.4, 117.2, 109.9, 109.6, 109.5, 104.3, 104.1, 69.6, 69.3, 68.6, 65.2, 63.6, 63.3, 62.1, 60.2, 56.6, 56.5, 49.6, 49.3, 48.4, 47.2, 46.9, 45.2, 44.0, 43.4, 43.1, 42.2, 35.8, 35.5, 35.4, 34.9, 33.6, 31.4, 26.6, 25.7, 22.8, 22.6, 22.5, 19.4 ppm. Mass spectrum, m/z [537.2] (M+H)+.

EXAMPLE 72

N-{1-[6-(3,4-Difluoro-phenoxymethyl)-4-pyrimidin-2-yl-hexahydro-pyrrolo[3,2-b]pyrrole-1-carbonyl]-2,2-dimethylpropyl}-2-methylamino-propionamide $^1$H NMR (CDCl$_3$, 300 MHz): δ8.35 (d, J=4.8 Hz, 2H), 7.86 (d, J=9.6 Hz, 1H), 7.00 (dd, J=9.0, 18.9 Hz, 1H), 6.66-6.56 (m, 1H), 6.53-6.49 (m, 1H), 4.72 (t, J=5.4 Hz, 1H), 4.63 (d, J=9.6 Hz, 1H), 4.55 (d, J=6.0 Hz, 1H), 4.14-3.96 (m, 3H), 3.84 (t, J=8.1 Hz, 1H), 3.62-3.56 (m, 1H), 3.49-3.40 (m, 1H), 3.14 (dd, J=6.6, 13.8 Hz, 1H), 2.96-2.86 (m, 3H), 2.49-2.42 (m, 4H), 2.23-2.10 (m, 1H), 1.33 (d, J=6.9 Hz, 3H), 1.07-1.03 (m, 9H), ppm; $^{13}$C NMR (CDCl$_3$, 75 MHz): δ174.5, 174.3, 170.0, 169.7, 159.9, 158.0, 155.0, 154.9, 154.8, 152.1, 151.9, 148.8, 148.6, 148.8, 146.6, 143.6, 143.4, 117.2, 117.0, 110.3, 110.0, 109.7, 109.6, 109.5, 104.3, 104.1, 69.7, 69.4, 64.6, 64.5, 62.4, 60.8, 60.1, 56.7, 56.4, 49.3, 49.2, 47.2, 45.2, 44.8, 42.6, 36.0, 35.6, 34.9, 31.3, 26.7, 26.6, 19.4 ppm. Mass spectrum, m/z [531.1] (M+H)+.

TABLE 9

| Example | Structure | K$_D$ (XIAP BIR3) μM | K$_D$ (c-IAP-1 BIR3) μM | CC$_{50}$ (SK-OV-3) μM | Mass spectrum, m/z |
|---|---|---|---|---|---|
| 62 | (structure) | A | A | A | 510.7 (M + H) |
| 63 | (structure) | A | A | A | 531.6 (M + H) |
| 64 | (structure) | A | A | A | 453.6 (M + H) |

TABLE 9-continued

| Example | Structure | $K_D$ (XIAP BIR3) μM | $K_D$ (c-IAP-1 BIR3) μM | $CC_{50}$ (SK-OV-3) μM | Mass spectrum, m/z |
|---|---|---|---|---|---|
| 65 | 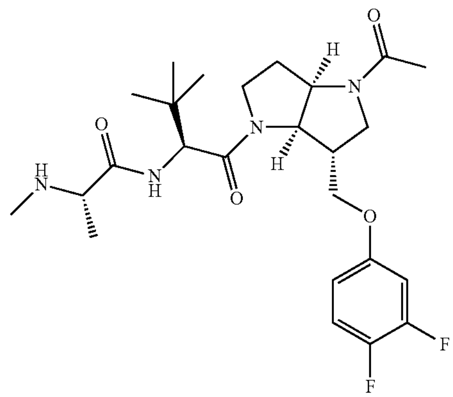 [SMILES: CN[C@@H](C)C(=O)N[C@H](C(=O)N1CC[C@@H]2[C@H]1[C@@H](COc1ccc(F)c(F)c1)CN2C(C)=O)C(C)(C)C] | A | A | A | 495.7 (M + H) |
| 66 | 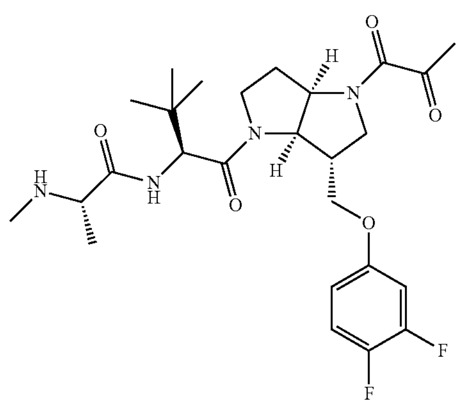 [SMILES: CN[C@@H](C)C(=O)N[C@H](C(=O)N1CC[C@@H]2[C@H]1[C@@H](COc1ccc(F)c(F)c1)CN2C(=O)C(C)=O)C(C)(C)C] | A | A | A | 523.7 (M + H) |
| 67 | 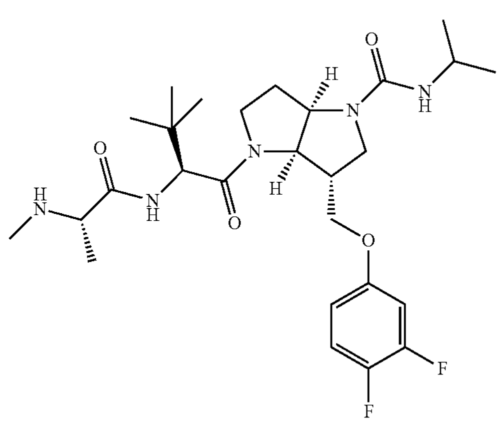 [SMILES: CN[C@@H](C)C(=O)N[C@H](C(=O)N1CC[C@@H]2[C@H]1[C@@H](COc1ccc(F)c(F)c1)CN2C(=O)NC(C)C)C(C)(C)C] | A | A | A | 538.7 (M + H) |

TABLE 9-continued

| Example | Structure | $K_D$ (XIAP BIR3) µM | $K_D$ (c-IAP-1 BIR3) µM | $CC_{50}$ (SK-OV-3) µM | Mass spectrum, m/z |
|---|---|---|---|---|---|
| 68 | 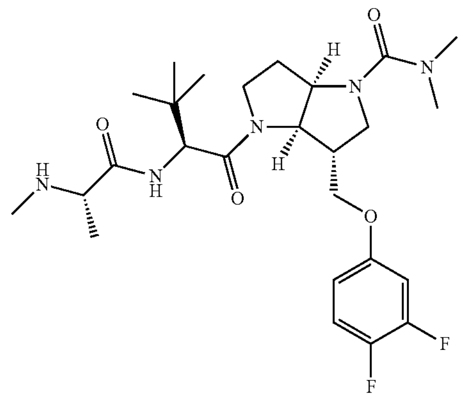 | A | A | A | 524.7 (M + H) |
| 69 | 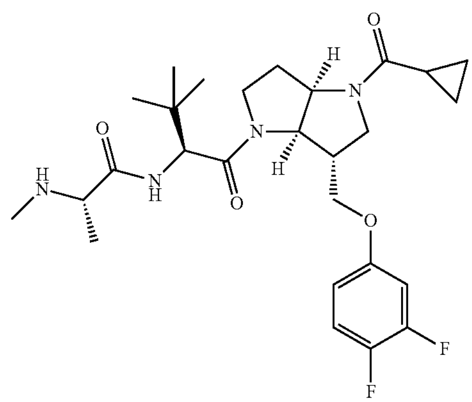 [SMILES: CN[C@@H](C)C(=O)N[C@H](C(=O)N1CC[C@@H]2[C@H]1[C@@H](COc1ccc(F)c(F)c1)CN2C(=O)C1CC1)C(C)(C)C] | B | A | A | 521.2 (M + H) |
| 70 | 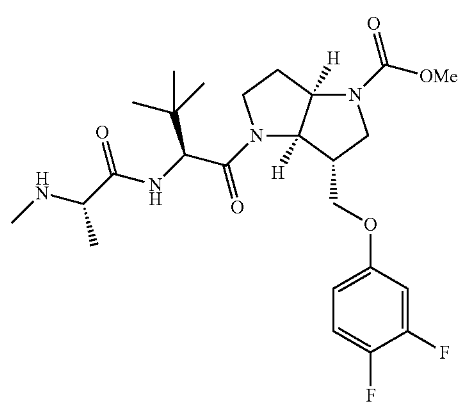 [SMILES: CN[C@@H](C)C(=O)N[C@H](C(=O)N1CC[C@@H]2[C@H]1[C@@H](COc1ccc(F)c(F)c1)CN2C(=O)OC)C(C)(C)C] | A | A | A | 511.1 (M + H) |

TABLE 9-continued

| Example | Structure | $K_D$ (XIAP BIR3) µM | $K_D$ (c-IAP-1 BIR3) µM | $CC_{50}$ (SK-OV-3) µM | Mass spectrum, m/z |
|---|---|---|---|---|---|
| 71 | 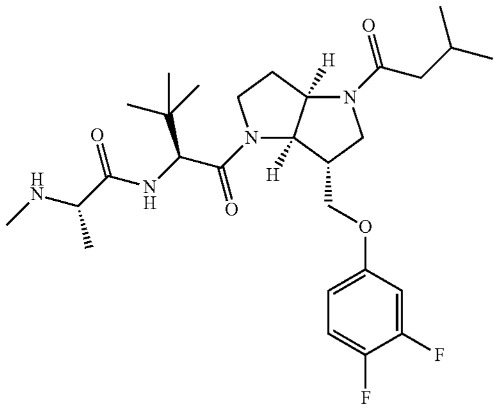 [SMILES: CN[C@@H](C)C(=O)N[C@H](C(=O)N1CC[C@@H]2[C@H]1[C@@H](COc1ccc(F)c(F)c1)CN2C(=O)CC(C)C)C(C)(C)C] | A | A | A | 537.2 (M + H) |
| 72 | 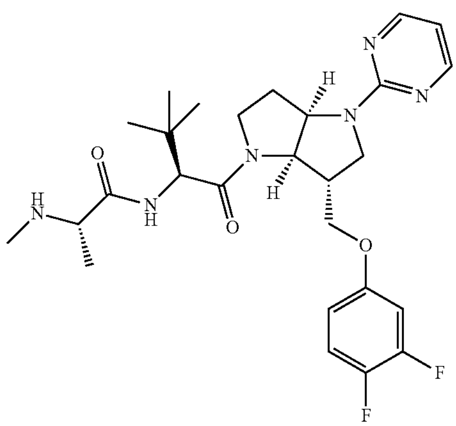 [SMILES: CN[C@@H](C)C(=O)N[C@H](C(=O)N1CC[C@@H]2[C@H]1[C@@H](COc1ccc(F)c(F)c1)CN2c1ncccn1)C(C)(C)C] | B | A | A | 531.1 (M + H) |

As noted above, dimers of the compounds generally and specifically described above can be prepared by a person of skill in the art. Illustrative dimers of the invention can be prepared, e.g., in accordance with the following general synthetic schemes and examples:

Scheme XC

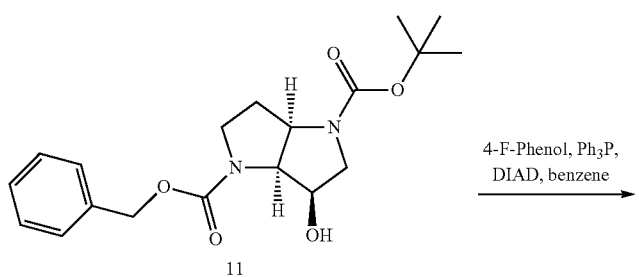

4-F-Phenol, Ph₃P, DIAD, benzene →

-continued
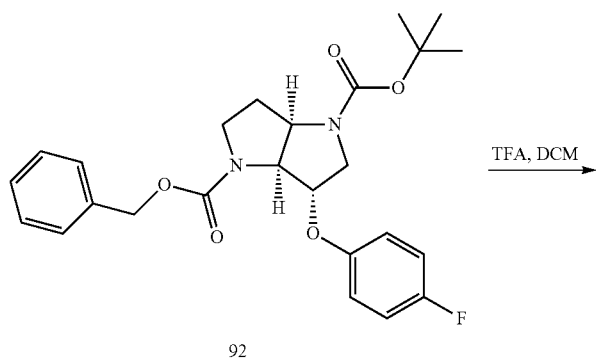
92
TFA, DCM →
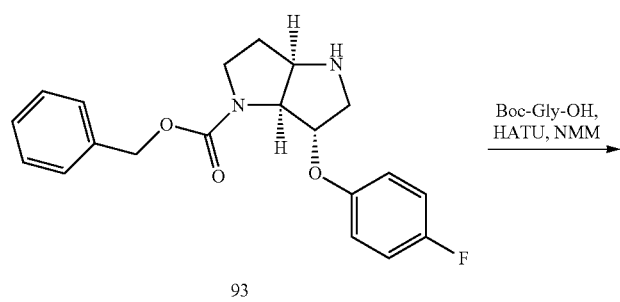
93
Boc-Gly-OH, HATU, NMM →
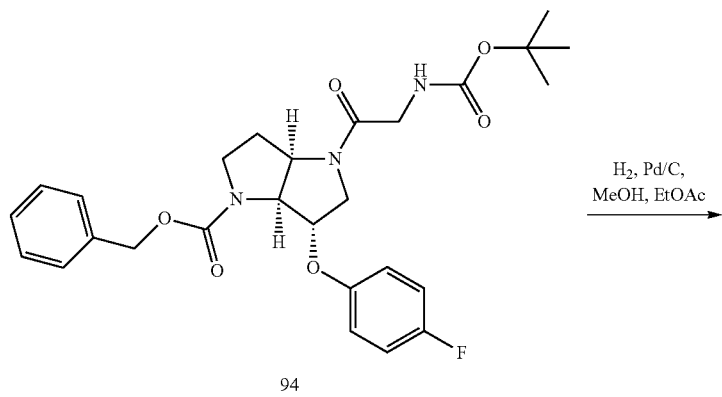
94
H₂, Pd/C, MeOH, EtOAc →
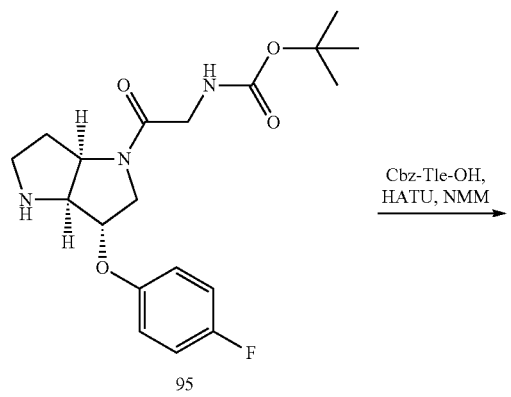
95
Cbz-Tle-OH, HATU, NMM →

-continued
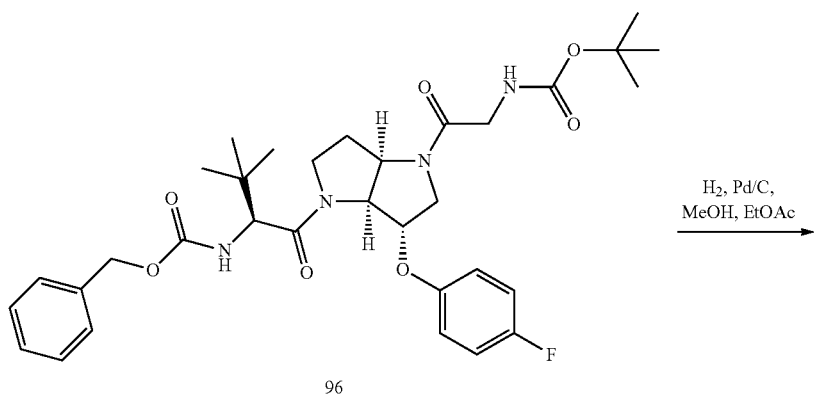
96
H₂, Pd/C,
MeOH, EtOAc →
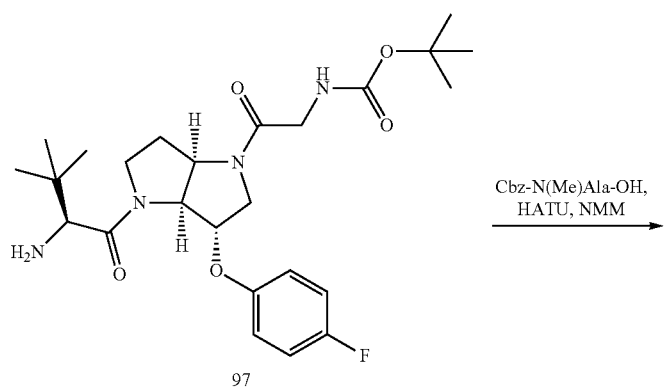
97
Cbz-N(Me)Ala-OH,
HATU, NMM →
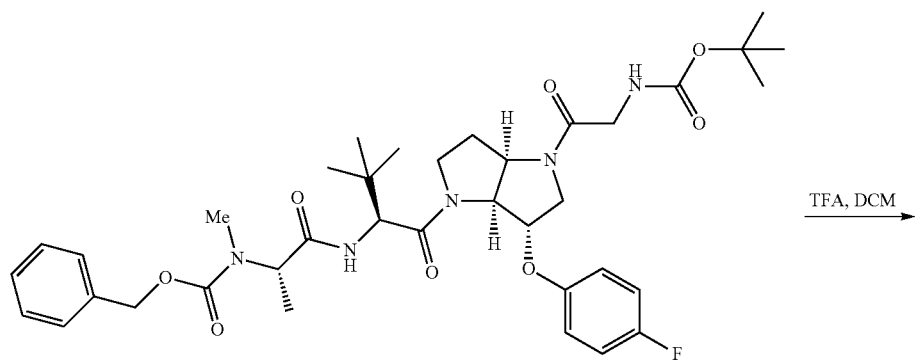
98
TFA, DCM →

-continued
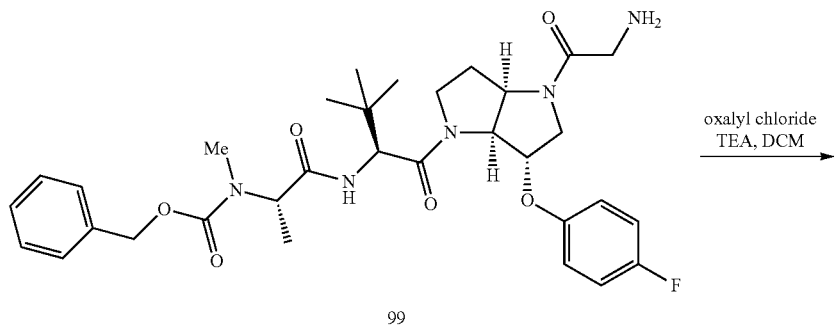
99
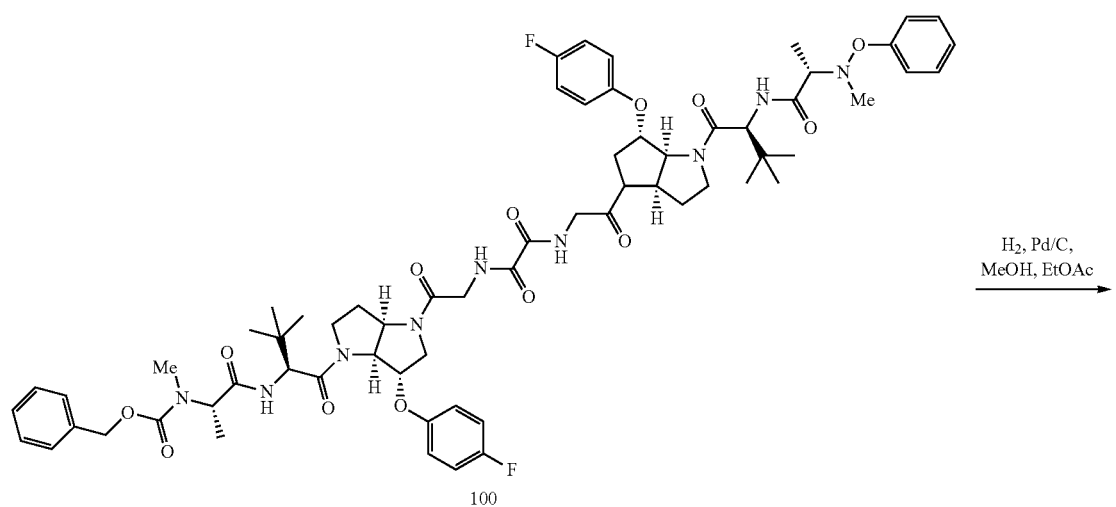
100
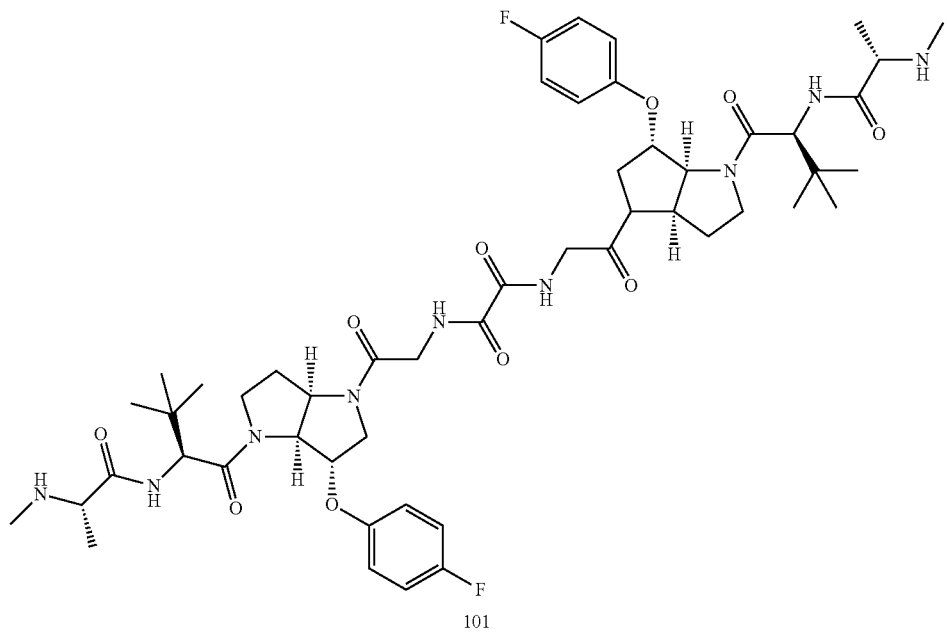
101

Scheme XCI
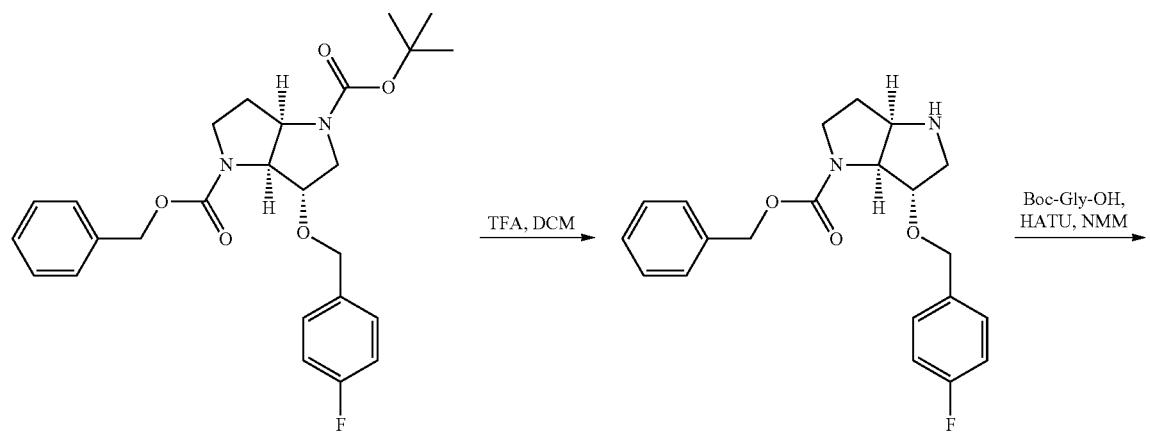
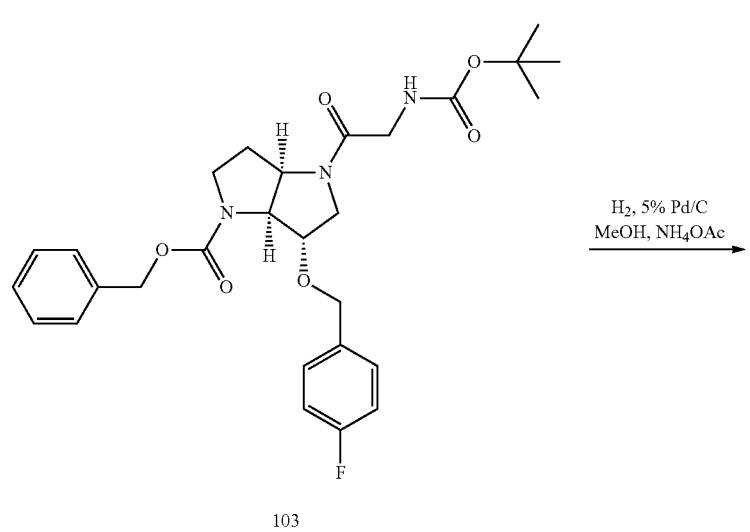
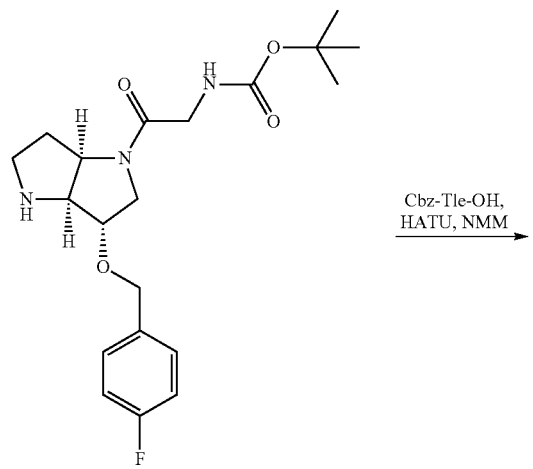

-continued
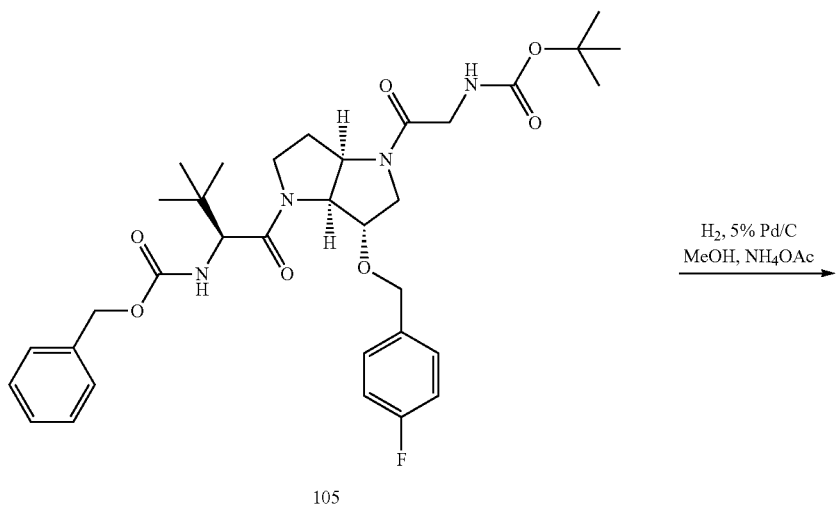
105
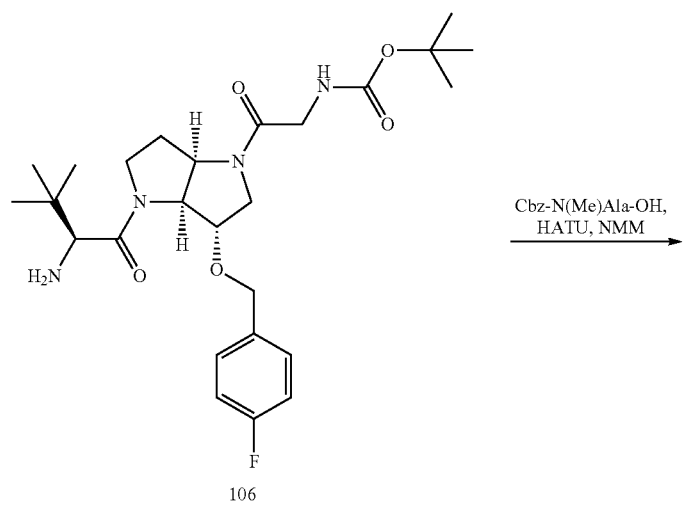
106
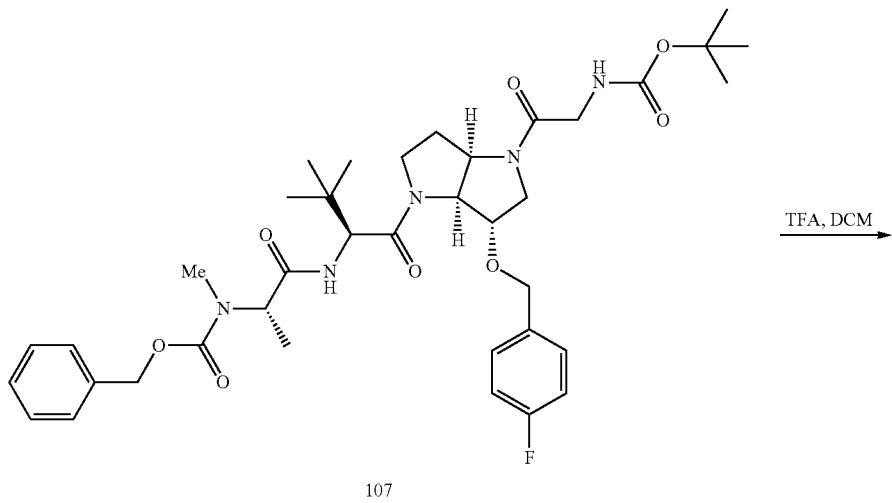
107

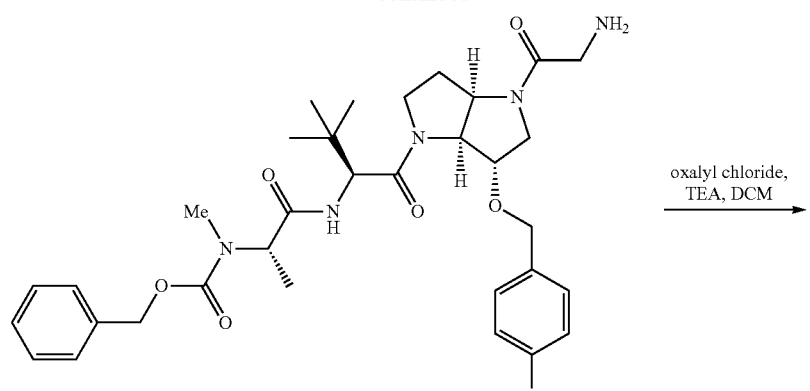
108
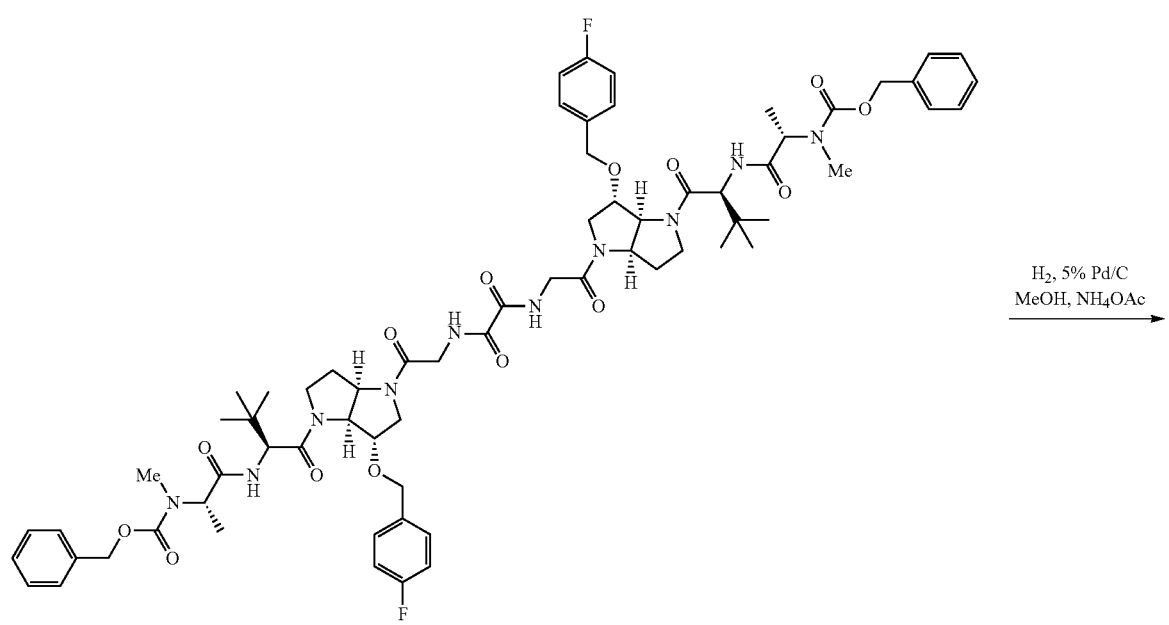
109

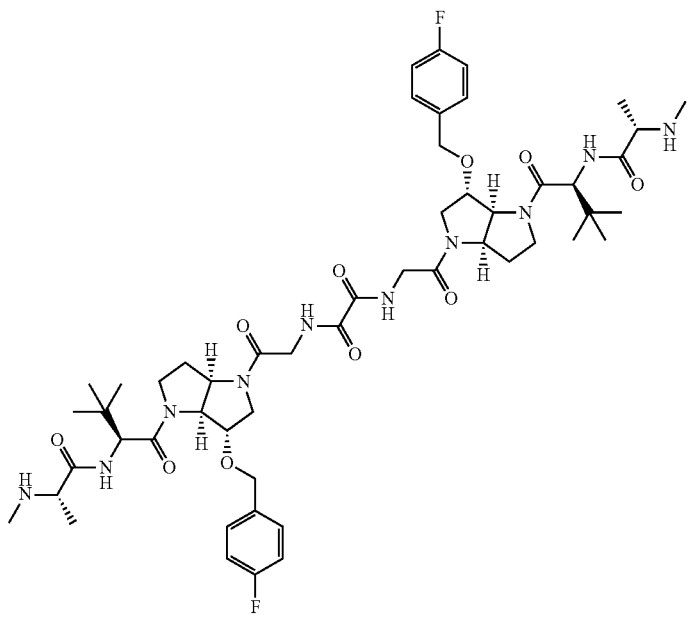
110
Scheme XCII
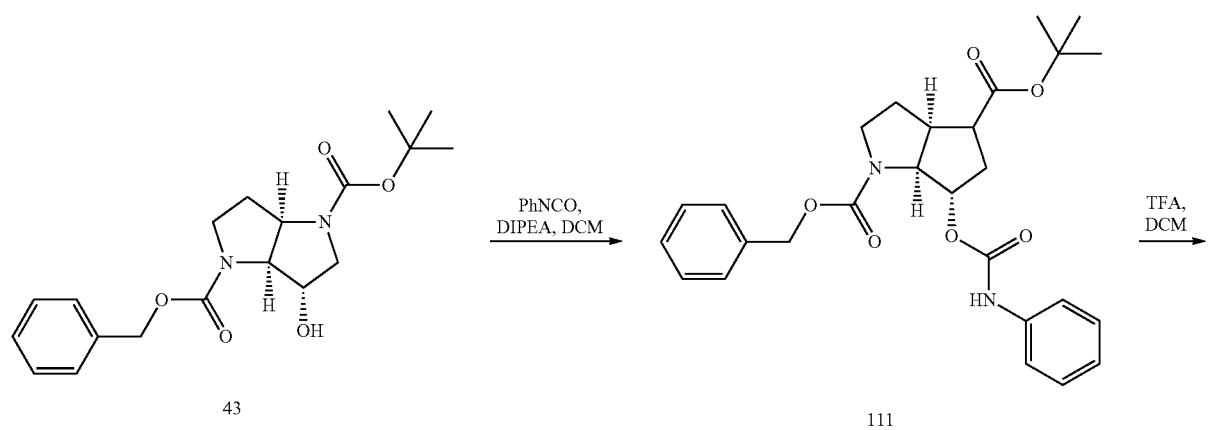
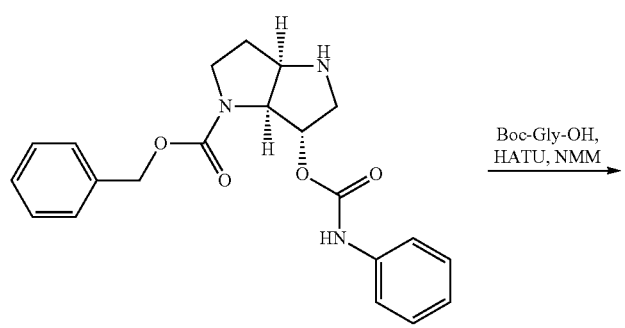

-continued
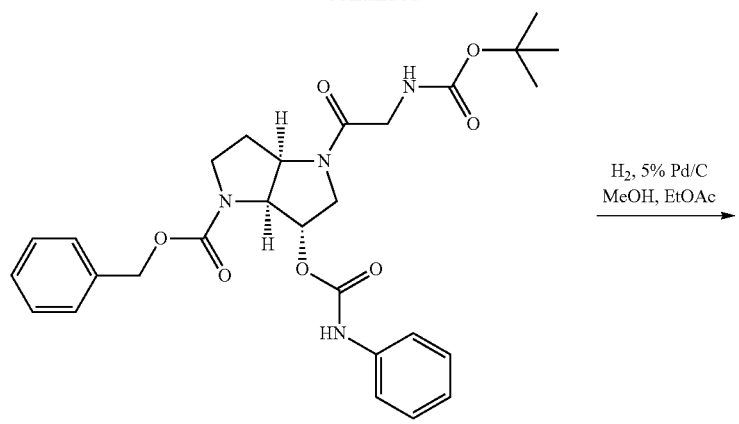
113
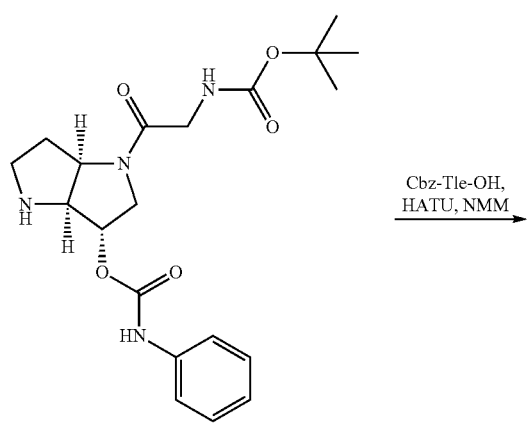
114
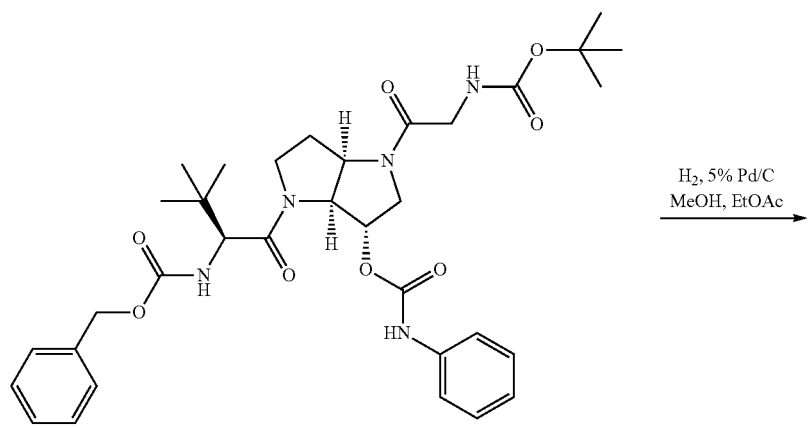
115

-continued
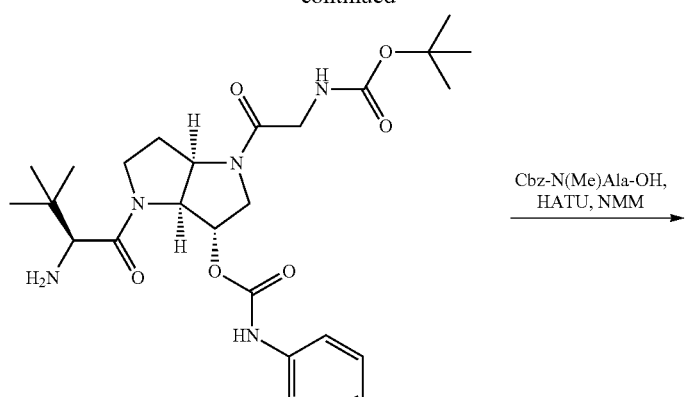
116
Cbz-N(Me)Ala-OH, HATU, NMM →
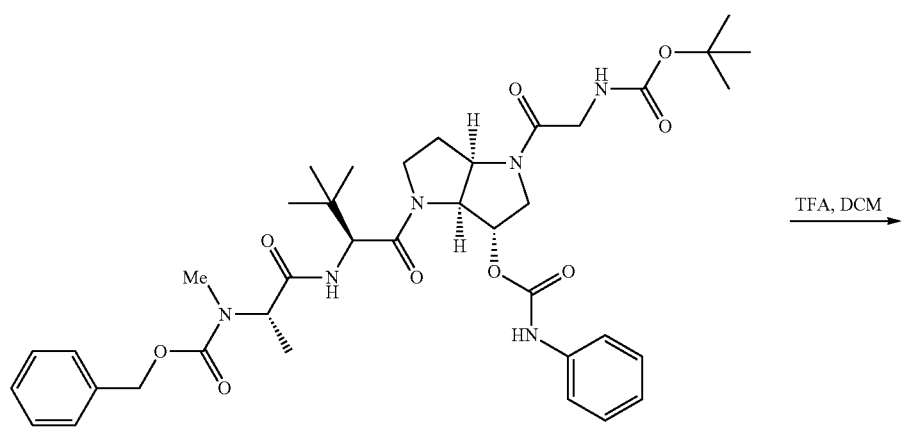
117
TFA, DCM →
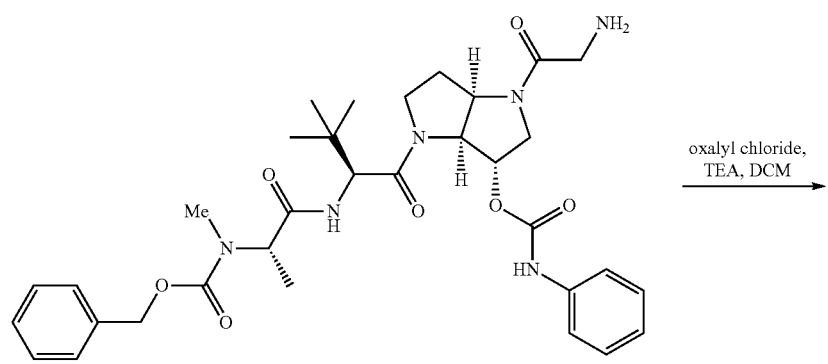
118
oxalyl chloride, TEA, DCM →

183 184
-continued
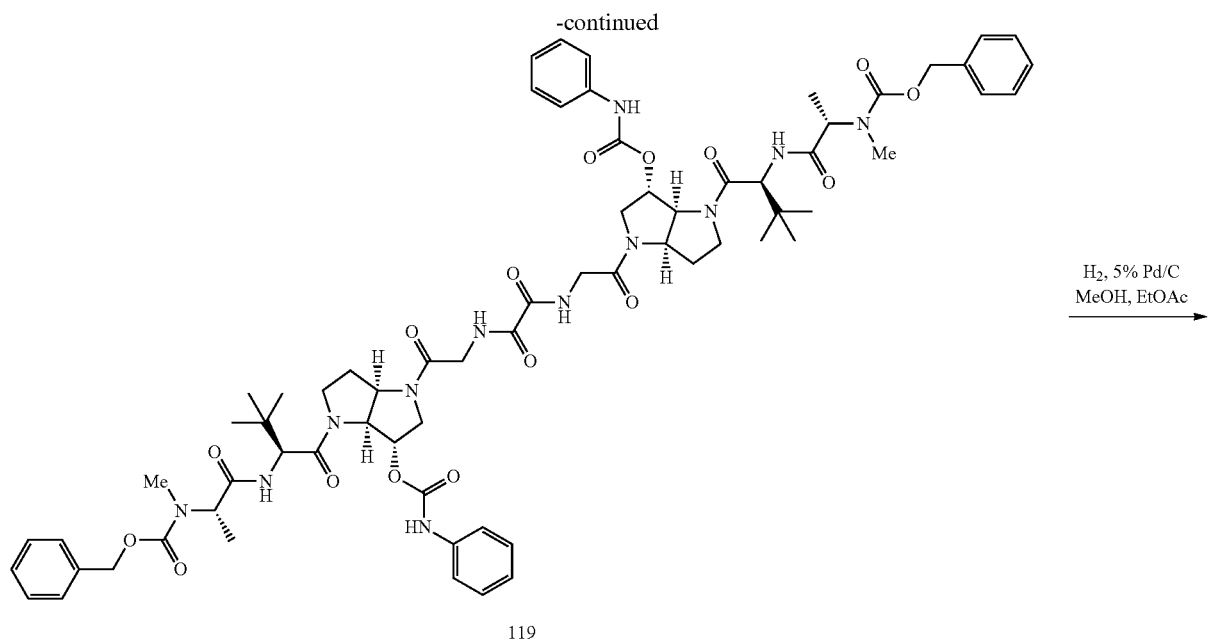
119
H₂, 5% Pd/C
MeOH, EtOAc
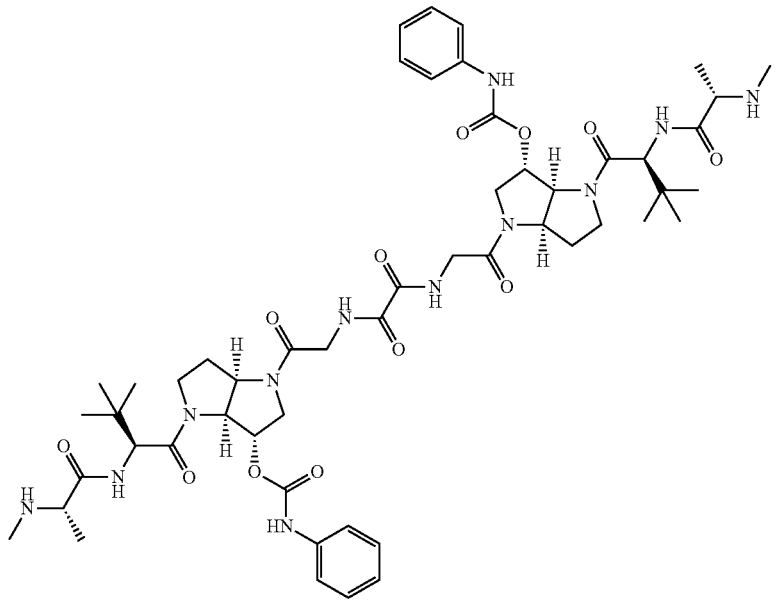
120
Scheme XCIII
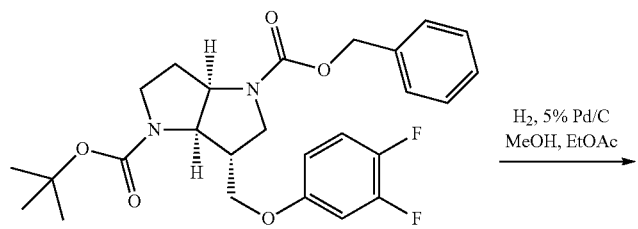
78
H₂, 5% Pd/C
MeOH, EtOAc -continued
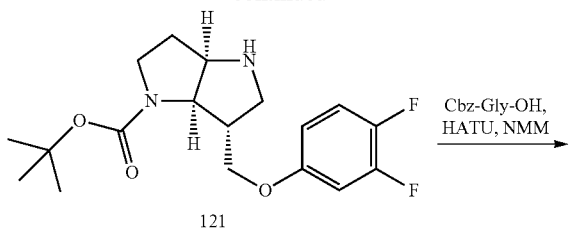
121
Cbz-Gly-OH, HATU, NMM →
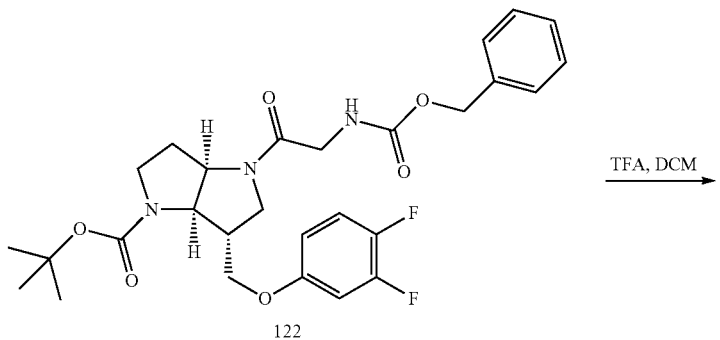
122
TFA, DCM →
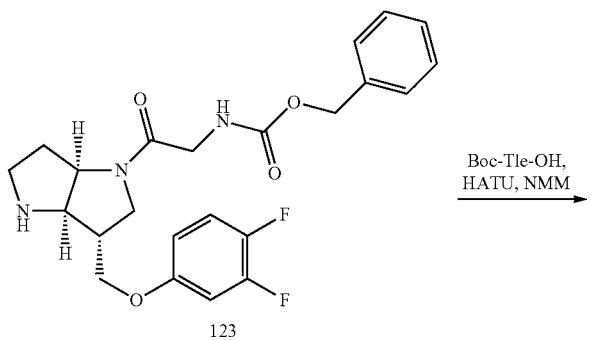
123
Boc-Tle-OH, HATU, NMM →
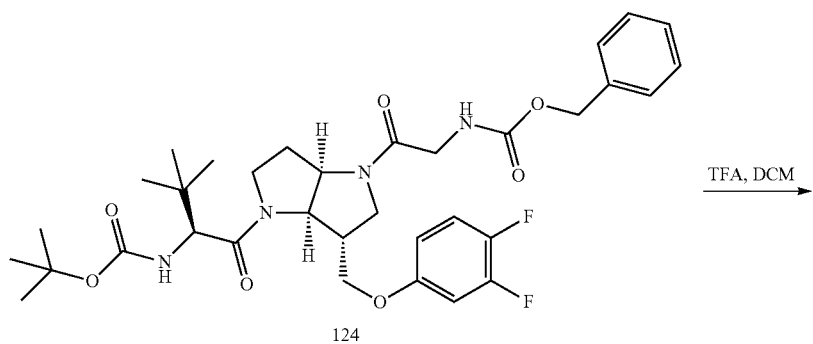
124
TFA, DCM →
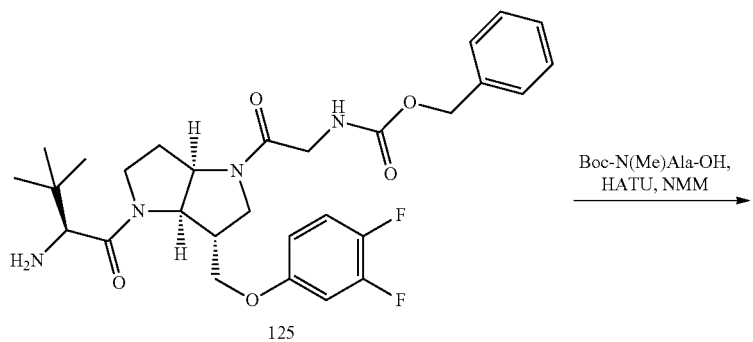
125
Boc-N(Me)Ala-OH, HATU, NMM →

-continued
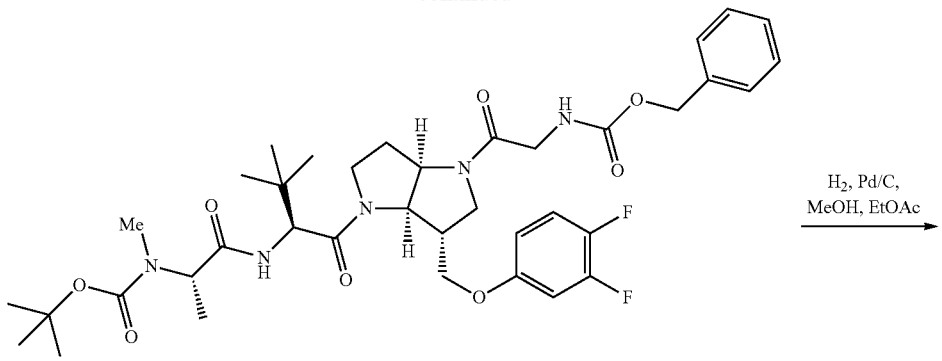
126
H₂, Pd/C,
MeOH, EtOAc
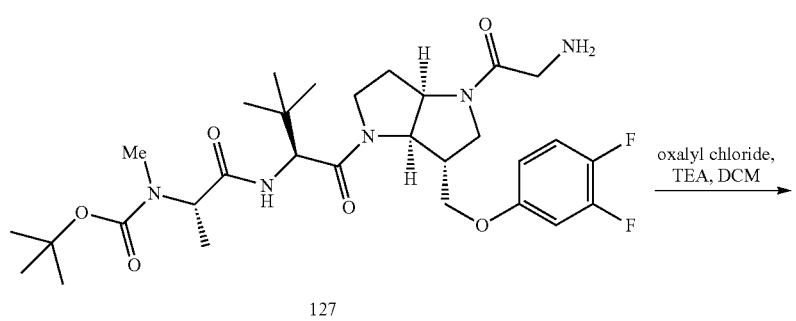
127
oxalyl chloride,
TEA, DCM
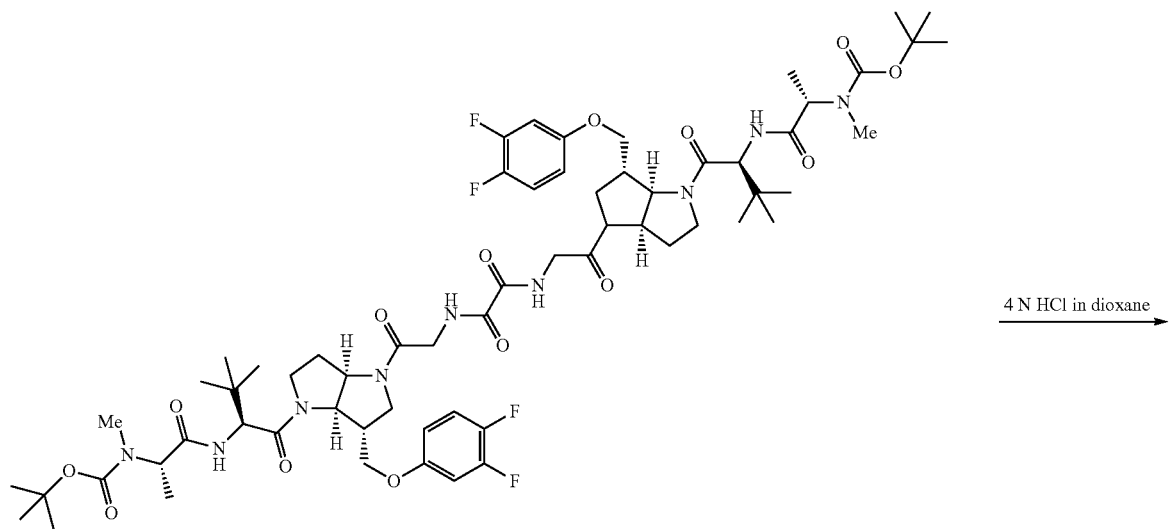
128
4 N HCl in dioxane

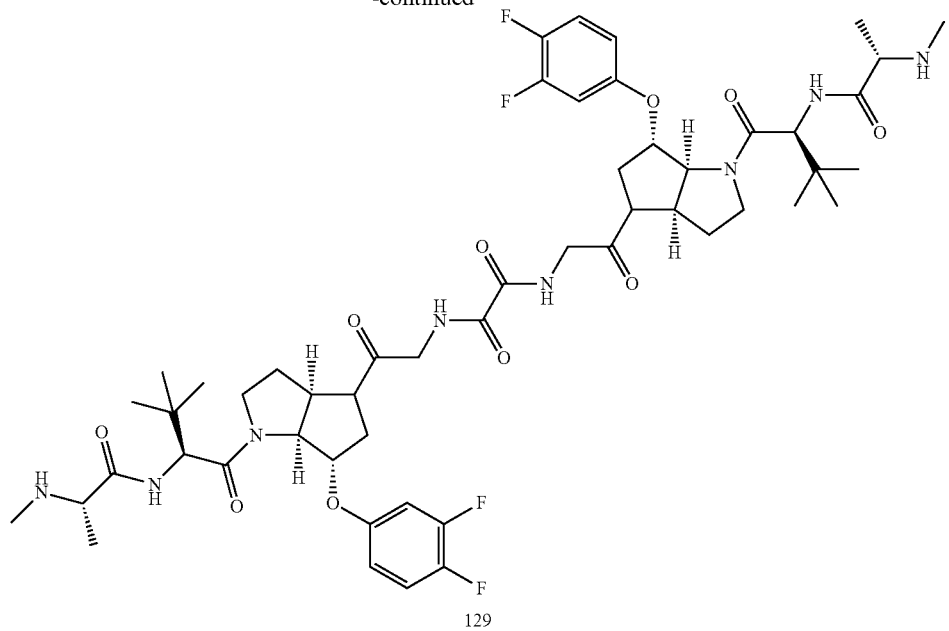

129

Additional bivalent ("dimeric") compounds can be prepared by linking two independently substituted monovalent compounds through the R2 and R2 positions as described by the following formula (the various substituents as defined throughout the application).

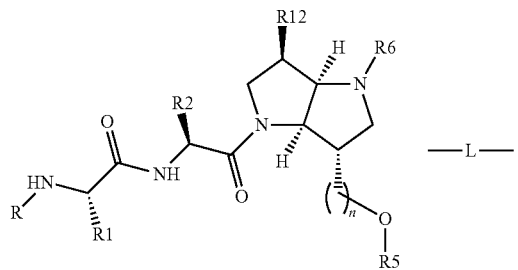

—L—

The synthetic preparation of such bivalent compounds is described in Schemes XCIV through CI following chemistry outlined in this application and described in U.S. Pat. No. 7,517,906, U.S. Pat. No. 7,309,792 which are herein incorporated by reference in their entireties.

Scheme XCIV

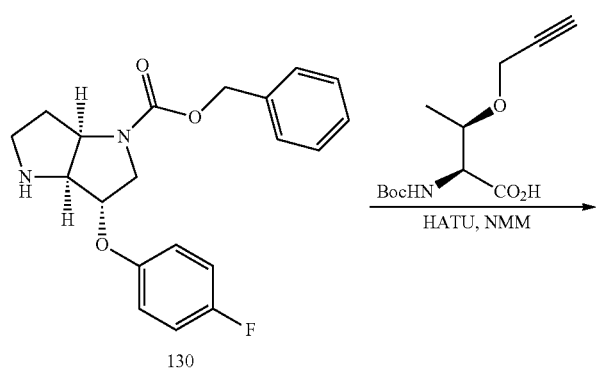

130

-continued
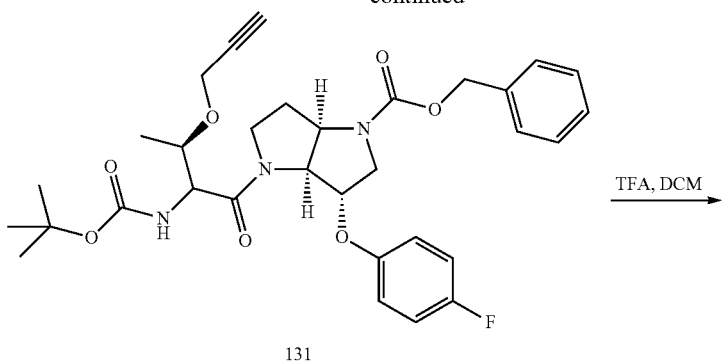
131
TFA, DCM →
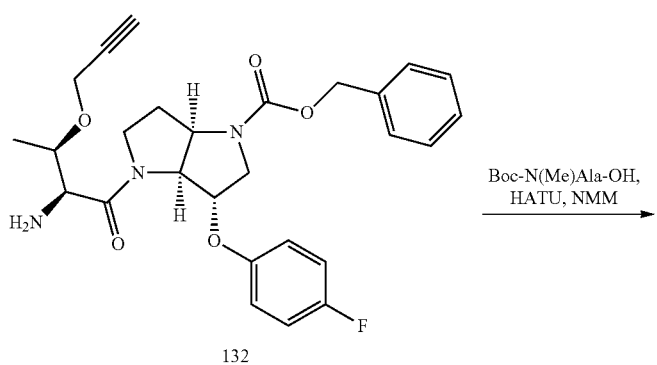
132
Boc-N(Me)Ala-OH, HATU, NMM →
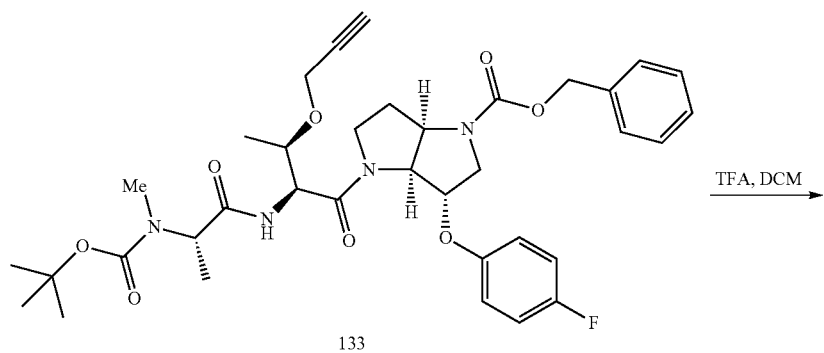
133
TFA, DCM →
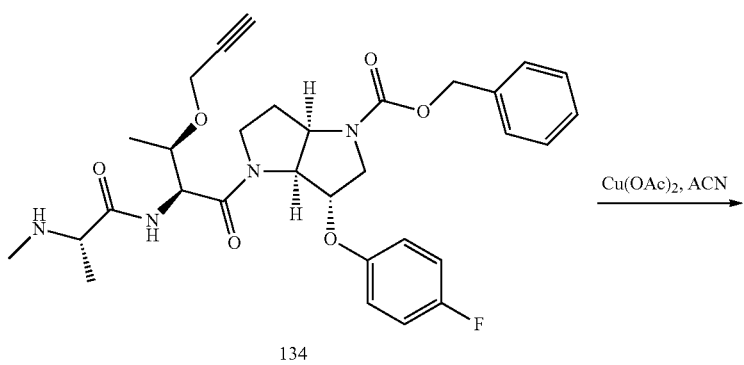
134
Cu(OAc)$_2$, ACN →

-continued
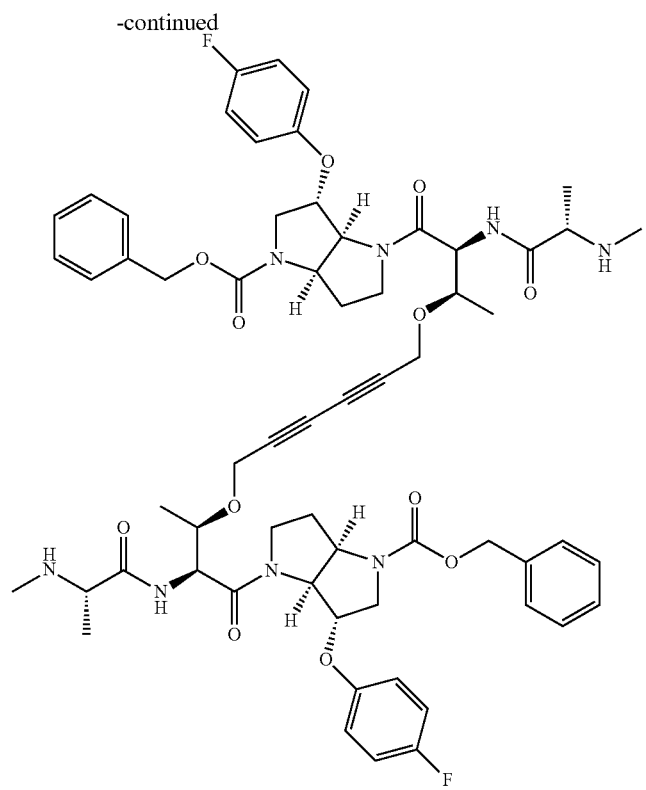
135
Scheme XCV
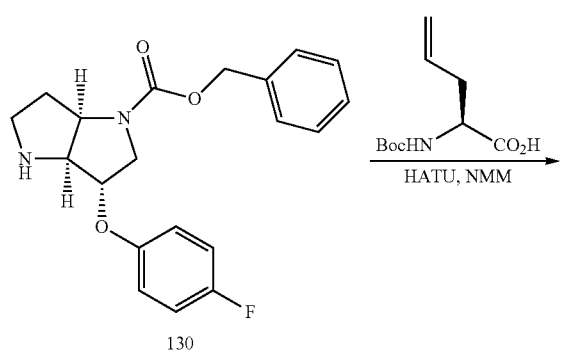
130
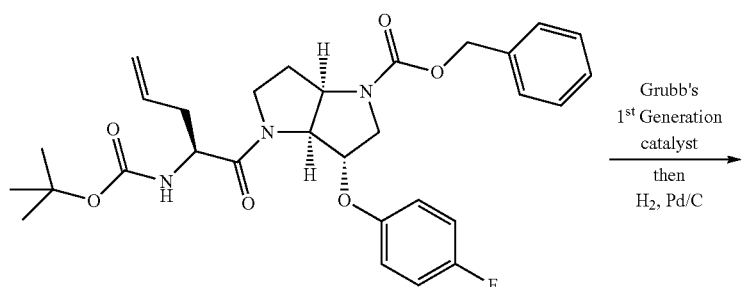
136

-continued
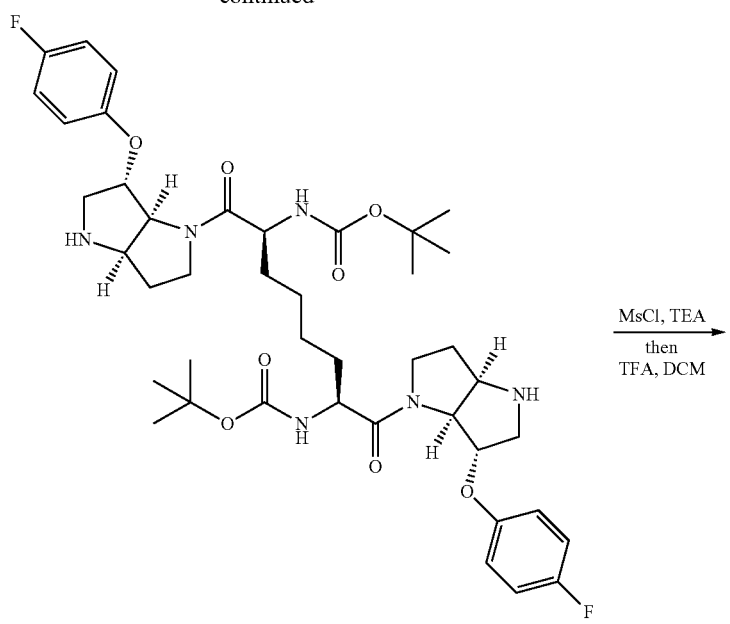
137
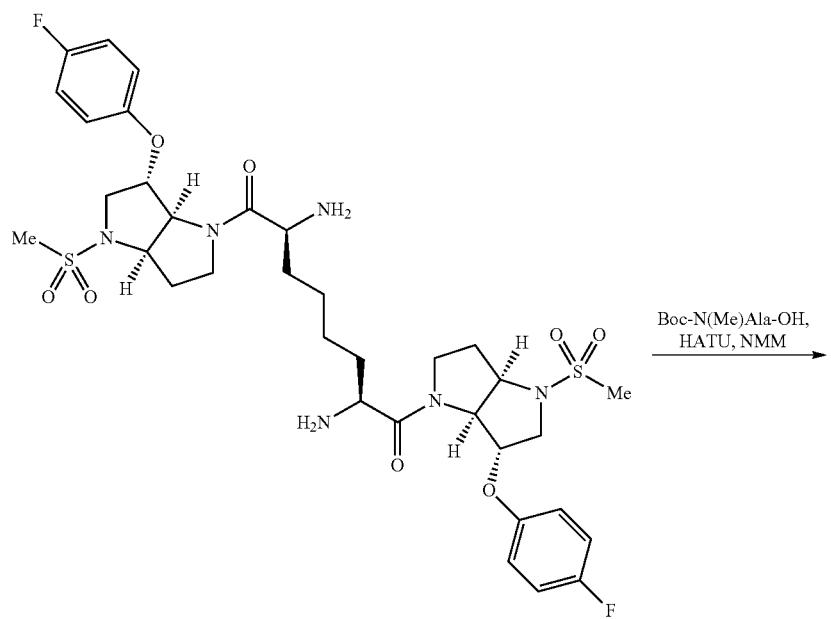
138

-continued
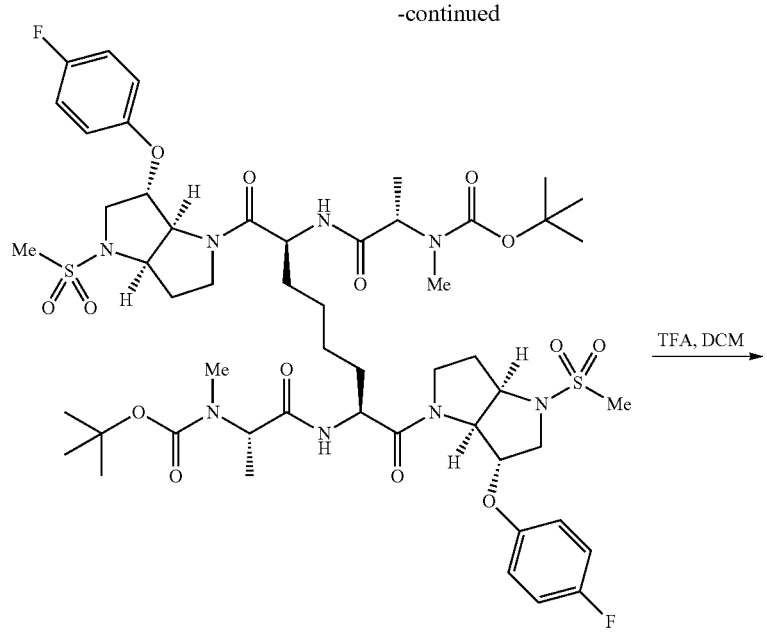
139
TFA, DCM →
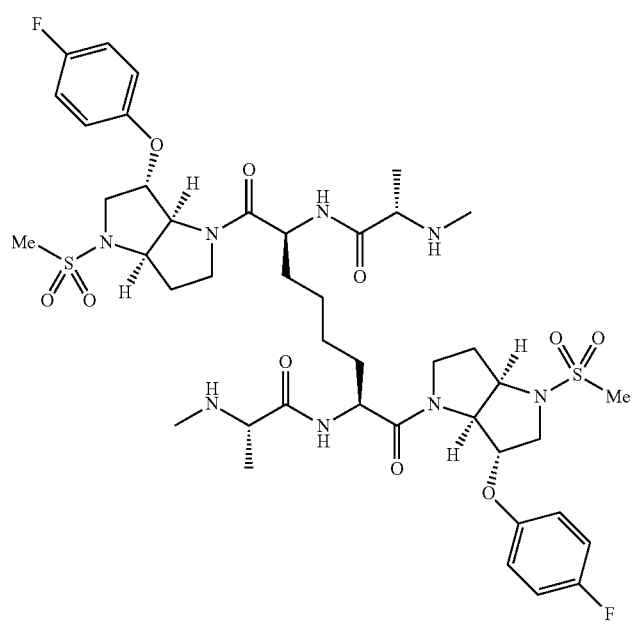
140

Scheme XCVI
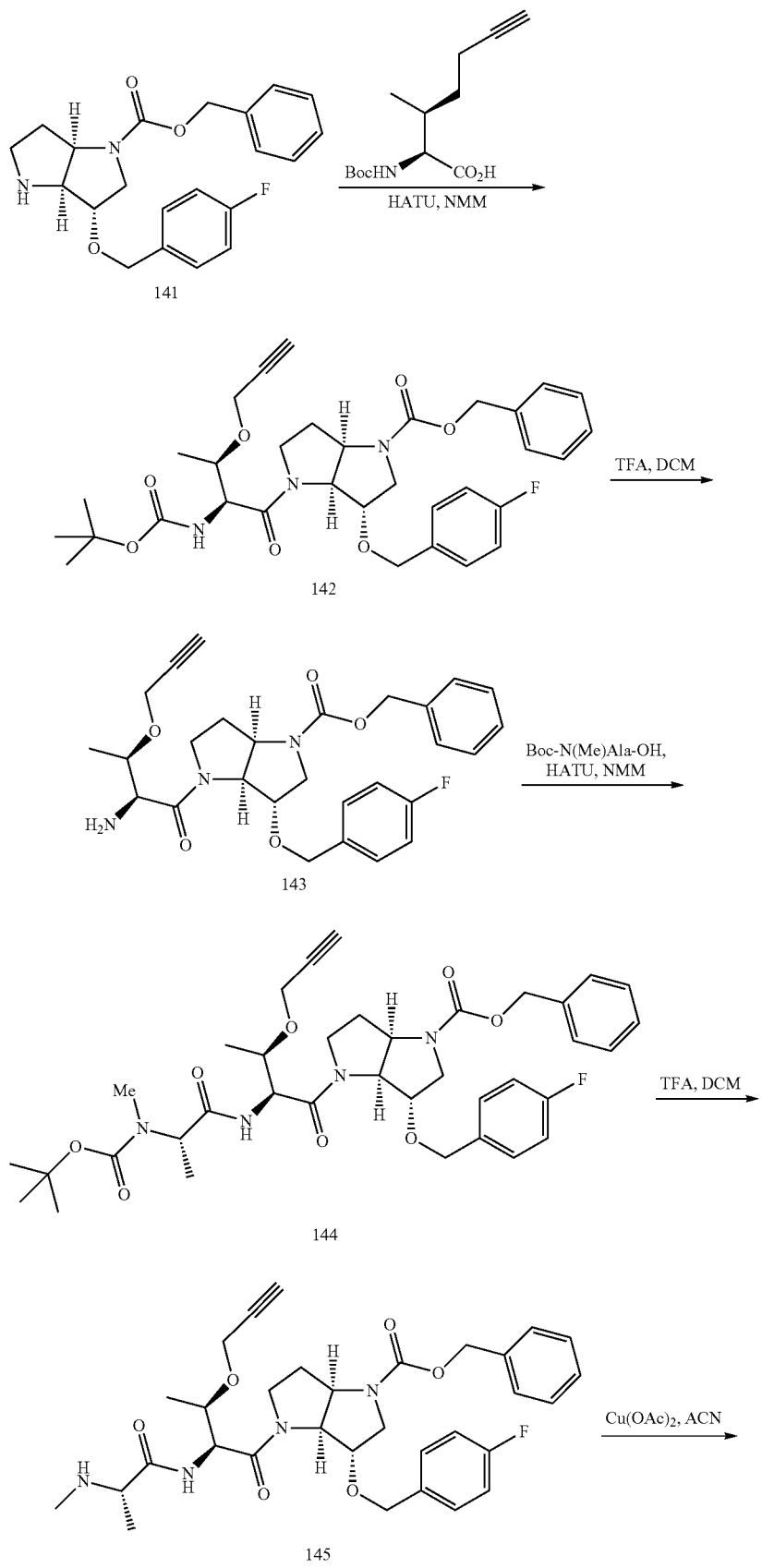

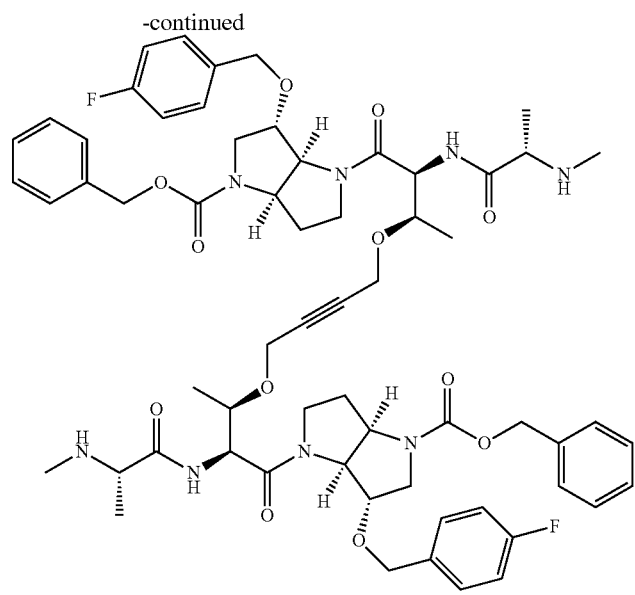
146
Scheme XCVII
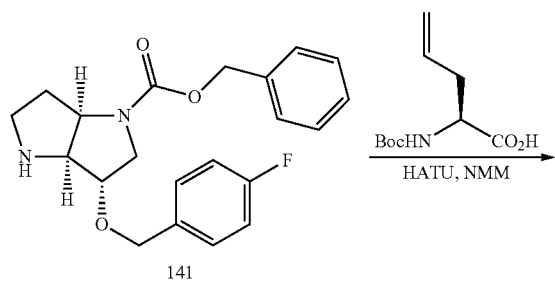
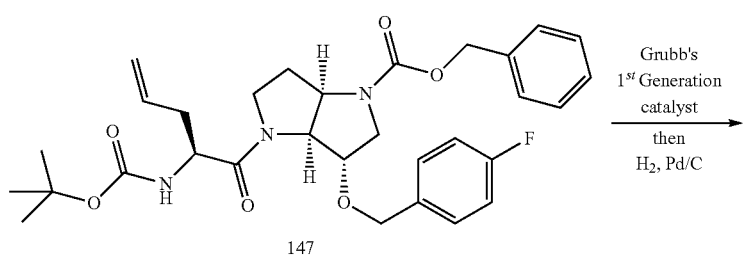
147

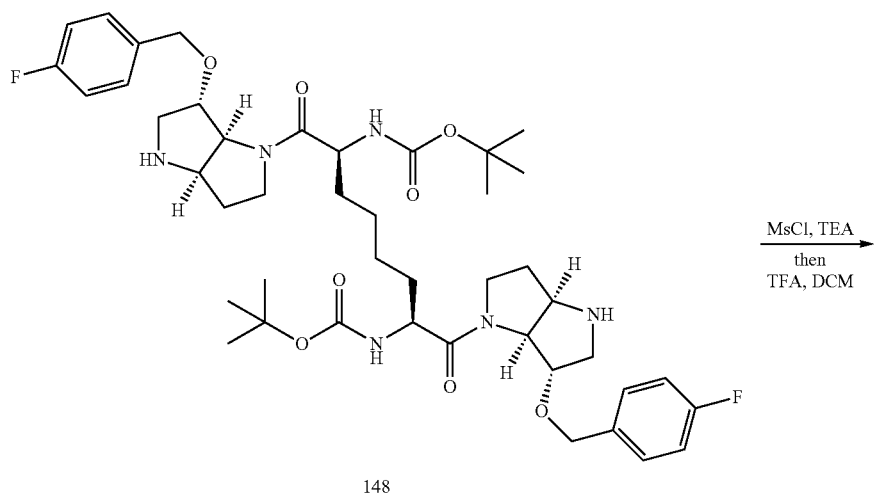
148
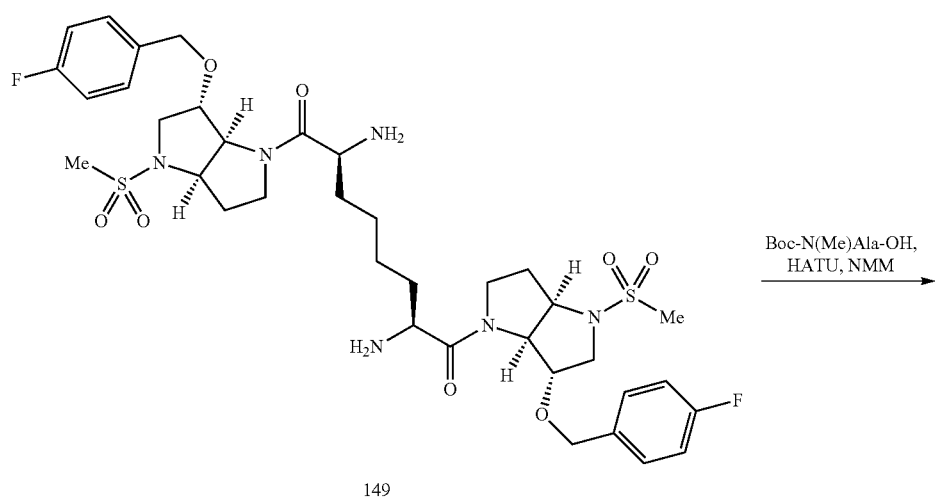
149
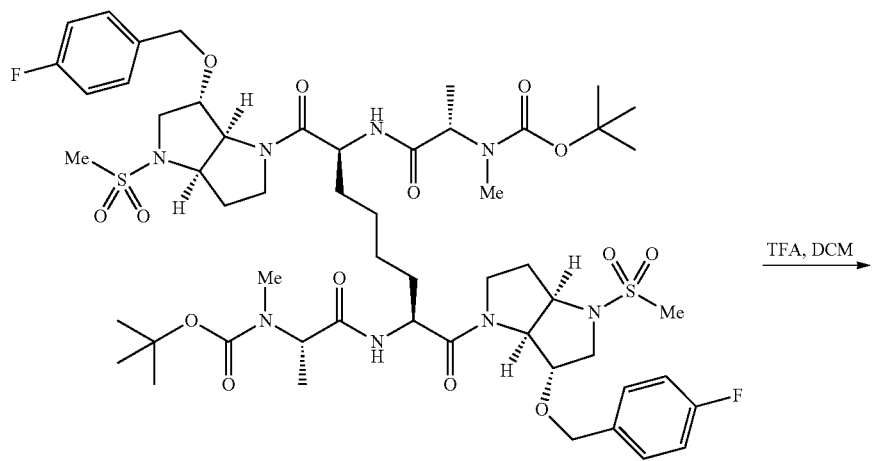
150

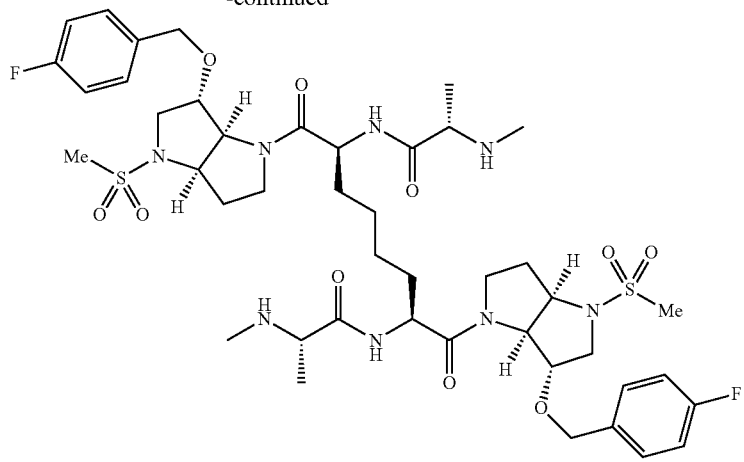
151
Scheme XCVIII
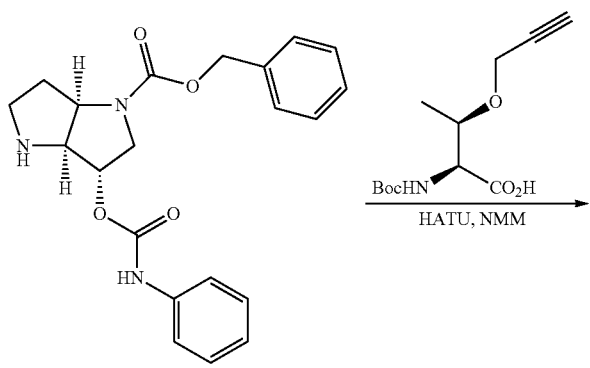
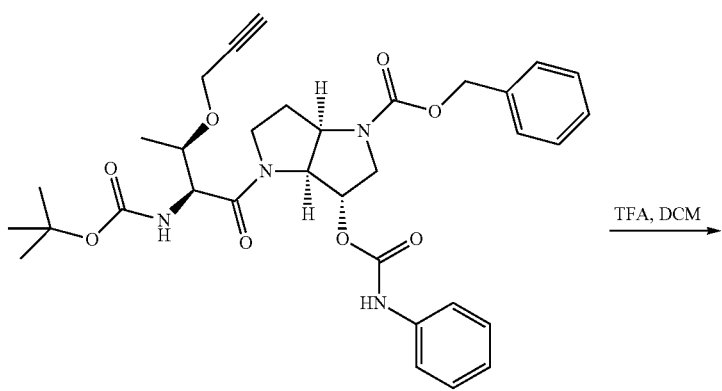
153

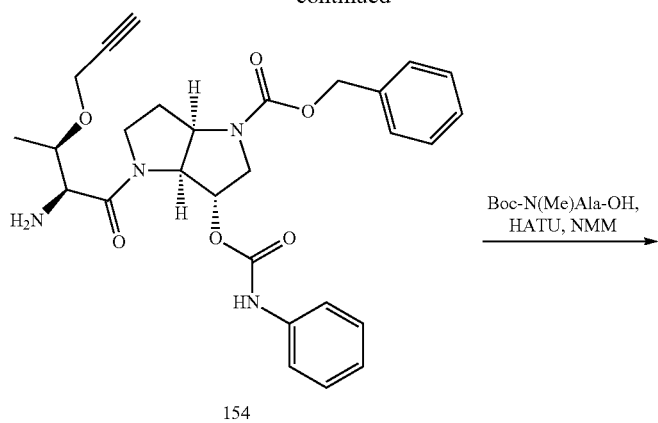
154
Boc-N(Me)Ala-OH, HATU, NMM →
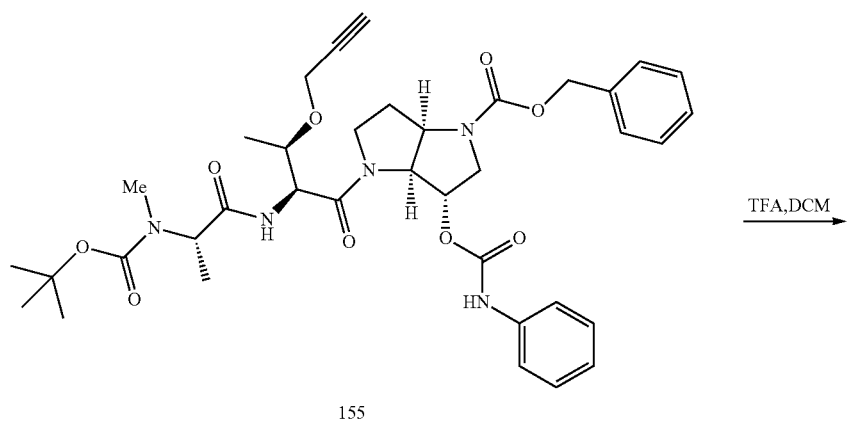
155
TFA, DCM →
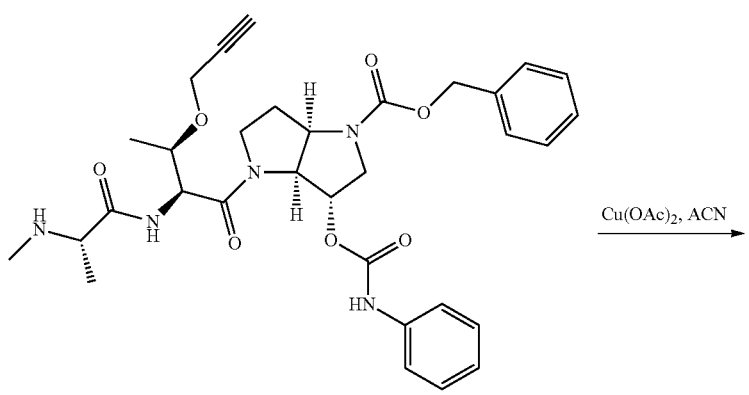
156
Cu(OAc)$_2$, ACN →

-continued
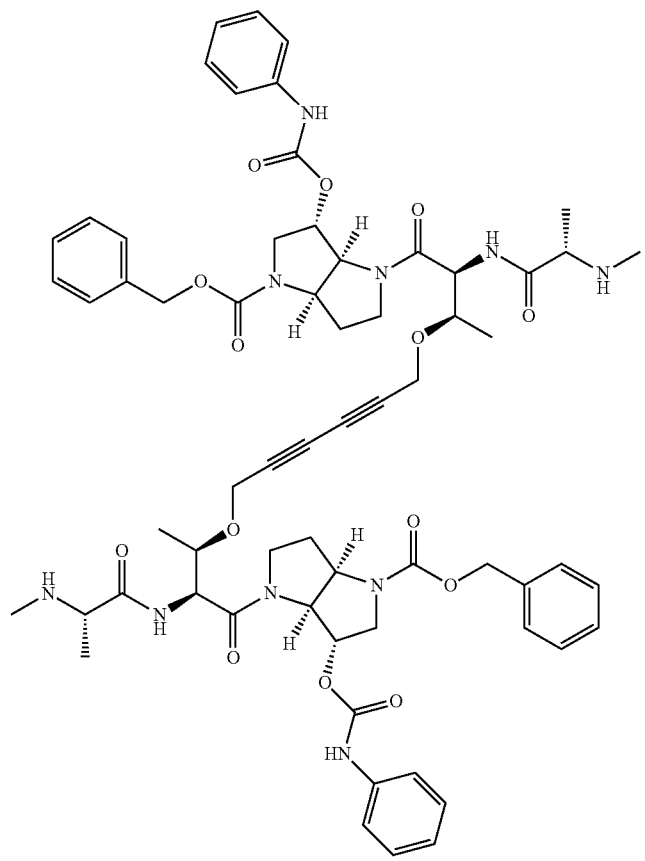
157
Scheme XCIX
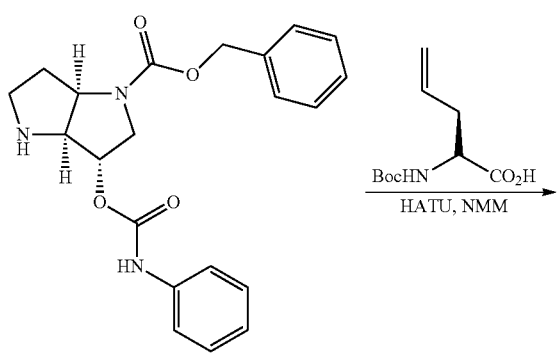
152

-continued
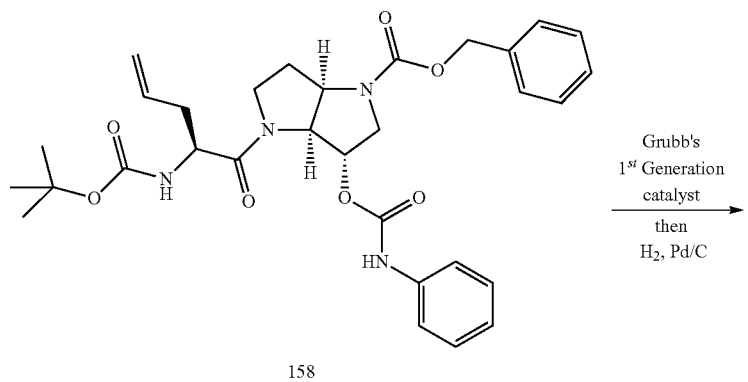
158
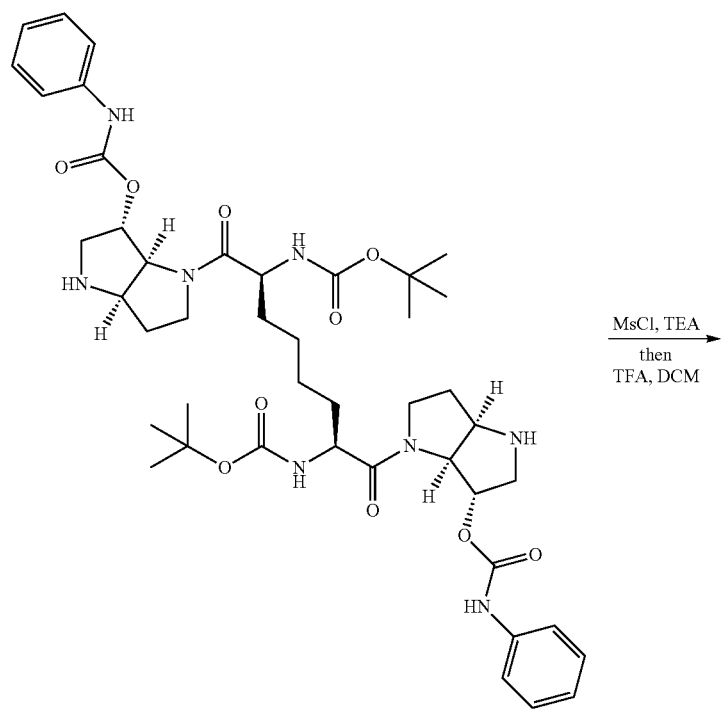
159

-continued
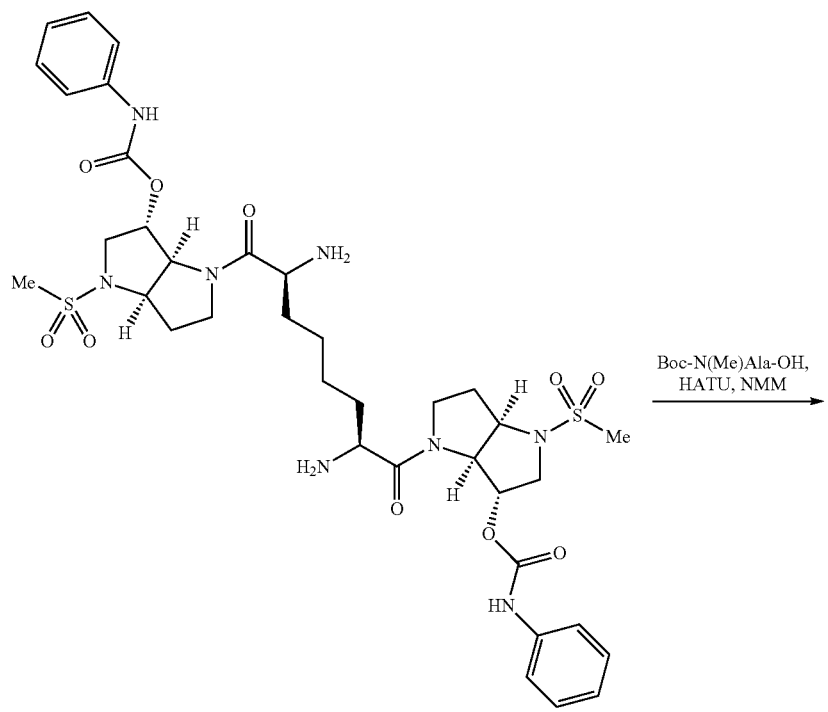
160
Boc-N(Me)Ala-OH, HATU, NMM →
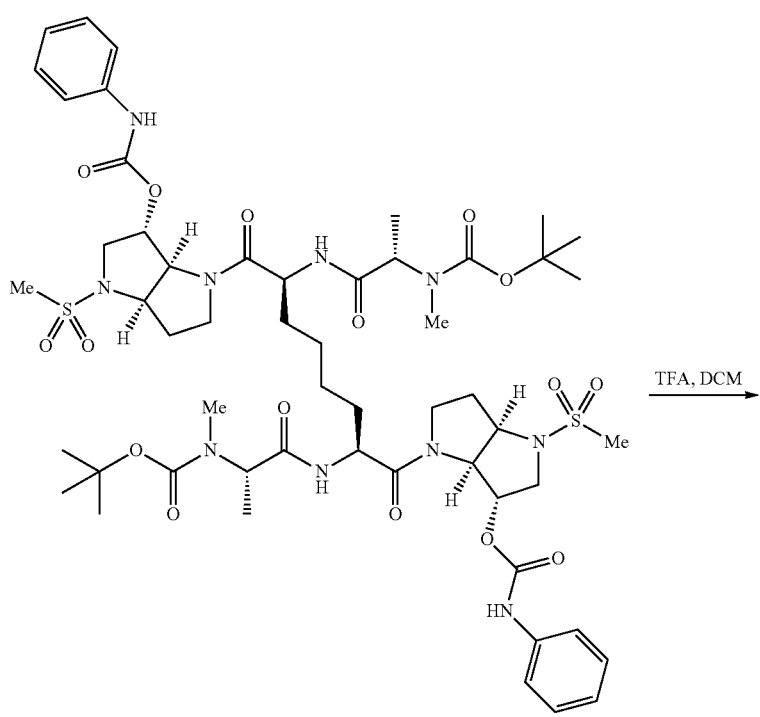
161
TFA, DCM →

-continued
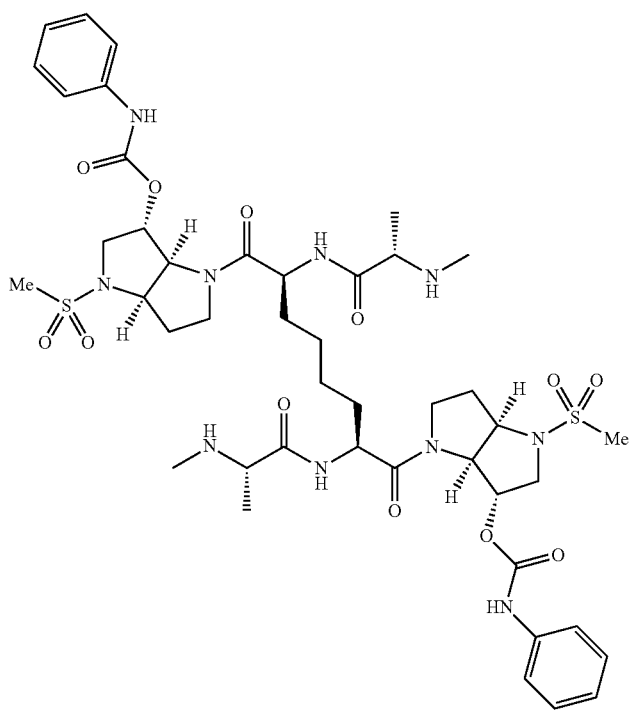
162
Scheme C
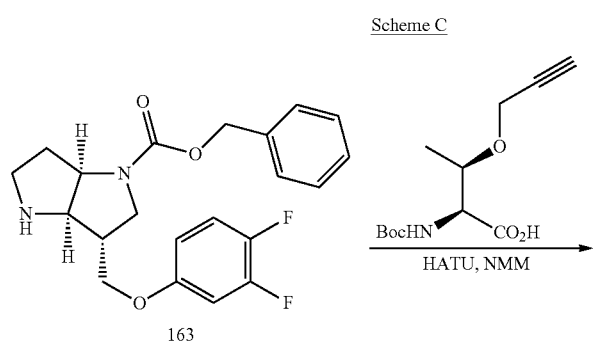
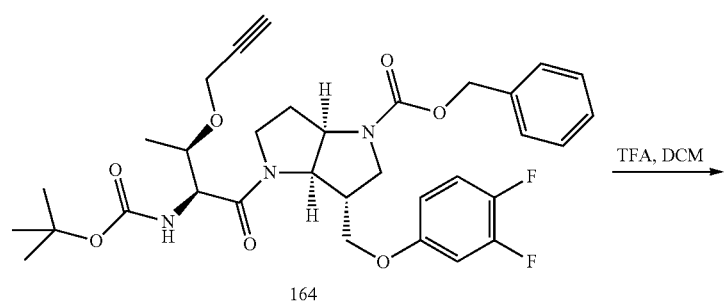

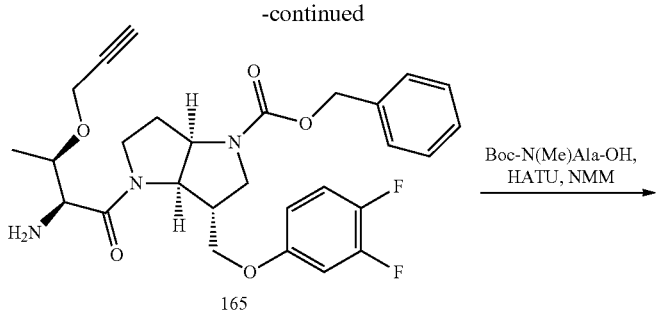
165
Boc-N(Me)Ala-OH, HATU, NMM →
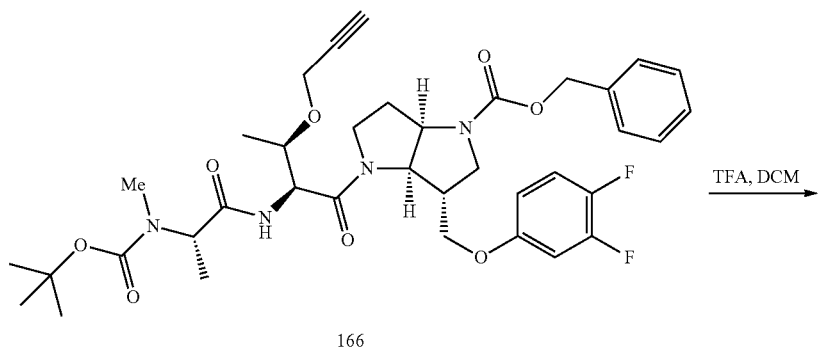
166
TFA, DCM →
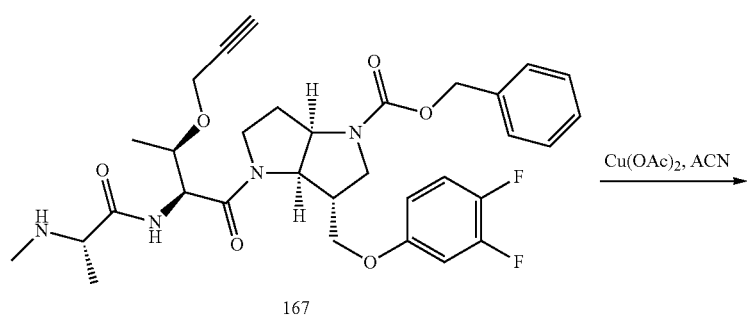
167
Cu(OAc)₂, ACN →
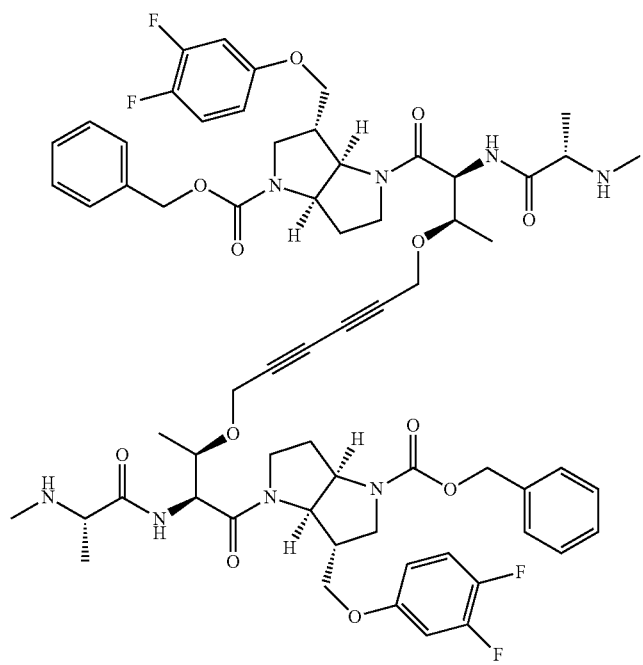
168

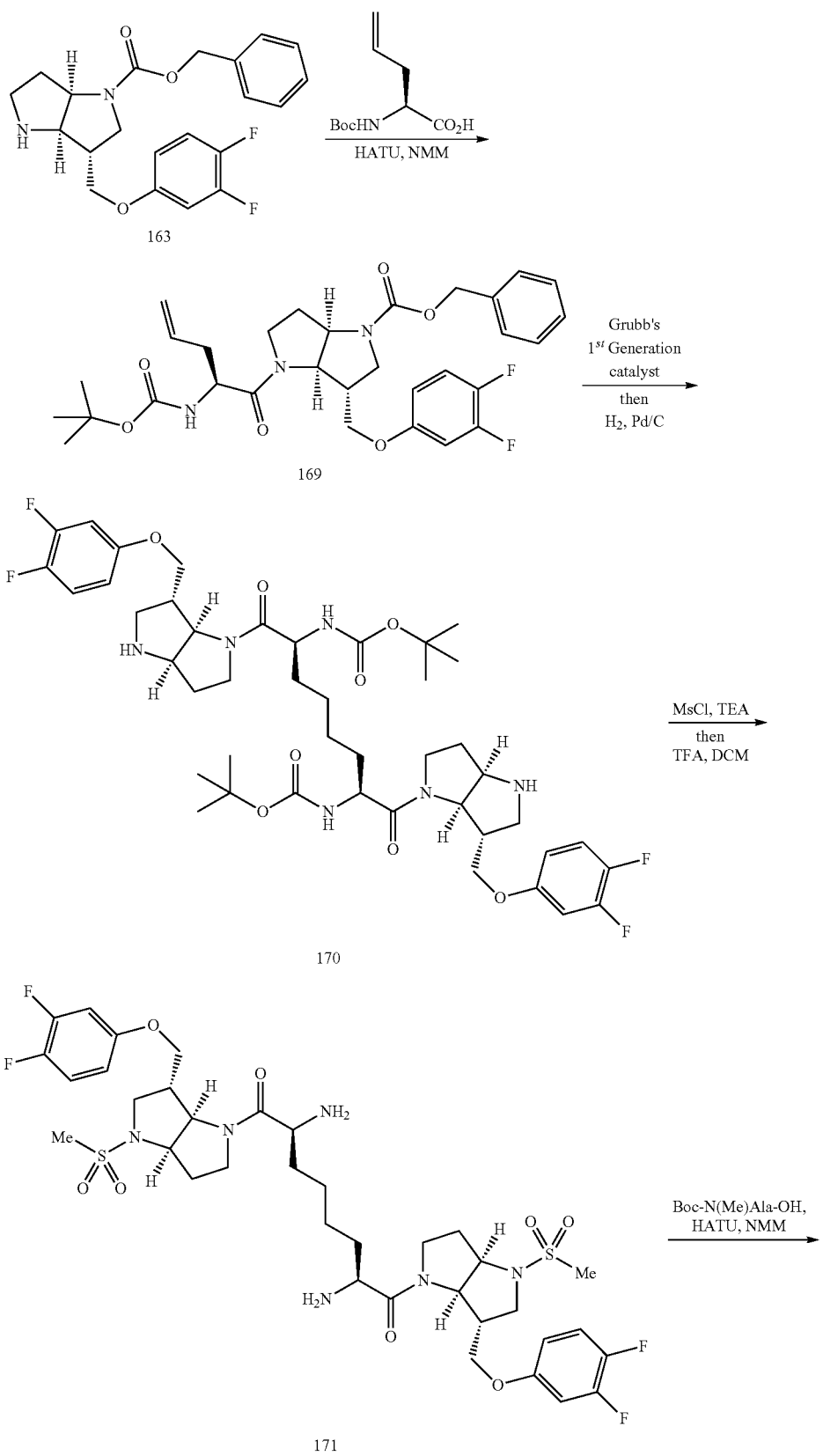

-continued

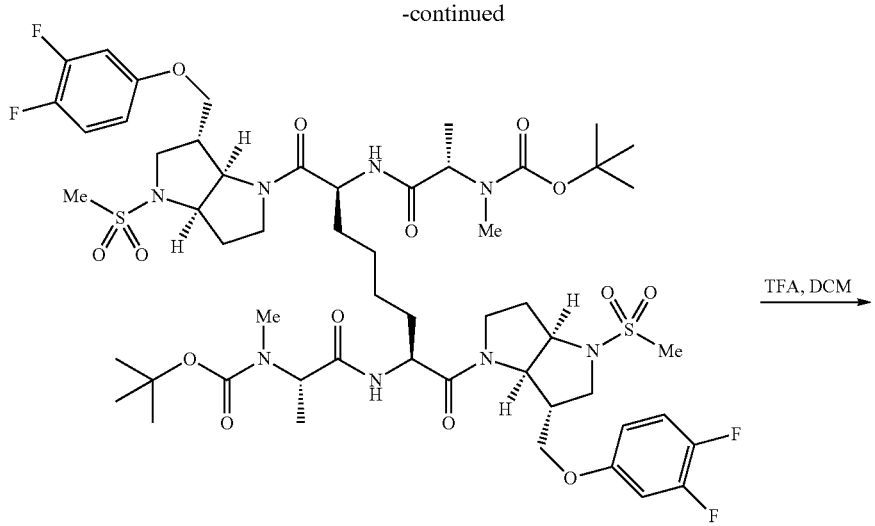

172

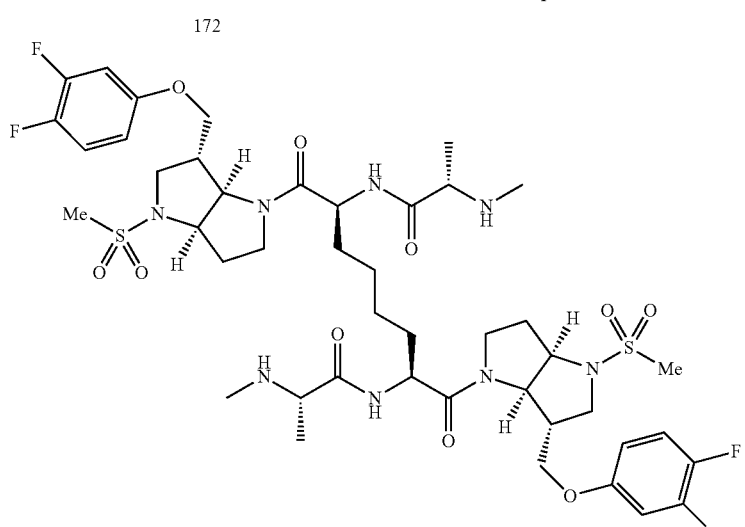

173

It is intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-enriched compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically enriched compounds of this invention can generally be prepared by substituting a readily available isotopically labelled reagent for a non-isotopically enriched reagent.

The compounds of the present invention may exist in unsolvated forms as well as solvated forms, including hydrated forms. The compounds of the present invention (e.g., compounds of Formula I, IS, and IR) also are capable of forming both pharmaceutically acceptable salts, including but not limited to acid addition and/or base addition salts. Furthermore, compounds of the present invention may exist in various solid states including an amorphous form (noncrystalline form), and in the form of clathrates, prodrugs, polymorphs, bio-hydrolyzable esters, racemic mixtures, non-racemic mixtures, or as purified stereoisomers including, but not limited to, optically pure enantiomers and diastereomers. In general, all of these forms can be used as an alternative form to the free base or free acid forms of the compounds, as described above and are intended to be encompassed within the scope of the present invention.

A "polymorph" refers to solid crystalline forms of a compound. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Different physical properties of polymorphs can affect their processing.

A "clathrate" means a compound or a salt thereof in the form of a crystal lattice that contains spaces (e.g., channels) that have a guest molecule (e.g., a solvent or water) trapped within.

As noted above, the compounds of the present invention can be administered, inter alia, as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N, N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

Compounds and salts of the present invention may also exist in tautomeric forms, such as an enol and an imine form, and the corresponding keto and enamine forms and geometric isomers and mixtures thereof. Tautomers exist as mixtures of a tautomeric set in solution. In solid form, usually one tautomer predominates. Even though only one tautomer may be described by the formulae above, the present invention includes all tautomers of the present compounds.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water, ethanol, and the like. The present invention contemplates and encompasses both the solvated and unsolvated forms.

The compounds of the present invention can be administered to a patient either alone or as a part of a pharmaceutical composition in a therapeutically effective amount. A variety of non-limiting methods for administering the compounds and related compositions to patients include orally, rectally, parenterally (intravenously, intramuscularly, or subcutaneously), intracisternally, intravaginally, intraperitoneally, intravesically, locally (powders, ointments, or drops), or as a buccal or nasal spray. In addition, the substance or compositions containing the active substances can be administered all at once, as for example, by a bolus injection, multiple times, such as by a series of tablets, or delivered substantially uniformly over a period of time, as for example, using transdermal delivery. It is also noted that the dose of the substances can be varied over time.

The compounds and related compositions of the present invention can be administered alone, or in combination with other pharmaceutically active substances. The other pharmaceutically active substances can be intended to treat the same disease or condition as the substances of the present invention or a different disease or condition. If the patient is to receive, or is receiving multiple pharmaceutically active substances, the substances can be administered simultaneously, or sequentially. For example, in the case of tablets, the active substances may be found in one tablet or in separate tablets, which can be administered at once or sequentially in any order. In addition, it should be recognized that the compositions may be different forms. For example, one or more substance may be delivered via a tablet, while another is administered via injection or orally as a syrup. All combinations, delivery methods and administration sequences are contemplated.

Pharmaceutical compositions to be used comprise a therapeutically effective amount of a compound as described above, or a pharmaceutically acceptable salt or other form thereof together with one or more pharmaceutically acceptable excipients. The phrase "pharmaceutical composition" refers to a composition suitable for administration in medical or veterinary use. It should be appreciated that the determinations of proper dosage forms, dosage amounts, and routes of administration for a particular patient are within the level of ordinary skill in the pharmaceutical and medical arts.

Compositions suitable for parenteral administration conveniently comprise a sterile aqueous preparation of a compound or composition of the invention, which is preferably isotonic with the blood of the recipient. This aqueous preparation may be formulated according to known methods using suitable dispersing or wetting agents, emulsifying and suspending agents. Various antibacterial and antifungal agents, for example, parabens, chlorobutanol, phenol, and sorbic acid also may be included. The sterile injectable preparation also may be a sterile injectable solution or suspension in a nontoxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Prolonged absorption of the injectable pharmaceutical form can be brought about by the use of agents delaying absorption, for example, aluminum monostearate and gelatin. Carrier formulation suitable for subcutaneous, intravenous, intramuscular, etc. administrations can be found in Remington's Pharmaceutical Sciences, Mack Publishing Co., Easton, Pa. which is incorporated herein in its entirety by reference thereto.

Solid dosage forms for oral administration include capsules, tablets, pills, powders, and granules. In such solid dosage forms, the compound is admixed with at least one inert pharmaceutically acceptable excipient such as (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid dosage forms such as tablets, dragees, capsules, pills, and granules also can be prepared with coatings and shells, such as enteric coatings and others well known in the art. The solid dosage form also may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients. Such solid dosage forms may generally contain from 1% to 95% (w/w) of the active compound. In certain embodiments, the active compound ranges from 5% to 70% (w/w).

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a substance of the present invention, and a second pharmaceutical substance. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a substance of the present invention can consist of one tablet or capsule, while a daily dose of the second substance can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Liquid dosage forms for oral administration include pharmaceutically acceptable emulsions, solutions, suspensions, syrups, and elixirs. In addition to the compound or composition, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances. Besides such inert diluents, the composition can also include adjuvants, such as wetting agents, emulsifying and suspending agents, sweetening, flavoring, and perfuming agents.

Compositions for rectal administrations are preferably suppositories which can be prepared by mixing compounds of the present invention with suitable non-irritating excipients or carriers such as cocoa butter, polyethyleneglycol or a low-melting, suppository wax, which are solid at ordinary temperatures but liquid at body temperature and therefore, melt in the rectum or vaginal cavity and release the active compound.

Dosage forms for topical administration of a compound of this invention include ointments, powders, sprays, and inhalants. The active compound is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds and compositions of the present invention also may benefit from a variety of delivery systems, including time-released, delayed release or sustained release delivery systems. Such option may be particularly beneficial when the compounds and composition are used in conjunction with other treatment protocols as described in more detail below.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, as used herein, means that the implant is constructed and arranged to deliver therapeutic levels of the active compound for at least 30 days, and preferably 60 days. Long-term sustained release implants are well-known to those of ordinary skill in the art and include some of the release systems described above.

In practicing the methods of the present invention, the compounds and compositions of the present invention are administered in a therapeutically effective amount. Generally, doses of active compounds would be from about 0.01 mg/kg per day to 1000 mg/kg per day. It is expected that doses ranging from 50-500 mg/kg will be suitable, preferably intravenously, intramuscularly, or intradermally, and in one or several administrations per day. The compounds of the present invention may also be used in combination with radiation therapy, hormone therapy, surgery and immunotherapy, which therapies are well know to those skilled in the art.

When practicing the conjoint or combination therapy described in more detail below, the administration of the compounds and compositions of the present invention can occur simultaneous with, subsequent to, or prior to chemotherapy or radiation, so long as the chemotherapeutic agent or radiation sensitizes the system to the compounds and compositions of the present invention.

In general, routine experimentation in clinical trials will determine specific ranges for optimal therapeutic effect for a particular compound and composition of the present invention and each administrative protocol, and administration to specific patients will be adjusted to within effective and safe ranges depending on the patient condition and responsiveness to initial administrations. However, the ultimate administration protocol will be regulated according to the judgment of the attending clinician considering such factors as age, condition and size of the patient, the potency of the compound or composition, the duration of the treatment and the severity of the disease being treated. For example, a dosage regimen of the compound or composition can be an oral administration of from 1 mg to 2000 mg/day, preferably 1 to 1000 mg/day, more preferably 50 to 600 mg/day, in two to four (preferably two) divided doses, to reduce tumor growth. Intermittent therapy (e.g., one week out of three weeks or three out of four weeks) may also be used.

In the event that a response in a subject is insufficient at the initial doses applied, higher doses (or effectively higher doses by a different, more localized delivery route) may be employed to the extent that the patient tolerance permits. Multiple doses per day are contemplated to achieve appropriate systemic levels of compounds. Generally, a maximum dose is used, that is, the highest safe dose according to sound medical judgment. Those of ordinary skill in the art will understand, however, that a patient may insist upon a lower dose or tolerable dose for medical reasons, psychological reasons or for virtually any other reason.

The compounds of the present invention and pharmaceutical compositions comprising a compound of the present invention can be administered to a subject suffering from cancer, an autoimmune disease or another disorder where a defect in apoptosis is implicated. In connection with such treatments, the patient can be treated prophylactically, acutely, or chronically using compounds and compositions of the present invention, depending on the nature of the disease. Typically, the host or subject in each of these methods is human, although other mammals may also benefit from the administration of a compound of the present invention.

As described in U.S. Pat. No. 7,244,851, the disclosure of which is incorporated herein by reference, IAP antagonists can be used for the treatment of all cancer types which fail to undergo apoptosis. Thus, compounds of the present invention can be used to provide a therapeutic approach to the treatment of many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia is also contemplated by this invention. Indications may include, but are not limited to brain cancers, skin cancers, bladder cancers, ovarian cancers, breast cancers, gastric cancers, pancreatic cancers, colon cancers, blood cancers, lung cancers and bone cancers. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

The inventors believe that the IAP antagonists of the present invention will be particularly active for treating human malignancies where cIAP1 and cIAP2 are over-expressed (e.g., lung cancers, see Dai et al, Hu. Molec. Genetics, 2003 v 12 pp 791-801; leukemias (multiple references), and other cancers (Tamm et al, Clin Cancer Res, 2000, v 6, 1796-1803). The inventors also expect that the IAP antagonists of the present invention will be active in disorders that may be driven by inflammatory cytokines such as TNF playing a pro-survival role (for example, there is a well defined role for TNF acting as a survival factor in ovarian carcinoma, similarly for gastric cancers (see Kulbe, et al, Cancer Res 2007, 67, 585-592).

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Examples of such autoimmune diseases include collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotony, Guillain-Barré syndrome (Müller-Fischer syndrome), stiff-man syndrome, cerebellar degeneration, ataxia, opsoklonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

The present invention also is directed to the use of the compounds and compositions as a chemopotentiating agent with other treatment approaches. The term "chemopotentiating agent" refers to an agent that acts to increase the sensitivity of an organism, tissue, or cell to a chemical compound, or treatment namely "chemotherapeutic agents" or "chemo drugs" or to radiation treatment. Thus, compounds and compositions of the present invention can be used for inhibiting tumor growth in vivo by administering them in combination with a biologic or chemotherapeutic agent or by using them in combination with chemoradiation. In these applications, the administration of the compounds and compositions of the present invention may occur prior to, and with sufficient time, to cause sensitization of the site to be treated. Alternatively, the compounds and compositions of the present invention may be used contemporaneously with radiation and/or additional anti-cancer chemical agents (infra). Such systems can avoid repeated administrations of the compounds and compositions of the present invention, increasing convenience to the subject and the physician, and may be particularly suitable for certain compositions of the present invention.

Biological and chemotherapeutics/anti-neoplastic agents and radiation induce apoptosis by activating the extrinsic or intrinsic apoptotic pathways, and, since the compounds and compositions of the present invention relieve antagonists of apoptotic proteins (IAPs) and, thus, remove the block in apoptosis, the combination of chemotherapeutics/anti-neoplastic agents and radiation with the compounds and compositions of the present invention should work synergistically to facilitate apoptosis.

A combination of a compound of the present invention and a chemotherapeutic/anti neoplastic agent and/or radiation therapy of any type that activates the intrinsic pathway may provide a more effective approach to destroying tumor cells. Compounds of the present invention interact with IAP's, such as XIAP, cIAP-1, cIAP-2, ML-IAP, etc., and block the IAP mediated inhibition of apoptosis while chemotherapeutics/anti neoplastic agents and/or radiation therapy kills actively dividing cells by activating the intrinsic apoptotic pathway leading to apoptosis and cell death. As is described in more detail below, embodiments of the invention provide combinations of a compound of the present invention and a chemotherapeutic/anti-neoplastic agent and/or radiation which provide a synergistic action against unwanted cell proliferation. This synergistic action between a compound of the present invention and a chemotherapeutic/anti-neoplastic agent and/or radiation therapy can improve the efficiency of the chemotherapeutic/anti-neoplastic agent and/or radiation therapies. This will allow for an increase in the effectiveness of current chemotherapeutic/anti-neoplastic agents or radiation treatments allowing the dose of the chemotherapeutic/anti-neoplastic agent to be lowered, therein providing both a more effective dosing schedule as well as use of a more tolerable dose of chemotherapeutic/anti-neoplastic agent and/or radiation.

In an embodiment of the present invention, the patient is treated by administering a compound or a pharmaceutical composition of the present invention at a time the patient is subject to concurrent or antecedent radiation or chemotherapy for treatment of a neoproliferative pathology of a tumor such as, but not limited to, bladder cancer, breast cancer, prostate cancer, lung cancer, pancreatic cancer, gastric cancer, colon cancer, ovarian cancer, renal cancer, hepatoma, melanoma, lymphoma, sarcoma, and combinations thereof.

In another embodiment of the present invention, the compound or composition of the present invention can be administered in combination with a chemotherapeutic and/or for use in combination with radiotherapy, immunotherapy, and/or photodynamic therapy, promoting apoptosis and enhancing the effectiveness of the chemotherapeutic, radiotherapy, immunotherapy, and/or photodynamic therapy.

Embodiments of the invention also include a method of treating a patient afflicted with cancer by the contemporaneous or concurrent administration of a chemotherapeutic agent. Such chemotherapeutic agents include but are not limited to the chemotherapeutic agents described in "Modern Pharmacology with Clinical Applications", Sixth Edition, Craig & Stitzel, Chpt. 56, pg 639-656 (2004), herein incorporated by reference. The chemotherapeutic agent can be, but is not limited to, alkylating agents, antimetabolites, anti-tumor antibiotics, plant-derived products such as taxanes, enzymes, hormonal agents, miscellaneous agents such as cisplatin, monoclonal antibodies, glucocorticoids, mitotic inhibitors, topoisomerase I inhibitors, topoisomerase II inhibitors, immunomodulating agents such as interferons, cellular growth factors, cytokines, and nonsteroidal anti-inflammatory compounds, cellular growth factors and kinase inhibitors. Other suitable classifications for chemotherapeutic agents include mitotic inhibitors and nonsteroidal antiestrogenic analogs.

Specific examples of suitable biological and chemotherapeutic agents include, but are not limited to, cisplatin, carmustine (BCNU), 5-fluorouracil (5-FU), cytarabine (Ara-C), gemcitabine, methotrexate, daunorubicin, doxorubicin, dexamethasone, topotecan, etoposide, paclitaxel, vincristine, tamoxifen, TNF-alpha, TRAIL, interferon (in both its alpha and beta forms), thalidomide, and melphalan. Other specific examples of suitable chemotherapeutic agents include nitrogen mustards such as cyclophosphamide, alkyl sulfonates, nitrosoureas, ethylenimines, triazenes, folate antagonists, purine analogs, pyrimidine analogs, anthracyclines, bleomycins, mitomycins, dactinomycins, plicamycin, vinca alkaloids, epipodophyllotoxins, taxanes, glucocorticoids, L-asparaginase, estrogens, androgens, progestins, luteinizing hormones, octreotide actetate, hydroxyurea, procarbazine, mitotane, hexamethylmelamine, carboplatin, mitoxantrone, monoclonal antibodies, levamisole, interferons, interleukins, filgrastim and sargramostim. Chemotherapeutic compositions also comprise other members, i.e., other than TRAIL, of the TNF superfamily of compounds.

Another embodiment of the present invention relates to the use of a compound or composition of the present invention in combination with topoisomerase inhibitors to potentiate their apoptotic inducing effect. Topoisomerase inhibitors inhibit DNA replication and repair, thereby promoting apoptosis and have been used as chemothemotherapeutic agents. Topoisomerase inhibitors promote DNA damage by inhibiting the enzymes that are required in the DNA repair process. Therefore, export of Smac from the mitochondria into the cell cytosol is provoked by the DNA damage caused by topoisomerase inhibitors. Topoisomerase inhibitors of both the Type I class (camptothecin, topotecan, SN-38 (irinotecan active metabolite)) and the Type II class (etoposide) are expected to show potent synergy with compounds of the present invention. Further examples of topoisomerase inhibiting agents that may be used include, but are not limited to, irinotecan, topotecan, etoposide, amsacrine, exatecan, gimatecan, etc. Other topoisomerase inhibitors include, for example, Aclacinomycin A, camptothecin, daunorubicin, doxorubicin, ellipticine, epirubicin, and mitaxantrone.

In another embodiment of the invention, the chemotherapeutic/anti-neoplastic agent for use in combination with the compounds and compositions of the present invention may be a platinum containing compound. In one embodiment of the invention, the platinum containing compound is cisplatin. Cisplatin can synergize with a compound of the present invention and potentiate the inhibition of an IAP, such as but not limited to XIAP, cIAP-1, c-IAP-2, ML-IAP, etc. In another embodiment a platinum containing compound is carboplatin. Carboplatin can synergize with a compound of the present invention and potentiate the inhibition of an IAP, including, but not limited to, XIAP, cIAP-1, c-IAP-2, ML-IAP, etc. In another embodiment a platinum containing compound is oxaliplatin. The oxaliplatin can synergize with a compound of the present invention and potentiate the inhibition of an IAP, including, but not limited to, XIAP, cIAP-1, c-IAP-2, ML-IAP, etc.

Platinum chemotherapy drugs belong to a general group of DNA modifying agents. DNA modifying agents may be any highly reactive chemical compound that bonds with various nucleophilic groups in nucleic acids and proteins and cause mutagenic, carcinogenic, or cytotoxic effects. DNA modifying agents work by different mechanisms, disruption of DNA function and cell death; DNA damage/the formation of cross-bridges or bonds between atoms in the DNA; and induction of mispairing of the nucleotides leading to mutations, to achieve the same end result. Three non-limiting examples of a platinum containing DNA modifying agents are cisplatin, carboplatin and oxaliplatin.

Cisplatin is believed to kill cancer cells by binding to DNA and interfering with its repair mechanism, eventually leading to cell death. Carboplatin and oxaliplatin are cisplatin derivatives that share the same mechanism of action. Highly reactive platinum complexes are formed intracellularly and inhibit DNA synthesis by covalently binding DNA molecules to form intrastrand and interstrand DNA crosslinks.

Non-steroidal anti-inflammatory drugs (NSAIDs) have been shown to induce apoptosis in colorectal cells. NSAIDs appear to induce apoptosis via the release of Smac from the mitochondria (PNAS, Nov. 30, 2004, vol. 101:16897-16902). Therefore, the use of NSAIDs in combination with the compounds and compositions of the present invention would be expected to increase the activity of each drug over the activity of either drug independently.

Many naturally occurring compounds isolated from bacterial, plant, and animals can display potent and selective biological activity in humans including anticancer and antineoplastic activities. In fact, many natural products, or semi-synthetic derivatives thereof, which possess anticancer activity, are already commonly used as therapeutic agents; these include paclitaxel, etoposide, vincristine, and camptothecin amongst others. Additionally, there are many other classes of natural products such as the indolocarbazoles and epothilones that are undergoing clinical evaluation as anticancer agents. A reoccurring structural motif in many natural products is the attachment of one or more sugar residues onto an aglycone core structure. In some instances, the sugar portion of the natural product is critical for making discrete protein-ligand interactions at its site of action (i.e., pharmacodynamics) and removal of the sugar residue results in significant reductions in biological activity. In other cases, the sugar moiety or moieties are important for modulating the physical and pharmacokinetic properties of the molecule. Rebeccamycin and staurosporine are representative of the sugar-linked indolocarbazole family of anticancer natural products with demonstrated anti-kinase and anti-topoisomerase activity.

Taxanes are anti-mitotic, mitotic inhibitors or microtubule polymerization agents. Taxanes are characterized as compounds that promote assembly of microtubules by inhibiting tubulin depolymerization, thereby blocking cell cycle progression through centrosomal impairment, induction of abnormal spindles and suppression of spindle microtubule dynamics. Taxanes include but are not limited to, docetaxel and paclitaxel. The unique mechanism of action of taxane is in contrast to other microtubule poisons, such as Vinca alkaloids, colchicine, and cryptophycines, which inhibit tubulin polymerization. Microtubules are highly dynamic cellular polymers made of alpha-beta-tubulin and associated proteins that play key roles during mitosis by participating in the organization and function of the spindle, assuring the integrity of the segregated DNA. Therefore, they represent an effective target for cancer therapy.

Yet another embodiment of the present invention is the therapeutic combination or the therapeutic use in combination of a compound or composition of the present invention with TRAIL or other chemical or biological agents which bind to and activate the TRAIL receptor(s). TRAIL has received considerable attention recently because of the finding that many cancer cell types are sensitive to TRAIL-induced apoptosis, while most normal cells appear to be resistant to this action of TRAIL. TRAIL-resistant cells may arise by a variety of different mechanisms including loss of the receptor, presence of decoy receptors, or overexpression of FLIP which competes for zymogen caspase-8 binding during DISC formation. In TRAIL resistance, a compound or composition of the present invention may increase tumor cell sensitivity to TRAIL leading to enhanced cell death, the clinical correlations of which are expected to be increased apoptotic activity in TRAIL resistant tumors, improved clinical response, increased response duration, and ultimately, enhanced patient survival rate. In support of this, reduction in XIAP levels by in vitro antisense treatment has been shown to cause sensitization of resistant melanoma cells and renal carcinoma cells to TRAIL (Chawla-Sarkar, et al., 2004). The compounds of the present invention bind to IAPs and inhibit their interaction with caspases, therein potentiating TRAIL-induced apoptosis.

Compounds and compositions of the present invention also can be used to augment radiation therapy (or radiotherapy), i.e., the medical use of ionizing radiation as part of cancer treatment to control malignant cells. Although radiotherapy is often used as part of curative therapy, it is occasionally used as a palliative treatment, where cure is not possible and the aim is for symptomatic relief. Radiotherapy is commonly used for the treatment of tumors. It may be used as the primary therapy. It is also common to combine radiotherapy with surgery and/or chemotherapy. The most common tumors treated with radiotherapy are breast cancer, prostate cancer, rectal cancer, head & neck cancers, gynecological tumors, bladder cancer and lymphoma. Radiation therapy is commonly applied just to the localized area involved with the tumor. Often the radiation fields also include the draining lymph nodes. It is possible but uncommon to give radiotherapy to the whole body, or entire skin surface. Radiation therapy is usually given daily for up to 35-38 fractions (a daily dose is a fraction). These small frequent doses allow healthy cells time to grow back, repairing damage inflicted by the radiation. Three main divisions of radiotherapy are external beam radiotherapy or teletherapy, brachytherapy or sealed source radiotherapy and unsealed source radiotherapy, which are all suitable examples of treatment protocol in the present invention. The differences relate to the position of the radiation source; external is outside the body, while sealed and unsealed source radiotherapy has radioactive material delivered internally. Brachytherapy sealed sources are usually extracted later, while unsealed sources are injected into the body.

Administration of the compounds and compositions of the present invention may occur prior to, concurrently with, or subsequent to the combination treatment protocol. A variety of administration routes are available. The particular mode selected will depend, of course, upon the particular chemotherapeutic drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, inhalation, intra-peritoneal, or parenteral routes. The term "parenteral" includes subcutaneous, intravenous, intramuscular, or infusion. Intravenous or intramuscular routes are particularly suitable for purposes of the present invention.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A compound of Formula (I):

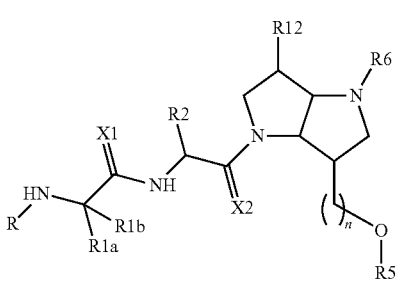

or a pharmaceutically acceptable salt thereof, wherein:

X1 and X2 are each independently O, or S:

n is 0 or 1;

R is selected from H; alkyl; substituted alkyl; alkenyl; substituted alkenyl; cycloalkyl; substituted cycloalkyl; aryl; substituted aryl; heteroaryl; or substituted heteroaryl;

R1a and R1b are each independently selected from H; alkyl; or substituted alkyl;

R2 is selected from H; alkyl; substituted alkyl; cycloalkyl; substituted cycloalkyl; heterocycloalkyl; substituted heterocycloalkyl; aryl; substituted aryl; heteroaryl; or substituted heteroaryl;

R5 is selected from H; alkyl; substituted alkyl; cycloalkyl; substituted cycloalkyl; aryl; substituted aryl; heterocycloalkyl; substituted heterocycloalkyl; heteroaryl; or substituted heteroaryl;

R6 is selected from H; alkyl; substituted alkyl; alkoxy; substituted alkoxy; alkylsulfonyl; arylsulfonyl; cycloalkyl; substituted cycloalkyl; heterocycloalkyl; substituted heterocycloalkyl; aryl; substituted aryl; heteroaryl; or substituted heteroaryl; and R12 is selected from H; or hydroxy.

2. The compound of claim 1, or a pharmaceutically acceptable salt thereof, wherein:

R is selected from H; alkyl; substituted alkyl; alkenyl; substituted alkenyl; aryl; substituted aryl; cycloalkyl; substituted cycloalkyl; heteroaryl; or substituted heteroaryl; wherein the substitutents for the substituted alkyl, the substituted alkenyl, the substituted aryl, the substituted cycloalkyl and the substituted heteroaryl are selected from the group consisting of halogen, hydroxy, oxo, mercapto, carboxyl, alkyl, cycloalkyl, aryl, alkoxy, amino, heteroaryl, and nitro;

R1a and R1b are each independently selected from H; alkyl; or substituted alkyl; wherein the substitutents are selected from the group consisting of halogen, hydroxy, oxo, mercapto, carboxyl, cycloalkyl, aryl, alkoxy, amino, heteroaryl, and nitro;

R2 is alkyl; substituted alkyl, wherein the substituents are selected from the group consisting of halogen, hydroxy, oxo, alkoxy, cycloalkyl, aryl, heterocycloalkyl and heteroaryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl, or substituted heteroaryl wherein the substituents are selected from the group consisting of halogen, hydroxy, mercapto, carboxyl, alkyl, cycloalkyl, aryl, alkoxy, amino, heteroaryl, and nitro;

R5 is selected from H; alkyl; substituted alkyl, wherein the alkyl substituents are selected from the group consisting of oxo, amino, alkoxy, carboxy, carboalkoxy, cycloalkyl, aryl, and substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro;

R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the group consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

3. The compound of claim 2, or a pharmaceutically acceptable salt thereof, wherein:

X1 and X1 are O;

R is selected from H; alkyl; substituted alkyl; alkenyl; or substituted alkenyl; wherein the alkyl and alkenyl substitutents are selected from the group consisting of halogen, hydroxy, oxo, mercapto, carboxyl, alkyl, cyclopropyl, alkoxy, amino, and nitro;

R1a and R1b are each independently selected from H; alkyl; or substituted alkyl, wherein the substituents are selected from the group consisting of halogen, hydroxy, oxo, mercapto, carboxyl, alkyl, cyclopropyl, alkoxy, amino, and nitro;

R2 is selected from alkyl; cycloalkyl; aryl; heterocycloalkyl; heteroaryl; or substituted alkyl, wherein the substituents are selected from the group consisting of halogen, hydroxy, oxo, alkoxy, cycloalkyl, aryl, heterocycloalkyl and heteroaryl;

R5 is selected from H; alkyl; substituted alkyl, wherein the alkyl substituents are selected from the group consisting of oxo, amino, aryl, and substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; aryl; substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; or heterocycloalkyl; and R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the group consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

4. The compound of claim 3, or a pharmaceutically acceptable salt thereof, wherein:

R is selected from H; or lower alkyl;

R1a and R1b are each independently selected from H; or lower alkyl optionally substituted with halogen;

R2 is selected from H; lower alkyl; cycloalkyl; or substituted lower alkyl wherein the substituents are selected from the group consisting of hydroxy, cycloalkyl and alkoxy; and R6 is selected from H; lower alkylsulfonyl; alkyl; substituted alkyl, wherein the alkyl substituents are selected from the group consisting of hydroxy, oxo, halogen, amino, alkoxy, cycloalkyl, aryl, and heteroaryl optionally substituted with lower alkyl or halogen; cycloalkyl; or heteroaryl optionally substituted with lower alkyl or halogen.

5. The compound of claim 4, or a pharmaceutically acceptable salt thereof, wherein:

R is methyl;

R1a is H and R1b is selected from methyl, or fluoromethyl;

R2 is selected from iso-propyl, t-butyl, 2-methoxy ethyl, or cyclohexyl;

R5 is selected from H; alkyl; substituted alkyl, wherein the alkyl substituents are selected from the group consisting of oxo, amino, heterocycloalkyl, and aryl optionally substituted with halogen; cycloalkyl; aryl; or substituted aryl wherein the aryl substituents are selected from the group consisting of halogen and phenyl;

R6 is selected from H; lower alkylsulfonyl; lower alkyl; substituted lower alkyl, wherein the substituents are selected from the group consisting of oxo, lower alkoxy, amino, and heteroaryl optionally substituted with lower alkyl or halogen; cycloalkyl; heterocycloalkyl; or heteroaryl, and R12 is H.

6. The compound of claim 5, or a pharmaceutically acceptable salt thereof, wherein amino comprises a group having a formula —NHR3 or —NR3R4, where the R3 and R4 group can be the same or different and are selected from the group consisting of alkyl, substituted alkyl, aryl, substituted aryl, cycloalkyl and heterocycloalkyl.

7. The compound of claim 6 wherein R5 is selected from H, phenyl, biphenyl, fluorophenyl, naphthyl, tetrahydronaphthyl, benzyl, fluorobenzyl, pyrrolidinyl carbonyl, piperidyl carbonyl, morpholinyl carbonyl, benzyl carbamoyl, phenyl carbamoyl, naphthyl carbamoyl, ethyl carbamoyl, n-butyl carbamoyl, isopropyl carbamoyl, tert-butyl carbamoyl, cyclopropyl carbamoyl, cyclohexyl carbamoyl, diphenylamino carbonyl, or methyl,phenyl amino carbonyl.

8. The compound of claim 7 wherein R6 is selected from H, ethyl, cyclopropyl, cyclohexyl, acetyl, tert-butoxy carbonyl, 3-methyl butyryl, 2-oxo-propionyl, methylsulfonyl, 2-methyl-propylsulfonyl, methyl carbamoyl, isopropyl carbamoyl, dimethyl carbamoyl, benzyl carbamoyl, tetrahydro pyanyl, or pyrimidinyl.

9. A compound of claim 1 where R1a is H and having the structure of formula (I—S):

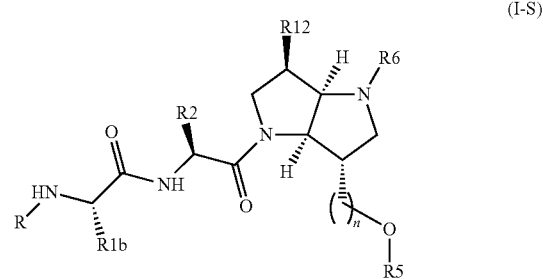

or a pharmaceutically acceptable salt thereof.

10. The compound of claim 9, or a pharmaceutically acceptable salt thereof, wherein:

R is selected from H; alkyl; substituted alkyl; alkenyl; substituted alkenyl; aryl; substituted aryl; cycloalkyl; substituted cycloalkyl; heteroaryl; or substituted heteroaryl;

wherein the alkyl, alkenyl, aryl, cycloalkyl and heteroaryl substituents are selected from the group consisting of halogen, hydroxy, oxo, mercapto, carboxyl, alkyl, cycloalkyl, aryl, alkoxy, amino, heteroaryl, and nitro;

R1b is selected from alkyl; or substituted alkyl, wherein the substitutents are selected from the group consisting of halogen, hydroxy, oxo, mercapto, carboxyl, cycloalkyl, aryl, alkoxy, amino, heteroaryl, and nitro;

R2 is alkyl; substituted alkyl, wherein the alkyl substituents are selected from the group consisting of halogen, hydroxy, oxo, alkoxy, cycloalkyl, aryl, heterocycloalkyl and heteroaryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; heteroaryl; or substituted heteroaryl wherein the heteroaryl substituents are selected from the group consisting of halogen, hydroxy, mercapto, carboxyl, alkyl, cycloalkyl, aryl, alkoxy, amino, heteroaryl, and nitro;

R5 is selected from H; alkyl; substituted alkyl, wherein the alkyl substituents are selected from the group consisting of oxo, amino, alkoxy, carboxy, carboalkoxy, cycloalkyl, aryl, and substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; and R6 is selected from H; alkylsulfonyl; arylsulfonyl; alkyl; substituted alkyl, wherein the alkyl substituents are selected from the groupg consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the group consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

11. The compound of claim 10, or a pharmaceutically acceptable salt thereof, wherein:

R is selected from H; alkyl; substituted alkyl; alkenyl; or substituted alkenyl, wherein the alkyl and alkenyl substitutents are selected from the group consisting of halogen, hydroxy, oxo, mercapto, carboxyl, alkyl, cyclopropyl, alkoxy, amino, and nitro;

R1b is selected from alkyl; or substituted alkyl, wherein the substitutents are selected from the group consisting of halogen, hydroxy, oxo, mercapto, carboxyl, alkyl, cyclopropyl, alkoxy, amino, and nitro, R2 is selected from alkyl; cycloalkyl; aryl; heterocycloalkyl; heteroaryl; or substituted alkyl, wherein the substituents are selected from the group consisting of halogen, hydroxy, oxo, alkoxy, cycloalkyl, aryl, heterocycloalkyl and heteroaryl;

R5 is selected from H; alkyl; substituted alkyl, wherein the alkyl substituents are selected from the group consisting of oxo, amino, aryl, and substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; aryl; substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; or heterocycloalkyl; and R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the group consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

12. The compound of claim 11, or a pharmaceutically acceptable salt thereof, wherein:

R is selected from H, or lower alkyl;

R1b is a lower alkyl optionally substituted with halogen;

R2 is selected from H; lower alkyl; cycloalkyl; or substituted lower alkyl wherein the substituents are selected from the group consisting of hydroxy, cycloalkyl and alkoxy; and R6 is selected from H; lower alkylsulfonyl; alkyl; substituted alkyl, wherein the alkyl substituents are selected from the group consisting of hydroxy, oxo, halogen, amino, alkoxy, cycloalkyl, aryl, and heteroaryl optionally substituted with lower alkyl or halogen; cycloalkyl; or heteroaryl optionally substituted with lower alkyl or halogen.

13. The compound of claim 12, or a pharmaceutically acceptable salt thereof, wherein:

R is methyl;

R1b is selected from methyl or fluoromethyl;

R2 is selected from iso-propyl, t-butyl, 2-methoxy ethyl, or cyclohexyl;

R5 is selected from H; alkyl; substituted alkyl; wherein the alkyl substituents are selected from the group consisting of oxo, amino, heterocycloalkyl, and aryl optionally substituted with halogen; cycloalkyl; aryl; or substituted aryl, wherein the aryl substituents are selected from the group consisting of halogen and phenyl;

R6 is selected from H; lower alkylsulfonyl; lower alkyl; substituted lower alkyl, wherein the substituents are selected from the group consisting of oxo, lower alkoxy, amino, and heteroaryl optionally substituted with lower alkyl or halogen; cycloalkyl; heterocycloalkyl; or heteroaryl, and R12 is H.

14. The compound of claim 13, or a pharmaceutically acceptable salt thereof, wherein amino comprises a group having a formula —NHR3 or —NR3R4, where the R3 and R4 group can be the same or different and are selected from the group consisting of alkyl, substituted alkyl, aryl, substituted aryl, cycloalkyl and heterocycloalkyl.

15. The compound of claim 14 wherein R5 is selected from H; phenyl, biphenyl, fluorophenyl, naphthyl, tetrahydronaphthyl, benzyl, fluorobenzyl, pyrrolidinyl carbonyl, piperidyl carbonyl, morpholinyl carbonyl, benzyl carbamoyl, phenyl carbamoyl, naphthyl carbamoyl, ethyl carbamoyl, n-butyl carbamoyl, isopropyl carbamoyl, tert-butyl carbamoyl, cyclopropyl carbamoyl, cyclohexyl carbamoyl, diphenylamino carbonyl, or methyl-phenyl amino carbonyl.

16. The compound of claim 15 wherein R6 is selected from H, ethyl, cyclopropyl, cyclohexyl, acetyl, tert-butoxy carbonyl, 3-methyl butyryl, 2-oxo-propionyl, methylsulfonyl, 2-methyl-propylsulfonyl, methyl carbamoyl, isopropyl carbamoyl, dimethyl carbamoyl, benzyl carbamoyl, tetrahydro pyanyl, or pyrimidinyl.

17. The compound of claim 1, selected from the group consisting of:

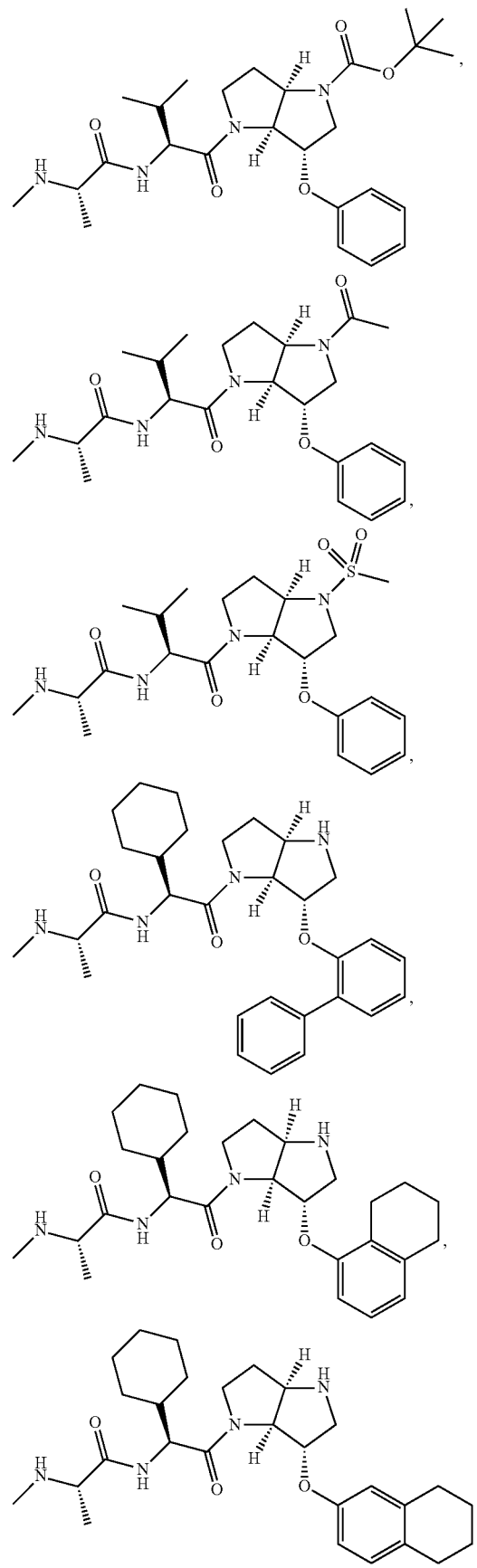

243
-continued
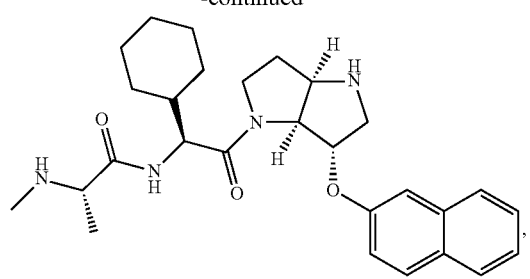
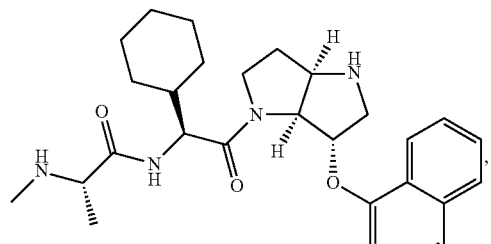
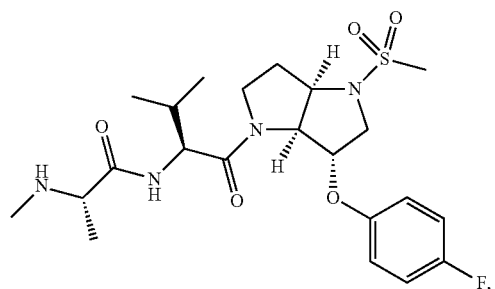
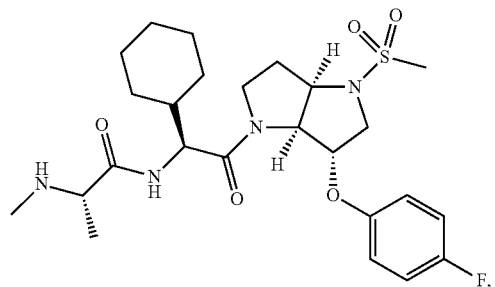
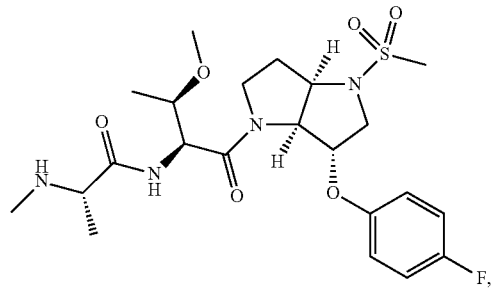
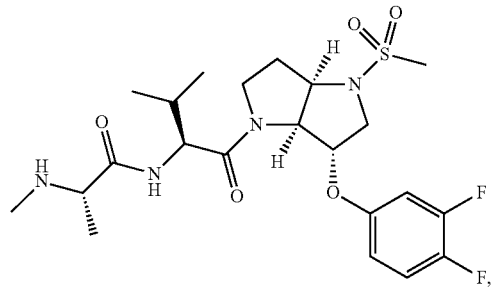
244
-continued
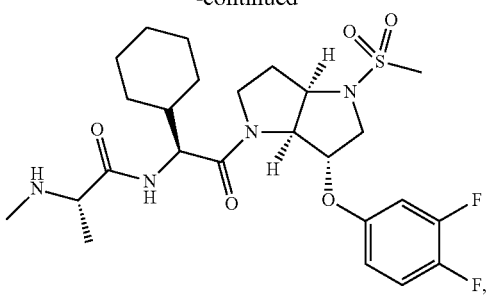
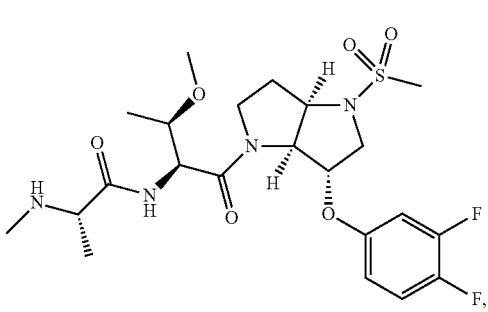
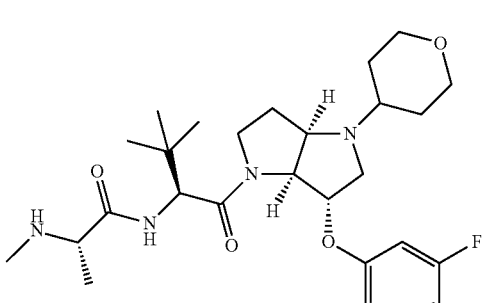
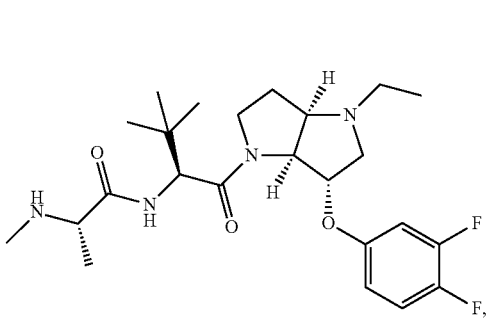
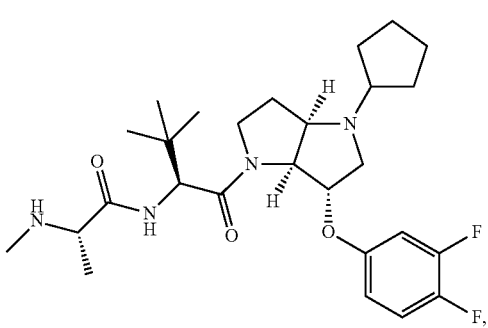

245
-continued
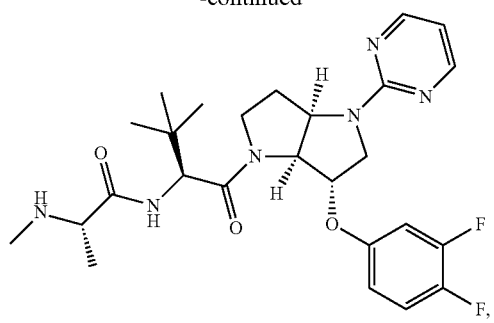
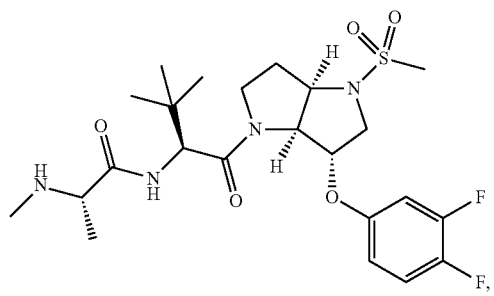
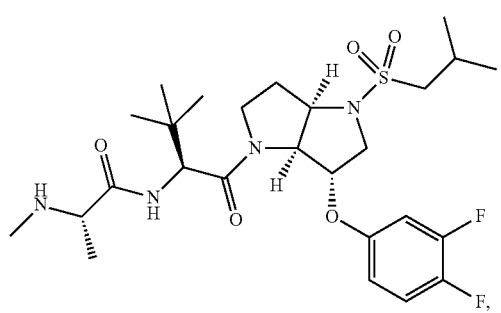
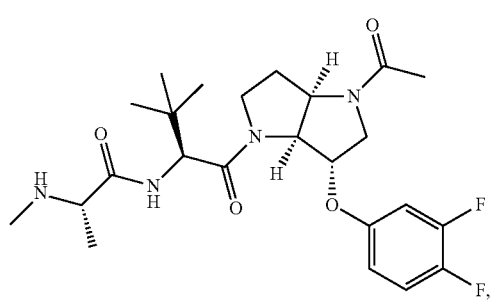
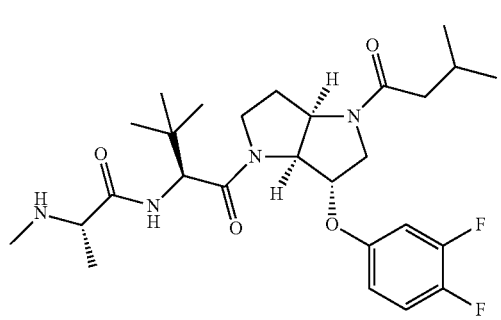
246
-continued
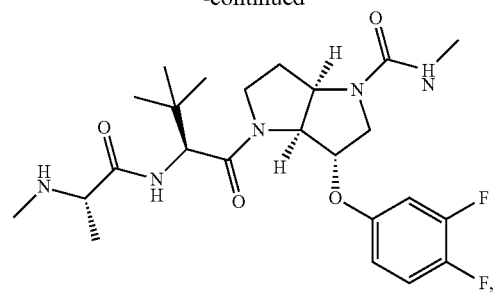
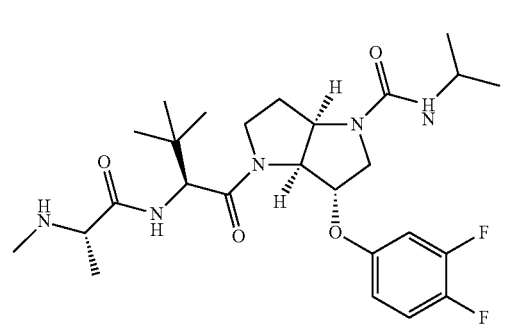
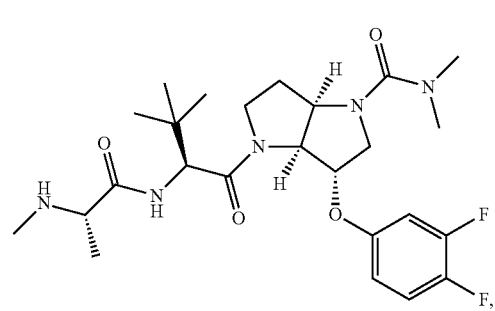
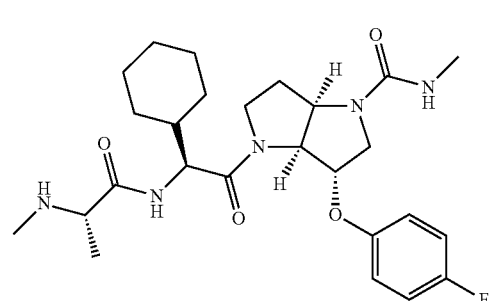
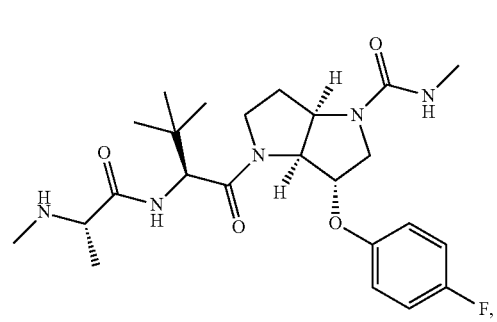

247
-continued
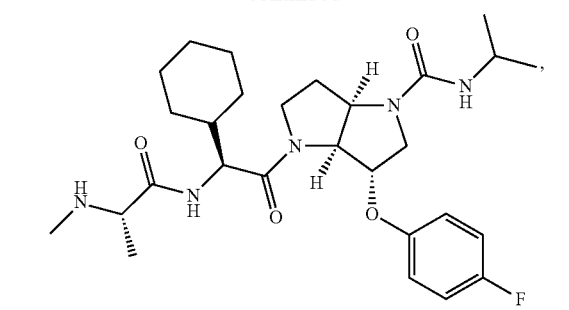
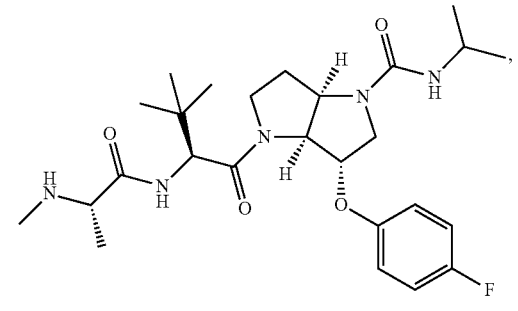
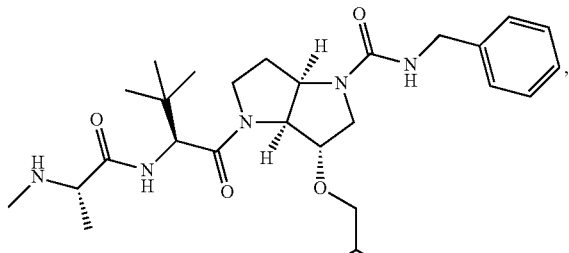
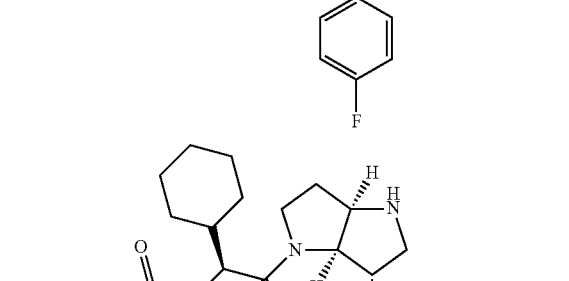
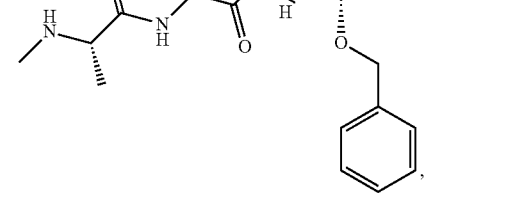
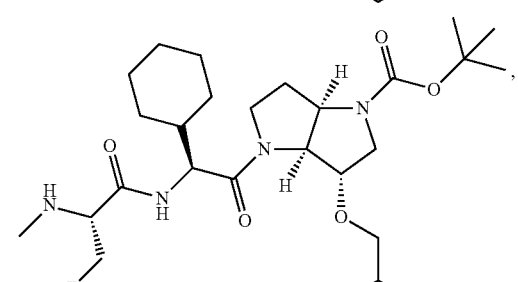
248
-continued
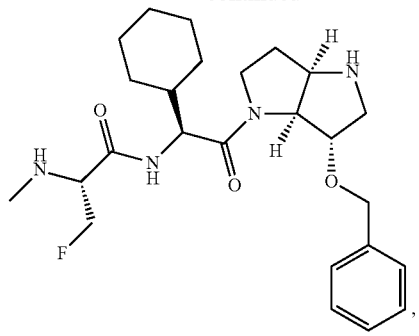
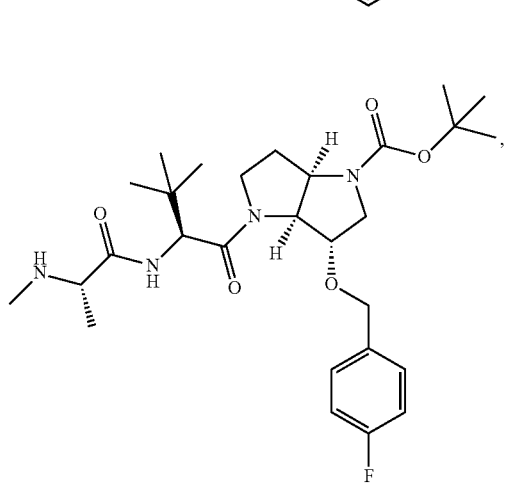
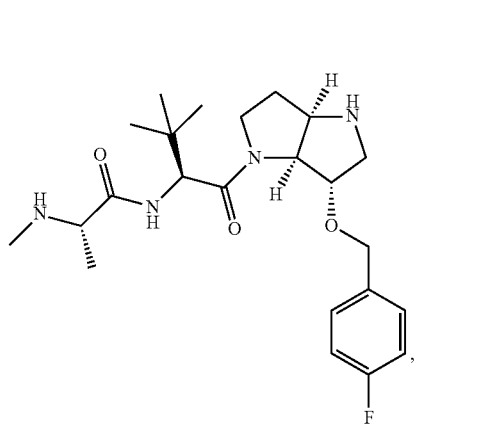
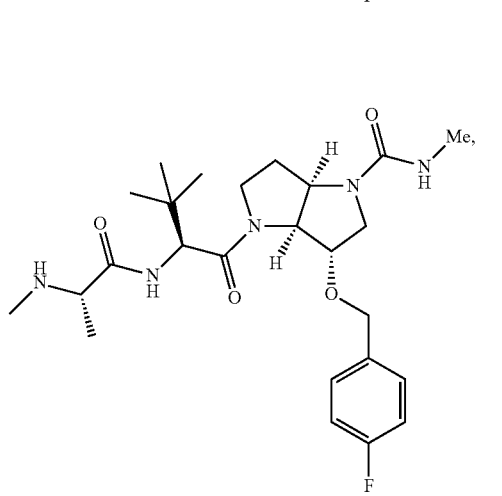

249
-continued
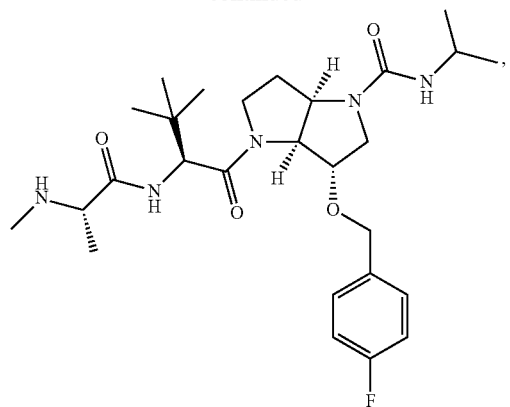
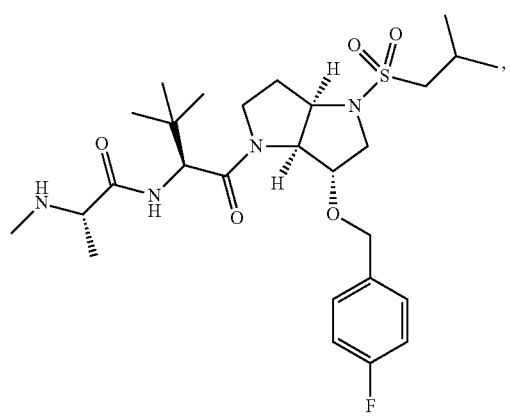
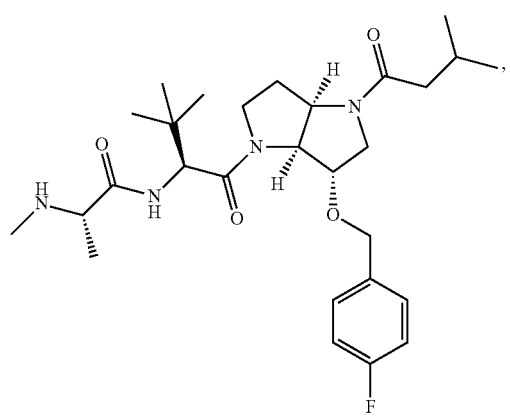
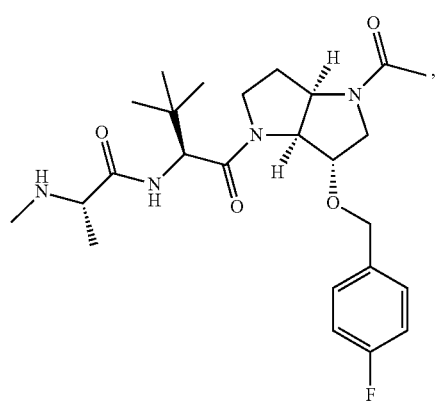
250
-continued
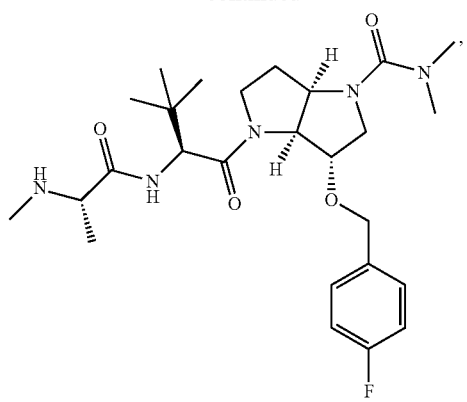
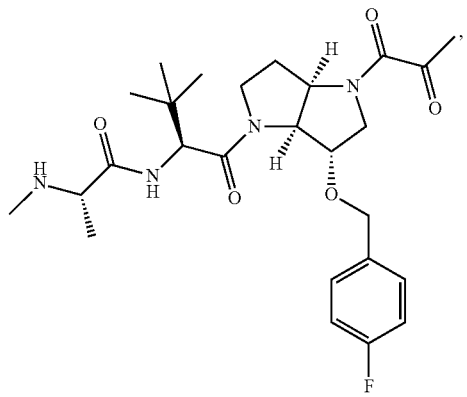
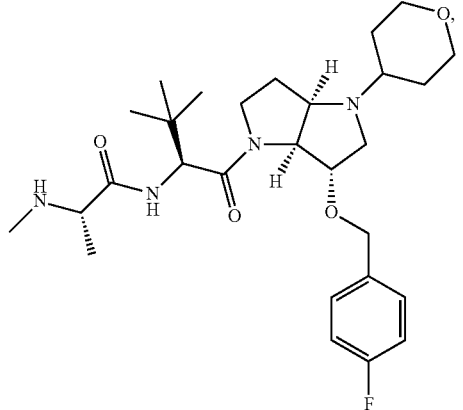
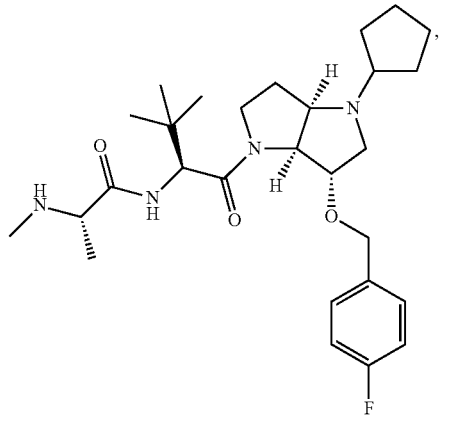

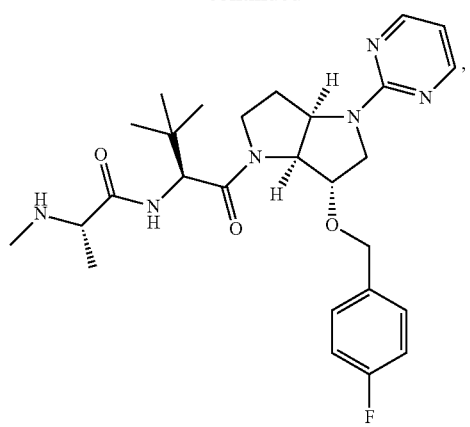
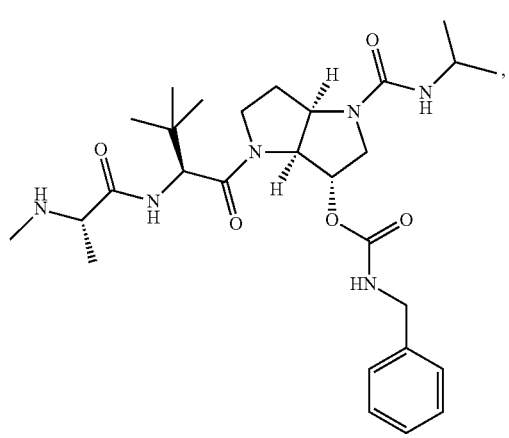
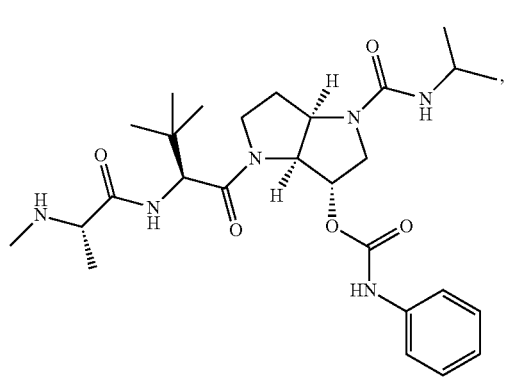
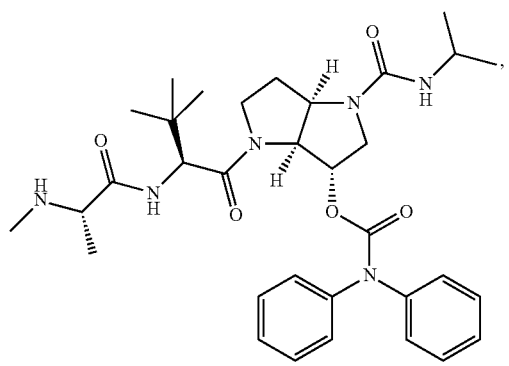
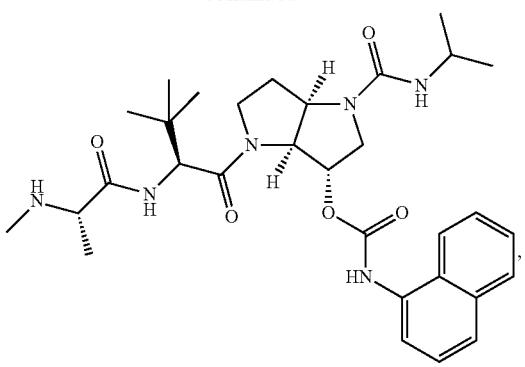
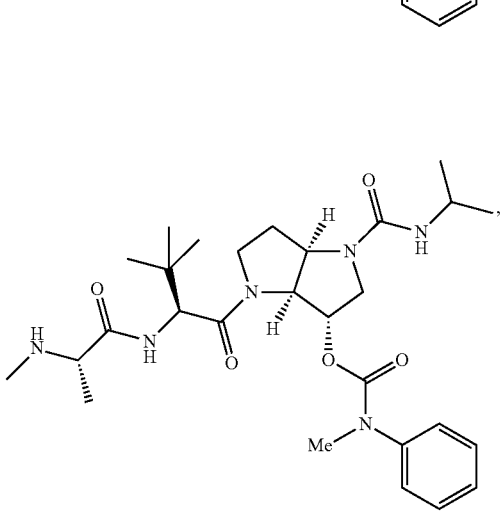
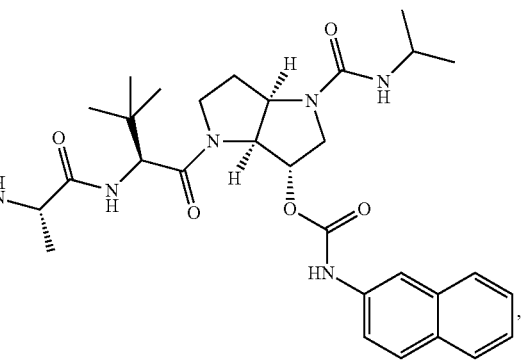
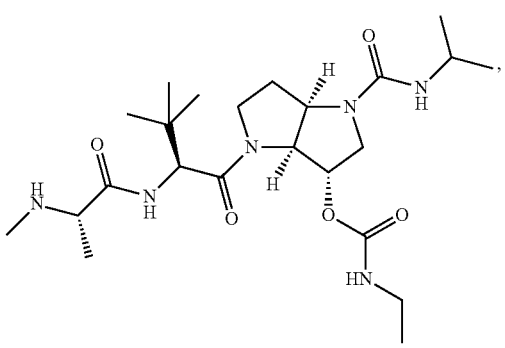

253
-continued
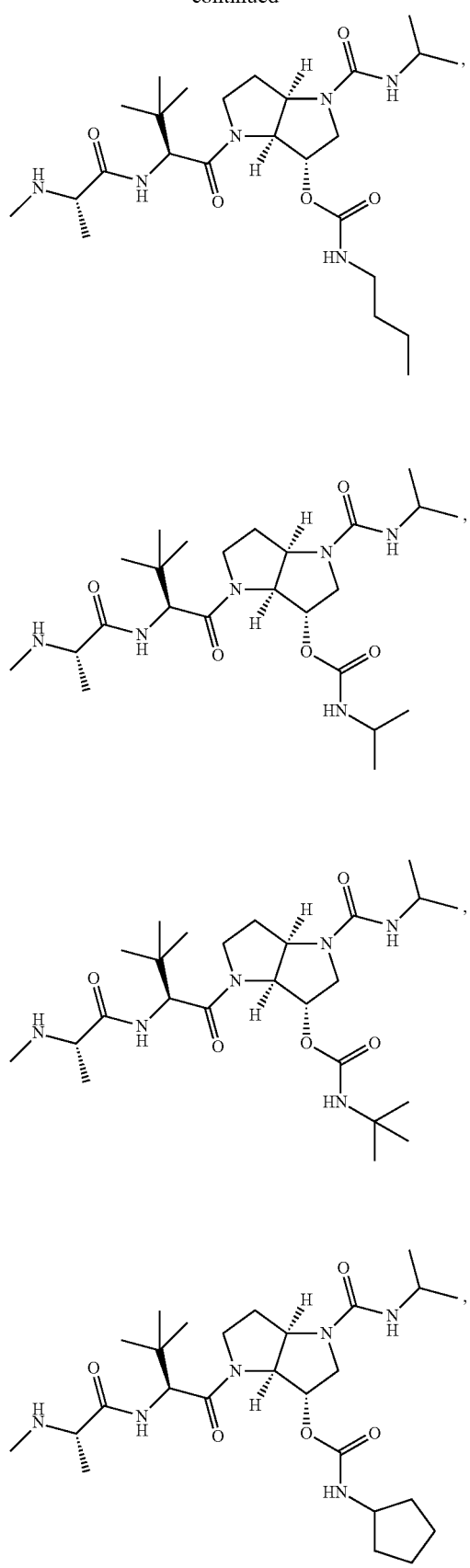
254
-continued
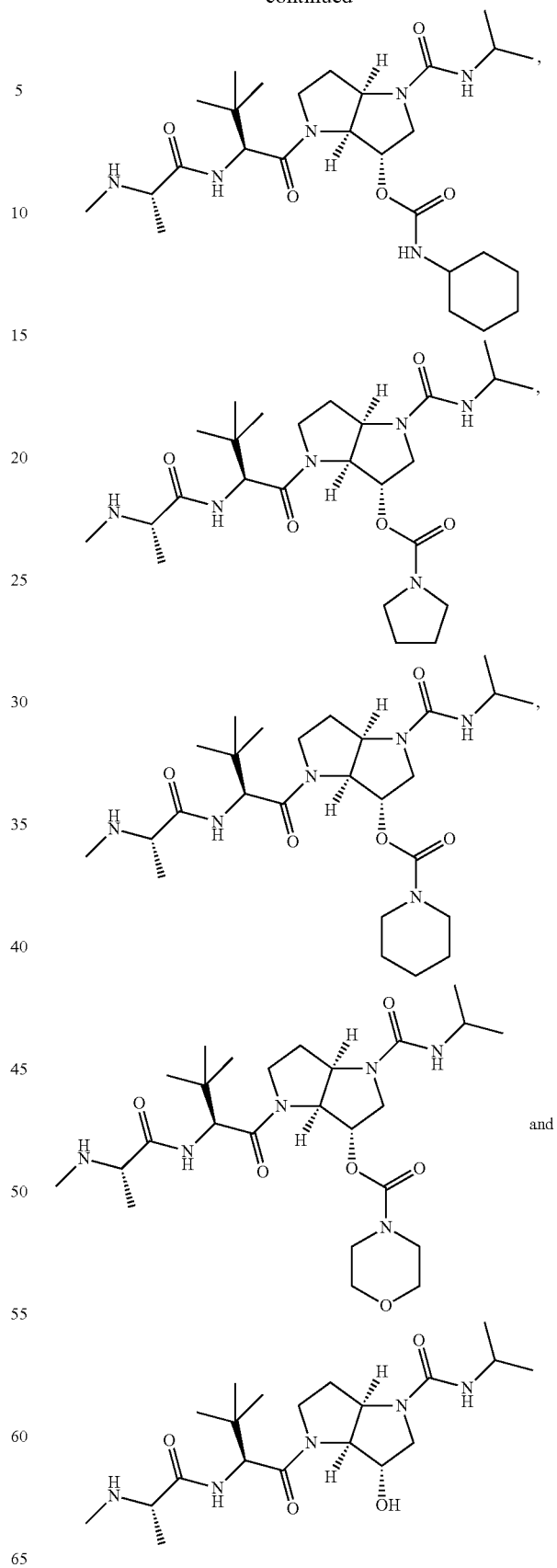
and pharmaceutically acceptable salts thereof.

18. The compound of claim 1, selected from the group consisting of
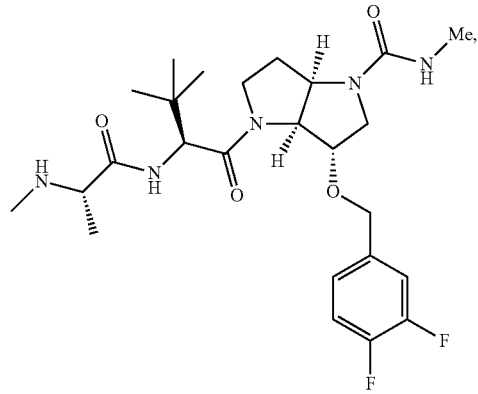
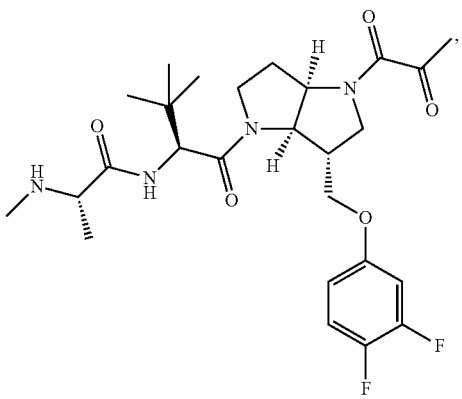
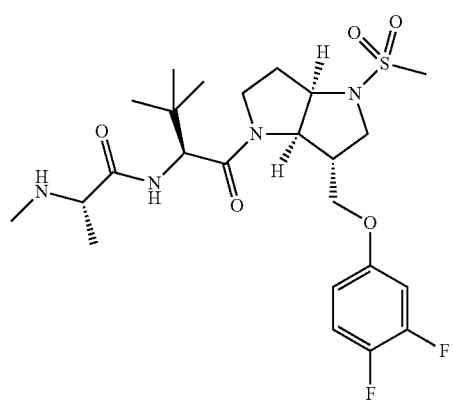
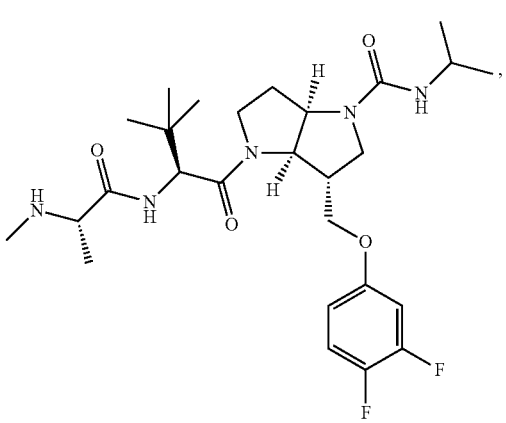
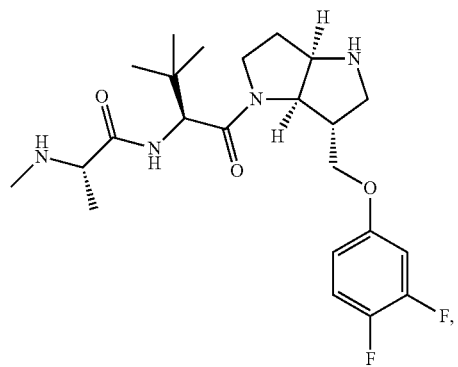
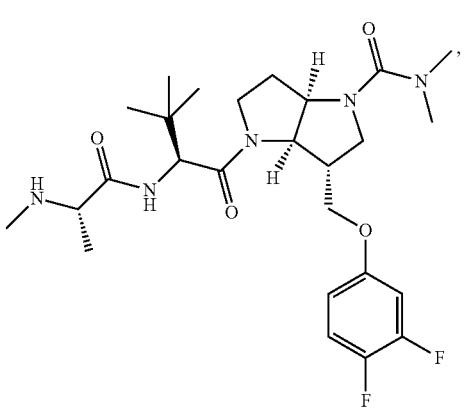
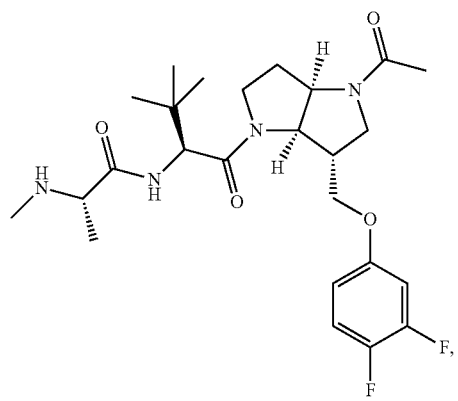
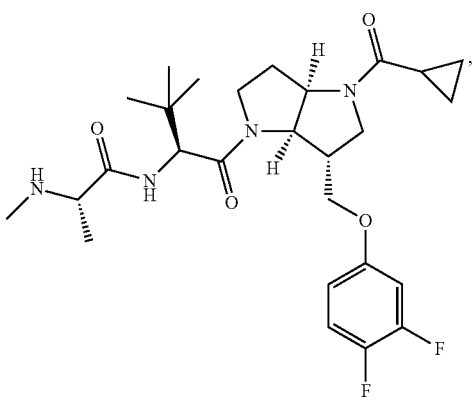

257

-continued

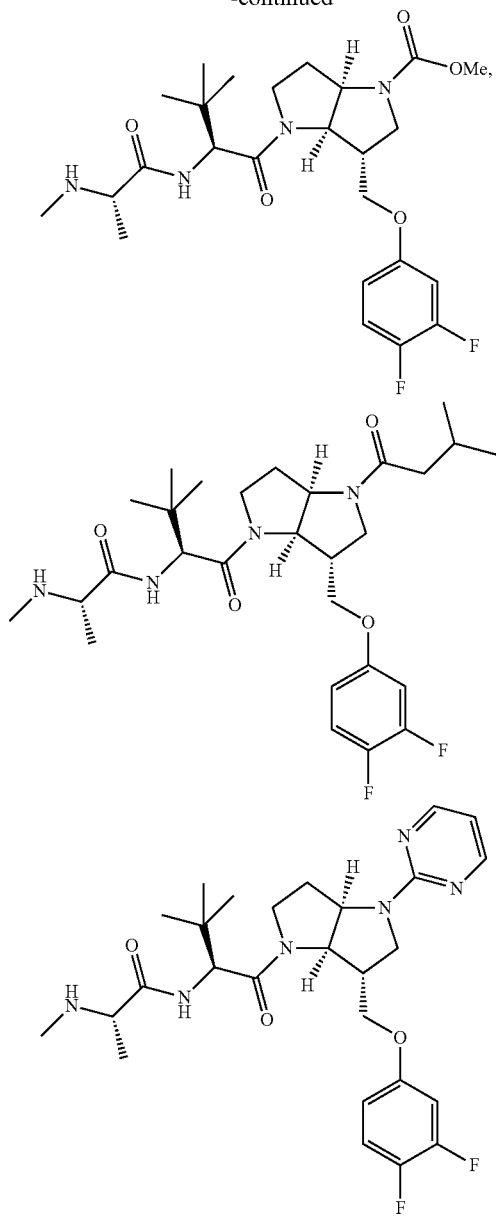

and pharmaceutically acceptable salts thereof.

19. A compound that is a dimer of two monomers of Formula (I) or of two monomers of Formula (I—S) or of one monomer of Formula (I—S) and one monomer of Formula (I-R),

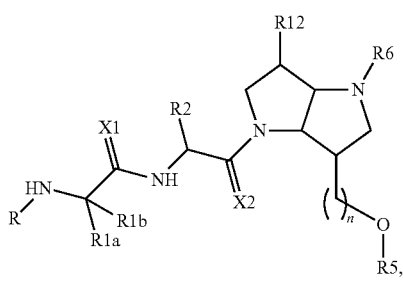
(I)

258

-continued

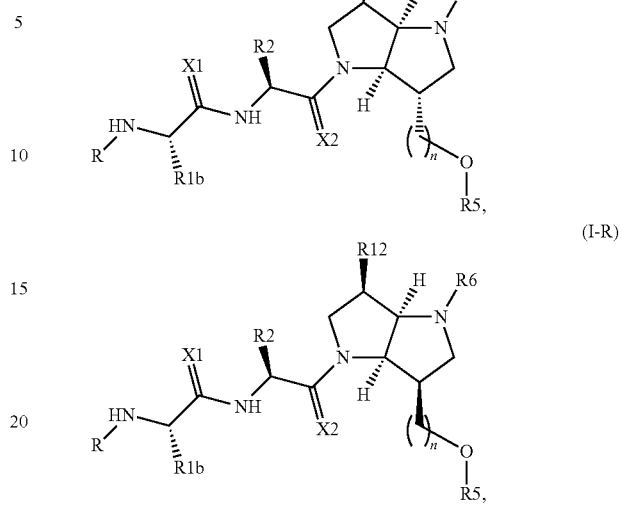

or a pharmaceutically acceptable salt of any such dimer, wherein:
both R2 groups together, or both R6 groups together, form -L-, linking the two monomers;
X1 is O or S:
X2 is O or S:
n is 0 or 1;
R is selected from H; alkyl; substituted alkyl; alkenyl; substituted alkenyl; cycloalkyl; substituted cycloalkyl; aryl; substituted aryl; heteroaryl; or substituted heteroaryl;
R1a and R1b are each independently selected from H; alkyl; or substituted alkyl;
when both R6 groups together form -L-, then each R2 is selected from H; alkyl; substituted alkyl; cycloalkyl; substituted cycloalkyl; heterocycloalkyl; substituted heterocycloalkyl; aryl; substituted aryl; heteroaryl; or substituted heteroaryl;
R5 is selected from H; alkyl; substituted alkyl; cycloalkyl; substituted cycloalkyl; aryl; substituted aryl; heterocycloalkyl; substituted heterocycloalkyl; heteroaryl; or substituted heteroaryl;
when both R2 groups together form -L-, then each R6 is selected from H; alkyl; substituted alkyl; alkoxy; substituted alkoxy; alkylsulfonyl; arylsulfonyl; cycloalkyl; substituted cycloalkyl; heterocycloalkyl; substituted heterocycloalkyl; aryl; substituted aryl; heteroaryl; or substituted heteroaryl;
L is a single or double covalent bont, or is a contiguous chain, branched or unbranched, substituted or unsubstituted, of 1 to about 100 atoms, and
R12 is selected from H; or hydroxy.

20. The compound of claim 19, or a pharmaceutically acceptable salt thereof, wherein:
R is selected from H; alkyl; substituted alkyl; alkenyl; substituted alkenyl; aryl; substituted aryl; cycloalkyl; substituted cycloalkyl; heteroaryl; or substituted heteroaryl; wherein the substitutents for the substituted alkyl, the substituted alkenyl, the substituted aryl, the substituted cycloalkyl and the substituted heteroaryl are selected from the group consisting of halogen, hydroxy, oxo, mercapto, carboxyl, alkyl, cycloalkyl, aryl, alkoxy, amino, heteroaryl, and nitro;

R1a and R1b are each independently selected from H; alkyl; or substituted alkyl; wherein the substitutents are selected from the group consisting of halogen, hydroxy, oxo, mercapto, carboxyl, cycloalkyl, aryl, alkoxy, amino, heteroaryl, and nitro;

when both R6 groups together form -L-, then R2 is alkyl; substituted alkyl, wherein the substituents are selected from the group consisting of halogen, hydroxy, oxo, alkoxy, cycloalkyl, aryl, heterocycloalkyl and heteroaryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl, or substituted heteroaryl wherein the substituents are selected from the group consisting of halogen, hydroxy, mercapto, carboxyl, alkyl, cycloalkyl, aryl, alkoxy, amino, heteroaryl, and nitro;

R5 is selected from H; alkyl; substituted alkyl, wherein the alkyl substituents are selected from the group consisting of oxo, amino, alkoxy, carboxy, carboalkoxy, cycloalkyl, aryl, and substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro;

when both R2 groups together form -L-, then R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the group consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro, and L is optionally substituted alkyl, alkylene, alkylyne, cycloalkyl, alkylcycloalkyl, alkylarylalkyl chain of 2 to 20 atoms with 1-3 heteroatoms selected from —O—, —NH— and —S—.

21. The compound of claim 20, or a pharmaceutically acceptable salt thereof, wherein:

X1 and X1 are O;

R is selected from H; alkyl; substituted alkyl; alkenyl; or substituted alkenyl; wherein the alkyl and alkenyl substitutents are selected from the group consisting of halogen, hydroxy, oxo, mercapto, carboxyl, alkyl, cyclopropyl, alkoxy, amino, and nitro;

R1a and R1b are each independently selected from H; alkyl; or substituted alkyl, wherein the substitutents are selected from the group consisting of halogen, hydroxy, oxo, mercapto, carboxyl, alkyl, cyclopropyl, alkoxy, amino, and nitro;

when both R6 groups together form -L-, then R2 is selected from alkyl; cycloalkyl; aryl; heterocycloalkyl; heteroaryl; or substituted alkyl, wherein the substituents are selected from the group consisting of halogen, hydroxy, oxo, alkoxy, cycloalkyl, aryl, heterocycloalkyl and heteroaryl;

R5 is selected from H; alkyl; substituted alkyl, wherein the alkyl substituents are selected from the group consisting of oxo, amino, aryl, and substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; aryl; substituted aryl, wherein the aryl substituents are selected from the group consisting of alkyl, halogen, hydroxy, mercapto, carboxyl, cycloalkyl, aryl, alkoxy, amino, heteroaryl, heterocycloalkyl, nitro, alkylsulfonyl and arylsulfonyl; or heterocycloalkyl; and when both R2 groups together form -L-, then R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the group consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro and L is optionally substituted alkyl, alkylene, alkylyne, cycloalkyl, alkylcycloalkyl, alkylarylalkyl chain of 2 to 20 atoms with 1-3 heteroatoms selected from —O—, —NH— and —S—.

22. The compound of claim 21, or a pharmaceutically acceptable salt thereof, wherein:

R is selected from H; or lower alkyl;

R1a and R1b are each independently selected from H; or lower alkyl optionally substituted with halogen;

when both R6 groups together form -L-, then R2 is selected from H; lower alkyl; cycloalkyl; or substituted lower alkyl wherein the substituents are selected from the group consisting of hydroxy, cycloalkyl and alkoxy; and when both R2 groups together form -L-, then R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen and L is —C(O)CH₂NHC(O)C(O)NHCH₂C(O)—.

23. The compound of claim 22, or a pharmaceutically acceptable salt thereof, wherein:

R is methyl;

R1a is H and R1b is selected from methyl, or fluoromethyl;

when both R6 groups together form -L-, then R2 is selected from iso-propyl, t-butyl, 2-methoxy ethyl, or cyclohexyl;

R5 is selected from H; alkyl; substituted alkyl, wherein the alkyl substituents are selected from the group consisting of oxo, amino, heterocycloalkyl, and aryl optionally substituted with halogen; cycloalkyl; aryl; or substituted aryl wherein the aryl substituents are selected from the group consisting of halogen and phenyl;

when both R2 groups together form -L-, then R6 is selected from H; lower alkylsulfonyl; lower alkyl; substituted lower alkyl, wherein the substituents are selected from the group consisting of oxo, lower alkoxy, amino, and heteroaryl optionally substituted with lower alkyl or halogen; cycloalkyl; heterocycloalkyl; or heteroaryl, L is —C(O)CH₂NHC(O)C(O)NHCH₂C(O)—, and R12 is H.

24. The compound of claim 23, or a pharmaceutically acceptable salt thereof, wherein amino comprises a group having a formula —NHR3 or —NR3R4, where the R3 and R4 group can be the same or different and are selected from the group consisting of alkyl, substituted alkyl, aryl, substituted aryl, cycloalkyl and heterocycloalkyl.

25. The compound of claim 24 wherein R5 is selected from H, phenyl, biphenyl, fluorophenyl, naphthyl, tetrahydronaphthyl, benzyl, fluorobenzyl, pyrrolidinyl carbonyl, piperidyl carbonyl, morpholinyl carbonyl, benzyl carbamoyl, phenyl carbamoyl, naphthyl carbamoyl, ethyl carbamoyl, n-butyl carbamoyl, isopropyl carbamoyl, tert-butyl carbamoyl, cyclopropyl carbamoyl, cyclohexyl carbamoyl, diphenylamino carbonyl, or methyl,phenyl amino carbonyl.

26. The compound of claim 25 wherein both R2 groups together form -L-, and R6 is selected from H, ethyl, cyclopropyl, cyclohexyl, acetyl, tert-butoxy carbonyl, 3-methyl butyryl, 2-oxo-propionyl, methylsulfonyl, 2-methyl-propylsulfonyl, methyl carbamoyl, isopropyl carbamoyl, dimethyl carbamoylbenzyl carbamoyl, tetrahydro pyanyl, or pyrimidinyl.

27. A pharmaceutical composition comprising a compound of claim 1, or a pharmaceutically acceptable salt thereof, and a pharmaceutically acceptable excipient.

28. A method for inducing apoptosis in a cell comprising contacting the cell with a compound, or a pharmaceutically acceptable salt thereof, selected from claim 1 in an amount sufficient to induce apoptosis in the cell.

29. The method of claim 28 wherein the cell is a cancer cell.

30. A method of treating a patient having cancer selected from the group consisting of; sarcomas, bladder cancers, ovarian cancers, breast cancers, brain cancers, pancreatic cancers, colon cancers, blood cancers, skin cancers, lung cancers and bone cancers, the method comprising administering a therapeutically effective amount of a compound, or a pharmaceutically acceptable salt thereof sufficient for inducing apoptosis, of claim 1 to a patient in need thereof.

31. The method of claim 30 wherein the cancers are selected from the group consisting of colorectal cancer, renal carcinoma, ovarian carcinoma, pancreatic carcinoma, prostate carcinoma, breast carcinoma, melanoma, glioblastoma, acute myeloid leukemia (AML), small cell lung carcinoma, non-small cell lung carcinoma, rhabdomyosarcoma, and basal cell carcinoma.

32. The method of claim 31 further comprising administering a second therapy selected from radiation, chemotherapy, immunotherapy, photodynamic therapy, or combinations thereof.

33. A method of treating patient having a autoimmune disease selected from the group consisting of; systemic lupus erythematosus, psoriasis and idiopathic thrombocytopenic purpura (Morbus Werlhof); the method comprising administering a therapeutically effective amount of a compound, or a pharmaceutically acceptable salt thereof sufficient for inducing apoptosis, of claim 1 to a patient in need thereof.

* * * * *

UNITED STATES PATENT AND TRADEMARK OFFICE
CERTIFICATE OF CORRECTION

PATENT NO. : 8,415,486 B2
APPLICATION NO. : 13/322709
DATED : April 9, 2013
INVENTOR(S) : Stephen M. Condon et al.

It is certified that error appears in the above-identified patent and that said Letters Patent is hereby corrected as shown below:

In the Claims

In Claim 2, Column 235, Line 46:
    Please delete "substitutents" and insert --substituents--.

In Claim 2, Column 235, Line 53:
    Please delete "substitutents" and insert --substituents--.

In Claim 3, Column 236, Line 66-67:
    Please delete "substitutents" and insert --substituents--.

In Claim 3, Column 237, Line 4:
    Please delete "substitutents" and insert --substituents--.

In Claim 10, Column 239, Line 2:
    Please delete "substitutents" and insert --substituents--.

In Claim 10, Column 239, Line 6:
    Please delete "substitutents" and insert --substituents--.

In Claim 10, Column 239, Line 56:
    Please delete "groupg" and insert --group--.

In Claim 11, Column 240, Line 18-19:
    Please delete "substitutents" and insert --substituents--.

In Claim 11, Column 240, Line 23:
    Please delete "substitutents" and insert --substituents--.

Signed and Sealed this
First Day of July, 2014

Michelle K. Lee
*Deputy Director of the United States Patent and Trademark Office*

CERTIFICATE OF CORRECTION (continued)
U.S. Pat. No. 8,415,486 B2

In Claim 17, Column 246, between lines 1-15:

Please replace 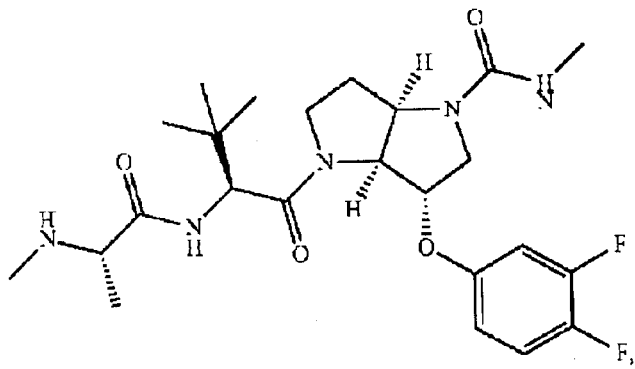

with 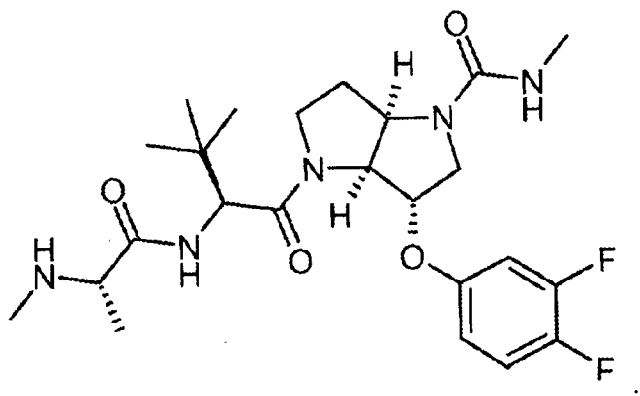

In Claim 17, Column 246, between lines 15-28:

Please replace 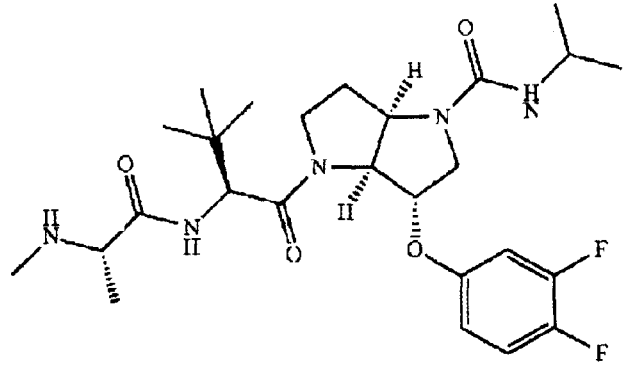

with 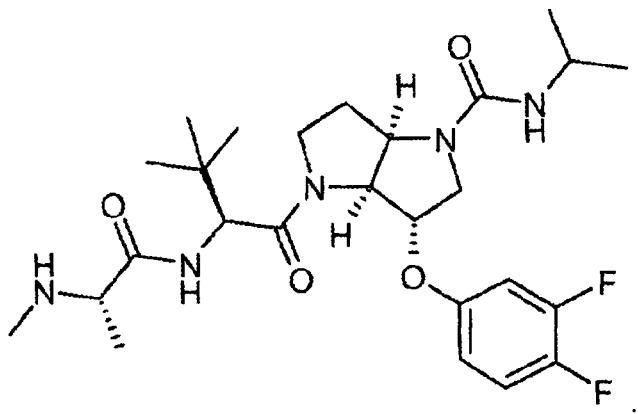

CERTIFICATE OF CORRECTION (continued)
U.S. Pat. No. 8,415,486 B2

In Claim 19, Column 258, Line 55:
    Please delete "bont" and insert --bond--.

In Claim 20, Column 258, Line 64:
    Please delete "substitutents" and insert --substituents--.

In Claim 20, Column 259, Line 4:
    Please delete "substitutents" and insert --substituents--.

In Claim 21, Column 259, Lines 22-23:
    Please delete "substitutents" and insert --substituents--.

In Claim 21, Column 259, Line 27:
    Please delete "substitutents" and insert --substituents--.